US011591398B2

(12) United States Patent
Hayes et al.

(10) Patent No.: US 11,591,398 B2
(45) Date of Patent: *Feb. 28, 2023

(54) SINGLE DOMAIN ANTIBODIES TO PROGRAMMED CELL DEATH PROTEIN 1 (PD-1)

(71) Applicant: CRESCENDO BIOLOGICS LIMITED, Cambridge (GB)

(72) Inventors: Phil Hayes, Cambridge (GB); James Legg, Cambridge (GB); Martyna Lewandowska, Cambridge (GB); Colette Johnston, Cambridge (GB); Brian McGuinness, Cambridge (GB); Mike Romanos, Cambridge (GB); Christine Rossant, Cambridge (GB); Yumin Teng, Cambridge (GB)

(73) Assignee: CRESCENDO BIOLOGICS LIMITED, Cambridge (GB)

( * ) Notice: Subject to any disclaimer, the term of this patent is extended or adjusted under 35 U.S.C. 154(b) by 9 days.

This patent is subject to a terminal disclaimer.

(21) Appl. No.: 16/475,597

(22) PCT Filed: Jan. 8, 2018

(86) PCT No.: PCT/GB2018/050036
§ 371 (c)(1),
(2) Date: Jul. 2, 2019

(87) PCT Pub. No.: WO2018/127710
PCT Pub. Date: Jul. 12, 2018

(65) Prior Publication Data
US 2020/0239573 A1    Jul. 30, 2020

(30) Foreign Application Priority Data

Jan. 6, 2017 (GB) ..................... 1700207
Jan. 6, 2017 (GB) ..................... 1700208
Jan. 6, 2017 (GB) ..................... 1700210

(51) Int. Cl.
| | | |
|---|---|---|
| *C07K 16/28* | (2006.01) | |
| *C12N 15/85* | (2006.01) | |
| *A61P 35/00* | (2006.01) | |
| *A01K 67/027* | (2006.01) | |
| *G01N 33/68* | (2006.01) | |
| *A61K 39/00* | (2006.01) | |
| *C07K 16/18* | (2006.01) | |

(52) U.S. Cl.
CPC ...... *C07K 16/2818* (2013.01); *A01K 67/0278* (2013.01); *A61P 35/00* (2018.01); *C07K 16/2803* (2013.01); *C12N 15/85* (2013.01); *G01N 33/6803* (2013.01); *A01K 2227/105* (2013.01); *A61K 2039/505* (2013.01); *C07K 16/18* (2013.01); *C07K 2317/24* (2013.01); *C07K 2317/31* (2013.01); *C07K 2317/33* (2013.01); *C07K 2317/35* (2013.01); *C07K 2317/565* (2013.01); *C07K 2317/569* (2013.01); *C07K 2317/70* (2013.01); *C07K 2317/76* (2013.01); *C07K 2317/92* (2013.01); *C07K 2317/94* (2013.01); *C07K 2319/00* (2013.01)

(58) Field of Classification Search
CPC .......... C07K 2317/569; C07K 2317/76; C07K 2317/56
See application file for complete search history.

(56) References Cited

U.S. PATENT DOCUMENTS

| | | | |
|---|---|---|---|
| 7,851,598 B2 | 12/2010 | Davis | |
| 9,872,852 B2 | 1/2018 | Chupak et al. | |
| 10,202,458 B2 | 2/2019 | Goetsch et al. | |
| 10,975,161 B2 | 4/2021 | Balloi et al. | |
| 11,236,174 B2 | 2/2022 | McGuinness et al. | |
| 11,312,771 B2 | 4/2022 | Edwards et al. | |
| 2010/0122358 A1 | 5/2010 | Bruggemann et al. | |
| 2013/0202623 A1* | 8/2013 | Chomont | G01N 33/56988 424/173.1 |
| 2014/0356908 A1 | 12/2014 | Grosveld et al. | |
| 2015/0201769 A1 | 7/2015 | Freeman et al. | |
| 2015/0210769 A1* | 7/2015 | Freeman | G01N 33/57484 424/136.1 |
| 2015/0210796 A1* | 7/2015 | Kim | C08G 18/325 252/586 |
| 2017/0240644 A1 | 8/2017 | Zhou et al. | |
| 2018/0362666 A1 | 12/2018 | Teng et al. | |
| 2019/0023807 A1 | 1/2019 | Balloi et al. | |
| 2019/0144561 A1 | 5/2019 | McGuinness et al. | |
| 2019/0322749 A1 | 10/2019 | Edwards et al. | |

(Continued)

FOREIGN PATENT DOCUMENTS

| | | |
|---|---|---|
| CN | 105384825 A | 3/2016 |
| EP | 2363404 A2 | 9/2011 |

(Continued)

OTHER PUBLICATIONS

Goel et al., Plasticity within the Antigen Combining Site May Manifest as Molecular Mimicry in the Humoral Immune Response. The Journal of Immunology 173(12):7358-7367, 2004.*
Lloyd et al., Modelling the human immune response: performance of a 1011 human antibody repertoire against a broad panel of therapeutically relevant antigens. Protein Engineering, Design & Selection 22(3):159-168, 2009.*

(Continued)

*Primary Examiner* — Hong Sang
(74) *Attorney, Agent, or Firm* — Sterne, Kessler, Goldstein & Fox P.L.L.C.

(57) ABSTRACT

The invention relates to PD-1 binding agents that block the interaction of PD-1 with its ligands, and the use of such binding agents in the treatment, prevention and detection of disease.

17 Claims, 7 Drawing Sheets

Figure 1A:
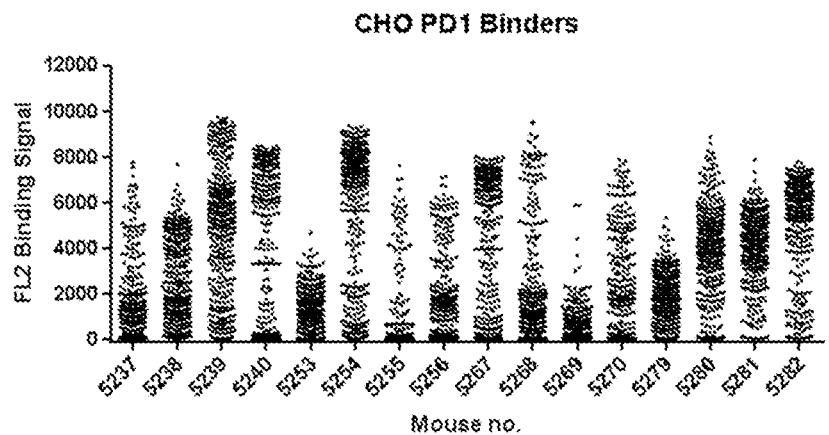

Specification includes a Sequence Listing.

(56) References Cited

U.S. PATENT DOCUMENTS

| | | | |
|---|---|---|---|
| 2020/0131274 | A1 | 4/2020 | Royle et al. |
| 2020/0239570 | A1 | 7/2020 | Edwards et al. |
| 2020/0362047 | A1 | 11/2020 | Brucklacher-Waldert et al. |
| 2020/0362051 | A1 | 11/2020 | Brucklacher-Waldert et al. |
| 2020/0392244 | A1 | 12/2020 | Balloi et al. |
| 2021/0015937 | A1 | 1/2021 | Edwards et al. |
| 2021/0340233 | A1 | 11/2021 | Edwards et al. |
| 2022/0112305 | A1 | 4/2022 | McGuinness et al. |
| 2022/0220215 | A1 | 7/2022 | Enever et al. |
| 2022/0227850 | A1 | 7/2022 | Dunlevy et al. |

FOREIGN PATENT DOCUMENTS

| | | |
|---|---|---|
| EP | 2363404 B1 | 9/2016 |
| EP | 3470426 A1 | 4/2019 |
| WO | WO-2003000737 A2 | 1/2003 |
| WO | WO-2004076618 A2 | 9/2004 |
| WO | WO-2006089230 A2 | 8/2006 |
| WO | WO-2007117264 A2 | 10/2007 |
| WO | 2009/114335 | 9/2009 |
| WO | WO-2009117335 A2 | 9/2009 |
| WO | WO-2010036959 A2 | 4/2010 |
| WO | WO-2011110621 A1 | 9/2011 |
| WO | WO-2012072731 A2 | 6/2012 |
| WO | WO-2013167883 A1 | 11/2013 |
| WO | WO-2014141192 A1 | 9/2014 |
| WO | WO-2015034820 A1 | 3/2015 |
| WO | WO 2015/112900 | 7/2015 |
| WO | WO-2015116539 A1 | 8/2015 |
| WO | WO-2015142675 A2 | 9/2015 |
| WO | WO-2015143079 A1 | 9/2015 |
| WO | WO-2015200119 A1 | 12/2015 |
| WO | WO 2016/020856 | 2/2016 |
| WO | WO-2016025880 A1 | 2/2016 |
| WO | WO-2016062990 A1 | 4/2016 |
| WO | WO 2016-073760 | 5/2016 |
| WO | WO 2016/106159 | 6/2016 |
| WO | WO-2016184882 A1 | 11/2016 |
| WO | WO 2016/197497 | 12/2016 |
| WO | WO-2017019846 A1 | 2/2017 |
| WO | WO-2017020801 A1 | 2/2017 |
| WO | WO-2017060144 A1 | 4/2017 |
| WO | WO-2017087589 A2 | 5/2017 |
| WO | WO-2017122017 A1 | 7/2017 |
| WO | WO-2017122018 A1 | 7/2017 |
| WO | WO-2017122019 A1 | 7/2017 |
| WO | WO-2017123650 A2 | 7/2017 |
| WO | WO-2017191476 A1 | 11/2017 |
| WO | WO-2017201488 A1 | 11/2017 |
| WO | WO-2018104444 A1 | 6/2018 |
| WO | WO-2018127709 A1 | 7/2018 |
| WO | WO-2018127710 A1 | 7/2018 |
| WO | WO-2018127711 A1 | 7/2018 |
| WO | WO-2018224439 A1 | 12/2018 |
| WO | WO-2019012260 A1 | 1/2019 |
| WO | WO-2019092451 A1 | 5/2019 |
| WO | WO-2019092452 A1 | 5/2019 |
| WO | WO-2019158942 A1 | 8/2019 |
| WO | WO-2020099871 A1 | 5/2020 |
| WO | WO-2020229842 A1 | 11/2020 |
| WO | WO-2020229844 A1 | 11/2020 |

OTHER PUBLICATIONS

Edwards et al.,The remarkable flexibility of the human antibody repertoire; isolation of over one thousand different antibodies to a single protein, BlyS. Journal of Molecular Biology 334:103-118, 2003.*
Padlan, Advances in Protein Chemistry, 1996, 49:57-133.*
Berglund et al, Protein Science, 2008, 17:606-613.*
Tzartos et al., Methods in Molecular Biology, 1996, 66:55-66.*
Chen, Sci Adv. Apr. 1, 2020;6(14):eaaz7825.*
Paul, Fundamental Immunology, 3rd Edition, 1993, pp. 292-295, under the heading "Fv Structure and Diversity in Three Dimensions".*
Rudikoff et al., Proc. Natl. Acad. Sci. USA, 79(6):1979-1983, Mar. 1982.*
Muyldermans et al, Annu. Rev. Biochem., 82:775-97, 2013.*
Vincke et al., . Biol. Chem., 2009, 284(5): 3273-3284.*
Muyldermans et al, Annu. Rev. Biochem., 2013, 82:775-97.*
Saerens et al., J Mol. Biol., 2005, 352: 597-607.*
Vincke et al., J. Biol. Chem., 2009, 284(5): 3273-3284.*
Zabetakis et al.,PLOS ONE, 2013, 8(10), 1-7.*
Caldas, C., et al., "Humanization of the anti-CD18 antibody 6.7: an unexpected effect of a framework residue in binding to antigen," *Molecular Immunology* 39(15):941-952, Elsevier, Netherlands (May 2003).
Du, J., et al., "Molecular basis of recognition of human osteopontin by 23C3, a potential therapeutic antibody for treatment of rheumatoid arthritis," *Journal of Molecular Biology* 382(4):835-842, Elsevier, Netherlands (published online Jul. 2008, published in print Oct. 2008).
Kunik, V., et al., "Structural consensus among antibodies defines the antigen binding site," *PLoS Comput Biol* 8(2):e1002388, 12 pages, Public Library of Science, United States (published online Feb. 2012).
Agata, Y., "Expression of the PD-1 antigen on the surface of stimulated mouse T and B lymphocytes," Int. Immunology, 8(5):765-772, Oxford University Press, United Kingdom (May 1996).
Bennett, F., et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," Journal of Immunology 170(2):711-718, The American Association of Immunologists, Inc., United States (2003).
Bruschi, C.V., and Gjuracic, K., "Yeast Artifical Chromosomes" in the Encyclopedia of Life Sciences, pp. 1-6, Macmillan Publishers Ltd., United Kingdom (2002).
Callahan, M.K., and Wolchok, J.D., "At the bedside: CTLA-4- and PD-1-blocking antibodies in cancer immunotherapy," J Leukoc Biol 94(1):41-53, Society for Leukocyte Biology, United States (2013).
Castelli, C., et al., "Lymphocyte activation gene-3 (LAG-3, CD223) in plasmacytoid dendritic cells (pDCs): a molecular target for the restoration of active antitumor immunity," Oncoimmunology, 3(11):e967146, 4 pages, Landes Bioscience, United States (Dec. 2014).
Dietz, L.J., et al., "Volumetric capillary cytometry: a new method for absolute cell enumeration," Cytometry 23(3):177-186, John Wiley & Sons, United States (1996).
D'Huyvetter, M., et al., "Radiolabeled nanobodies as theranostic tools in targeted radionuclide therapy of cancer," Expert Opin. Drug Deliv., 11(12): 1939-54, Taylor and Francis Ltd., United Kingdom (Dec. 2014).
Francisco, L., et al., "The PD-1 pathway in tolerance and autoimmunity," Immunol. Rev., 236:219-242, Wiley-Blackwell Publishing Ltd., United Kingdom (Jul. 2010).
GenBank, "Alpha-synuclein," Accession No. P37840.1, accessed at https://www.ncbi.nlm.nih.gov/protein/P37840, accessed on Sep. 24, 2020, 13 pages.
GenBank, "C-type lectin domain family 4 member G isoform 1 [*Homo sapiens*]," Accession No. NP_940894.1, accessed at https://www.ncbi.nlm.nih.gov/protein/NP_940894, accessed on Sep. 24, 2020, 3 pages.
GenBank, "E3 ubiquitin-protein ligase CBL-B isoform b [*Homo sapiens*]," Accession No. NP_001308717.1, accessed at https://www.ncbi.nlm.nih.gov/protein/NP_001308717, accessed on Sep. 24, 2020, 4 pages.
GenBank, "galectin-3 [*Homo sapiens*]," Accession No. BAA22164.1, accessed at https://www.ncbi.nlm.nih.gov/protein/BAA22164, accessed on Sep. 24, 2020, 2 pages.
GenBank, "*Homo sapiens* lymphocyte activating 3 (LAG3), mRNA," Accession No. NM_002286.6, accessed at https://www.ncbi.nlm.nih.gov/nuccore/NM_002286, accessed on Sep. 24, 2020, 5 pages.
GenBank, "Human hPD-1 (hPD-1) mRNA, complete cds," Accession No. U64863.1, accessed at https://www.ncbi.nlm.nih.gov/nuccore/U64863, accessed on Sep. 24, 2020, 3 pages.
GenBank, "Macaca fascicularis chromosome 11, Macaca_fascicularis_5.0, whole genome shotgun sequence," Accession No. NC_022282.

(56) References Cited

OTHER PUBLICATIONS 1, accessed at https://www.ncbi.nlm.nih.gov/nuccore/NC_ 022282, accessed on Sep. 24, 2020, 2 pages.
GenBank, "Macaca mulatta lymphocyte activating 3 (LAG3), mRNA," Accession No. XM_001108923.4, accessed at https://www.ncbi.nlm.nih.gov/nuccore/XM_001108923, accessed on Sep. 24, 2020, 2 pages.
Grosso, J., et al., "LAG-3 regulates CD8+ T cell accumulation and effector function in murine self- and tumor-tolerance systems," J. Clin. Invest., 117(11):3383-92, American Society for Clinical Investigation, United States (Nov. 2007).
He, J., et al., "Development of PD-1/PD-L1 Pathway in Tumor Immune Microenvironment and Treatment for Non-Small Cell Lung Cancer," Scientific Reports 5:13110, 9 pages, Nature Publishing Group, United Kingdom (2015).
Holt, L., et al., "Domain antibodies: proteins for therapy," Trends Biotechnol., 21(11):484-90, Elsevier Ltd., Netherlands (Nov. 2003).
Huang, C., et al., "Role of LAG-3 in regulatory T cells," Immunity, 21(4):503-13, Cell Press, United States (Oct. 2004).
Huang, R., et al., "Compensatory upregulation of PD-1, LAG-3, and CTLA-4 limits the efficacy of single-agent checkpoint blockade in metastatic ovarian cancer," Oncoimmunol. 6(1):e1249561, 13 pages, Taylor and Francis Group, United Kingdom (Oct. 2016).
Huard, B., et al., "Characterization of the major histocompatibility complex class II binding site on LAG-3 protein," Proc. Natl. Acad. Sci., 94(11):5744-5749, National Academy of Sciences, United States (May 1997).
Huard, B., et al., "Lymphocyte-activation gene 3/major histocompatibility complex class II interaction modulates the antigenic response of CD4+ T lymphocytes," Eur. J. Immunol., 24(12):3216-21, Wiley-VCH Verlag, Germany (Dec. 1994).
Huard, B., et al., "T cell major histocompatibility complex class II molecules down-regulate CD4+ T cell clone responses following LAG-3 binding," Eur. J. Immunol., 26(5):1180-6, Wiley-VCH Verlag, Germany (May 1996).
International Preliminary Report on Patentability of the International Searching Authority directed to related International Patent Application No. PCT/GB2018/050035, dated Jul. 9, 2019, 11 pages.
International Preliminary Report on Patentability of the International Searching Authority directed to related International Patent Application No. PCT/GB2018/050036, dated Jul. 9, 2019, 11 pages.
International Preliminary Report on Patentability of the International Searching Authority directed to related International Patent Application No. PCT/GB2018/050037, dated Jul. 9, 2019, 12 pages.
International Preliminary Report on Patentability of the International Searching Authority directed to related International Patent Application No. PCT/GB2019/050425, dated Aug. 18, 2020, 7 pages.
International Search Report and Written Opinion of the International Searching Authority directed to related International Patent Application No. PCT/GB2018/050035, dated Apr. 25, 2018, 16 pages.
International Search Report and Written Opinion of the International Searching Authority directed to related International Patent Application No. PCT/GB2018/050036, dated May 3, 2018, 16 pages.
International Search Report and Written Opinion of the International Searching Authority directed to related International Patent Application No. PCT/GB2018/050037, dated Apr. 25, 2018, 18 pages.
International Search Report and Written Opinion of the International Searching Authority directed to related International Patent Application No. PCT/GB2019/050425, dated Apr. 17, 2019; 10 pages.
Ishida, Y., et al., "Induced expression of PD-1, a novel member of the immunoglobulin gene superfamily, upon programmed cell death," Embo J., 11(11): 3887-3895, Nature Publishing Group on behalf of the European Molecular Biology Organization, United Kingdom (Nov. 1992).

Karwacz, K., et al., "PD-L1 co-stimulation contributes to ligand-induced T cell receptor down-modulation on CD8+ T cells," EMBO Mol. Med., 3(10): 581-592, Nature Publishing Group on behalf of the European Molecular Biology Organization, United Kingdom (Oct. 2011).
Keir, M.E., et al., "Programmed death-1 (PD-1):PD-ligand 1 interactions inhibit TCR-mediated positive selection of thymocytes," J Immunol 175(11):7372-7379, The American Association of Immunologists, Inc., United States (2005).
Kisielow, M., et al., "Expression of lymphocyte activation gene 3 (LAG-3) on B cells is induced by T cells," Eur. J. Immunol., 35(7):2081-8, Wiley-VCH Verlag, Germany (Jul. 2005).
Kouo, T., et al., "Galectin-3 Shapes Antitumor Immune Responses by Suppressing CD8+ T Cells via LAG-3 and Inhibiting Expansion of Plasmacytoid Dendritic Cells," Cancer Immunol. Res., 3(4):412-423, American Association for Cancer Research Inc., United States (Apr. 2015).
Kraman, M., et al., "A LAG-3/PD-L1 bispecific antibody inhibits tumor growth in two syngeneic colon carcinoma models," Society for Immunotherapy of Cancer (SITC) Conference, 1 page, BioMed Central Ltd., United Kingdom (Nov. 2016).
Lowther, D.E., et al., "PD-1 marks dysfunctional regulatory T cells in malignant gliomas," JCI Insight 1(5):e85935, 15 pages, The American Society for Clinical Investigation, United States (2016).
Main, S., et al., "A potent human anti-eotaxin1 antibody, CAT-213: isolation by phage display and in vitro and in vivo efficacy," J Pharmacol Exp Ther 319(3): 1395-404, American Society for Pharmacology and Experimental Therapeutics, United States (2006).
Marks, J.D., and Bradbury, A., "Chapter 8: Selection of Human Antibodies from Phage Display Libraries" in Methods in Molecular Biology, Antibody Engineering: Methods and Protocols, Lo, B., ed., pp. 161-176, Springer Nature, Switzerland (2004).
Marks, J.D., "Chapter 19: Antibody Affinity Maturation by Chain Shuffling" in Methods in Molecular Biology, Antibody Engineering: Methods and Protocols, Lo, B., ed., pp. 327-343, Springer Nature, Switzerland (2004).
Matsuzaki, J., et al., "Tumor-infiltrating NY-ESO-1-specific CD8+ T cells are negatively regulated by LAG-3 and PD-1 in human ovarian cancer," Proc. Natl. Acad. Sci., 107(17):7875-7880, National Academy of Science, United States (Apr. 2010).
Mcguinness, B., "Humabody fragments: Small and perfectly formed," Biopharmadealmakers, accessed at www.crescendobiologics.com, pp. B12-B13, 2 pages (2013).
Miraglia, S., et al., "Homogeneous Cell- and Bead-Based Assays for High Throughput Screening Using Fluorometric Microvolume Assay Technology," J Biomol Screening 4(4):193-204, SAGE Journals, United States (1999).
NCT02061761, "Safety Study of Anti-LAG-3 in Relapsed or Refractory Hematologic Malignancies," ClinicalTrials.gov, posted Feb. 13, 2014, accessed at https://www.clinicaltrials.gov/ct2/show/NCT02061761 on Dec. 14, 2020, 4 pages.
NCT02460224, "Safety and Efficacy of LAG525 Single Agent and in Combination With PDR001 in Patients With Advanced Malignancies," ClinicalTrials.gov, posted Jun. 2, 2015, accessed at https://www.clinicaltrials.gov/ct2/show/NCT02460224 on Dec. 14, 2020, 5 pages.
Nishimura, H., et al., "Autoimmune dilated cardiomyopathy in PD-1 receptor-deficient mice," Science, 291(5502):319-322, American Association for the Advancement of Science, United States (2001).
Nishimura, H., et al., "Development of lupus-like autoimmune diseases by disruption of the PD-1 gene encoding an ITIM motif-carrying immuno receptor," Immunity, 11(2):141-151, Cell Press, United States (Aug. 1999).
Posthumus, W.P., et al., "Analysis and simulation of a neutralizing epitope of transmissible gastroenteritis virus," J Virology 64(7):3304-3309, American Society for Microbiology, United States (1990).
Ren, L., et al., "Silencing of the immunoglobulin heavy chain locus by removal of all eight constant-region genes in a 200-kb region," Genomics, 84(4):686-695, Academic Press Inc., United States (Oct. 2004).

(56) References Cited

OTHER PUBLICATIONS

Riley, J., "PD-1 signaling in primary T cells," Immunol Rev., 229(1):114-125, Wiley-Blackwell Publishing Ltd., United Kingdom (May 2009).
Roe, M., "Superior Human Single Domain VH Antibody Fragments from a Transgenic Mouse," Biopharmadealmakers, accessed at www.crescendobiologics.com, p. B23, 1 page (2013).
Rudikoff, S., et al., "Single Amino Acid Substitution Altering Antigen-Binding Specificity," Proc. Natl. Acad. Sci., 79(6):1979-1983, National Academy of Science, United States (Mar. 1982).
Triebel, F., et al., "LAG-3, a novel lymphocyte activation gene closely related to CD4," J. Exp. Med., 171(5):1393-1405, Rockefeller University Press, United States (May 1990).
Tseng, S., et al., "B7-DC, a new dendritic cell molecule with potent costimulatory properties for T cells," J. Exp. Med., 193(7):839-45, Rockefeller University Press, United States (Apr. 2001).
UK Search Report for Application No. GB1700207.2, dated Nov. 24, 2017; 4 pages.
UniParc, "UPI0000119BF0," accessed at https://www.uniprot.org/uniparc/UPI0000H9BF0, accessed on Sep. 24, 2020, 1 page.
UniProt, "E3 ubiquitin-protein ligase CBL," Accession No. P22681, accessed at https://www.uniprot.org/uniprot/P22681, accessed on Sep. 24, 2020, 10 pages.
UniProt, "E3 ubiquitin-protein ligase CBL-B," Accession No. Q13191, accessed at https://www.uniprot.org/uniprot/Q13191, accessed on Sep. 24, 2020, 10 pages.
UniProt, "Programmed cell death protein 1," Accession No. Q15116, accessed at https://www.uniprot.org/uniprot/Q15116, accessed on Sep. 24, 2020, 7 pages.
Wang, C., et al., "In vitro characterization of the anti-PD-1 antibody nivolumab, BMS-936558, and in vivo toxicology in non-human primates," Cancer Immunol Res 2(9):846-856, American Association for Cancer Research, United States (2014).
Wang, W., et al., "PD1 blockade reverses the suppression of melanoma antigen-specific CTL by CD4+ $CD25^{Hi}$ regulatory T cells," Int Immunol 21(9):1065-1077, Oxford University Press, United Kingdom (2009).
Wesolowski, J., et al., "Single domain antibodies: promising experimental and therapeutic tools in infection and immunity," Medical Microbiology and Immunology, 198(3)157-174, Springer Verlag, Germany (Aug. 2009).
Wong, Y., et al., "Structural Requirements for a Specificity Switch and for Maintenance of Affinity Using Mutational Analysis of a Phase-Displayed Anti-Arsonate Antibody of Fab Heavy Chain First Complementarily-Determining Region," J. Immunol., 160(12):5990-7, American Association of Immunologists, United States (Jun. 1998).
Workman, C., et al., "Cutting edge: molecular analysis of the negative regulatory function of lymphocyte activation gene-3," J. Immunol., 169(10):5392-5395, American Association of Immunologists, United States (Nov. 2002).
Xu, F., et al., "LSECtin expressed on melanoma cells promotes tumor progression by inhibiting antitumor T-cell responses," Cancer Res., 74(13):3418-3428, American Association for Cancer Research, United States (Jul. 2014).
Yokosuka, T., et al., "Programmed cell death 1 forms negative costimulatory microclusters that directly inhibit T cell receptor signaling by recruiting phosphatase SHP2," J. Exp. Med., 209(6):1201-1217, Rockefeller University Press, United States (Jun. 2012).
Zhang, X., et al., "Structural and functional analysis of the costimulatory receptor programmed death-1," Immunity, 20(3):337-347, Cell Press, United States (Mar. 2004).
Zou, X., et al., "Block in development at the pre-B-II to immature B cell stage in mice without Ig kappa and Ig lambda light chain," J. Immunol., 170(3):1354-61, American Association of Immunologists, United States (Feb. 2003).
Geng, Yu, et al., "$2^{nd}$ International Conference on Antibodies and Therapeutics." Confer-enceseries.com. Jul. 11-12, 2016, Philadelphia, USA,.

Holt, L.J., et al., "Anti-serum albumin domain antibodies for extending the half-lives of short lived drugs," Protein Eng. Des. Sel. 21(5):283-288, Oxford University Press, United Kingdom (2008).
Colman, P.M., et al., "Effects of amino acid sequence changes on antibody-antigen interactions," Research in Immunology 145(1):33-36, Elsevier, Netherlands (1994).
Office action dated Jun. 11, 2021, in U.S. Appl. No. 16/475,599, inventor Edwards; C., et al., int'l filing date Jan. 8, 2018, 10 pages.
Office action dated Sep. 20, 2021, in U.S. Appl. No. 16/475,590, inventor Edwards; B., et al., int'l filing date Jan. 8, 2018, 15 pages.
Drabek, D., et al., "Expression Cloning and Production of Human Heavy-Chain-Only Antibodies from Murine Transgenic Plasma Cells," Frontiers in Immunology 7(619): 1-10, Frontiers Media SA, United States (Dec. 2016).
Trinklein, N., et al., "Abstract LB-090: Sequence-based discovery of fully human anti-CD3 and anti-PDL 1 single domain antibodies using novel transgenic rats," Cancer Research 76(14):1-4, American Association of cancer Research, United States (Jul. 2016).
Gordon, S.R., et al., "PD-1 expression by tumor-associated macrophages inhibits phagocytosis and tumour immunity," Nature 545(7655): 495-499, Nature Publishing Group, United Kingdom (May 2017).
Legg, J.W., et al., "CB307: A novel T-cell costimulatory Humabody® VH therapeutic for PSMA-positive tumors," retrieved from: https://www.crescendobiologics.com/wp-content/uploads/2019/08/20190412-CB307-A-novel-T-cell-costimulatory-Humabody%C2%AE-VH-therapeutic-for-PSMA-positive-tumors.pdf, 1 page, (Apr. 2019).
Perez-Ruiz, E., et al., "Anti-CD137 and PD-1/PD-L1 Antibodies En Route toward Clinical Synergy," Clinical Cancer Research 23(18):5326-5328, American Cancer Research, United States (Aug. 2017).
International Search Report and Written Opinion in Application No. PCT/GB2020/051201, E.P.O., Netherlands, dated Oct. 13, 2020, 23 pages.
Homayouni, V., et al., "Preparation and characterization of novel nanobody against T-cell immunoglobulin and mucin-3 (TIM-3)," Iranian Journal of Basic Medical Sciences 19(11):1201 -1208, Mashhad University of Medical Sciences, Iran (2016).
Japanese Office Action dated Dec. 13, 2021, in Japanese Patent Application No. 2019-536937, filed Jan. 18, 2018, 21 pages.
Japanese Office Action dated Dec. 6, 2021, in Japanese Patent Application No. 2019-536936, filed Jan. 8, 2018, 17 pages.
Crescendo Biologics, "Humabody Fragments: Small and Perfectly Formed," BioPharma Dealmakers: B12-B13, retrieved from: https://www.crescendobiologics.com/wp-content/uploads/2016/03/20150309-Crescendo0315.pdf, retrieved on Jan. 20, 2022, dated Mar. 2016, 2 pages.
Co-Pending U.S. Appl. No. 17/610,330, Int'l filing Date May 15, 2020, inventor Enever, C., et al., (Unpublished).
An, Z., ed., "Section 3.4.3—Glycan Profiles of Recombinant IgG Produced in Rodent Cell Lines," in *Therapeutic Monoclonal Antibodies: From Bench to Clinic*, pp. 73-76, John Wiley & Sons, United States (2009).
Bahara, N.H.H., et al., "Construction of a Semisynthetic Human VH Single-Domain Antibody Library and Selection of Domain Antibodies against a-Crystalline of *Mycobacterium tuberculosis*," Journal of Biomolecular Screening 21(1):35-43, Sage Publications, United States (Jan. 2016).
Bander, N.H., et al., "Targeted Systemic Therapy of Prostate Cancer with a Monoclonal Antibody to Prostate-Specific Membrane Antigen," Seminars in Oncology 30(5):667-676, W.B. Saunders, United States (Oct. 2003).
Barve, A., et al., "Prostate Cancer Relevant Antigens and Enzymes For Targeted Drug Delivery," Journal of Control Release 187:118-132, Elsevier Science Publishers, Netherlands (Aug. 2014).
Bayachou, M., et al., "Catalytic Two-Electron Reductions of $N_2O$ and $N_3$ by Myoglobin in Surfactant Films," Inorganic Chemistry 39(2):289-293, American Chemical Society, United States (Jan. 2000).
Bruggemann, M., et al., "A Repertoire of Monoclonal Antibodies With Human Heavy Chains From Transgenic Mice," Proc Natl Acad Sci USA 86(17):6709-6713, National Academy of Sciences, United States (Sep. 1989).

(56) References Cited

OTHER PUBLICATIONS

Bulliard, Y., et al., "OX40 Engagement Depletes Intratumoral Tregs via Activating FcγRs, Leading to Antitumor Efficacy," Immunology and Cell Biology 92(6):475-480, Nature Publishing Group, United Kingdom (2014).
Chalupny, N.J., et al., "T-cell Activation Molecule 4-1BB Binds to Extracellular Matrix Proteins," Proc Natl Acad Sci USA 89(21):10360-10364, National Academy of Sciences, United States (Nov. 1992).
Chatalic, K.L.S., et al.,"A Novel" '"In-Labeled Anti-Prostate-Specific Membrane Antigen Nanobody for Targeted SPECT/CT Imaging of Prostate Cancer," The Journal of Nuclear Medicine 56(7):1094-1099, Society of Nuclear Medicine and Molecular Imaging, United States (Jul. 2015).
Chen, L., et al. "Epitope-directed antibody selection by site-specific photocrosslinking." Science Advances 6(14): eaaz7825, 9 pages, American Association for the Advancement of Science, United States (2020).
Chothia, C. and Lesk, A. M., "Canonical Structures for the Hypervariable Regions of Immunoglobulins," Journal of Molecular Biology 196(4):901-917, Elsevier, United Kingdom (Aug. 1987).
Cizeau, J., et al., "Abstract 5770: Engineering and Characterization of Anti-PSMA Humabody-deBouganin Fusion Proteins," Cancer Research 78(13 Suppl):5770, AACR Annual Meeting 2018 (Apr. 4-18, 2018), 2 pages, American Association for Cancer Research, United States (2018).
ClinicalTrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.
Communication from the Examining Division for EP Application No. EP 17 700 734.1, European Patent Office, Munich, Germany, dated Jul. 24, 2020, 10 pages.
Communication from the Examining Division for EP Application No. EP 17 701 006.3, European Patent Office, Munich, Germany, dated Jun. 5, 2019, 6 pages.
Communication from the Examining Division for EP Application No. EP 17 724 869.7, European Patent Office, Munich, Germany, dated Dec. 4, 2019, 6 pages.
Communication from the Examining Division for EP Application No. EP 19 707 094.9, European Patent Office, Munich, Germany, dated Nov. 22, 2021, 4 pages.
Conrath, E., et al., "Camel Single-Domain Antibodies as Modular Building Units in Bispecific and Bivalent Antibody Constructs," Journal of Biological Chemistry 276(10):7346-7350, American Society for Biochemistry and Molecular Biology, United States (Mar. 2001).
Dubrot, J., et al., "Treatment With Anti-CD137 mAbs Causes Intense Accumulations of Liver T Cells Without Selective Antitumor Immunotherapeutic Effects in This Organ," Cancer Immunology, Immunotherapy 59(8):1223-1233, Springer Verlag, Germany (2010).
Elsadek, B. and Kratz, F., "Impact of Albumin on Drug Delivery—New Applications on the Horizon," Journal of Controlled Release 157(1):4-28, Elsevier Science Publishers, Netherlands (Jan. 2012).
Evazalipour, M., et al., "Camel Heavy Chain Antibodies against Prostate-Specific Membrane Antigen," Hybridoma (Larchmt) 31(6):424-429, Mary Ann Liebert Inc., United States (Dec. 2012).
Evazalipour, M., et al., "Generation and Characterization of Nanobodies Targeting PSMA For Molecular Imaging of Prostate Cancer," Contrast Media & Molecular Imaging 9(3):211-220, Hindawi in collaboration with John Wiley & Sons, Inc, United Kingdom (May-Jun. 2014).
Fan, G., et al., "Bispecific Antibodies and their Applications," Journal of Hematology & Oncology 8, Article No. 130, 14 pages, BioMed Central: Part of Springer Nature, United Kingdom (Dec. 2015).
Fan, X., et al., "Ultrasonic nanobubbles carrying anti-PSMA nanobody: construction and application in prostate cancer-targeted imaging," PLOS One, 10(6):e0127419, 13 pages, Public Library of Science, United States (Jun. 2015).

Fisher, T.S., et al., "Targeting of 4-1BB by monoclonal antibody PF-05082566 enhances T-cell function and promotes anti-tumor activity," Cancer Immunology Immunotherapy, 61: 1721-1733, Springer Nature Limited, Germany (2012).
Gauttier, V., et al., "Agonistic anti-CD137 Antibody Treatment Leads to Antitumor Response in Mice with Liver Cancer," International Journal of Cancer 135(2):2857-2867, Wiley-Liss Inc., United States (Dec. 2014).
Genbank, "*Homo sapiens* TNF receptor superfamily member 9 (TNFRSF9), mRNA," NCBI Reference Sequence: NM_001561.6, https://www.ncbi.nlm.nih.gov/nuccore/NM001561, last accessed on May 19, 2020, 5 pages.
GenBank, "tumor necrosis factor receptor superfamily member 9 precursor [*Homo sapiens*]," Accession No. NP_001552.2, accessed on https://www.ncbi.nlm.nih.gov/protein/NP001552, Oct. 7, 2016, 4 pages.
Guo, Y., et al., "Chimeric Antigen Receptor-Modified T Cells for Solid Tumors: Challenges and Prospects," Journal of Immunology Research 2016:3850839, 11 pages, Hindawi Publishing Corporation, Egypt (2016).
Henry, K. A., et al., "Identification of Cross-reactive Single-domain Antibodies Against Serum Albumin Using Next-generation DNA Sequencing," Protein Engineering, Design & Selection 28(10):379-383, Oxford University Press, United Kingdom (Aug. 2015).
Holliger, P, and Hudson, P.J., "Engineered Antibody Fragments and the Rise of Single Domains," Nature Biotechnology 23(9): 1126-1136, Nature America Publishing, United States (2005).
Houot, R., et al., "Therapeutic Effect of CD137 Immunomodulation in Lymphoma and Its Enhancement by $T_{reg}$ Depletion," Blood 114(16):3431-3438, American Society of Hematology, United States (2009).
International Preliminary Report on Patentability for International Application No. PCT/GB2019/053220, The International Bureau of WIPO, Switzerland, dated May 18, 2021, 11 pages.
International Preliminary Report on Patentability for International Application No. PCT/GB2020/051199, The International Bureau of WIPO, Switzerland, dated Nov. 16, 2021, 8 pages.
International Preliminary Report on Patentability for International Application No. PCT/GB2020/051201, The International Bureau of WIPO, Switzerland, dated Nov. 16, 2021, 17 pages.
International Preliminary Report on Patentability for International Application No. PCT/GB2017/050074, The International Bureau of WIPO, Switzerland, dated Jul. 17, 2018, 11 pages.
International Preliminary Report on Patentability for International Application No. PCT/GB2017/051272, The International Bureau of WIPO, Switzerland, dated Nov. 6, 2018, 11 pages.
International Preliminary Report on Patentability for International Application No. PCT/GB2018/051941, The International Bureau of WIPO, Switzerland, dated Jan. 14, 2020, 6 pages.
International Preliminary Report on Patentability for International Application No. PCT/GB2018/053279, The International Bureau of WIPO, Switzerland, dated May 19, 2020, 11 pages.
International Preliminary Report on Patentability for International Application No. PCT/GB2018/053280, The International Bureau of WIPO, Switzerland, dated May 19, 2020, 12 pages.
International Preliminary Report on Patentability for International Application No. PCT/GB2017/050075, The International Bureau of WIPO, Switzerland, dated Jul. 17, 2018, 7 pages.
International Search Report and Written Opinion for International Application No. PCT/GB2017/050074, European Patent Office, Netherlands, dated May 30, 2017, 17 pages.
International Search Report and Written Opinion for International Application No. PCT/GB2017/050075, European Patent Office, Netherlands, dated Mar. 23, 2017, 12 pages.
International Search Report and Written Opinion for International Application No. PCT/GB2017/051272, European Patent Office, Netherlands, dated Sep. 11, 2017, 17 pages.
International Search Report and Written Opinion for International Application No. PCT/GB2018/051941, European Patent Office, Netherlands, dated Sep. 14, 2018, 11 pages.
International Search Report and Written Opinion for International Application No. PCT/GB2018/053279, European Patent Office, Netherlands, dated Feb. 1, 2019, 15 pages.

(56) References Cited

OTHER PUBLICATIONS

International Search Report and Written Opinion for International Application No. PCT/GB2018/053280, European Patent Office, Netherlands, dated Feb. 11, 2019, 17 pages.

International Search Report and Written Opinion for International Application No. PCT/GB2019/050425, European Patent Office, Netherlands, dated Apr. 17, 2019, 10 pages.

International Search Report and Written Opinion for International Application No. PCT/GB2019/053220, European Patent Office, Netherlands, dated Apr. 3, 2020, 17 pages.

International Search Report and Written Opinion for International Application No. PCT/GB2020/051199, European Patent Office, Netherlands, dated Aug. 20, 2020, 13 pages.

Jamnani, F.R., et al., "T Cells Expressing VHH-Directed Oligoclonal Chimeric Her2 Antigen Receptors: Towards Tumor-Directed Oligoclonal T Cell Therapy," Biochimica et Biophysica Acta 1840(1):378-386, Elsevier Pub. Co, Netherlands (Jan. 2014).

Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (1971).

Kabat, E.A., et al., "Sequences of proteins of immunological interest," 5th Edition, NIH publication No. 91-3242, pp. 1-1137, U.S. Department of Public Health and Human Services, National Institutes of Health, United States (1991).

Kunik, V., et al., "The Indistinguishability of Epitopes From Protein Surface is Explained By the Distinct Binding Preferences of Each of the Six Antigen-Binding Loops," Protein Engineering, Design and Selection 26(10):599-609, Oxford University Press, United Kingdom (Oct. 2013).

Kwon, B.S., and Weissman, S.M., "cDNA Sequences of Two Inducible T-Cell Genes," Proc Natl Acad Sci USA 86(6):1963-1967, National Academy of Science, United States (Mar. 1989).

Lefranc, M.P., et al., "IMGT Unique Numbering for Immunoglobulin and T Cell Receptor Constant Domains and Ig Superfamily C-like Domains," Developmental and Comparative Immunology 29(3):185-203, Elsevier Science, United States (2005).

Madireddi, S., et al., "Galectin-9 Controls the Therapeutic Activity of 4-1BB-Targeting Antibodies," The Journal of Experimental Medicine 211(7): 1433-1448, The Rockefeller University Press, United States (Jun. 2014).

Mcguinness, B., et al., "Abstract 5766: Multifunctional biologies for targeted T-cell therapy based on in vivo matured fully human VH domains," Cancer Research 78(13_Suppl):5766, AACR Annual Meeting 2018 (Apr. 4-18, 2018), 2 pages, American Association for Cancer Research, United States (2018).

Muyldermans, S., et al., "Recognition of Antigens by Single-Domain Antibody Fragments: the Superfluous Luxury of Paired Domains," Trends in Biochemical Sciences 26(4):230-235, Elsevier Trends Journals, United Kingdom (Apr. 2001).

Muyldermans, S., "Single Domain Camel Antibodies: Current Status," Reviews in Molecular Biotechnology 74(4):277-302, Elsevier Science Publishers, Netherlands (2001).

Muyldermans, S., et al., "Nanobodies: Natural Single-domain Antibodies," Annual Review of Biochemistry, 82:17.1-17.23, Annual Reviews, United States (2013).

Translation of Japanese Office Action dated Jul. 4, 2022, in Japanese Patent Application No. 2019-536936, filed Jan. 18, 2018, 5 pages.

Office Action for Japanese Patent Application No. 2018-537519, dated Feb. 5, 2021, Japan Patent Office, Japan, 9 pages.

Office Action for Japanese Patent Application No. 2018-537533, dated Feb. 16, 2021, Japan Patent Office, Japan, 6 pages.

Zak, K.M., et al., "Structural basis for small molecule targeting of the programmed death ligand 1 (PD-L1)," Oncotarget 7:30323-30335, Impact Journals, United States (Apr. 2016).

Office Action dated Aug. 11, 2020, in U.S. Appl. No. 16/069,495, Balloi, E., et al., filed Jul. 11, 2018, 18 pages.

Office Action dated Mar. 1, 2022, in U.S. Appl. No. 16/475,590, inventor Edwards; B., et al., int'l filing date Jan. 8, 2018, 17 pages.

Zare, H., et al., "Production of Nanobodies against Prostate-Specific Membrane Antigen (PSMA) Recognizing LnCaP Cells," and supplemental figures, Int J Biol Markers 29(2):e169-e179 (12 total pages), SAGE Publications, United States (Jun. 2014).

Patei,, T. P., et al., "Different Culture Methods Lead to Differences in Glycosylation of a Murine IgG Monoclonal Antibody," Biochemical Journal 285(Pt 3):839-845, Portland Press on behalf of the Biochemical Society, United Kingdom (1992).

Roovers, R.C., et al., "A Biparatopic Anti-EGFR Nanobody Efficiently Inhibits Solid Tumour Growth," International Journal of Cancer 129(8):2013-2024, Wiley-Liss Inc., United States (Oct. 2011).

Sanchez-Paulete, A.R., et al., "Deciphering CD137 (4-1BB) Signaling in T-cell Costimulation for Translation Into Successful Cancer Immunotherapy," European Journal of Immunology 46(3):513-522, Wiley-VCH Verlag GmbH & Co. KGaA, Germany (Mar. 2016).

Segal, N.H., et al., "Results from an Integrated Safety Analysis of Urelumab, an Agonist Anti-CD137 Monoclonal Antibody," Clinical Cancer Research 23(8): 1929-1936, American Association for Cancer Research, United States (Oct. 2016).

Strohl, W.R., "Fusion Proteins for Half-Life Extension of Biologies as a Strategy to Make Biobetters," BioDrugs 29(4):215-239, Springer International, New Zealand (Jul. 2015).

UniProtKB, "Glutamate carboxypeptidase 2," UniProtKB-Q04609 (FOLH1_Human), https://www.uniprot.org/uniprot/Q04609, last accessed on May 19, 2020, 24 pages.

UniProtKB, "Tumor necrosis factor receptor superfamily member 9," UniProtKB-Q07011 (TNR9 Human), https://www.uniprot.org/uniprot/Q07011, last accessed on May 19, 2020, 12 pages.

Vinay, D. S., and Kwon, B. S., "Therapeutic Potential of Anti-CD137 (4-1BB) Monoclonal Antibodies," Expert Opinion on Therapeutic Targets 20(3):361-373, Informa Healthcare, United Kingdom (2016).

Vinay, D.S., and Kwon, B.S., "4-1BB (CD137), an Inducible Costimulatory Receptor, as a Specific Target For Cancer Therapy," BMB Reports 47(3):122-129, The Korean Society for Biochemistry and Molecular Biology, South Korea (Mar. 2014).

Vinay, D.S and Kwon, B.S., "Immunotherapy of cancer with 4-1BB," Molecular Cancer Therapeutics 11(5): 1062-1070, American Association for Cancer Research, United States (May 2012).

Vinay, D.S., and Kwon, B.S., "Role of 4-1BB in Immune Responses," Seminars in Immunology 10(6):481-489, Article No. si980157, Academic Press, United Kingdom (Dec. 1998).

Vincke, C., and Muyldermans, S., "Introduction to Heavy Chain Antibodies and Derived Nanobodies," Methods in Molecular Biology 911:15-26, Springer Science + Business Media, Germany (2012).

Viuff, D., et al., "Generation of a Double Transgenic Humanized Neonatal Fc Receptor (FcRn)/Albumin Mouse to Study the Pharmacokinetics of Albumin-Linked Drugs," Journal of Controlled Release 223:22-30, Elsevier Science Publishers, Netherlands (Feb. 2016).

Ward, E. S., et al., "Binding Activities of a Repertoire of Single Immunoglobulin Variable Domains Secreted from *Escherichia coli*," Nature 341(6242):544-546, Nature Publishing Group, United Kingdom (Oct. 1989).

Zapata, J.M., et al., "CD137 (4-1BB) Signalosome: Complexity is a Matter of TRAFs," Frontiers in Immunology 9:2618, 12 pages, Frontiers Research Foundation, Switzerland (Nov. 2018).

Co-pending U.S. Appl. No. 17/706,839, filed Mar. 29, 2022, inventor Edwards; C., et al., (Unpublished).

* cited by examiner a)

b)

c)

a)

b)

c)

a)

b)

c)

SINGLE DOMAIN ANTIBODIES TO PROGRAMMED CELL DEATH PROTEIN 1 (PD-1)

CROSS-REFERENCE TO RELATED APPLICATIONS

This application is a 35 U.S.C. § 371 National Phase Application of International Application No. PCT/GB2018/050036, filed Jan. 8, 2018, which claims the benefit of GB Application No. 1700207.2, filed Jan. 6, 2017, GB Application No. 1700208.0, filed Jan. 6, 2017, and GB Application No. 1700210.6, filed Jan. 6, 2017, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 105011.txt; Size: 305,715 bytes; and Date of Creation: Dec. 12, 2019) is herein incorporated by reference in its entirety.

FIELD OF THE INVENTION

The invention relates to PD-1 binding agents, in particular anti-PD-1 $V_H$ single domain antibodies (sdAb), and the use of such binding agents in the treatment, prevention and detection of disease.

INTRODUCTION

Antibody-based therapeutics have emerged as important components of therapies for an increasing number of human diseases in such fields as oncology, inflammatory and infectious diseases. Indeed, antibodies are one of the best-selling classes of drugs today; five of the top ten best selling drugs are antibodies.

The Programmed Death 1 (PD-1) protein is encoded by the PDCD1 gene and expressed as a 55 kDa type I transmembrane protein (Agata 1996 Int Immunol 8(5):765-72). PD-1 is an immunoglobulin superfamily member (Ishida 1992 EMBO 11(11):3887-95) and it is an inhibitory member of the extended CD28/CTLA-4 family of T cell regulators. Other members of this family include CD28, CTLA-4, ICOS and BTLA. PD-1 exists as a monomer, lacking the unpaired cysteine residue characteristic of other CD28 family members (Zhang 2004 Immunity 20:337-47). Its cytoplasmic domain contains an immunoreceptor tyrosine-based inhibitory motif (ITIM) and an immunoreceptor tyrosine-based switch motif (ITSM) that are phosphorylated during signal transduction (Riley 2009 Immunol Rev 229(1):114-25).

PD-1 is expressed on B cells, T cells, and monocytes (Agata 1996). The role of PD-1 in maintaining immunologic self-tolerance was demonstrated in PDCD1–/– mice, which develop autoimmune disorders (Nishimura 1999 Immunity 11:141-51, Nishimura 2001 Science 291(5502):319-22). The PD-1 pathway therefore regulates antigen responses, balancing autoimmunity and tolerance.

There are two ligands for PD-1 that mediate its regulatory function. PD-L1 (B7-H1) is normally expressed on dendritic cells, macrophages, resting B cells, bone marrow-derived mast cells and T cells as well as non-hematopoietic cell lineages (reviewed in Francisco 2010 Immunol Rev 236: 219-42). PD-L2 (B7-DC) is largely expressed on dendritic cells and macrophages (Tseng 2001 J Exp Med 193(7):839-45). Ligand expression is influenced by local mediators and can be upregulated by inflammatory cytokines.

PD-1 is known as an immunoinhibitory protein that negatively regulates TCR signals. The interaction between PD-1 and PD-L1 can act as an immune checkpoint, which can lead to, e.g., a decrease in tumour infiltrating lymphocytes, a decrease in T-cell receptor mediated proliferation, and/or immune evasion by cancerous cells. Immune suppression can be reversed by inhibiting the local interaction of PD-1 with PD-L1 or PD-L2; the effect is additive when the interaction of PD-1 with both PD-L1 and PD-L2 is blocked1.

As T cells become activated and co-stimulated by antigen-presenting cells (APCs), T cell expression of PD-1 is induced. PD-1 engagement with ligand on the APC cross-links PD-1 and clusters it into the T cell receptor (TCR) complex within the immunological synapse (Yokosuka 2012 J Exp Med 209(9):1201-17). Within the T cell cytoplasm, PD-1 signalling domains ITIM and ITSM are phosphorylated. This induces Src-homology-2 domain-containing tyrosine phosphatase (SHP1/2) that attenuates various components of the T cell receptor (TCR) signalling. T cell activation is dampened, which leads to a reduction in cytokine response, proliferation and cytolytic activity. This downregulation of T cell function serves to prevent overstimulation, tolerising cells against weakly immunogenic self-antigen.

The PD-1 pathway can be exploited in cancer or infection, whereby tumours or viruses can evade effective immune recognition and T cells demonstrate an 'exhausted' phenotype. PD-L1 has also been shown to be expressed in many tumour types including urothelial, ovarian, breast, cervical, colon, pancreatic, gastric, melanoma, glioblastoma and non-small cell lung carcinoma (reviewed in Callahan 2014 J Leukoc Biol 94(1):41-53). The cytokines produced by cancer stromal cells can further upregulate PD-L1 in the tumour microenvironment (He 2015 Nature Scientific Reports 5:13110). As a result, tumour-specific T cells become unresponsive through PD-1 signalling and therefore fail to eliminate their target. T regulatory cells (T regs) have also been shown to express high levels of PD-1 and they suppress the anti-tumour response further (Lowther 2016 JCI Insight 1(5):85935).

Disruption of the PD-1:PD-L1 interaction enhances T cell activity. An anti-PD-1 monoclonal antibody demonstrates blockade of the interaction between PD-1 and its ligands (Wang 2014 Cancer Immunol Res 2(9):846-56). T cell function in-vitro can be enhanced by PD-1 blockade, as demonstrated by improved proliferation and cytokine responses in mixed lymphocyte reactions of T cells and dendritic cells. cytotoxic lymphocytes (CTLs) derived from melanoma patients has also been shown to be enhanced by PD-1 blockade in vitro using the antibody OPDIVO (nivolumab), and can become resistant to Treg suppression (Wang 2009 Int Immunol 21(9):1065-1077). This antibody has been tested in clinical dose escalation studies in melanoma, non-small cell lung carcinoma (NSCLC), renal cell cancer (RCC) and others. It shows improved overall survival rates compared to chemotherapy in NSCLC patients. Another PD-1 blocking antibody, KEYTRUDA® (pembrolizumab), demonstrates responses in NSCLC patients refractory to CTLA-4 blockade. OPDIVO® and KEYTRUDA® both functionally block the interaction of human PD-1 with its ligands.

It is possible to induce PD-1 signalling by cross-linking it on the membrane with a combination of anti-PD-1 plus anti-CD3 antibodies (Bennett 2003 J Immunol 170:711-18, Keir 2005 J Immunol 175:7372-7379). This function could be detrimental during an anti-tumour response because T cell activity would be suppressed. If suppression of T cell responses were desired, agonistic anti-PD-1 antibodies or those with effector functions could be used to treat immune-related diseases such as rheumatoid arthritis.

The aim of the present invention is to address the need of alternative antibody-based treatments for use in the treatment of disease, in particular in the treatment of cancer.

SUMMARY OF THE INVENTION

The invention provides isolated single domain antibodies, in particular $V_H$ single domain antibodies that bind to PD-1 and that exhibit a number of desirable properties.

The single domain antibodies of the present invention bind to human PD-1 and modulate the interaction of PD-1 with PD-L1 and/or PD-L2. The anti-PD-1 antibodies preferably bind to PD-1 with high affinity and block the functional interaction of PD-1 with PD-L1 and/or PD-L2. In some embodiments, the blocking antibodies of the invention may block the binding of PD-1 to PD-L1, PD-L2 and/or stimulate or enhance T-cell activation. In some embodiments, the blocking antibodies may be useful for stimulating or enhancing the immune response and/or for treating a subject suffering from cancer and other diseases.

Thus, in one aspect, the invention provides isolated single domain antibody that binds to human PD-1 comprising a CDR3 sequence selected from a CDR3 of table 1.

In one embodiment, the single domain antibody comprises a CDR1 as shown in SEQ ID No. 1 or a sequence with at least 80% homology thereto, a CDR2 as shown in SEQ ID No. 2 or a sequence with at least 80% homology thereto and a CDR3 as shown in SEQ ID No. 3 or a sequence with at least 80% homology thereto.

In one embodiment, the isolated single domain antibody comprises CDR1, CDR2 and CDR3 sequences selected from CDR1, CDR2 and CDR3 sequences as shown Table 1.

In one embodiment, the single domain antibody comprises a sequence selected from SEQ ID Nos. 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 252, 256, 260, 264, 268, 272, 276, 280, 284, 288, 292, 369, 373, 377, 381, 385, 389, 393, 397, 401, 405, 409, 413, 417 421, 425, 429, 433, 437, 441, 445, 449, 453, 457, 461, 465, 469, 473, 477, 481, 485, 489, 493, 497, 501, 505, 509, 513. 517, 521, 525, 529 or 533 or a sequence with at least 70%, 80% or 90% homology thereto.

In one embodiment, the single domain antibody is conjugated to a toxin, enzyme, radioisotope, half-life extending moiety, label, therapeutic molecule or other chemical moiety.

In one embodiment, the isolated single domain antibody is obtained or obtainable from a transgenic rodent that expresses a transgene comprising human V, D and J regions.

The invention also provides an isolated binding agent that binds to essentially the same epitope as the single domain antibody described herein.

The invention also provides an isolated binding agent that competes for binding to human PD-1 with the single domain antibody described herein.

The invention also provides an isolated binding agent comprising a single domain antibody described herein.

In one embodiment, said single domain antibody is linked to a second binding molecule that does not bind to PD-1.

In one embodiment, said second single domain antibody binds to an immonooncology target.

In one embodiment, said single domain antibody is linked to a second binding molecule that binds to PD-1.

The invention also provides the use of a single domain antibody described herein in a multispecific or multivalent binding agent.

The invention also provides an immunoconjugate comprising a single domain antibody or a binding agent described herein linked to a therapeutic agent.

The invention also provides a pharmaceutical composition comprising a single domain antibody described herein, a binding agent described herein or an immunoconjugate described herein and a pharmaceutical carrier.

The invention also provides a method for treating a cancer, an immune disorder, neurological disease, inflammatory disorder, allergy, transplant rejection, viral infection, immune deficiency or other immune system-related disorder comprising administering a therapeutically effective amount of a comprising a single domain antibody, an immunoconjugate or a pharmaceutical composition according to claim described herein.

The invention also provides the use of a single domain antibody, a binding agent, an immunoconjugate or a pharmaceutical composition described herein in the manufacture of a medicament for the treatment of a cancer, an immune disorder, neurological disease, inflammatory disorder, allergy, transplant rejection, viral infection, immune deficiency or other immune system-related disorder.

The invention also provides a single domain antibody, a binding agent, an immunoconjugate or a pharmaceutical composition described herein for use as medicament.

The invention also provides single domain antibody, a binding agent, an immunoconjugate or a pharmaceutical composition described herein for use in the treatment of a cancer, an immune disorder, neurological disease, inflammatory disorder, allergy, transplant rejection, viral infection, immune deficiency, and other immune system-related disorder.

The invention also provides an isolated nucleic acid molecule comprising a nucleotide sequence encoding a single domain antibody described herein.

The invention also provides a method for producing a single domain antibody described herein comprising expressing a nucleic acid encoding said binding molecule in a host cell and isolating the binding molecule from the host cell.

The invention also provides a kit comprising a single domain antibody, a binding agent, an immunoconjugate or a pharmaceutical composition described herein.

The invention also provides a method for detecting the presence of human PD-1 in a test sample comprising contacting said sample with a single domain antibody described herein and at least one detectable label and detecting binding of said single domain antibody to human PD-1.

The invention also provides a method for producing a single $V_H$ domain antibody that binds to human PD-1 comprising
a) immunising a transgenic animal that expresses a nucleic acid construct comprising human heavy chain V genes and that is not capable of making functional endogenous light or heavy chains with an PD-1 antigen,
b) generating a library from said animal
c) isolating single $V_H$ domain antibodies from said libraries and
d) identifying a single $V_H$ domain antibody that binds to human PD-1 and
e) isolating said antibody.

The invention also provides a single $V_H$ domain antibody obtained or obtainable by the method above.

The invention also provides an isolated heavy chain only antibody comprising a $V_H$ domain that binds to human PD-1.

The invention also provides a heavy chain only antibody comprising a $V_H$ domain that binds to human PD-1 obtained or obtainable from a transgenic mouse which expresses human V, D and J loci and does not produce functional endogenous lambda and kappa light chains and heavy chain.

The invention also provides bispecific molecule comprising the single domain antibody described above linked to a second functional moiety having a different binding specificity than said single domain antibody.

Another aspect of the invention pertains to methods of modulating immune responses using anti-PD-1 single domain antibodies described herein.

The invention further provides a method of inhibiting growth of tumor cells in vivo using anti-PD-1 single domain antibodies described herein.

FIGURES

The invention is further described in the following non-limiting figures.

FIG. 1: a) Binding Assay: $V_H$ were identified that bound to the CHO human PD-1 and b) Inhibition Assay: Inhibition of PD-1 binding to PD-L1.

Figure 2:
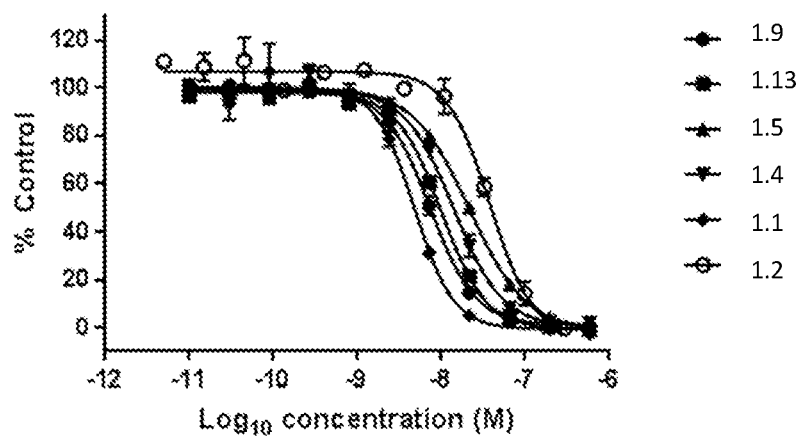

FIG. 2: PD-1/PD-L2 inhibition assay using different single domain antibodies.

Figure 3:
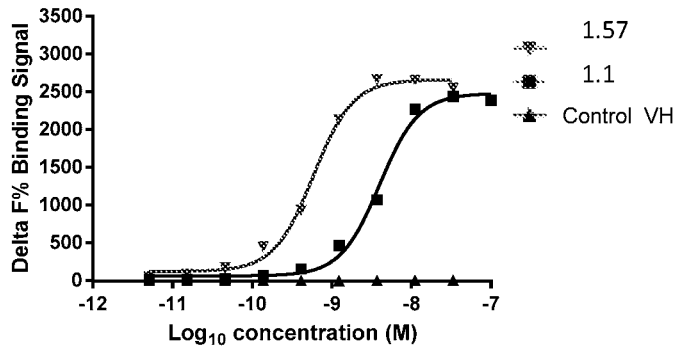
Figure 3:
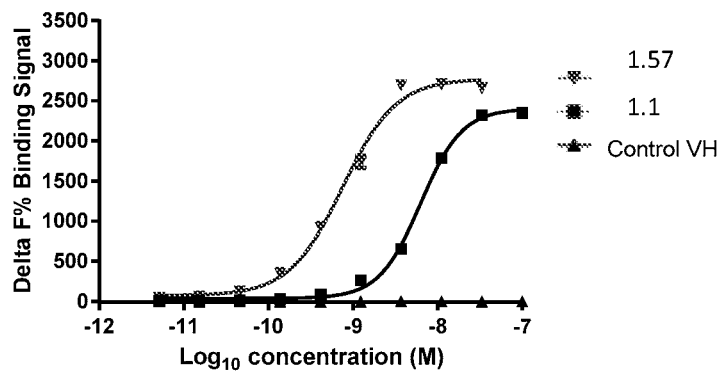
Figure 3:
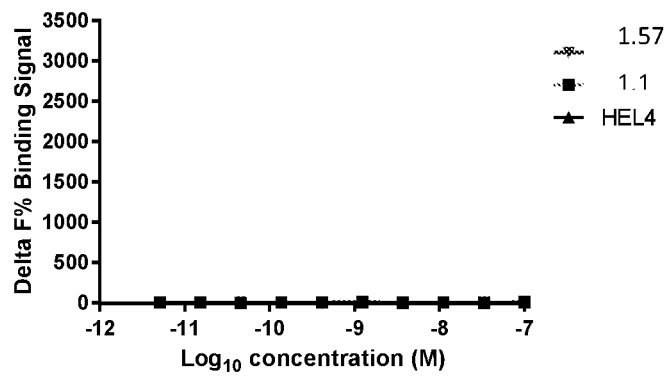

FIG. 3: Species cross reactivity testing. a) $V_H$ single domain antibody 1.1 and 1.57 binding to human PD-1 b) $V_H$ single domain antibody 1.1 and 1.57 binding to cynomolgus PD-1 recombinant protein c) $V_H$ single domain antibody 1.1 and 1.57 binding to mouse PD-1 protein.

Figure 4:
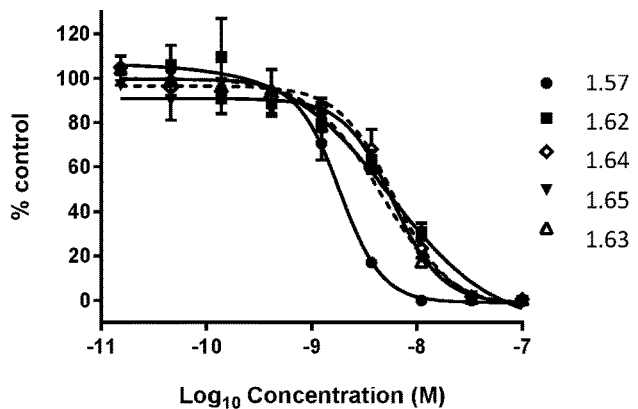
Figure 4:
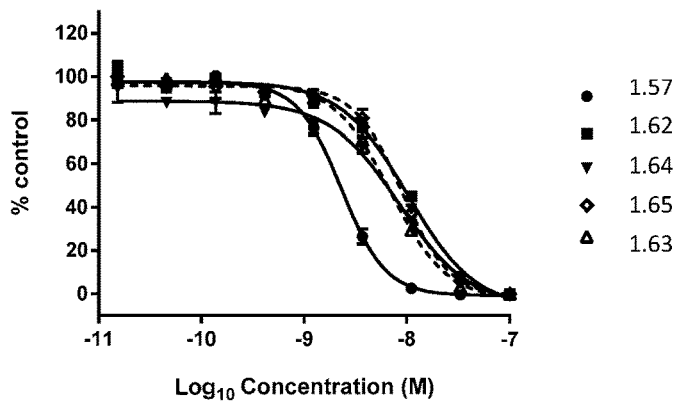
Figure 4:
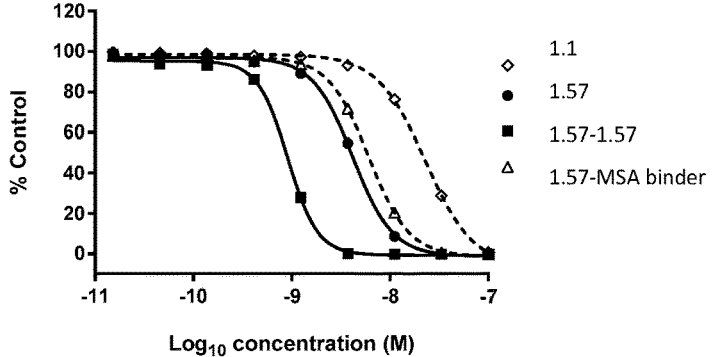

FIG. 4: FMAT Inhibition assay using $V_H$ single domain antibodies. a) CHO PD-1/PD-L1 assay with monovalent $V_H$ single domain antibodies; b) CHO PD-1/PD-L2 assay with monovalent $V_H$ single domain antibodies; c) CHO PD-1/PD-L1 assay with bivalent agents.

Figure 5:
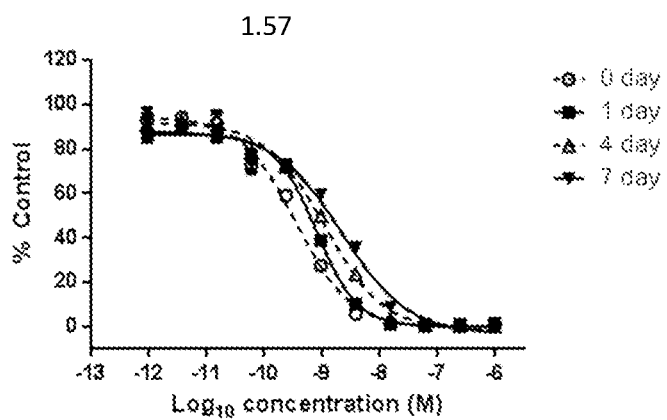
Figure 5:
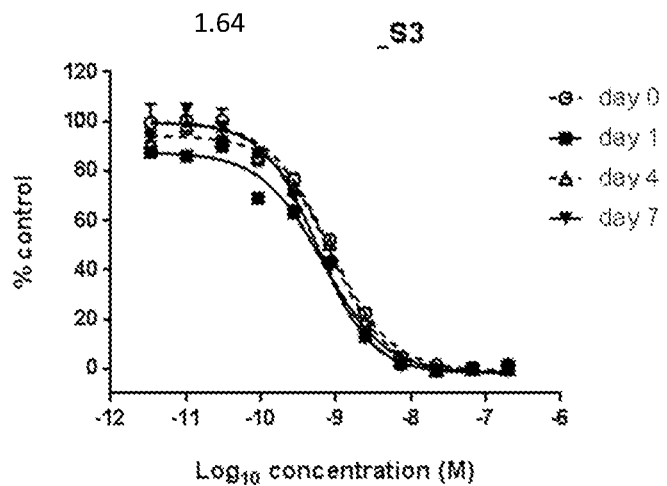
Figure 5:
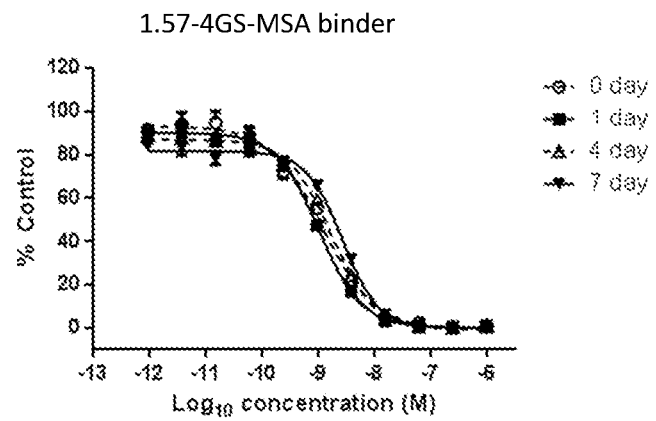

FIG. 5: Serum stability of different $V_H$ single domain antibodies. a) serum stability of 1.57 $V_H$ single domain antibodies b) serum stability of 1.64 $V_H$ single domain antibodies c) serum stability of formatted $V_H$ 1.57-4GS-MSA binder FIG. 6: Binding of $V_H$ single domain antibody to CD4 T-cells.

Figure 7A:
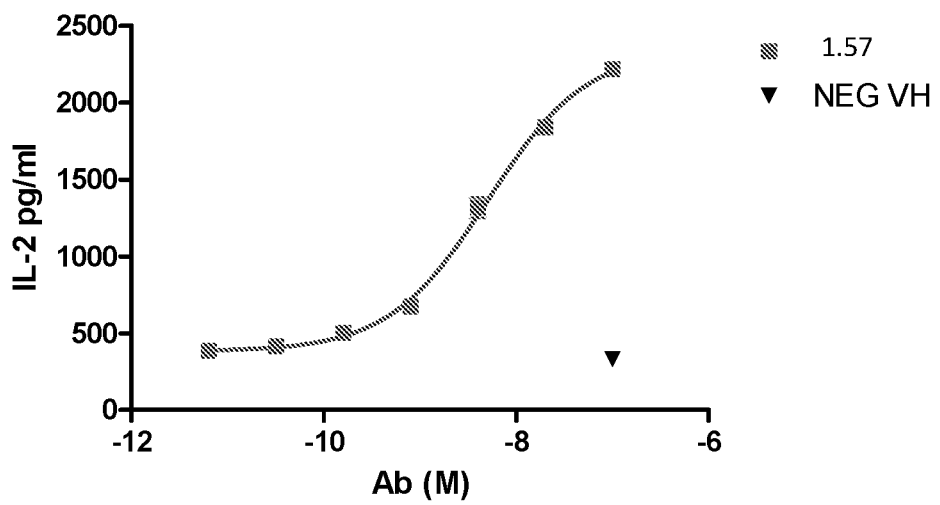
Figure 7B:
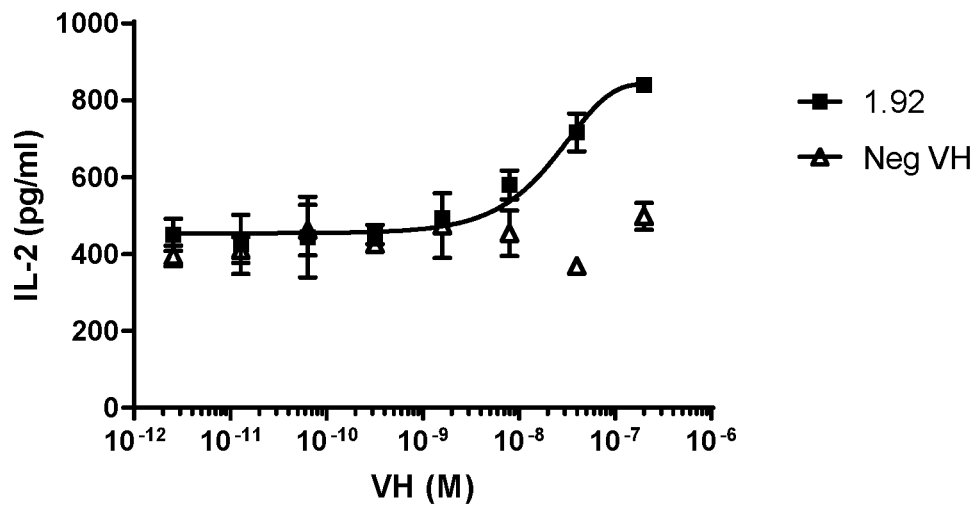

FIG. 7: shows a co-culture of dendritic cells and CD4+ T cells.: a) Effects of PD-1 specific Humabody® 1.57 on human T cell activation in a Mixed Lymphocyte Reaction b) Effects of PD-1 specific Humabody® 1.92 on human T cell activation in a Mixed Lymphocyte Reaction.

Figure 8:
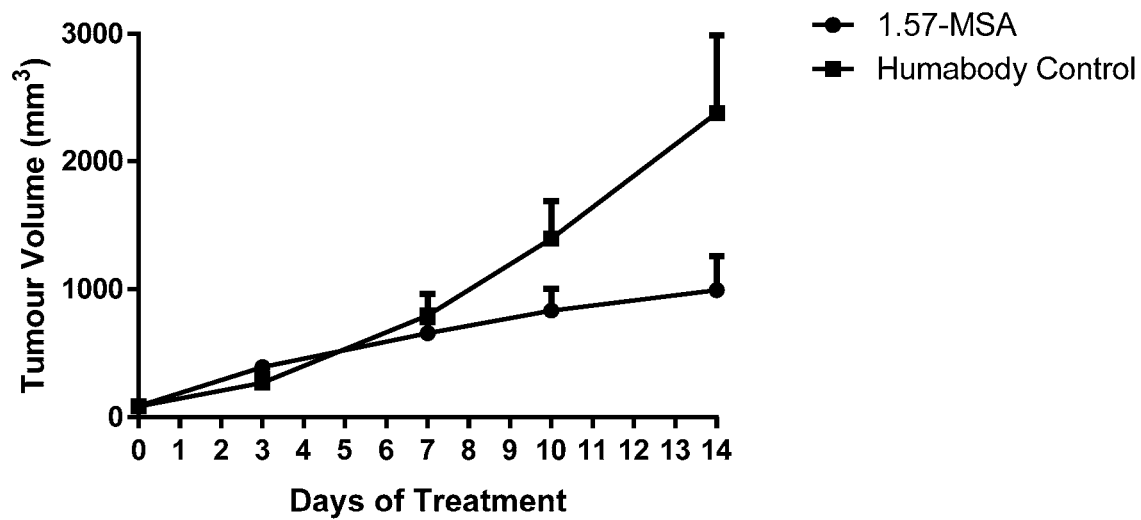

FIG. 8: In Vivo Efficacy of Humabody® Compounds in HuGEMM PD-1 Model with Subcutaneous MC38 Mouse Colon Adenocarcinoma.

Figure 9:
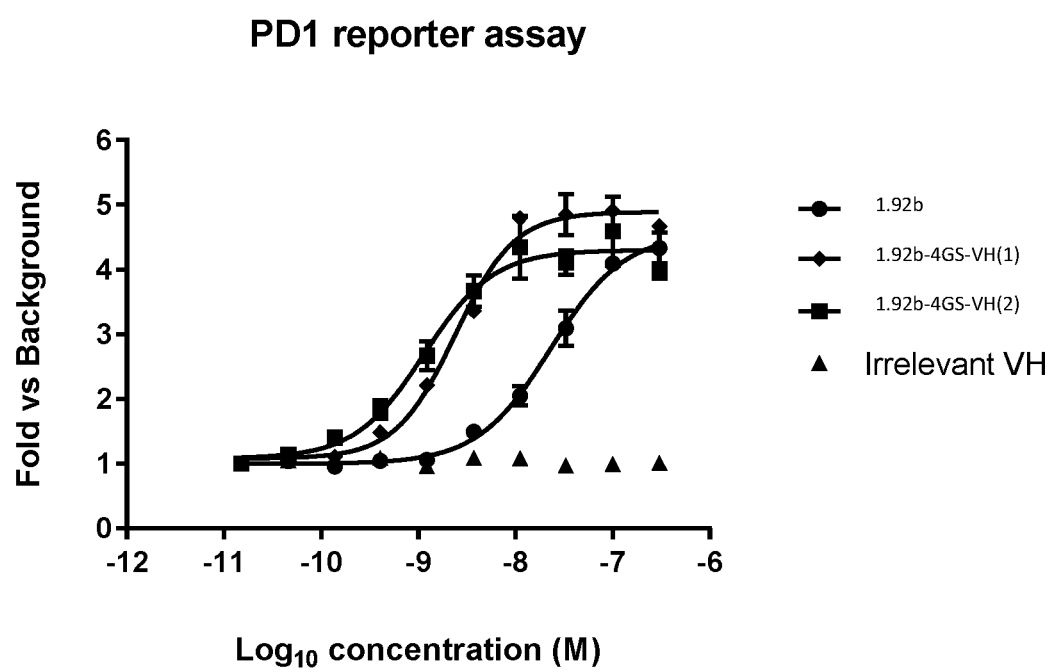

FIG. 9: Monovalent $V_H$ single domain antibody and biparatopic in the functional reporter assay.

DETAILED DESCRIPTION

The various aspects and embodiments will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012); Therapeutic Monoclonal Antibodies: From Bench to Clinic, Zhiqiang An (Editor), Wiley, (2009); and Antibody Engineering, 2nd Ed., Vols 1 and 2, Ontermann and Dubel, eds., Springer-Verlag, Heidelberg (2010).

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The invention thus provides isolated single domain antibodies that bind human PD-1 and block the interaction of PD-1 with PD-L1 and/or the interaction of PD-1 with PD-L2, pharmaceutical compositions comprising such binding molecules, as well as isolated nucleic acids, isolated recombinant expression vectors and isolated host cells for making such binding proteins. Also provided are methods of using the single domain antibodies disclosed herein to detect human PD-1 and methods of treating disease. In another aspect, the invention provides binding molecules comprising a single domain antibody that binds human PD-1 and block the interaction of PD-1 with PD-L1 and/or the interaction of PD-1 with PD-L2 as described herein.

In one aspect, the invention relates to a single domain antibody, wherein the single domain antibody exhibits one or more of the following properties:

(a) binds to human PD-1 with a KD as measured in the examples;

(b) increases IL-2 secretion in an MLR assay;

(c) binds to human PD-1 and cynomolgus monkey PD-1;

(d) does not bind to mouse PD-1;

(e) inhibits the binding of PD-L1 and/or PD-L2 to PD-1;

(f) inhibits tumor cell growth in vivo (e.g. as measured in the examples).

Suitable assays to measure the properties as set out above are described in the examples.

In preferred embodiments, the single domain antibody is a single domain antibody wherein the domain is a human variable heavy chain ($V_H$) domain. Thus, in certain embodiments, the invention provides isolated single domain antibodies that bind human PD-1, wherein the domain is a variable heavy chain domain, preferably a $V_H$ domain and wherein said single domain antibodies bind to human PD-1 and block the interaction of PD-1 with PD-L1 and/or the interaction of PD-1 with PD-L2.

The properties of the single domain antibodies of the invention as described above can be exploited in therapeutic methods and uses as described herein.

In particular, as explained below, the single domain antibodies of the invention can be used in a multivalent or multispecific format. Thus, the invention also relates to multifunctional binding agents comprising a single domain antibody as described herein.

Molecules of the invention bind specifically to wild type human PD-1 (UniProt Accession No. Q15116, GenBank Accession No. U64863, SEQ ID No. 576). Residues 1-20 correspond to the pre-sequence, residues 171 and beyond make up the transmembrane helix and the intracellular domain of PD-1.

Unless otherwise specified, the term PD-1 as used herein refers to human PD-1. The terms "Programmed Death 1," "Programmed Cell Death 1," "Protein PD-1," "PD-1," PD1," "PDCD1," "hPD-1" and "hPD-1" are used interchangeably, and include variants, isoforms, species homologs of human PD-1.

The terms "PD-1 binding molecule/protein/polypeptide/agent", "PD-1 antigen binding molecule protein/polypeptide/agent", "anti-PD-1 single domain antibody", "anti-PD-1 single immunoglobulin variable domain", "anti-PD1 heavy chain only antibody" or "anti-PD-1 antibody" all refer to a molecule capable of specifically binding to the human PD-1 antigen. The binding reaction may be shown by standard methods, for example with reference to a negative control test using an antibody of unrelated specificity. The term "PD-1 binding molecule/agent" includes a PD-1 binding protein.

An antibody or binding molecule of the invention, including a single domain antibody and multivalent or multispecific binding agent described herein, "which binds" or is "capable of binding" an antigen of interest, e.g. PD-1, is one that binds the antigen with sufficient affinity such that the antibody is useful as a therapeutic agent in targeting a cell or tissue expressing the antigen.

Binding molecules of the invention, including the single domain antibodies and multivalent or multispecific binding agents described herein, bind specifically to human PD-1. In other words, binding to the PD-1 antigen is measurably different from a non-specific interaction. As demonstrated in the examples, the single domain antibodies of the invention do not cross react with mouse PD-1. Preferably, the single domain antibodies of the invention bind to human PD-1 and also bind to cyno PD-1.

The term "specific binding" or "specifically binds to" or is "specific for" a particular polypeptide or an epitope on a particular polypeptide target as used herein can be exhibited, for example, by a molecule having a KD for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The term "antibody" broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art.

In a full-length antibody, each heavy chain is comprised of a heavy chain variable region or domain (abbreviated herein as HCVR) and a heavy chain constant region. The heavy chain constant region is comprised of three domains, $C_H1$, $C_H2$ and $C_H3$. Each light chain is comprised of a light chain variable region or domain (abbreviated herein as LCVR) and a light chain constant region. The light chain constant region is comprised of one domain, $C_L$.

The heavy chain and light chain variable regions can be further subdivided into regions of hypervariability, termed complementarity determining regions (CDR), interspersed with regions that are more conserved, termed framework regions (FR). Each heavy chain and light chain variable region is composed of three CDRs and four FRs, arranged from amino-terminus to carboxy-terminus in the following order: FR1, CDR1, FR2, CDR2, FR3, CDR3, FR4.

Immunoglobulin molecules can be of any type (e.g., IgG, IgE, IgM, IgD, IgA and IgY), class (e.g., IgG 1, IgG2, IgG 3, IgG4, IgA1 and IgA2) or subclass. The term "CDR" refers to the complementarity-determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs can be defined differently according to different systems known in the art.

The Kabat Complementarity Determining Regions (CDRs) are based on sequence variability and are the most commonly used (Kabat et al., (1971) Ann. N.Y. Acad. Sci. 190:382-391 and Kabat, et al., (1991) Sequences of Proteins of Immunological Interest, Fifth Edition, U.S. Department of Health and Human Services, NIH Publication No. 91-3242). Chothia refers instead to the location of the structural loops (Chothia and Lesk J. Mol. Biol. 196:901-917 (1987)). The Kabat numbering system is generally used when referring to a residue in the variable domain (approximately residues 1-107 of the light chain and residues 1-113 of the heavy chain).

The system described by Kabat is used herein unless otherwise specified. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion.

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

The term "antigen binding site" refers to the part of the antibody or antibody fragment that comprises the area that specifically binds to an antigen. An antigen binding site may be provided by one or more antibody variable domains. Preferably, an antigen binding site is comprised within the associated $V_H$ and $V_L$ of an antibody or antibody fragment.

An antibody fragment is a portion of an antibody, for example as F(ab')$_2$, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs.

scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv).

The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore has either the $V_H$ or $V_L$ domain.

In one aspect, the invention relates to an isolated single domain antibody, an isolated variable single domain or an isolated immunoglobulin single variable domain wherein said isolated single domain antibody, isolated variable single domain or isolated immunoglobulin single variable domain binds to human PD-1 and blocks the interaction of PD-1 and PD-L1 or PD-L2.

The terms "single domain antibody, variable single domain or immunoglobulin single variable domain (ISV)" are all well known in the art and describe the single variable fragment of an antibody that binds to a target antigen. These terms are used interchangeably herein. As explained below, preferred embodiments of the various aspects of the invention relate to single heavy chain variable domain antibodies/immunoglobulin heavy chain single variable domains which bind a PD-1 antigen in the absence of light chain. Human heavy chain single variable domain antibodies are particularly preferred. Such binding molecules are also termed Humabody® herein. Humabody® is a registered trademark of Crescendo Biologics Ltd.

Thus, in some preferred embodiments, the isolated binding agents/molecules of the invention comprise or consist of at least one single domain antibody wherein said domain is a human heavy chain variable domain. Thus, in one aspect, the binding agents of the invention comprise or consist of at least one human immunoglobulin single variable heavy chain domain; they are devoid of $V_L$ domains.

The term "isolated" single domain antibody refers to a single domain antibody that is substantially free of other single domain antibodies, antibodies or antibody fragments having different antigenic specificities. Moreover, an isolated single domain antibody may be substantially free of other cellular material and/or chemicals.

A "blocking single domain antibody or antibody" or a "neutralizing single domain antibody or antibody", as used herein refers to an antibody whose binding to PD-1 results in inhibition of at least one biological activity of PD-1. For example, a single domain antibody of the invention may prevent or block PD-1 binding to PD-L1 and/or PD-L2. In one embodiment, the single domain antibody of the invention blocks PD-1 binding to PD-L1. In one embodiment, the single domain antibody of the invention blocks PD-1 binding to PD-L2.

Each single $V_H$ domain antibody comprises three CDRs and four FRs, arranged from amino-terminus to carboxy-terminus in the following order: FR1-CDR1-FR2-CDR2-FR3-CDR3-FR4. Thus, in one embodiment of the invention, the domain is a human variable heavy chain ($V_H$) domain with the following formula FR1-CDR1-FR2-CDR2-FR3-CDR3-FR4.

Modifications to the C or N-terminal $V_H$ framework sequence may be made to the single domain antibodies of the invention to improve their properties. For example, the $V_H$ domain may comprise C or N-terminal extensions or deletions. C-terminal extensions can be added to the C-terminal end of a $V_H$ domain which terminates with the residues VTVSS (SEQ ID No. 585).

In one embodiment, the single domain antibodies of the invention comprise C-terminal extensions or deletions of from 1 to 50 residues, for example 1 to 25, e.g. 1, 2, 3, 4, 5, 6, 7, 8, 9 or 10 additional amino acids. In one embodiment, the single domain antibodies of the invention comprise additional amino acids of the human $C_H1$ domain thus that the C terminal end extends into the $C_H1$ domain. In one embodiment, said extension comprises at least one alanine residue, for example a single alanine residue, a pair of alanine residues or a triplet of alanine residues.

Additional C or N-terminal residues can be linkers that are used to conjugate the single domain antibodies of the invention to another moiety, or tags that aid the detection of the molecule. Such tags are well known in the art and include for, example linker His tags, e.g., hexa-His (HHHHHH, SEQ ID No. 586) or myc tags.

As used herein, the term "homology" generally refers to the percentage of amino acid residues in a sequence that are identical with the residues of the reference polypeptide with which it is compared, after aligning the sequences and in some embodiments after introducing gaps, if necessary, to achieve the maximum percent homology, and not considering any conservative substitutions as part of the sequence identity. Thus, the percent homology between two amino acid sequences is equivalent to the percent identity between the two sequences. Neither N- or C-terminal extensions, tags or insertions shall be construed as reducing identity or homology. Methods and computer programs for the alignment are well known. The percent identity between two amino acid sequences can be determined using well known mathematical algorithms.

According to the various aspects and embodiments of the invention, the variable domain of the single domain antibodies of the invention is preferably a human variable domain ($V_H$). As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples. In one embodiment, a human $V_H$ domain can also include a $V_H$ domain that is derived from or based on a human $V_H$ domain amino acid or nucleic acid sequence encoding such $V_H$ domain. Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified. For example, a substantially human $V_H$ domain the $V_H$ domain may include up to 10, for example 1, 2, 3, 4 or 5 amino acid modifications compared to a fully human sequence.

However, the term "human $V_H$ domain" or "substantially human $V_H$ domain", as used herein, is not intended to include antibodies in which CDR sequences derived from the germline of another mammalian species, such as a mouse, have been grafted onto human framework sequences. Preferably, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

In one embodiment, the invention relates to an isolated single $V_H$ domain antibody that binds to human PD-1 comprising a CDR3 sequence as shown Table 1 below or a sequence with at least 60%, 70%, 80%, 90%, 95% or more sequence identity thereto. For example, the single $V_H$ domain antibody capable of binding to human PD-1 may comprise a CDR3 sequence selected from SEQ ID Nos. 3 or 441 or a sequence with at least 60%, 70%, 80%, 90%, 95% or more sequence homology to one of these sequences. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment, said sequence homology is at least 90%, 91%, 92%, 93%, 94%, 95%, 96%, 97%, 98% or 99%.

In one embodiment, the $V_H$ single domain antibody has a CDR1 as shown in SEQ ID No. 1 or SEQ ID No. 1 with 1 or 2 amino acid substitutions, a CDR2 as shown in SEQ ID No. 2 or SEQ ID No. 2 with 1 to 5 amino acid substitutions and a CDR3 as shown in SEQ ID No. 3 or SEQ ID No. 3 with 1 to 5 amino acid substitutions.

In one embodiment, the $V_H$ single domain antibody has a CDR3 sequence comprising SEQ ID No. 3 or a sequence having at least 70%, at least 80%, at least 90%, or at least 95% homology to SEQ ID No. 3. In one embodiment, said sequence homology is at least 90%, 91%, 92%, 93%, 94%, 95%, 96%, 97%, 98% or 99%.

In one embodiment, the $V_H$ single domain antibody comprises a combination of CDR1, 2 and 3 sequences selected from the CDR1, 2 and 3 sequences in Table 1 or combinations thereof. In one embodiment, the $V_H$ single domain antibody comprises a set of CDR1, 2 and 3 sequences selected from the sets of CDR1, 2 and 3 sequences as shown for the any of the clones in Table 1. Thus, in one aspect, the isolated single domain antibody comprises a CDR1, CDR2 and CDR3 selected from CDRs1-3 of full length sequences SEQ ID Nos: 4, 8, 12, 16, 20, 24, 28, 32, 36, 40, 44, 48, 52, 56, 60, 64, 68, 72, 76, 80, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 252, 256, 260, 264, 268, 272, 276, 280, 284, 288, 292, 369, 373, 377, 381, 385, 389, 393, 397, 401, 405, 409, 413, 417 421, 425, 429, 433, 437, 441, 445, 449, 453, 457, 461, 465, 469, 473, 477, 481, 485, 489, 493, 497, 501, 505, 509, 513, 517, 521, 525, 529 or 533.

Accordingly, in one embodiment, the $V_H$ single domain antibody comprises CDR1 having SEQ ID No. 1, CDR2 having SEQ ID No. 2 and CDR3 having SEQ ID No. 3 (CDRs of SEQ ID NO. 4), a CDR1 having SEQ ID No. 5, CDR2 having SEQ ID No. 6 and CDR3 having SEQ ID No. 7 (CDRs of SEQ ID NO. 8) and so forth. Thus, the $V_H$ single domain antibody comprises one of the following CDR combinations: SEQ ID Nos. 1, 2, 3; SEQ ID Nos. 5, 6, 7; SEQ ID Nos. 9, 10, 11; SEQ ID Nos. 13, 14, 15; SEQ ID Nos. 17, 18, 19; SEQ ID Nos. 21, 22, 23; SEQ ID Nos. 25, 26, 27; SEQ ID Nos. 29, 30, 31; SEQ ID Nos. 33, 34, 35; SEQ ID Nos. 37, 38, 39; SEQ ID Nos. 41, 42, 43, SEQ ID Nos. 45, 46, 47; SEQ ID Nos. 49, 50, 51; SEQ ID Nos. 53, 54, 55; SEQ ID Nos. 57, 58, 59; SEQ ID Nos. 61, 62, 63; SEQ ID Nos. 65, 66, 67; SEQ ID Nos. 69, 70, 71; SEQ ID Nos. 73. 74. 75; SEQ ID Nos. 77. 78, 79; SEQ ID Nos. 101, 102, 103; SEQ ID Nos. 105, 106, 107; SEQ ID Nos. 109, 110, 111; SEQ ID Nos. 113, 114, 115; SEQ ID Nos. 117, 118, 119; SEQ ID Nos. 121, 122, 123; SEQ ID Nos. 125, 126, 127; SEQ ID Nos. 129; 130; 131; SEQ ID Nos. 133, 134, 15; SEQ ID Nos. 137, 18, 139; SEQ ID Nos. 141, 142, 143; SEQ ID Nos. 145, 146, 147; SEQ ID Nos. 149, 150, 151; SEQ ID Nos. 153, 154, 155; SEQ ID Nos. 157, 158, 159; SEQ ID Nos. 161, 162, 163; SEQ ID Nos. 165, 166, 167; SEQ ID Nos. 169, 170, 171; SEQ ID Nos. 173, 174, 175; SEQ ID Nos. 177, 178, 179; SEQ ID Nos. 181, 182, 183; SEQ ID Nos. 185, 186, 187; SEQ ID Nos. 189, 190, 191; SEQ ID Nos. 193, 194, 195; SEQ ID Nos. 197, 198, 199; SEQ ID Nos. 201, 202, 203; SEQ ID Nos. 205, 206, 207; SEQ ID Nos. 209, 210, 211; SEQ ID Nos. 213, 214, 215; SEQ ID Nos. 217, 218, 219; SEQ ID Nos. 221, 222, 223, SEQ ID Nos. 225, 226, 227; SEQ ID Nos. 229, 230, 231; SEQ ID Nos. 233, 234, 235; SEQ ID Nos. 237, 238, 239; SEQ ID Nos. 241, 242, 243; SEQ ID Nos. 245, 246, 247; SEQ ID Nos. 249, 250, 251; SEQ ID Nos. 253, 254, 255; SEQ ID Nos. 257, 258, 259; SEQ ID Nos. 261, 262, 263; SEQ ID Nos. 265, 266, 267; SEQ ID Nos. 269, 270, 271; SEQ ID Nos. 273, 274, 275; SEQ ID Nos. 277, 278, 279; SEQ ID Nos. 281, 282, 283; SEQ ID Nos. 285, 286, 287; SEQ ID Nos. 289, 290, 291; SEQ ID Nos. 366, 367, 368; SEQ ID Nos. 370, 371, 372; SEQ ID Nos. 374, 375, 376; SEQ ID Nos. 378, 379, 380; SEQ ID Nos. 382, 383, 384; SEQ ID Nos. 386, 387, 388; SEQ ID Nos. 390, 391, 392; SEQ ID Nos. 394, 395, 396; SEQ ID Nos. 398, 399, 400; SEQ ID Nos. 403, 403, 404; SEQ ID Nos. 406, 407, 408; SEQ ID Nos. 410, 411, 412; SEQ ID Nos. 414, 415, 416; SEQ ID Nos. 418, 419, 420; SEQ ID Nos. 422, 423, 425; SEQ ID Nos. 426, 427, 428; SEQ ID Nos. 430, 431, 432; SEQ ID Nos. 434, 436, 436; SEQ ID Nos. 438, 439, 440; SEQ ID Nos. 442, 443, 444; SEQ ID Nos. 446, 447, 448; SEQ ID Nos. 450, 451, 452; SEQ ID Nos. 454, 455, 456; SEQ ID Nos. 458, 459, 460; SEQ ID Nos. 462, 463, 464; SEQ ID Nos. 466, 467, 468; SEQ ID Nos. 470, 471, 472, SEQ ID Nos. 474, 475, 476; SEQ ID Nos. 478, 479, 480; SEQ ID Nos. 482, 483, 484; SEQ ID Nos. 486, 487, 488; SEQ ID Nos. 490, 491, 492; SEQ ID Nos. 494, 495, 496; SEQ ID Nos. 498, 499, 500; SEQ ID Nos. 502, 503, 504; SEQ ID Nos. 506, 507, 508; SEQ ID Nos. 510, 511, 512; SEQ ID Nos. 514, 515, 516; SEQ ID Nos. 518, 519, 520; SEQ ID Nos. 522, 523, 524; SEQ ID Nos. 526, 527, 528; SEQ ID Nos. 530, 531, 532. In one embodiment, the CDRs are SEQ ID NO. 438, 439, 440.

In another embodiment, said CDR1 comprises or consists of the amino acid sequence SEQ ID NO. 1 or a sequence with at least at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID No. 2 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR3 comprises or consists of the amino acid sequence SEQ ID No. 3 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto.

In another embodiment, the $V_H$ single domain antibody comprises or consists of a polypeptide sequence as shown for any one of $V_H$ single domain antibodies 1.1 to 1.115 in Table 1 or a sequence with at least 60%, 70%, 80%, 90%, 95% or more sequence homology thereto. In one embodiment, the invention relates to a $V_H$ single domain antibody which has combinations of CDR1, CDR2 and CDR3 as shown for any of $V_H$ single domain antibody 1.41 to 1.115. In one embodiment, the invention relates to a $V_H$ single domain antibody which has a CDR1, CDR2 and CDR3 sequence as shown for $V_H$ single domain antibody 1.57. In one embodiment, the invention relates to a $V_H$ single domain antibody which has combinations of CDR1, CDR2 and CDR3 as shown for any of $V_H$ single domain antibody 1.62 to 1.73. In one embodiment, the invention relates to a $V_H$ single domain antibody which has combinations of CDR1, CDR2 and CDR3 as shown for any of $V_H$ single domain antibody 1.74 to 1.115. In one embodiment, the invention relates to a $V_H$ single domain antibody which has combinations of CDR1, CDR2 and CDR3 as for $V_H$ single domain antibody 1.92.

In one embodiment, the $V_H$ single domain antibody comprises or consists of an amino acid sequence selected from SEQ ID Nos. 4, 8, 12, 16, 20, 24, 28, 32, 36, 40, 44, 48, 52, 56, 60, 64, 68, 72, 76, 80, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 252, 256, 260, 264, 268, 272, 276, 280, 284, 288, 292, 369, 373, 377, 381, 385, 389, 393, 397, 401, 405, 409, 413, 417 421, 425, 429, 433, 437, 441, 445, 449, 453, 457, 461, 465, 469, 473, 477, 481, 485, 489, 493, 497, 501, 505, 509, 513. 517, 521, 525, 529 or 533 or a sequence with at least 60%, 70%, 80%, 90%, 95% or more sequence homology thereto. In one embodiment, the $V_H$ single domain antibody comprises or consists of a sequence selected from SEQ ID Nos. 4, 228, 232, 236, 240, 244, 248, 252, 256, 260, 369, 373, 377, 381, 385, 389, 393, 397, 401, 405, 409, 413, 417 421, 425, 429, 433, 437, 441, 445, 449, 453, 457, 461, 465, 469, 473, 477, 481, 485, 489, 493, 497, 501, 505, 509, 513. 517, 521, 525, 529 or 533 or a sequence with at least 60%, 70%, 80%, 90%, 95% or more sequence homology thereto. In one embodiment, the $V_H$ single domain antibody comprises or consists of a sequence selected from SEQ ID No. 4, 228, 381, 176, 381,441 or a sequence with at least 60%, 70%, 80%, 90%, 95% or more sequence homology thereto. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment, the $V_H$ single domain antibody comprises or consists of SEQ ID No. 441.

TABLE 1

Full length sequences and CDR sequences of VH single domain antibodies

| Name | CDR1 | CDR2 | CDR3 | Full length |
|---|---|---|---|---|
| 1.1 | DYTMT SEQ NO. 1 | YISTGGTIKY YTDSVKG SEQ NO. 2 | EAPLRLGESPHD AFDI SEQ NO. 3 | SEQ NO. 4 QVQLVESGGGLVKPGGSLRLSCAASGFTFSDYTMT WMRQAPGKGLEWVSYISTGGTIKYYTDSVKGRFTIS RDNAKNSLYLQMNSLRADDTAVYYCAREAPLRLGES PHDAFDIWGQGTMVTVSS |
| 1.2 | DYTMT SEQ NO. 5 | YISTGGSIKY YTDSVKG SEQ NO. 6 | EAPLRLGESPHD AFDI SEQ NO. 7 | SEQ NO. 8 EVQLLESGGGLVKPGGSLRLSCAASGFTFSDYTMTW MRQAPGKGLEWVSYISTGGSIKYYTDSVKGRFTISRD NAKNSLYLQMNSLRADDTAVYYCAREAPLRLGESPH DAFDIWGQGTMVTVSS |
| 1.3 | DYTMT SEQ NO. 9 | YISTGGSIKY YTDSVKG SEQ NO. 10 | EAPLRLGESPHD AFDI SEQ NO. 11 | SEQ NO. 12 QVQLVESGGGLVKPGGSLRLSCAASGFTFSDYTMT WMRQAPGKGLEWVSYISTGGSIKYYTDSVKGRFTIS RDNAKNSLYLQMNSLRADDTAVYYCAREAPLRLGES PHDAFDIWGQGTMVTVSS |
| 1.4 | DYYMI SEQ NO. 13 | YISGGGTTK YYTDSVKG SEQ NO. 14 | EAPLRLGETPHD AFDI SEQ NO. 15 | SEQ NO. 16 QVQLVESGGGLVKPGGSLRLSCAASGFTFSDYYMIW MRQAPGKGLEWVSYISGGGTTKYYTDSVKGRFTISR DNAKNSLYLQMNSLRADDTAVYYCAREAPLRLGETP HDAFDIWGQGTMVTVSS |
| 1.5 | DYTMT SEQ NO. 17 | YISTGGNTK YYTDSVKG SEQ NO. 18 | EAPLRLGESPHD AFDI SEQ NO. 19 | SEQ NO. 20 EVQLVESGGGLVKPGGSLRLSCAASGFTFSDYTMTW MRQAPGKGLEWVSYISTGGNTKYYTDSVKGRFTISR DNAKNSLYLQMNSLRADDTAVYYCAREAPLRLGESP HDAFDIWGQGTMVTVSS |
| 1.6 | DYTMT SEQ NO. 21 | YISTGGTIKY YTDSVKG SEQ NO. 22 | EAPLRLGESPHD AFDI SEQ NO. 23 | SEQ NO. 24 EVQLLESGGGLVKPGGSLRLSCAASGFTFSDYTMTW MRQAPGKGLEWVSYISTGGTIKYYTDSVKGRFTISRD |

TABLE 1-continued

Full length sequences and CDR sequences of VH single domain antibodies

| Name | CDR1 | CDR2 | CDR3 | Full length |
|---|---|---|---|---|
| | | | | NAKNSLYLQMSSLRADDTAVYYCAREAPLRLGESPH DAFDIWGQGTMVTVSS |
| 1.7 | DYTMT SEQ NO. 25 | YISTGGTIKY YTDSVKG SEQ NO. 26 | EAPLRLGESPHD AFDI SEQ NO. 27 | SEQ NO. 28 EVQLVESGGGLVKPGGSLRLSCAASGFTFSDYTMTW MRQAPGKGLEWVSYISTGGTIKYYTDSVKGRFTISRD NAKNSLYLQMNSLRADDTAVYYCAREAPLRLGESPH DAFDIWGQGTMVTVSS |
| 1.8 | DYTMT SEQ NO. 29 | YISTGGSIKY YTDSVKG SEQ NO. 30 | EAPLRLGESPHD AFDI SEQ NO. 31 | SEQ NO. 32 EVQLVESGGGLVKPGGSLRLSCAASGFTFSDYTMTW MRQAPGKGLEWVSYISTGGSIKYYTDSVKGRFTISRD NAKNSLYLQMNSLRAGDTAVYYCAREAPLRLGESPH DAFDIWGQGTMVTVSS |
| 1.9 | DYTMT SEQ NO. 33 | YISTGGTIKY YTDSVKG SEQ NO. 34 | EAPLRLGESPHD AFDI SEQ NO. 35 | SEQ NO. 36 QVQLVESGGGLVKPGGSLRLSCAASGFTFGDYTMT WMRQAPGKGLEWVSYISTGGTIKYYTDSVKGRFTIS RDNAKNSLYLQMDSLRADDTAVYYCAREAPLRLGES PHDAFDIWGQGTMVTVSS |
| 1.10 | DYTMS SEQ NO. 37 | YISLGGNTK YYTDSVKG SEQ NO. 38 | EAPLRLGESPHD AFDI SEQ NO. 39 | SEQ NO. 40 QVQLVESGGGLVKPGGSLRLSCAASGFTFSDYTMS WMRQAPGKGLEWISYISLGGNTKYYTDSVKGRFTIS RDNAKNSLYLQMNSLRADDTAVYYCAREAPLRLGES PHDAFDIWGQGTMVTVSS |
| 1.11 | DYDMT SEQ NO. 41 | YISRGGSTK YYADSVKG SEQ NO. 42 | EAPLRLGETPHD AFDI SEQ NO. 43 | SEQ NO. 44 EVQLLESGGGLVKPGGSLRLSCAASGFTFSDYDMTW IRQAPGKGQEWVSYISRGGSTKYYADSVKGRFTISRD NAKNSLYLQMNSLRAEDTAVYYCAREAPLRLGETPH DAFDIWGQGTMVTVSS |
| 1.12 | DYYMG SEQ NO. 45 | YISSSGSTIY YADSVKG SEQ NO. 46 | EAPLRLGESPHD AFDI SEQ NO. 47 | SEQ NO. 48 EVQLLESGGGVVKPGGSLRLSCAASGFTFSDYYMG WIRQAPGKGLEWISYISSSGSTIYYADSVKGRFTISRD NAKNSLYLQMNSLRAEDTAVYYCAREAPLRLGESPH DAFDIWGQGTMVTVSS |
| 1.13 | DYTMT SEQ NO. 49 | YISTGGTIKY YTDSVKG SEQ NO. 50 | EAPLRLGESPHD AFDI SEQ NO. 51 | SEQ NO. 52 EVQLLESGGGLVKPGGSLRLSCAASGFTFSDYTMTW MRQAPGKGLEWVSYISTGGTIKYYTDSVKGRFTISRD NAKNSLYLQMNSLRADDTAVYYCAREAPLRLGESPH DAFDIWGQGTMVTVSS |
| 1.14 | DYTMT SEQ NO. 53 | YISTGGTIKY YTDSVKG SEQ NO. 54 | EAPLRLGESPHD AFDI SEQ NO. 55 | SEQ NO. 56 EVQLVESGGGLVQPGRSLRLSCAASGFTFSDYTMT WMRQAPGKGLEWVSYISTGGTIKYYTDSVKGRFTIS RDNAKNSLYLQMNSLRADDTAVYYCAREAPLRLGES PHDAFDIWGQGTMVTVSS |
| 1.15 | DNSMS SEQ NO. 57 | YISSSGSTIY YADSVKG SEQ NO. 58 | EAPLRLGESPHD AFDI SEQNO. 59 | SEQ NO. 60 EVQLVESGGGLVKPGGSLRLSCAASGFTFSDNSMS WIRQAPGKGLEWVSYISSSGSTIYYADSVKGRFTISR DNAKNSLYLQMNTLRAEDTAVYYCAKEAPLRLGESP HDAFDIWGQGTMVTVSS |
| 1.16 | DYTMS SEQ NO. 61 | YISTGGSIKY YTDSVKG SEQ NO. 62 | EAPLRLGESPHD AFDI SEQ NO. 63 | SEQ NO. 64 EVQLVESGGGLVKPGGSLRLSCAASGFTFSDYTMSW MRQAPGKGLEWVSYISTGGSIKYYTDSVKGRFTISRD NAKNSLYLQMNSLRADDTAVYYCAREAPLRLGESPH DAFDIWGQGTMVTVSS |
| 1.17 | DYTMT SEQ NO. 65 | YISTGGSIKY YTDSVKG SEQ NO. 66 | EAPLRLGESPHD AFDI SEQ NO. 67 | SEQ NO. 68 EVQLVESGGGLVKPGGSLRLSCAASGFTFSDYTMTW MRQAPGKGLEWVSYISTGGSIKYYTDSVKGRFTISRD NAKNSLYLQMNSLRVDDTAVYYCAREAPLRLGESPH DAFDIWGQGTMVTVSS |
| 1.18 | DYTMT SEQ NO. 69 | YISTGGTIKY YTDSVKG SEQ NO. 70 | EAPLRLGESPHD AFDI SEQ NO. 71 | SEQ NO. 72 QVQLLESGGGLVKPGGSLRLSCAASGFTFSDYTMT WMRQAPGKGLEWVSYISTGGTIKYYTDSVKGRFTIS RDNAKNSLYLQMNSLRADDTAVYYCAREAPLRLGES PHDAFDIWGQGTMVTVSS |

TABLE 1-continued

Full length sequences and CDR sequences of VH single domain antibodies

| Name | CDR1 | CDR2 | CDR3 | Full length |
|---|---|---|---|---|
| 1.19 | DYTMT SEQ NO. 73 | YISTGGSIKY YTDSVKG SEQ NO. 74 | EAPLRLGETPHD AFDI SEQ NO. 75 | SEQ NO. 76 QVQLVESGGGLVKPGGSLRLSCAASGFTFSDYTMT WMRQAPGKGLEWVSYISTGGSIKYYTDSVKGRFTIS RDNAKNSLYLQMNSLRAEDTAVYYCAREAPLRLGET PHDAFDIWGQGTMVTVSS |
| 1.20 | DYTMT SEQ NO. 77 | YISSGGSIKF YADSVKG SEQ NO. 78 | EAPLRLGESPHD AFDI SEQ NO. 79 | SEQ NO. 80 EVQLLESGGGLVKPGGSLRLSCAASGFTFSDYTMTW MRQAPGKGLEWVSYISSGGSIKFYADSVKGRFTISRD NAKNSLYLQMNSLRAEDTAVYYCAREAPLRLGESPH DAFDIWGQGTMVTVSS |
| 1.21 | DYTMT SEQ NO. 81 | YISTGGSIKY YTDSVKG SEQ NO. 82 | EAPLRLGESPHD AFDT SEQ NO. 83 | SEQ NO. 84 EVQLVESGGGLVKPGGSLRLSCAASGFTFSDYTMTW MRQAPGKGLEWVSYISTGGSIKYYTDSVKGRFTISRD NAKNSLYLQMNSLRADDTAVYYCAREAPLRLGESPH DAFDTWGQGTMVTVSS |
| 1.22 | DYTMT SEQ NO. 85 | YISTGGSIKY YTDSVKG SEQ NO. 86 | EAPLRLGESPHD AFDI SEQ NO. 87 | SEQ NO. 88 EVQLVESGGGLVKPGGSLRLSCAASGFTFSDYTMTW MRQAPGKGLEWVSYISTGGSIKYYTDSVKGRFTISRD NAKNSLYLQMNSLRADDTAVYYCAREAPLRLGESPH DAFDIWGQGTMVTVSS |
| 1.23 | DYTMS SEQ NO. 89 | YISTGGTIKY YTDSVKG SEQ NO. 90 | EAPLRLGESPHD AFDI SEQ NO. 91 | SEQ NO. 92 QITLKESGGGLVKPGGSLRLSCAASGFTFSDYTMSW MRQAPGKGLEWVSYISTGGTIKYYTDSVKGRFTISRD NAKNSLYLQMNSLRADDTAVYYCAREAPLRLGESPH DAFDIWGQGTMVTVSS |
| 1.24 | DYDMY SEQ NO. 93 | YISRGGSVT YYADSVKG SEQ NO. 94 | EAPLRLGETPHA AFDI SEQ NO. 95 | SEQ NO. 96 QVTLKESGGGLVKPGGSLRLSCAASGFTFSDYDMY WIRQAPGKGLEWVSYISRGGSVTYYADSVKGRFTI RDNAKNALYLQMNSLRAEDMAVYFCATEAPLRLGE TPHAAFDIWGQGTMVTVSS |
| 1.25 | DYYMS SEQ NO. 97 | FISSSGSTTY YADSVKG SEQ NO. 98 | EAPLRLGESPHD AFDF SEQ NO. 99 | SEQ NO. 100 QVTLKESGGGLVKPGGSLRLSCAASGFTFSDYYMSW FRQAPGKEREWISFISSSGSTTYYADSVKGRFTISRDN AKNSLYLQMNSLRAEDTAVYYCAREAPLRLGESPHD AFDFWGQGTMVTVSS |
| 1.26 | DNSMS SEQ NO. 101 | YISSSGSTIY YADSVKG SEQ NO. 102 | EAPLRLGESPHD AFDI SEQ NO. 103 | SEQ NO. 104 QVTLKESGGGLVKPGGSLRLSCAASGFTFSDNSMS WIRQAPGKGLEWVSYISSSGSTIYYADSVKGRFTISR DNAKNSLYLQMNTLRAEDTAVYYCAKEAPLRLGESP HDAFDIWGQGTMVTVSS |
| 1.27 | DYTMT SEQ NO. 105 | YISTGGSIKY YTDSVKG SEQ NO. 106 | EAPLRLGESPHD AFDI SEQ NO. 107 | SEQ NO. 108 QVTLKESGGGLVKPGGSLRLSCAASGFTFSDYTMTW MRQAPGKGLEWVSYISTGGSIKYYTDSVKGRFTISRD NAKNSLYLQMNSLRADDTAVYYCAREAPLRLGESPH DAFDIWGQGTMVTVSS |
| 1.28 | DYDMY SEQ NO. 109 | YISRGGSVT YYADSVKG SEQ NO. 110 | EAPLRLGETPHA AFDI SEQ NO. 111 | SEQ NO. 112 QITLKESGGGLVKPGGSLRLSCAASGFTFSDYDMYWI RQAPGKGLEWVSYISRGGSVTYYADSVKGRFTISRD NAKNALYLQMNSLRAEDMAVYFCATEAPLRLGETP HAAFDIWGQGTMVTVSS |
| 1.29 | DYTMS SEQ NO. 113 | YISTGGTIKY YTDSVKG SEQ NO. 114 | EAPLRLGESPHD AFDI SEQ NO. 115 | SEQ NO. 116 QVTLKESGGGLVKPGGSLRLSCAASGFTFSDYTMSW MRQAPGKGLEWVSYISTGGTIKYYTDSVKGRFTISRD NAKNSLYLQMNSLRADDTAVYYCAREAPLRLGESPH DAFDIWGQGTMVTVSS |
| 1.30 | DYTMT SEQ NO. 117 | YISTGGSIKY YTDSVKG SEQ NO. 118 | EAPLRLGESPHD AFDI SEQ NO. 119 | SEQ NO. 120 QVTLKESGGGLVKPGGSLRLSCAASGFTFSDYTMTW MRQAPGKGLEWVSYISTGGSIKYYTDSVKGRFTISRD NARNSLYLQMNSLRAEDTAVYYCAREAPLRLGESPH DAFDIWGQGTMVTVSS |
| 1.31 | DYTMT SEQ NO. | YISTGGSTK YYTDSVKG SEQ NO. | EAPLRLGESPHD AFDI SEQ NO. 123 | SEQ NO. 124 QVTLKESGGGLVKPGGSLRLSCAASGFTFSDYTMTW MRQAPGKGLEWVSYISTGGSTKYYTDSVKGRFTISR |

TABLE 1-continued

Full length sequences and CDR sequences of VH single domain antibodies

| Name | CDR1 | CDR2 | CDR3 | Full length |
|---|---|---|---|---|
| | | 121 | 122 | DNAKNSLYLQMNSLRADDTAVYYCAREAPLRLGESPHDAFDIWGQGTMVTVSS |
| 1.32 | DDYMM SEQ NO. 125 | YISSGGSIIYY ADSVKG SEQ NO. 126 | EAPLRLGESPHD AFDI SEQ NO. 127 | SEQ NO. 128 QVTLKESGGGLVKPGGSLRLSCAASGFTFSDDYMM WIRQAPGKGLEWVSYISSGGSIIYYADSVKGRFTISR DNAKNSLYLQMNSLRAEDTAVYYCAREAPLRLGESP HDAFDIRGQGTMVTVSS |
| 1.33 | DYDMY SEQ NO. 129 | YISRGGSVT YYADSVKG SEQ NO. 130 | EAPLRLGETPHA AFDI SEQ NO. 131 | SEQ NO. 132 QITLKESGGGLVKPGGSLRLSCAASGFTFSDYDMYW VRQAPGKGLEWVSYISRGGSVTYYADSVKGRFTISR DNAKNALYLQMNSLRAEDMAVYFCATEAPLRLGET PHAAFDIWGQGTMVTVSS |
| 1.34 | DYTMT SEQ NO. 133 | YISTGGSVK YYTDSVKG SEQ NO. 134 | EAPLRLGESPHD AFDI SEQ NO. 135 | SEQ NO. 136 EVQLVESGGGLVKPGGSLRLSCAASGFTFSDYTMTW MRQAPGKGLEWVSYISTGGSVKYYTDSVKGRFTISR DNAKNSLYLQMNSLRADDTAVYYCAREAPLRLGESP HDAFDIWGQGTMVTVSS |
| 1.35 | DYTMT SEQ NO. 137 | YISTGGSIKY YTDSVKG SEQ NO. 138 | EAPLRLGESPHD AFDI SEQ NO. 139 | SEQ NO. 140 EVQLLESGGGLVKPGGSLRLSCAASGFTFSDYTMTW MRQAPGKGLEWVSYISTGGSIKYYTDSVKGRFTISRD NAKNSLYLQMNSLRVDDTAVYYCAREAPLRLGESPH DAFDIWGQGTMVTVSS |
| 1.36 | DYTMT SEQ NO. 141 | YISTGGTIKY YTDSVKG SEQ NO. 142 | EAPLRLGESPHD AFDI SEQ NO. 143 | SEQ NO. 144 EVQLVESGGGLVKPGGSLRLSCAASGFTFSDYTMTW MRQAPGKGLEWVSYISTGGTIKYYTDSVKGRFTISRD NAKNSLFLQMNSLRADDTAVYYCAREAPLRLGESPH DAFDIWGQGTMVTVSS |
| 1.37 | DYTMT SEQ NO. 145 | YISTGGSIKY YTDSVKG SEQ NO. 146 | EAPLRLGESPHD AFDI SEQ NO. 147 | SEQ NO. 148 QVQLVESGGGLVKPGGSLRLSCAASGFTFSDYTMT WMRQAPGKGLEWVSYISTGGSIKYYTDSVKGRFTIS RDNAKNSLFLQMNSLRADDTAVYYCAREAPLRLGES PHDAFDIWGQGTMVTVSS |
| 1.38 | DYTMT SEQ NO. 149 | YISTGGTIKY YTDSVKG SEQ NO. 150 | EAPLRLGESPHD AFDI SEQ NO. 151 | SEQ NO. 152 EVQLVESGGGLVQPGGSLRLSCAASGFTFSDYTMT WMRQAPGKGLEWVSYISTGGTIKYYTDSVKGRFTIS RDNAKNSLYLQMNSLRADDTAVYYCAREAPLRLGES PHDAFDIWGQGTMVTVSS |
| 1.39 | DYTMT SEQ NO. 153 | YISTGGSIKY YTDSVKG SEQ NO. 154 | EAPLRLGESPHD AFDI SEQ NO. 155 | SEQ NO. 156 QVQLQESGGGLVKPGGSLRLSCAASGFTFSDYTMT WMRQAPGKGLEWVSYISTGGSIKYYTDSVKGRFTIS RDNAKNSLYLQMNSLRADDTAVYYCAREAPLRLGES PHDAFDIWGQGTMVTVSS |
| 1.40 | DSSMS SEQ NO. 157 | YISSGGGIIY YTDSVKG SEQ NO. 158 | EAPLRLGESPHD AFDI SEQ NO. 159 | SEQ NO. 160 EVQLVESGGGLVKPGGSLRLSCAASGFTFSDSSMSW IRQAPGRGLEWISYISSGGGIIYYTDSVKGRFTISRDN AKNSLYLQMNSLRVEDTAVYYCAKEAPLRLGESPHD AFDIWGHGTMVTVSS |
| 1.41 | DNSMT SEQ NO. 161 | YISSGGGVIF YADSVKG SEQ NO. 162 | EAPLRLGESPHD AFDI SEQ NO. 163 | SEQ NO. 164 QVQLVESGGGLVKPGGSLRLSCAASGFTFSDNSMT WMRQAPGKGLEWVSYISSGGGVIFYADSVKGRFTIS RDNAKNSLYLQMNSLRADDTAVYYCAREAPLRLGES PHDAFDIWGQGTMVTVSS |
| 1.42 | DNSMT SEQ NO. 165 | YISSGGGVK FYADSVKG SEQ NO. 166 | EAPLRLGESPHD AFDI SEQ NO. 167 | SEQ NO. 168 QVQLVESGGGLVKPGGSLRLSCAASGFTFSDNSMT WMRQAPGKGLEWVSYISSGGGVKFYADSVKGRFTI SRDNAKNSLYLQMNSLRADDTAVYYCAREAPLRLGE SPHDAFDIWGQGTMVTVSS |
| 1.43 | DSSMT SEQ NO. 169 | YISSGGGVIF YADSVKG SEQ NO. 170 | EAPLRLGESPHD AFDI SEQ NO. 171 | SEQ NO. 172 QVQLVESGGGLVKPGGSLRLSCAASGFTFSDSSMT WMRQAPGKGLEWVSYISSGGGVIFYADSVKGRFTIS RDNAKNSLYLQMNSLRADDTAVYYCAREAPLRLGES PHDAFDIWGQGTMVTVSS |

TABLE 1-continued

Full length sequences and CDR sequences of VH single domain antibodies

| Name | CDR1 | CDR2 | CDR3 | Full length |
|---|---|---|---|---|
| 1.44 | DNSMT SEQ NO. 173 | YISSGGAVK FYADSVKG SEQ NO. 174 | EAPLRLGESPHD AFDI SEQ NO. 175 | SEQ NO. 176 QVQLVESGGGLVKPGGSLRLSCAASGFTFSDNSMT WMRQAPGKGLEWVSYISSGGAVKFYADSVKGRFTI SRDNAKNSLYLQMNSLRADDTAVYYCAREAPLRLGE SPH DAFDIWGQGTMVTVSS |
| 1.45 | DYSMS SEQ NO. 177 | YISSGGGVIF YADSVKG SEQ NO. 178 | EAPLRLGESPHD AFDI SEQ NO. 179 | SEQ NO. 180 QVQLVESGGGLVKPGGSLRLSCAASGFTFSDYSMS WMRQAPGKGLEWVSYISSGGGVIFYADSVKGRFTIS RDNAKNSLYLQMNSLRADDTAVYYCAREAPLRLGES PHDAFDIWGQGTMVTVSS |
| 1.46 | DSSMS SEQ NO. 181 | YISSGGGVIF YADSVKG SEQ NO. 182 | EAPLRLGESPHD AFDI SEQ NO. 183 | SEQ NO. 184 QVQLVESGGGLVKPGGSLRLSCAASGFTFSDSSMS WMRQAPGKGLEWVSYISSGGGVIFYADSVKGRFTIS RDNAKNSLYLQMNSLRADDTAVYYCAREAPLRLGES PHDAFDIWGQGTMVTVSS |
| 1.47 | DNSMS SEQ NO. 185 | YISSGGGVIF YADSVKG SEQ NO. 186 | EAPLRLGESPHD AFDI SEQ NO. 187 | SEQ NO. 188 QVQLVESGGGLVKPGGSLRLSCAASGFTFSDNSMS WMRQAPGKGLEWVSYISSGGGVIFYADSVKGRFTIS RDNAKNSLYLQMNSLRADDTAVYYCAREAPLRLGES PHDAFDIWGQGTMVTVSS |
| 1.48 | DSSMT SEQ NO. 189 | YISSGGGVK FYADSVKG SEQ NO. 190 | EAPLRLGESPHD AFDI SEQ NO. 191 | SEQ NO. 192 QVQLVESGGGLVKPGGSLRLSCAASGFTFSDSSMT WMRQAPGKGLEWVSYISSGGGVKFYADSVKGRFTI SRDNAKNSLYLQMNSLRADDTAVYYCAREAPLRLGE SPHDAFDIWGQGTMVTVSS |
| 1.49 | DSSMS SEQ NO. 193 | YISTGGGVK FYADSVKG SEQ NO. 194 | EAPLRLGESPHD AFDI SEQ NO. 195 | SEQ NO. 196 QVQLVESGGGLVKPGGSLRLSCAASGFTFSDSSMS WMRQAPGKGLEWVSYISTGGGVKFYADSVKGRFTI SRDNAKNSLYLQMNSLRADDTAVYYCAREAPLRLGE SPHDAFDIWGQGTMVTVSS |
| 1.50 | DNSMT SEQ NO. 197 | YISSGGTIKF YADSVKG SEQ NO. 198 | EAPLRLGESPHD AFDI SEQ NO. 199 | SEQ NO. 200 QVQLVESGGGLVKPGGSLRLSCAASGFTFSDNSMT WMRQAPGKGLEWVSYISSGGTIKFYADSVKGRFTIS RDNAKNSLYLQMNSLRADDTAVYYCAREAPLRLGES PHDAFDIWGQGTMVTVSS |
| 1.51 | DSSMT SEQ NO. 201 | YISSGGAVK FYTDSVKG SEQ NO. 202 | EAPLRLGESPHD AFDI SEQ NO. 203 | SEQ NO. 204 QVQLVESGGGLVKPGGSLRLSCAASGFTFSDSSMT WMRQAPGKGLEWVSYISSGGAVKFYTDSVKGRFTI SRDNAKNSLYLQMNSLRADDTAVYYCAREAPLRLGE SPHDAFDIWGQGTMVTVSS |
| 1.52 | DNSMT SEQ NO. 205 | YISSGGGVK YYADSVKG SEQ NO. 206 | EAPLRLGESPHD AFDI SEQ NO. 207 | SEQ NO. 208 QVQLVESGGGLVKPGGSLRLSCAASGFTFSDNSMT WMRQAPGKGLEWVSYISSGGGVKYYADSVKGRFTI SRDNAKNSLYLQMNSLRADDTAVYYCAREAPLRLGE SPHDAFDIWGQGTMVTVSS |
| 1.53 | DNSMT SEQ NO. 209 | YISSGGSVK FYADSVKG SEQ NO. 210 | EAPLRLGESPHD AFDI SEQ NO. 211 | SEQ NO. 212 QVQLVESGGGLVKPGGSLRLSCAASGFTFSDNSMT WMRQAPGKGLEWVSYISSGGSVKFYADSVKGRFTI SRDNAKNSLYLQMNSLRADDTAVYYCAREAPLRLGE SPHDAFDIWGQGTMVTVSS |
| 1.54 | DDSMT SEQ NO. 213 | YISSGGGVIF YADSVKG SEQ NO. 214 | EAPLRLGESPHD AFDI SEQ NO. 215 | SEQ NO. 216 QVQLVESGGGLVKPGGSLRLSCAASGFTFSDDSMT WMRQAPGKGLEWVSYISSGGGVIFYADSVKGRFTIS RDNAKNSLYLQMNSLRADDTAVYYCAREAPLRLGES PHDAFDIWGQGTMVTVSS |
| 1.55 | DNSMT SEQ NO. 217 | YISSGGGVK FYADSVKG SEQ NO. 218 | EAPLRLGESPHD AFDI SEQ NO. 219 | SEQ NO. 220 QVQLVESGGGLVKPGGSLRLSCAASGFTFSDNSMT WMRQAPGKGLEWVSYISSGGGVKFYADSVKGRFTI SRDNAKNSLYLQMNSLRADDTAVYYCAREAPLRLGE SPHDAFDISGQGTMVTVSS |
| 1.56 | DNSMT SEQ NO. | YISSGGAVK FYADSVKG SEQ NO. | EAPLRLGESPHD AFDI SEQ NO. 223 | SEQ NO. 224 QVQLVESGGGLVKPGGSLRLSCAASGFTFSDNSMT WMRQAPGKGLEWVSYISSGGAVKFYADSVKGRFTI |

TABLE 1-continued

Full length sequences and CDR sequences of VH single domain antibodies

| Name | CDR1 | CDR2 | CDR3 | Full length |
|------|------|------|------|-------------|
|      | 221  | 222  |      | SRDNAKNSLYLQMNSLRADDTAVYYCAREAPLRLGE<br>SPHDAFDILGQGTMVTVSS |
| 1.57 | DNSMT<br>SEQ<br>NO.<br>225 | YISSGGGVIF<br>YADSVKG<br>SEQ NO.<br>226 | EAPLRLGESPHD<br>AFDI<br>SEQ NO. 227 | SEQ NO. 228<br>QVQLVESGGGLVKPGGSLRLSCAASGFTFSDNSMT<br>WMRQAPGKGLEWVSYISSGGGVIFYADSVKGRFTIS<br>RDNAKNSLYLQMNSLRADDTAVYYCAREAPLRLGES<br>PHDAFDISGQGTMVTVSS |
| 1.58 | DNTMT<br>SEQ<br>NO. 229 | YISTGGGVK<br>FYADSVKG<br>SEQ NO.<br>230 | EAPLRLGESPHD<br>AFDI<br>SEQ NO. 231 | SEQ NO. 232<br>QVQLVESGGGLVKPGGSLRLSCAASGFTFSDYTMT<br>WMRQAPGKGLEWVSYISTGGTIKYYTDSVKGRFTIS<br>RDNAKNSLYLQMNSLRADDTAVYYCAREAPLRLGES<br>PHDAFDIWGQGTMVTVSS |
| 1.59 | DNSMS<br>SEQ<br>NO.<br>233 | YISSGGSVK<br>FYADSVKG<br>SEQ NO.<br>234 | EAPLRLGESPHD<br>AFDI<br>SEQ NO. 235 | SEQ NO. 236<br>QVQLVESGGGLVKPGGSLRLSCAASGFTFSDNTMT<br>WMRQAPGKGLEWVSYISTGGGVKFYADSVKGRFTI<br>SRDNAKNSLYLQMNSLRADDTAVYYCAREAPLRLGE<br>SPHDAFDIWGQGTMVTVSS |
| 1.60 | DNSMT<br>SEQ<br>NO.<br>237 | YISTGGGVK<br>YYADSVKG<br>SEQ NO.<br>238 | EAPLRLGESPHD<br>AFDI<br>SEQ NO. 239 | SEQ NO. 240<br>QVQLVESGGGLVKPGGSLRLSCAASGFTFSDNSMS<br>WMRQAPGKGLEWVSYISSGGSVKFYADSVKGRFTI<br>SRDNAKNSLYLQMNSLRADDTAVYYCAREAPLRLGE<br>SPHDAFDIWGQGTMVTVSS |
| 1.61 | DYTMS<br>SEQ<br>NO.<br>241 | YISTGGGVK<br>FYADSVKG<br>SEQ NO.<br>242 | EAPLRLGESPHD<br>AFDI<br>SEQ NO. 243 | SEQ NO. 244<br>QVQLVESGGGLVKPGGSLRLSCAASGFTFSDNSMT<br>WMRQAPGKGLEWVSYISTGGGVKYYADSVKGRFTI<br>SRDNAKNSLYLQMNSLRADDTAVYYCAREAPLRLGE<br>SPHDAFDIWGQGTMVTVSS |
| 1.62 | DSSMT<br>SEQ<br>NO.<br>245 | YISSGGAVK<br>FYTDSVKG<br>SEQ NO.<br>246 | EAPLRLGESPHD<br>AFDI<br>SEQ NO. 247 | SEQ NO. 248<br>QVQLVESGGGLVKPGGSLRLSCAASGFTFSDSSMT<br>WMRQAPGKGLEWVSYISSGGAVKFYTDSVKGRFTI<br>SRDNAKNSLYLQMNSLRADDTAVYYCAREAPLRLGE<br>SPHDAFDISGQGTMVTVSS |
| 1.63 | DSSMT<br>SEQ<br>NO.<br>249 | YISSGGGVK<br>FYTDSVKG<br>SEQ NO.<br>250 | EAPLRLGESPHD<br>AFDI<br>SEQ NO. 251 | SEQ NO. 252<br>EVQLVESGGGLVKPGGSLRLSCAASGFTFSDSSMTW<br>MRQAPGKGLEWVSYISSGGGVKFYTDSVKGRFTISR<br>DNAKNSLYLQMNSLRADDTAVYYCAREAPLRLGESP<br>HDAFDISGQGTMVTVSS |
| 1.64 | DSSMT<br>SEQ<br>NO.<br>253 | YISSGGGVK<br>FYADSVKG<br>SEQ NO.<br>254 | EAPLRLGESPHD<br>AFDI<br>SEQ NO. 255 | SEQ NO. 256<br>EVQLVESGGGLVKPGGSLRLSCAASGFTFSDSSMTW<br>MRQAPGKGLEWVSYISSGGGVKFYADSVKGRFTISR<br>DNAKNSLYLQMNSLRADDTAVYYCAREAPLRLGESP<br>HDAFDISGQGTMVTVSS |
| 1.65 | DSSMT<br>SEQ<br>NO.<br>257 | YISSGGGVK<br>FYADSVKG<br>SEQ NO.<br>258 | EAPLRLGESPHD<br>AFDI<br>SEQ NO. 259 | SEQ NO. 260<br>QVQLVESGGGLVKPGGSLRLSCAASGFTFSDSSMT<br>WMRQAPGKGLEWVSYISSGGGVKFYADSVKGRFTI<br>SRDNAKNSLYLQMNSLRADDTAVYYCAREAPLRLGE<br>SPHDAFDISGQGTMVTVSS |
| 1.66 | DSSMT<br>SEQ<br>NO.<br>261 | YISSGGGVK<br>FYTDSVKG<br>SEQ NO.<br>262 | EAPLRLGESPHD<br>AFDT<br>SEQ NO. 263 | SEQ NO. 264<br>QVQLVESGGGLVKPGGSLRLSCAASGFTFSDSSMT<br>WMRQAPGKGLEWVSYISSGGGVKFYTDSVKGRFTI<br>SRDNAKNSLYLQMDSLRADDTAVYYCAREAPLRLGE<br>SPHDAFDTSGQGTMVTVSS |
| 1.67 | GSSMT<br>SEQ<br>NO.<br>265 | YISSGGGVIF<br>YADSVKG<br>SEQ NO.<br>266 | EAPLRLGESPHD<br>AFDI<br>SEQ NO. 267 | SEQ NO. 268<br>QVQLVESGGGLVKPGGSLRLSCAASGFTFSGSSMT<br>WMRQAPGKGLEWVSYISSGGGVIFYADSVKGRFTIS<br>RDNAKNSLYLQMNSLRADDTAVYYCAREAPLRLGES<br>PHDAFDISGQGTMVTVSS |
| 1.68 | DNSMT<br>SEQ<br>NO.<br>269 | YISSGGGVIF<br>YADSVKG<br>SEQ NO.<br>270 | EAPLRLGESPHD<br>AFDI<br>SEQ NO. 271 | SEQ NO. 272<br>QVQLVESGGGLVKPGGSLRLSCAASGFTFGDNSMT<br>WMRQAPGKGLEWVSYISSGGGVIFYADSVKGRFTIS<br>RDNAKNSLYLQMNSLRADDTAVYYCAREAPLRLGES<br>PHDAFDISGRGTTVTVSS |

TABLE 1-continued

Full length sequences and CDR sequences of VH single domain antibodies

| Name | CDR1 | CDR2 | CDR3 | Full length |
|---|---|---|---|---|
| 1.69 | DNSMS SEQ NO. 273 | YISSGGGVIF YADSVKG SEQ NO. 274 | EAPLRLGESPHD AFDI SEQ NO. 275 | SEQ NO. 276 QVQLVESGGGLVKPGGSLRLSCAASGFTFSDNSMS WMRQAPGKGLEWVSYISSGGGVIFYADSVKGRFTIS RDNAKNSLYLQMNSLRADDTAVYYCAREAPLRLGES PHDAFDISGQGTMVTVSS |
| 1.70 | DSSMT SEQ NO. 277 | YISSGGAVK FYTDSVKG SEQ NO. 278 | EAPLRLGESPHD AFDI SEQ NO. 279 | SEQ NO. 280 QVQLVESGGGLVKPGGSLRLSCAASGFTFGDSSMT WMRQAPGKGLEWVSYISSGGAVKFYTDSVKGRFTI SRDNAKNSLYLQMNSLRADDTAVYYCAREAPLRLGE SPHDAFDISGQGTMVTVSS |
| 1.71 | GSSMT SEQ NO. 281 | YISSGGGVK FYTDSVKG SEQ NO. 282 | EAPLRLGESPHD AFDI SEQ NO. 283 | SEQ NO. 284 QVQLVESGGGLVKPGGSLRLSCAASGFTFGGSSMT WMRQAPGKGLEWVSYISSGGGVKFYTDSVKGRFTI SRDNAKNSLYLQMNSLRADDTAVYYCAREAPLRLGE SPHDAFDISGQGTMVTVSS |
| 1.72 | DSSMS SEQ NO. 285 | YISSGGGVIF YADSVKG SEQ NO. 286 | EAPLRLGESPHD AFDI SEQ NO. 287 | SEQ NO. 288 QVQLVESGGGLVKPGGSLRLSCAASGFTFSDSSMS WMRQAPGKGLEWVSYISSGGGVIFYADSVKGRFTIS RDNAKNSLYLQMNSLRADDTAVYYCAREAPLRLGES PHDAFDISGQGTMVTVSS |
| 1.73 | DSSMT SEQ NO. 289 | YISAGGGVR FYTDSVKG SEQ NO. 290 | EAPLRLGESPHD AFDI SEQ NO. 291 | SEQ NO. 292 QVQLVESGGGLVKPGGSLRLSCAATGFTFSDSSMT WMRQAPGKGLEWVSYISAGGGVRFYTDSVKGRFTI SRDNAKNSLYLQMNSLRADDTAVYYCAREAPLRLGE SPHDAFDISGQGTMVTVSS |
| 1.74 | SEQ ID NO: 366 DSSMT | SEQ ID NO: 367 YISSGGGVK FYTDSVKG | SEQ ID NO: 368 EAPLRLGESPHD AFDI | SEQ ID NO: 369 EVQLVESGGGLVKPGGSLRLSCAASGFTFSDSSMTW IRQAPGKGLEWVSYISSGGGVKFYTDSVKGRFTISRD NAKNSLYLQMNSLRADDTAVYYCAREAPLRLGESPH DAFDISGQGTMVTVSS |
| 1.75 | SEQ ID NO: 370 DSSMT | SEQ ID NO: 371 YISSGGGVK FYTDSVKG | SEQ ID NO: 372 EAPLRLGESPHD AFDI | SEQ ID NO: 373 EVQLVESGGGLVKPGGSLRLSCAASGFTFSDSSMTW IRQAPGKGLEWVSYISSGGGVKFYTDSVKGRFTISRD NAKNSLYLQMNSLRAEDTAVYYCAREAPLRLGESPH DAFDISGQGTMVTVSS |
| 1.76 | SEQ ID NO: 374 DSSMT | SEQ ID NO: 375 YISSGGGVK FYADSVKG | SEQ ID NO: 376 EAPLRLGESPHD AFDI | SEQ ID NO: 377 EVQLVESGGGLVKPGGSLRLSCAASGFTFSDSSMTW IRQAPGKGLEWVSYISSGGGVKFYADSVKGRFTISRD NAKNSLYLQMNSLRADDTAVYYCAREAPLRLGESPH DAFDISGQGTMVTVSS |
| 1.77 | SEQ ID NO: 378 DSSMT | SEQ ID NO: 379 YISSGGGVK FYTDSVKG | SEQ ID NO: 380 EAPLRLGESPHD AFDI | SEQ ID NO: 381 EVQLVESGGGLVKPGGSLRLSCAASGFTFSDSSMTW MRQAPGKGLEWVSYISSGGGVKFYTDSVKGRFTISR DNAKNSLYLQMNSLRAEDTAVYYCAREAPLRLGESP HDAFDISGQGTMVTVSS |
| 1.78 | SEQ ID NO: 382 DSSMT | SEQ ID NO: 383 YISSGGGVK FYADSVKG | SEQ ID NO: 384 EAPLRLGESPHD AFDI | SEQ ID NO: 385 EVQLVESGGGLVKPGGSLRLSCAASGFTFSDSSMTW IRQAPGKGLEWVSYISSGGGVKFYADSVKGRFTISRD NAKNSLYLQMNSLRAEDTAVYYCAREAPLRLGESPH DAFDISGQGTMVTVSS |
| 1.79 | SEQ ID NO: 386 DSSMT | SEQ ID NO: 387 YISSGGGVK FYADSVKG | SEQ ID NO: 388 EAPLRLGESPHD AFDI | SEQ ID NO: 389 EVQLVESGGGLVKPGGSLRLSCAASGFTFSDSSMTW KRQAPGKGLEWVSYISSGGGVKFYADSVKGRFTISR DNAKNSLYLQMNSLRAEDTAVYYCAREAPLRLGESP HDAFDISGQGTMVTVSS |
| 1.80 | SEQ ID NO: 390 DSSMT | SEQ ID NO: 391 YISSGGGVK FYADSVKG | SEQ ID NO: 392 EAPLRLGESPHD AFDI | SEQ ID NO: 393 EVQLVESGGGLVKPGGSLRLSCAASGFTFSDSSMTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.81 | SEQ ID NO: 394 DSSMT | SEQ ID NO: 395 YISSGGGVK | SEQ ID NO: 396 EAPLRLGESPHD | SEQ ID NO: 397 EVQLVESGGGLVKPGGSLRLSCAASGFTFSDSSMTW VRQAPGKGLEWVSYISSGGGVKFYADSVKGRFTISR |

TABLE 1-continued

Full length sequences and CDR sequences of VH single domain antibodies

| Name | CDR1 | CDR2 | CDR3 | Full length |
|---|---|---|---|---|
| | | FYADSVKG | AFDI | DNAKNSLYLQMNSLRAEDTAVYYCAREAPLRLGESP<br>HDAFDISGQGTMVTVSS |
| 1.82 | SEQ ID<br>NO: 398<br>DTSMT | SEQ ID<br>NO: 399<br>YISSGGGVK<br>FYTDSVKG | SEQ ID<br>NO: 400<br>EAPLRLGESPHD<br>AFDI | SEQ ID NO: 401<br>EVQLVESGGGLVKPGGSLRLSCAASGFTFSDTSMT<br>WMRQAPGKGLEWVSYISSGGGVKFYTDSVKGRFTI<br>SRDNAKNSLYLQMNSLRAEDTAVYYCAREAPLRLGE<br>SPHDAFDISGQGTMVTVSS |
| 1.83 | SEQ ID<br>NO: 402<br>DESMT | SEQ ID<br>NO: 403<br>YISSGGGVK<br>FYTDSVKG | SEQ ID<br>NO: 404<br>EAPLRLGESPHD<br>AFDI | SEQ ID NO: 405<br>EVQLVESGGGLVKPGGSLRLSCAASGFTFSDESMT<br>WFRQAPGKGLEWVSYISSGGGVKFYTDSVKGRFTIS<br>RDNAKNSLYLQMNSLRAEDTAVYYCAREAPLRLGES<br>PHDAFDISGQGTMVTVSS |
| 1.84 | SEQ ID<br>NO:<br>406<br>DESMT | SEQ ID NO:<br>407<br>YISSGGGVK | SEQ ID NO: 408<br>EAPLRLGESPHD<br>AFDI<br>FYTDSVKG | SEQ ID NO: 409<br>EVQLVESGGGLVKPGGSLRLSCAASGFTFSDESMT<br>WMRQAPGKGLEWVSYISSGGGVKFYTDSVKGRFTI<br>SRDNAKNSLYLQMNSLRAEDTAVYYCAREAPLRLGE<br>SPHDAFDISGQGTMVTVSS |
| 1.85 | SEQ ID<br>NO:<br>410<br>DYSMT | SEQ ID NO:<br>411<br>YISSGGGVK<br>FYTDSVKG | SEQ ID NO: 412<br>EAPLRLGESPHD<br>AFDI | SEQ ID NO: 413<br>EVQLVESGGGLVKPGGSLRLSCAASGFTFSDYSMT<br>WMRQAPGKGLEWVSYISSGGGVKFYTDSVKGRFTI<br>SRDNAKNSLYLQMNSLRAEDTAVYYCAREAPLRLGE<br>SPHDAFDISGQGTMVTVSS |
| 1.86 | SEQ ID<br>NO:<br>414<br>DASMT | SEQ ID NO:<br>415<br>YISSGGGVK<br>FYTDSVKG | SEQ ID NO: 416<br>EAPLRLGESPHD<br>AFDI | SEQ ID NO: 417<br>EVQLVESGGGLVKPGGSLRLSCAASGFTFSDASMT<br>WMRQAPGKGLEWVSYISSGGGVKFYTDSVKGRFTI<br>SRDNAKNSLYLQMNSLRAEDTAVYYCAREAPLRLGE<br>SPHDAFDISGQGTMVTVSS |
| 1.87 | SEQ ID<br>NO:<br>418<br>DKSMT | SEQ ID NO:<br>419<br>YISSGGGVK<br>FYTDSVKG | SEQ ID NO: 420<br>EAPLRLGESPHD<br>AFDI | SEQ ID NO: 421<br>EVQLVESGGGLVKPGGSLRLSCAASGFTFSDKSMT<br>WMRQAPGKGLEWVSYISSGGGVKFYTDSVKGRFTI<br>SRDNAKNSLYLQMNSLRAEDTAVYYCAREAPLRLGE<br>SPHDAFDISGQGTMVTVSS |
| 1.88 | SEQ ID<br>NO:<br>422<br>DRSMT | SEQ ID NO:<br>423<br>YISSGGGVK<br>FYTDSVKG | SEQ ID NO: 424<br>EAPLRLGESPHD<br>AFDI | SEQ ID NO: 425<br>EVQLVESGGGLVKPGGSLRLSCAASGFTFSDRSMT<br>WMRQAPGKGLEWVSYISSGGGVKFYTDSVKGRFTI<br>SRDNAKNSLYLQMNSLRAEDTAVYYCAREAPLRLGE<br>SPHDAFDISGQGTMVTVSS |
| 1.89 | SEQ ID<br>NO:<br>426<br>DYSMT | SEQ ID NO:<br>427<br>YISSGGGVK<br>FYADSVKG | SEQ ID NO: 428<br>EAPLRLGESPHD<br>AFDI | SEQ ID NO: 429<br>EVQLVESGGGLVKPGGSLRLSCAASGFTFSDYSMT<br>WMRQAPGKGLEWVSYISSGGGVKFYADSVKGRFTI<br>SRDNAKNSLYLQMNSLRAEDTAVYYCAREAPLRLGE<br>SPHDAFDISGQGTMVTVSS |
| 1.90 | SEQ ID<br>NO:<br>430<br>DVSMT | SEQ ID NO:<br>431<br>YISSGGGVK<br>FYADSVKG | SEQ ID NO: 432<br>EAPLRLGESPHD<br>AFDI | SEQ ID NO: 433<br>EVQLVESGGGLVKPGGSLRLSCAASGFTFSDVSMT<br>WMRQAPGKGLEWVSYISSGGGVKFYADSVKGRFTI<br>SRDNAKNSLYLQMNSLRAEDTAVYYCAREAPLRLGE<br>SPHDAFDISGQGTMVTVSS |
| 1.91 | SEQ ID<br>NO:<br>434<br>DQSMT | SEQ ID NO:<br>435<br>YISSGGGVK<br>FYADSVKG | SEQ ID NO: 436<br>EAPLRLGESPHD<br>AFDI | SEQ ID NO: 437<br>EVQLVESGGGLVKPGGSLRLSCAASGFTFSDQSMT<br>WMRQAPGKGLEWVSYISSGGGVKFYADSVKGRFTI<br>SRDNAKNSLYLQMNSLRAEDTAVYYCAREAPLRLGE<br>SPHDAFDISGQGTMVTVSS |
| 1.92 | SEQ ID<br>NO:<br>438<br>DESMT | SEQ ID NO:<br>439<br>YISSGGGVK<br>FYADSVKG | SEQ ID NO: 440<br>EAPLRLGESPHD<br>AFDI | SEQ ID NO: 441<br>EVQLVESGGGLVKPGGSLRLSCAASGFTFSDESMT<br>WMRQAPGKGLEWVSYISSGGGVKFYADSVKGRFTI<br>SRDNAKNSLYLQMNSLRAEDTAVYYCAREAPLRLGE<br>SPHDAFDISGQGTMVTVSS |
| 1.93 | SEQ ID<br>NO:<br>442<br>DASMT | SEQ ID NO:<br>443<br>YISSGGGVK<br>FYADSVKG | SEQ ID NO: 444<br>EAPLRLGESPHD<br>AFDI | SEQ ID NO: 445<br>EVQLVESGGGLVKPGGSLRLSCAASGFTFSDASMT<br>WMRQAPGKGLEWVSYISSGGGVKFYADSVKGRFTI<br>SRDNAKNSLYLQMNSLRAEDTAVYYCAREAPLRLGE<br>SPHDAFDISGQGTMVTVSS |

TABLE 1-continued

Full length sequences and CDR sequences of VH single domain antibodies

| Name | CDR1 | CDR2 | CDR3 | Full length |
|---|---|---|---|---|
| 1.94 | SEQ ID NO: 446 DWSMT | SEQ ID NO: 447 YISSGGGVK FYADSVKG | SEQ ID NO: 448 EAPLRLGESPHD AFDI | SEQ ID NO: 449 EVQLVESGGGLVKPGGSLRLSCAASGFTFSDWSMT WMRQAPGKGLEWVSYISSGGGVKFYADSVKGRFTI SRDNAKNSLYLQMNSLRAEDTAVYYCAREAPLRLGE SPHDAFDISGQGTMVTVSS |
| 1.95 | SEQ ID NO: 450 DGSMT | SEQ ID NO: 451 YISSGGGVK FYADSVKG | SEQ ID NO: 452 EAPLRLGESPHD AFDI | SEQ ID NO: 453 EVQLVESGGGLVKPGGSLRLSCAASGFTFSDGSMT WMRQAPGKGLEWVSYISSGGGVKFYADSVKGRFTI SRDNAKNSLYLQMNSLRAEDTAVYYCAREAPLRLGE SPHDAFDISGQGTMVTVSS |
| 1.96 | SEQ ID NO: 454 DTSMT | SEQ ID NO: 455 YISSGGGVK FYADSVKG | SEQ ID NO: 456 EAPLRLGESPHD AFDI | SEQ ID NO: 457 EVQLVESGGGLVKPGGSLRLSCAASGFTFSDTSMT WMRQAPGKGLEWVSYISSGGGVKFYADSVKGRFTI SRDNAKNSLYLQMNSLRAEDTAVYYCAREAPLRLGE SPHDAFDISGQGTMVTVSS |
| 1.97 | SEQ ID NO: 458 DISMT | SEQ ID NO: 459 YISSGGGVK FYADSVKG | SEQ ID NO: 460 EAPLRLGESPHD AFDI | SEQ ID NO: 461 EVQLVESGGGLVKPGGSLRLSCAASGFTFSDISMTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.98 | SEQ ID NO: 462 DKSMT | SEQ ID NO: 463 YISSGGGVK FYADSVKG | SEQ ID NO: 464 EAPLRLGESPHD AFDI | SEQ ID NO: 465 EVQLVESGGGLVKPGGSLRLSCAASGFTFSDKSMT WMRQAPGKGLEWVSYISSGGGVKFYADSVKGRFTI SRDNAKNSLYLQMNSLRAEDTAVYYCAREAPLRLGE SPHDAFDISGQGTMVTVSS |
| 1.99 | SEQ ID NO: 466 DRSMT | SEQ ID NO: 467 YISSGGGVK FYADSVKG | SEQ ID NO: 468 EAPLRLGESPHD AFDI | SEQ ID NO: 469 EVQLVESGGGLVKPGGSLRLSCAASGFTFSDRSMT WMRQAPGKGLEWVSYISSGGGVKFYADSVKGRFTI SRDNAKNSLYLQMNSLRAEDTAVYYCAREAPLRLGE SPHDAFDISGQGTMVTVSS |
| 1.100 | SEQ ID NO: 470 DLSMT | SEQ ID NO: 471 YISSGGGVK FYADSVKG | SEQ ID NO: 472 EAPLRLGESPHD AFDI | SEQ ID NO: 473 EVQLVESGGGLVKPGGSLRLSCAASGFTFSDLSMTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.101 | SEQ ID NO: 474 DFSMT | SEQ ID NO: 475 YISSGGGVK FYADSVKG | SEQ ID NO: 476 EAPLRLGESPHD AFDI | SEQ ID NO: 477 EVQLVESGGGLVKPGGSLRLSCAASGFTFSDFSMTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.102 | SEQ ID NO: 478 DESVT | SEQ ID NO: 479 YISSGGGVK FYTDSVKG | SEQ ID NO: 480 EAPLRLGESPHD AFDI | SEQ ID NO: 481 EVQLVESGGGLVKPGGSLRLSCAASGFTFSDESVTW MRQAPGKGLEWVSYISSGGGVKFYTDSVKGRFTISR DNAKNSLYLQMNSLRAEDTAVYYCAREAPLRLGESP HDAFDISGQGTMVTVSS |
| 1.103 | SEQ ID NO: 482 DESQT | SEQ ID NO: 483 YISSGGGVK FYTDSVKG | SEQ ID NO: 484 EAPLRLGESPHD AFDI | SEQ ID NO: 485 EVQLVESGGGLVKPGGSLRLSCAASGFTFSDESQTW MRQAPGKGLEWVSYISSGGGVKFYTDSVKGRFTISR DNAKNSLYLQMNSLRAEDTAVYYCAREAPLRLGESP HDAFDISGQGTMVTVSS |
| 1.104 | SEQ ID NO: 486 DESFT | SEQ ID NO: 487 YISSGGGVK FYTDSVKG | SEQ ID NO: 488 EAPLRLGESPHD AFDI | SEQ ID NO: 489 EVQLVESGGGLVKPGGSLRLSCAASGFTFSDESFTW MRQAPGKGLEWVSYISSGGGVKFYTDSVKGRFTISR DNAKNSLYLQMNSLRAEDTAVYYCAREAPLRLGESP HDAFDISGQGTMVTVSS |
| 1.105 | SEQ ID NO: 490 DESLT | SEQ ID NO: 491 YISSGGGVK FYTDSVKG | SEQ ID NO: 492 EAPLRLGESPHD AFDI | SEQ ID NO: 493 EVQLVESGGGLVKPGGSLRLSCAASGFTFSDESLTW MRQAPGKGLEWVSYISSGGGVKFYTDSVKGRFTISR DNAKNSLYLQMNSLRAEDTAVYYCAREAPLRLGESP HDAFDISGQGTMVTVSS |
| 1.106 | SEQ ID NO: 494 | SEQ ID NO: 495 YISSGGGVK | SEQ ID NO: 496 EAPLRLGESPHD AFDI | SEQ ID NO: 497 EVQLVESGGGLVKPGGSLRLSCAASGFTFSDESKTW MRQAPGKGLEWVSYISSGGGVKFYTDSVKGRFTISR |

TABLE 1-continued

Full length sequences and CDR sequences of VH single domain antibodies

| Name | CDR1 | CDR2 | CDR3 | Full length |
|---|---|---|---|---|
| | DESKT | FYTDSVKG | | DNAKNSLYLQMNSLRAEDTAVYYCAREAPLRLGESPHDAFDISGQGTMVTVSS |
| 1.107 | SEQ ID NO: 498 DESYT | SEQ ID NO: 499 YISSGGGVK FYTDSVKG | SEQ ID NO: 500 EAPLRLGESPHD AFDI | SEQ ID NO: 501 EVQLVESGGGLVKPGGSLRLSCAASGFTFSDESYTW MRQAPGKGLEWVSYISSGGGVKFYTDSVKGRFTISR DNAKNSLYLQMNSLRAEDTAVYYCAREAPLRLGESP HDAFDISGQGTMVTVSS |
| 1.108 | SEQ ID NO: 502 DESAT | SEQ ID NO: 503 YISSGGGVK FYADSVKG | SEQ ID NO: 504 EAPLRLGESPHD AFDI | SEQ ID NO: 505 EVQLVESGGGLVKPGGSLRLSCAASGFTFSDESATW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.109 | SEQ ID NO: 506 DESFT | SEQ ID NO: 507 YISSGGGVK FYADSVKG | SEQ ID NO: 508 EAPLRLGESPHD AFDI | SEQ ID NO: 509 EVQLVESGGGLVKPGGSLRLSCAASGFTFSDESFTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.110 | SEQ ID NO: 510 DESNT | SEQ ID NO: 511 YISSGGGVK FYADSVKG | SEQ ID NO: 512 EAPLRLGESPHD AFDI | SEQ ID NO: 513 EVQLVESGGGLVKPGGSLRLSCAASGFTFSDESNTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.111 | SEQ ID NO: 514 DESWT | SEQ ID NO: 515 YISSGGGVK FYADSVKG | SEQ ID NO: 516 EAPLRLGESPHD AFDI | SEQ ID NO: 517 EVQLVESGGGLVKPGGSLRLSCAASGFTFSDESWT WMRQAPGKGLEWVSYISSGGGVKFYADSVKGRFTI SRDNAKNSLYLQMNSLRAEDTAVYYCAREAPLRLGE SPHDAFDISGQGTMVTVSS |
| 1.112 | SEQ ID NO: 518 DESIT | SEQ ID NO: 519 YISSGGGVK FYADSVKG | SEQ ID NO: 520 EAPLRLGESPHD AFDI | SEQ ID NO: 521 EVQLVESGGGLVKPGGSLRLSCAASGFTFSDESITW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.113 | SEQ ID NO: 522 DESST | SEQ ID NO: 523 YISSGGGVK FYADSVKG | SEQ ID NO: 524 EAPLRLGESPHD AFDI | SEQ ID NO: 525 EVQLVESGGGLVKPGGSLRLSCAASGFTFSDESSTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.114 | SEQ ID NO: 526 DESHT | SEQ ID NO: 527 YISSGGGVK FYADSVKG | SEQ ID NO: 528 EAPLRLGESPHD AFDI | SEQ ID NO: 529 EVQLVESGGGLVKPGGSLRLSCAASGFTFSDESHTW MRQAPGKGLEWVSYISSGGGVKFYADSVKGRFTISR DNAKNSLYLQMNSLRAEDTAVYYCAREAPLRLGESP HDAFDISGQGTMVTVSS |
| 1.115 | SEQ ID NO: 530 DESGT | SEQ ID NO: 531 YISSGGGVK FYADSVKG | SEQ ID NO: 532 EAPLRLGESPH D AFDI | SEQ ID NO: 533 EVQLVESGGGLVKPGGSLRLSCAASGFTFSDESGTW MRQAPGKGLEWVSYISSGGGVKFYADSVKGRFTISR DNAKNSLYLQMNSLRAEDTAVYYCAREAPLRLGESP HDAFDISGQGTMVTVSS |

In some embodiments, the invention provides a $V_H$ single domain antibody that is a variant of any of the above single $V_H$ domain antibodies having one or more amino acid substitutions, deletions, insertions or other modifications, and which retains a biological function of the single domain antibody. Thus, variant $V_H$ single domain antibody can be sequence engineered. Modifications may include one or more substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. A variant of a $V_H$ single domain antibody described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology to the non-variant molecule, preferably at least 90%, 91%, 92%, 93%, 94%, 95%, 96%, 97%, 98% or 99% sequence homology.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the invention can be replaced with other amino acid residues from the same side chain family and the altered antibody can be tested for retained function (i.e., the functions set forth in (c) through (I) above) using the functional assays described herein.

In some embodiments, the invention provides a $V_H$ single domain antibody that is a variant of a single domain antibody selected from those shown in Table 1 that comprises one or more sequence modification and has improvements in one or more of a property such as binding affinity, specificity, thermostability, expression level, effector function, glycosylation, reduced immunogenicity, or solubility as compared to the unmodified single domain antibody.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived.

To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

In one embodiment, the variant $V_H$ single domain antibody is selected from any one of SEQ ID Nos. 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 252, 256, 260, 264, 268, 272, 276, 280, 284, 288 or 292, but comprises one or more amino acid substitutions, for example 1 to 20 for example 1, 2, 3, 4, 5, 6, 7, 8, 9 or 10 amino acid substitutions compared to these sequences. In one embodiment, the variant $V_H$ single domain antibody is selected from SEQ ID No. 4. In one embodiment, the variant $V_H$ single domain antibody is selected from SEQ ID No. 228, 256 or 441. In one embodiment, the one or more amino acid substitution is in one or more of the framework areas. In another embodiment, the one or more amino acid substitution is in one or more of the CDRs. In one embodiment, the amino acid substitutions are in the framework and CDR sequences. In one embodiment, the single domain antibody comprises or consists of SEQ ID No. 4, 228, 441 or a sequence which comprises one or more amino acid substitutions, for example 1, 2, 3, 4, 5, 6, 7, 8, 9 or 10 amino acid substitutions.

Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity. Abbreviations for the amino acid residues that comprise polypeptides and peptides described herein, and conservative substitutions for these amino acid residues are shown in Table 3 below.

TABLE 3

Amino Acid Residues and Examples of
Conservative Amino Acid Substitutions

| Original residue Three letter code, single letter code | Conservative substitution |
|---|---|
| Alanine, Ala, A | Gly, Ser |
| Arginine, Arg, R | Lys, His |
| Asparagine, Asn, N | Gln, His |
| Aspartic acid Asp, D | Glu, Asn |
| Cysteine, Cys, C | Ser, Ala |
| Glutamine, Gln, Q | Asn |
| Glutamic acid, Glu, E | Asp, Gln |
| Glycine, Gly, G | Ala |
| Histidein, His, H | Asn, Gln |
| Isoleucine, Ile, I | Leu, Val |
| Leucine, Leu, L | Ile, Val |
| Lysine, lys, K | Ar, His |
| Methionine, Met, M | Leu, Ile, Tyr |
| Phenylalanine, Phe, F | Tyr, Met, Leu |
| Proline, Pro, P | Ala |
| Serine, Ser, S | Thr |

TABLE 3-continued

Amino Acid Residues and Examples of
Conservative Amino Acid Substitutions

| Original residue Three letter code, single letter code | Conservative substitution |
| --- | --- |
| Threonine, Thr, T | Ser |
| Tryptophan, Trp, W | Tyr, Phe |
| Tyrosine, Tyr, Y | Try, Phe |
| Valine, Val, V | Ile, Leu |

In one embodiment, a Q at position 1 is replaced with E.

In one embodiment, the variant $V_H$ single domain antibody comprises SEQ ID No. 4 (Humabody® 1.1) but with amino acid substitutions at one or more the following positions: Y32, T33, T53, T56, I57, K58, Y59, T61 and/or W115.

In one embodiment, the $V_H$ single domain antibody comprises SEQ ID No. 4 (Humabody® 1.1) but with the following amino acid substitutions: Y32→N, T33→S, T53→S, T56→G, I57→V, K58→I, Y59→F, W115→S (Humabody® 1.57)

In one embodiment, the variant $V_H$ single domain antibody comprises SEQ ID No. 228 (Humabody® 1.57) but with amino acid substitutions at one or more or all of the following positions: D31, N32, I58, A61, T35, S30, G56, S25Q117, M120 and/or Q1.

In one embodiment, the variant $V_H$ single domain antibody comprises SEQ ID No. 228 (Humabody® 1.57) but with amino acid substitutions selected from one of the following
1) D31→G, N32→S (Humabody® 1.67);
2) S30→G, D31→G, N32→S, A61→T (Humabody® 1.71);
3) T35→S (1.69);
4) S30→G, N32→S, A61→T (Humabody® 1.70);
5) S25→J, N32→S, A61→T (Humabody® 1.73);
6) N32→S, N84→D, I114→T (Humabody® 1.66);
7) S30→G, Q117→R, M120→J (Humabody® 1.68);
8) N32→S, T35→S (Humabody® 1.72);
9) N32→S, G56→A, A61→T (Humabody® 1.62);
10) N32→S, (Humabody® 1.65);
11) Q1→E, N32→S, (Humabody® 1.64);
12) Q1→E, N32→S, A61→T (Humabody® 1.63).

In one embodiment, the variant $V_H$ single domain antibody comprises SEQ ID No. 256 (Humabody® 1.64) but with amino acid substitutions at one or more or all of the following positions: S32, D90 and/or A61.

In one embodiment, the variant $V_H$ single domain antibody comprises SEQ ID No. 256 (Humabody® 1.64) but with amino acid substitutions selected from one of the following
1. S32→E, D90→E (Humabody® 1.92)
2. S32→R, D90→E (Humabody® 1.99)
3. S32→N, D90→E (Humabody® 1.89)
4. S32→E, D90→E A61→T (Humabody® 1.84)
5. D85→E A60→T (Humabody® 1.77)
6. S32→J, D90→E A60→T (Humabody® 1.82)

The numbering used above is based on the actual position of the residue.

$V_H$ single domain antibodies of the invention have shown excellent stability. Furthermore, $V_H$ single domain antibodies of the invention also show specificity for human PD-1, bind to cyno PD-1 and have fast on rates (see examples).

The $V_H$ single domain antibodies of the invention preferably have KD, $IC_{50}$ and/or $EC_{50}$ values as further described herein and as shown in the examples. $V_H$ single domain antibodies specifically bind to human PD-1 with high affinity, the KD can be least about $10^{-8}$ M to $10^{-12}$ such as $10^{-8}$M, $10^{-9}$M, $10^{-10}$ M, $10^{-11}$M or $10^{-12}$M as measured by surface plasmon resonance (biomolecular interaction analysis, BIAcore®) analysis. Single domain antibodies according to the invention preferably has an IC50 value for inhibition of PD-1 in $10^{-8}$M to $10^{-9}$ M range as determined in functional assay.

The term "KD" refers to the "equilibrium dissociation constant" and refers to the value obtained in a titration measurement at equilibrium, or by dividing the dissociation rate constant (Koff) by the association rate constant (Kon). "KA" refers to the affinity constant. The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® assay can be used.

The present invention further provides an isolated nucleic acid encoding a single domain antibody of the present invention. Nucleic acid may include DNA and/or RNA. In one aspect, the present invention provides a nucleic acid that codes for a CDR, for example CDR3, a set of two or three CDRs or for a $V_H$ single domain antibody as shown in Table 1 and as further defined above.

In one aspect, the invention thus also relates to a nucleic acid sequences comprising or consisting of a sequence selected from SEQ ID Nos. 293 to 365 and 534 to 575. These nucleic acid sequences encode $V_H$ single domain antibodies as shown in Table 1.

In one embodiment, the nucleic acid sequence has at least 60%, 70%, 80%, 90%, 95% or more sequence homology to a sequence selected from SEQ ID Nos. 293 to 365. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

A nucleic acid according to the present invention may comprise DNA or RNA and may be wholly or partially synthetic or recombinantly produced. Reference to a nucleotide sequence as set out herein encompasses a DNA molecule with the specified sequence, and encompasses a RNA molecule with the specified sequence in which U is substituted for T, unless context requires otherwise.

Furthermore, the invention relates to a nucleic acid construct comprising at least one nucleic acid as defined above. The construct may be in the form of a plasmid, vector, transcription or expression cassette.

The invention also relates to an isolated recombinant host cell comprising one or more nucleic acid construct as described above. The host cell may be a bacterial, viral, insect, plant, mammalian or other suitable host cell. In one embodiment, the cell is an E. coli cell. In another embodiment, the cell is a yeast cell. In another embodiment, the cell is a Chinese Hamster Ovary (CHO) cell.

In one embodiment, a method of making an anti-PD-1 single domain antibody as described herein is provided, wherein the method comprises culturing the host cell under conditions suitable for expression of the polynucleotide encoding the single domain antibody, and isolating the single domain antibody.

In another aspect, the invention provides binding molecules, e.g. antibodies, antibody fragments or antibody mimetics that bind to the same epitope on human PD-1 as any of the PD-1 single domain antibodies of the invention (i.e. antibodies that have the ability to cross-compete for binding to PD-1 with any of the single domain antibodies of Table 1. The single domain antibodies of the invention can thus be used as a reference antibody). In preferred embodiments, the reference antibody for cross-competition studies is single domain antibody 1.1 (SEQ ID No. 4), 1.57 (SEQ ID No. 228) or 1.92 (SEQ ID NO. 441).

Such cross-competing antibodies can be identified based on their ability to cross-compete with any of single domain antibodies 1.1 to 1.115 in standard PD-1 binding assays. For example, BIAcore® analysis, ELISA assays or flow cytometry may be used to demonstrate cross-competition with the single domain antibodies of the current invention.

In one embodiment, the invention provides a binding agent capable of binding human PD-1 wherein any one of the single domain antibodies described above displaces the binding agent in a competitive assay. In one embodiment, said single domain antibody is selected from 1.1 (SEQ ID No. 4), 1.57 (SEQ ID No. 228) or 1.92 (SEQ ID NO. 441). In some embodiments, the binding agent is an antibody, a functional fragment thereof, for example a single domain antibody, or an antibody mimetic protein. In another aspect, invention provides a binding agent capable of binding human PD-1 wherein the binding agent displaces any one of the single domain antibodies described above in a competitive assay. In one embodiment, said single domain antibody is selected from SEQ ID No. 1.1 (SEQ ID No. 4), 1.57 (SEQ ID No. 228), or 1.92 (SEQ ID NO. 441). In another aspect, invention provides a binding agent capable of binding human PD-1 wherein the binding agent binds to essentially the same epitope as the single domain antibody of the invention.

In another aspect, the invention provides an isolated heavy chain only antibody comprising a $V_H$ domain as described herein and listed in Table 1 or with at least 70%, 80% or 90% homology thereto.

In one aspect, the invention relates to a binding agent comprising a single domain antibody according to the invention and at least a second moiety. Thus, the invention also provides multifunctional molecules. In one embodiment, the at least second moiety is a binding molecule, for example selected from an antibody or antibody fragment (e.g., a Fab, F(ab')2, Fv, a single chain Fv fragment (scFv) or single domain antibody, for example a $V_H$ domain) or antibody mimetic protein. In one embodiment, the at least second moiety is a $V_H$ domain. In one embodiment, the single domain antibody of the invention can be linked to an antibody Fc region or fragment thereof, comprising one or both of $C_H2$ and $C_H3$ domains, and optionally a hinge region.

The binding agent may be multivalent, for example bivalent, or multiparatopic, for example biparatopic. Thus, the binding molecule may comprise a first $V_H$ single domain antibody and $V_H(A)$ and a second $V_H$ single domain antibody and $V_H(B)$ and thus has the following formula: $V_H(A)$-$V_H(B)$.

Each $V_H$ comprises CDR and FR regions. Thus, the binding molecule may have the following formula: FR1(A)-CDR1(A)-FR2(A)-CDR2(A)-FR3(A)-CDR3(A)-FR4(A)-FR1 (B)-CDR1(B)-FR2(B)-CDR2(BA)-FR3(B)-CDR3(B)-FR4(B). The order of the immunoglobulin single variable domains A and B is not particularly limited, so that, within a polypeptide of the invention, immunoglobulin single variable domain A may be located N-terminally and immunoglobulin single variable domain B may be located C-terminally, or vice versa. The $V_H$ domain antibodies are typically connected via a linker.

In one embodiment, the binding molecule is biparatopic or bispecific. Thus, in one aspect, the invention relates to a bispecific molecule comprising the single domain antibody described herein linked to a second functional moiety having a different binding specificity than said single domain antibody.

In one embodiment, biparatopic binding molecules are provided that comprise a first and a second binding molecule that bind to the target protein PD-1, but on different or overlapping sites. Complete or partial blocking can be seen in epitope binning studies. The first binding molecule is a single domain antibody according to the invention. In one embodiment, the second binding molecule is a PD-1 inhibitor that blocks the interaction of human PD-1 with one of its ligands. In one embodiment, the second binding molecule blocks the interaction of PD-1 with PD-L1. In one embodiment, the second binding molecule blocks the interaction of PD-1 with PD-L2. In one embodiment, the second binding molecule blocks the interaction of PD-1 with PD-L1 and PD-L2. The order of the first and second binding molecule is not particularly limited and can be reversed.

In one embodiment, the PD-1 inhibitor is a $V_H$ single domain antibody. Thus, another aspect relates to a binding molecule has the following formula: $V_H(A)$-L-$V_H(B)$ wherein $V_H(A)$-is a $V_H$ single domain antibody as disclosed herein and wherein $V_H(B)$ is a $V_H$ single domain antibody that blocks binding of PD-1 to PD-L1 and/or PD-L2. L is a linker. Suitable linkers include for example a linker with GS residues such as $(Gly_4Ser)n$, where n=from 1 to 20, e.g., 1 to 10, e.g. 1, 2, 3, 4, 5, 6, 7, 8, 9 or 10. In one embodiment, the linker is $(Gly_4Ser)n$, where n=4 or more. In another embodiment, the orientation is $V_H(B)$-L-$V_H(A)$.

As demonstrated herein, we have surprisingly shown that a binding molecule has the following formula: $V_H(A)$-L-$V_H$(B) wherein $V_H(A)$ is a blocking molecule and B a non blocking molecule as described above provides an enhanced effect compared to a $V_H$ single domain antibody that blocks binding of PD-1 to PD-L1 and/or PD-L2 and is not linked to a non-blocking $V_H$ single domain antibody. The effect is 10 to 25 fold compare d to a monovalent blocker. Thus, the $V_H$ single domain antibodies described herein find particular use for combination with a $V_H$ single domain antibody that does not block binding of PD-1 to PD-L1 and/or PD-L2 in a biparatopic molecule.

In one embodiment, the PD-1 inhibitor is an anti-PD-1 antibody chosen from Nivolumab®, Pembrolizumab® or Pidilizumab®. In some embodiments, the anti-PD-1 antibody is Nivolumab®. Alternative names for Nivolumab® include MDX-1106, MDX-1106-04, ONO-4538, or BMS-936558. In other embodiments, the anti-PD-1 antibody is Pembrolizumab®. Pembrolizumab® (Trade name KEYTRUDA® formerly Lambrolizumab®, also known as Merck 3745, MK-3475 or SCH-900475) is a humanized IgG4 monoclonal antibody that binds to PD-1. In some embodiments, the anti-PD-1 antibody is Pidilizumab®. Pidilizumab® (CT-011; Cure Tech) is a humanized IgG1k monoclonal antibody that binds to PD-1.

In one embodiment, the PD-1 inhibitor is a $V_H$ single domain antibody.

In another embodiment, the second binding molecule is a PD-1 inhibitor that binds to PD-1, but does not block the interaction of human PD-1 with one of its ligands. Thus, the invention also relates to the use of single domain antibodies of the invention in a biparatopic construct together with a molecule, for example a single domain antibody that binds to PD-1 but does not block the functional interaction of PD-1 and its ligands.

In one embodiment, the binding molecule is multivalent, for example bivalent. Bivalent binding molecules comprise two $V_H$ single domain antibodies that bind to the same target protein; e.g. human PD-1, at the same sites. In one embodiment, such molecules may comprise the same Humabody® $V_H$. In another embodiment, such molecules may comprise two $V_H$ single domain antibodies that are part of the same family, i.e. selected from the sequences shown in Table 1. In another embodiment, such molecules may comprise two $V_H$ single domain antibodies that are not part of the same family, but bind to the same site on human PD-1.

Biparatopic and bivalent binding molecules of the present invention can be constructed using methods known in the art.

In certain embodiments, the binding agent is in the form of a multispecific, for example bispecific, binding agent providing multiple functionalities. Such multispecific agent comprises a single domain antibody according to the invention that has a first binding specificity to PD-1 and at least one further binding molecule with a second binding specificity. Said further binding molecule can be selected from an antibody, an antibody fragment or antibody mimetic. In one embodiment, said antibody fragment is selected from $F(ab')_2$, Fab, Fv, sFv or domain antibody. In one embodiment, said antibody fragment is a $V_H$ single domain antibody.

In one embodiment, the binding agent is bispecific and comprises a single domain antibody according to the invention that has a first binding specificity to PD-1 and a second binding molecule with a second binding specificity. In one embodiment, the second binding molecule binds to an immunomodulatory agent, a checkpoint modulator, an agent involved in T-cell activation, a tumor microenvironment modifier (TME) or a tumour-specific target.

For example, the immunomodulator can be an inhibitor of an immune checkpoint molecule selected from an inhibitor of one or more of PD-L1, PD-L2, CTLA-4, TIM-3, LAG-3, CEACAM, VISTA, BTLA, TIGIT, LAIR1, CD160, 2B4 or TGFR beta. In another embodiment, the immunomodulator can be an activator of a costimulatory molecule selected from an agonist of one or more of IL-2, IL-12, OX40, OX40L, CD2, CD3, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, B7-H4 or CD83 ligand, CD3, CD8, CD28, CD4 or ICAM-1. In one embodiment, the immunomodulator is an inhibitor of LAG-3.

In one embodiment, the binding agent described above comprises further binding molecules. Thus, the binding agent can be trispecific or tetraspecific. Additional specificities are also envisaged. Any combination of the aforesaid molecules can be made in a multispecific binding agent, for example, a trispecific binding agent that includes a single domain antibody of the invention and a second and third binding specificity.

In another embodiment, the at least second moiety may serve to prolong the half-life of the binding molecule. The second moiety may comprise a protein, for example an antibody, or part thereof that binds a serum albumin, e.g., human serum albumin (HSA) or mouse serum albumin (MSA). The second moiety may comprise a $V_H$ domain that binds serum albumin, e.g., human serum albumin (HSA) or mouse serum albumin (MSA).

The second moiety may comprise a serum albumin, e.g. a human serum albumin (HSA) or a variant thereof such as HSA C34S. Further provided is binding molecule as described herein comprising a $V_H$ domain and an Fc domain, e.g., wherein the $V_H$ domain is fused to an Fc domain. Further provided is a binding molecule that comprises a second variable domain that specifically binds a second antigen, where the second antigen is an antigen other than human PD-1. The second antigen may be a cluster of differentiation (CD) molecule or a Major Histocompatibility Complex (MHC) Class II molecule.

In one embodiment, the anti-PD-1 single domain antibodies or multivalent binding agents of the invention are labelled with a detectable or functional label. A label can be any molecule that produces or can be induced to produce a signal, including but not limited to fluorophores, fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In still other embodiments, the anti-PD-1 single domain antibodies or multivalent binding agents of the invention are coupled to at least one therapeutic moiety, such as a drug, an enzyme or a toxin. In one embodiment, the therapeutic moiety is a toxin, for example a cytotoxic radionuclide, chemical toxin or protein toxin.

In another aspect, the anti-PD-1 single domain antibodies or multivalent binding agents of the invention are modified to increase half-life, for example by a chemical modification, especially by PEGylation, or by incorporation in a liposome or using a serum albumin protein.

Half-life may be increased by at least 1.5 times, preferably at least 2 times, such as at least 5 times, for example at least 10 times or more than 20 times, greater than the half-life of the corresponding $V_H$ single domain antibodies of the invention. For example, increased half-life may be more than 1 hours, preferably more than 2 hours, more preferably more than 6 hours, such as more than 12 hours, or even more than 24, 48 or 72 hours, compared to the corresponding $V_H$ single domain antibodies of the invention.

To generate a multivalent binding agent as described above, two binding molecules are connected by a linker, for example a polypeptide linker. Suitable linkers include for example a linker with GS residues such as $(Gly_4Ser)n$, where n=from 1 to 10, e.g., 1, 2, 3, 4, 5, 6, 7, 8, 9 or 10.

A single domain antibody described herein can be obtained from a transgenic rodent that expresses heavy chain only antibodies upon stimulation with a PD-1 antigen. The transgenic rodent, for example a mouse, preferably has a reduced capacity to express endogenous antibody genes. Thus, in one embodiment, the rodent has a reduced capacity to express endogenous light and/or heavy chain antibody genes. The rodent may therefore comprise modifications to disrupt expression of endogenous kappa and lambda light and/or heavy chain antibody genes so that no functional light and/or heavy chains are produced, for example as further explained below.

The invention also relates to a method for producing a human heavy chain only antibodies capable of binding human PD-1 said method comprising
   a) immunising a transgenic rodent with an PD-1 antigen wherein said rodent expresses a nucleic acid construct comprising unrearranged human heavy chain V genes and is not capable of making functional endogenous light or heavy chains,
   b) isolating human heavy chain only antibodies.

Further steps can include isolating a $V_H$ domain form said heavy chain only antibody, for example by generating a library of sequences comprising $V_H$ domain sequences from said mouse and isolating sequences comprising $V_H$ domain sequences from said libraries.

The invention also relates to a method for producing a single $V_H$ domain antibody capable of binding human PD-1 said method comprising
  a) immunising a transgenic rodent with an PD-1 antigen wherein said rodent expresses a nucleic acid construct comprising unrearranged human heavy chain V genes and is not capable of making functional endogenous light or heavy chains,
  b) generating a library of sequences comprising $V_H$ domain sequences from said mouse and
  c) isolating sequences comprising $V_H$ domain sequences from said libraries.

Further steps may include identifying a single $V_H$ domain antibody or heavy chain only antibody that binds to human PD-1 and blocks the interaction of PD-1 and PD-L1 and isolating said antibody, for example by using functional assays as shown in the examples.

Methods for preparing or generating the polypeptides, nucleic acids, host cells, products and compositions described herein using in vitro expression libraries can comprise the steps of:
a) providing a set, collection or library of nucleic acid sequences encoding amino acid sequences; and
b) screening said set, collection or library for amino acid sequences that can bind to/have affinity for PD-1 and
c) isolating the amino acid sequence(s) that can bind to/have affinity for PD-1.

In the above method, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

Libraries, for example phage libraries, are generated by isolating a cell or tissue expressing an antigen-specific, heavy chain-only antibody, cloning the sequence encoding the $V_H$ domain(s) from mRNA derived from the isolated cell or tissue and displaying the encoded protein using a library. The $V_H$ domain(s) can be expressed in bacterial, yeast or other expression systems.

The invention also relates to an isolated $V_H$ single domain antibody or an isolated heavy chain only antibody comprising a $V_H$ domain binding to PD-1 comprising an amino acid product of or derived from a human $V_H$ germline sequence. The heavy chain only antibody may be fully human or comprise mouse sequences.

In the various aspects and embodiments of the invention as out herein, the term rodent may relate to a mouse or a rat.

In one embodiment, the rodent is a mouse. The mouse may comprise a non-functional endogenous lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be deleted or rendered non-functional through insertion or other modification as described above. In one embodiment, the locus is functionally silenced so that the mouse does not make a functional lambda light chain.

Furthermore, the mouse may comprise a non-functional endogenous kappa light chain locus. Thus, the mouse does not make a functional endogenous kappa light chain. In one embodiment, the kappa light chain locus is deleted in part or completely or rendered non-functional through insertion, inversion, a recombination event, gene editing or gene silencing. In one embodiment, the locus is functionally silenced so that the mouse does not make a functional kappa light chain.

The mouse having functionally-silenced endogenous lambda and kappa L-chain loci may, for example, be made as disclosed in WO 2003/000737, which is hereby incorporated by reference in its entirety.

Furthermore, the mouse may comprise a non-functional endogenous heavy chain locus. Thus, the mouse does not make a functional endogenous heavy chain. In one embodiment, the heavy chain locus is deleted in part or completely or rendered non-functional through insertion, inversion, a recombination event, gene editing or gene silencing. In one embodiment, the locus is functionally silenced so that the mouse does not make a functional heavy chain.

For example, as described in WO 2004/076618 (hereby incorporated by reference in its entirety), all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and ε are absent and the flanking genes μ and α are partially absent to the extent that they are rendered non-functional, or genes μ, δ, γ3, γ1, γ2a, γ2b and ε are absent and α is partially absent to the extent that it is rendered non-functional, or δ, γ3, γ1, γ2a, γ2b, ε and α are absent and μ is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

In one embodiment, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse may comprise a vector, for example a Yeast Artificial Chromosome (YAC) for expressing a heterologous, preferably a human, heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002 Macmillan Publishers Ltd, Nature Publishing Group).

For example, the YAC may comprise a plethora of unrearranged human $V_H$, D and J genes in combination with mouse immunoglobulin constant region genes lacking $C_H1$ domains, mouse enhancer and regulatory regions. The human $V_H$, D and J genes are human $V_H$, D and J loci and they are unrearranged genes that are fully human. An example of such a YAC is provided in the example section.

Alternative methods known in the art may be used for deletion or inactivation of endogenous mouse or rat immunoglobulin genes and introduction of human $V_H$, D and J genes in combination with mouse immunoglobulin constant region genes lacking $C_H1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos. Regardless of how the genetic material is introduced, the manipulated embryos are transferred to pseudopregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, either conventional or with the inclusion of an IVF step to give efficient scaling of the process. However, it is also possible to include the TKO background during the transgenesis procedure. For example, for microinjection, the oocytes may be derived from TKO donors. Similarly, ES cells from TKO embryos can be derived for use in transgenesis.

Triple knock-out mice into which transgenes have been introduced to express immunoglobulin loci are referred to herein as TKO/Tg.

In one embodiment, the mouse is as described in WO2016/062990.

The invention also relates to a rodent, preferably a mouse which expresses a human heavy chain locus and which has been immunized with a PD-1 antigen. The invention also relates to a rodent as described above, preferably a mouse which expresses a heavy chain only antibody comprising a human $V_H$ domain that binds to human PD-1. Preferably, said rodent is not capable of making functional endogenous kappa and lambda light and/or heavy chains. The human heavy chain locus is located on a transgene which can be as described above.

The invention also relates to an anti-human PD-1 single $V_H$ domain antibody or an anti-human PD-1 heavy chain only antibody comprising a human $V_H$ domain or obtained or obtainable from a rodent, preferably a mouse, immunised with a human PD-1 antigen and which expresses a human heavy chain locus. Preferably, said rodent is not capable of making functional endogenous kappa and lambda light and/or heavy chains. The human heavy chain locus is located on a transgene which can be as described above.

In another aspect of the present invention, there is provided a pharmaceutical composition comprising a single domain antibody according to the present invention and optionally a pharmaceutically acceptable carrier. A single domain antibody of the present invention or the pharmaceutical composition of the invention can be administered by any convenient route, including but not limited to oral, topical, parenteral, sublingual, rectal, vaginal, ocular, intranasal, pulmonary, intradermal, intravitrial, intramuscular, intraperitoneal, intravenous, subcutaneous, intracerebral, transdermal, transmucosal, by inhalation, or topical, particularly to the ears, nose, eyes, or skin or by inhalation.

Parenteral administration includes, for example, intravenous, intramuscular, intraarterial, intraperitoneal, intranasal, rectal, intravesical, intradermal, topical or subcutaneous administration. Preferably, the compositions are administered parenterally.

The pharmaceutically acceptable carrier or vehicle can be particulate, so that the compositions are, for example, in tablet or powder form. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the single domain antibody of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The pharmaceutical composition of the invention can be in the form of a liquid, e.g., a solution, emulsion or suspension. The liquid can be useful for delivery by injection, infusion (e.g., IV infusion) or sub-cutaneously.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e.g. a gelatin capsule), it can contain, in addition to materials of the above type, a liquid carrier such as polyethylene glycol, cyclodextrin or a fatty oil.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Compositions can take the form of one or more dosage units.

In specific embodiments, it can be desirable to administer the composition locally to the area in need of treatment, or by intravenous injection or infusion.

The amount of the single domain antibody of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

Typically, the amount is at least about 0.01% of a single domain antibody of the present invention by weight of the composition. When intended for oral administration, this amount can be varied to range from about 0.1% to about 80% by weight of the composition. Preferred oral compositions can comprise from about 4% to about 50% of the sdAb of the present invention by weight of the composition.

Preferred compositions of the present invention are prepared so that a parenteral dosage unit contains from about 0.01% to about 2% by weight of the single domain antibody of the present invention.

For administration by injection, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

The invention provides methods of treating PD-1-mediated diseases or disorders in a mammal, e.g., a human patient, comprising administering an effective amount of an antibody of the present invention to a mammal in need thereof. In particular, the invention furthermore relates to a method for the prevention and/or treatment of a disorder selected from cancer, an immune disorder, neurological disease, inflammatory disorder, allergy, transplant rejection, viral infection, immune deficiency, and other immune system-related disorder said method comprising administering, to a subject in need thereof, a pharmaceutically active amount of a single domain antibody or pharmaceutical composition of the invention, or of a pharmaceutical composition of the invention.

As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the term "effective amount" means an amount of an anti-PD-1 antibody, that when administered alone or in combination with an additional therapeutic agent to a cell, tissue, or subject, is effective to achieve the desired therapeutic or prophylactic effect under the conditions of administration The invention also relates to a single domain antibody or pharmaceutical composition of the invention for use in the treatment or prevention of a disease.

In another aspect, the invention relates to a single domain antibody or pharmaceutical composition of the invention for use in the treatment or prevention of cancer, an immune disorder, neurological disease, inflammatory disorder, allergy, transplant rejection, viral infection, immune deficiency, and other immune system-related disorder.

In another aspect, the invention relates to the use of a single domain antibody or pharmaceutical composition of the invention in the treatment or prevention of a disease.

In another aspect, the invention relates to the use of a single domain antibody or pharmaceutical composition of the invention in the manufacture of a medicament for the treatment or prevention of cancer, an immune disorder, neurological disease, inflammatory disorder, allergy, transplant rejection, viral infection, immune deficiency, and other immune system-related disorder.

The cancer can be selected from a solid or non-solid tumor. For example, the cancer may be selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, urothelial carcinoma leukemia, prostate cancer, mesothelioma, adrenocortical carcinoma, lymphomas, such as such as Hodgkin's disease, non-Hodgkin's, gastric cancer, and multiple myelomas.

In one embodiment, the tumor is a solid tumor. Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS, neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

In one embodiment, the tumor is a non-solid tumor. Examples of non-solid tumors include leukemia, multiple myeloma and lymphoma.

In one aspect, the cancer is identified as a PD-L1 positive cancer. In one aspect, the cancer is locally advanced unresectable, metastatic, or recurrent cancer.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer).

In one embodiment, the cancer has progressed after another treatment, for example chemotherapy.

The single domain antibodies and pharmaceutical compositions of the present invention are particularly useful for the treatment of cancers that are associated with cells (e.g., exhausted T cells, B cells, monocytes, etc.) that express abnormally high levels of PD-1. Other preferred cancers include those characterized by elevated expression of PD-1 and/or its ligands PD-L1 and/or PD-L2. In one embodiment, the cancer is selected from a cancer that has high levels of cancer-associated genetic mutations and/or high levels of expression of tumour antigens. In another embodiment, the cancer is selected from a cancer known to be immunogenic or that is able to become immunogenic upon treatment with other cancer therapies.

The immune disorder can be selected from graft vs. host disease, arthritis, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

The neurological disease can be selected from Alzheimer's disease, epilepsy, Parkinson's disease, dementia, multiple sclerosis, peripheral neuropathy or post-herpetic neuralgia.

The single domain antibody or pharmaceutical composition of the invention may be administered as the sole active ingredient or in combination with one or more other therapeutic agent. A therapeutic agent is a compound or molecule which is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. An antibody molecule includes a full antibody or fragment thereof (e.g., a Fab, F(ab')2, Fv, a single chain Fv fragment (scFv) or a single domain antibody, for example a $V_H$ domain, or antibody mimetic protein.

In one embodiment, the single domain antibody is used in combination with an existing therapy or therapeutic agent, for example an anti-cancer therapy. Thus, in another aspect, the invention also relates to a combination therapy comprising administration of a single domain antibody or pharmaceutical composition of the invention and an anti-cancer therapy. The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the single domain antibody is used in combination with surgery.

In one embodiment, the single domain antibody or pharmaceutical composition of the invention is administered together with an immunomodulator, a checkpoint modulator, an agent involved in T-cell activation, a tumor microenvironment modifier (TME) or a tumour-specific target. For example, the immunomodulator can be an inhibitor of an immune checkpoint molecule selected from an inhibitor of one or more of PD-1, PD-L1, PD-L2, CTLA-4, TIM-3, LAG-3, CEACAM, VISTA, BTLA, TIGIT, LAIR1, CD160, 2B4 or TGFR beta. In another embodiment, the immunomodulator can be an activator of a costimulatory molecule selected from an agonist of one or more of OX40, OX40L, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand, CD3, CD8, CD28, CD4 or ICAM-1.

In one embodiment, the PD-1 inhibitor is an anti-PD-1 antibody chosen from Nivolumab®, Pembrolizumab® or Pidilizumab®.

In a specific embodiment of the present invention, the composition is administered concurrently with a chemotherapeutic agent or with radiation therapy. In another specific embodiment, the chemotherapeutic agent or radiation therapy is administered prior or subsequent to administration of the composition of the present invention, preferably at least an hour, five hours, 12 hours, a day, a week, a month, more preferably several months (e.g. up to three months), prior or subsequent to administration of composition of the present invention.

In some embodiments, the single domain antibodies of the invention may be administered with two or more therapeutic agents. In some embodiments, the binding agents of the invention may be administered with two or more therapeutic agents.

The single domain antibody or pharmaceutical composition of the invention may be administered at the same time or at a different time as the other therapy or therapeutic compound or therapy, e.g., simultaneously, separately or sequentially.

In yet another aspect, the invention provides a method of modulating an immune response in a subject comprising administering to the subject the single domain antibody of the invention such that the immune response in the subject is modulated. Preferably, the antibody of the invention enhances, stimulates or increases the immune response in the subject.

In a further aspect, the invention provides a method of inhibiting growth of tumor cells in a subject, comprising administering to a subject a therapeutically effective amount of an anti-PD-1 single domain antibody of the invention.

In another aspect, the invention relates to an immunoconjugate comprising a single domain antibody of the invention conjugated to at least one therapeutic and/or diagnostic agent.

In another aspect, the invention provides a kit for the treatment or prevention of a disease or an immune response and/or for detecting PD-1 for diagnosis, prognosis or monitoring disease comprising a single domain antibody of the invention. Such a kit may contain other components, packaging, instructions, or material to aid in the detection of PD-1 protein. The kit may include a labeled single domain antibody of the invention as described above and one or more compounds for detecting the label.

The invention in another aspect provides a single domain antibody of the invention packaged in lyophilized form, or packaged in an aqueous medium.

The invention also relates to a single domain antibody as described herein with reference to the figures and examples.

In another aspect, single domain antibodies of the invention are used for non-therapeutic purposes, such as diagnostic tests and assays. A method for detecting the presence of human PD-1 in a test sample comprises contacting said sample with a single domain antibody according to the invention and at least one detectable label and detecting binding of said single domain antibody to human PD-1.

In one embodiment, the invention relates to a method of diagnosing a PD-1-mediated adaptive immune resistance in a patient who has cancer. The method comprises contacting a sample with a single domain antibody disclosed herein that has been labelled with a detectable moiety; and detecting expression of PD-1 on immune cells, e.g., CD8+ T cells; B cells; and macrophages. The sample may be tumor tissue.

Modifications of antibodies for diagnostic purposes are well known in the art. For example, antibodies may be modified with a ligand group such as biotin, or a detectable marker group such as a fluorescent group, a radioisotope, or an enzyme. Compounds of the invention can be labelled using conventional techniques. Suitable detectable labels include but are not limited to fluorophores, chromophores, radioactive atoms, electron-dense reagents, enzymes, and ligands having specific binding partners.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene accession numbers and references to patent publications. "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1. Construction of Tg/TKO Mice

Mice carrying a human heavy-chain antibody transgenic locus in germline configuration within a background that is silenced for endogenous heavy and light chain antibody expression (triple knock-out, or TKO) were created as previously described (WO2004/076618, WO2003/000737, Ren et al., Genomics, 84, 686, 2004; Zou et al., J. Immunol., 170, 1354, 2003 and WO2016/062990). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002, Macmillan Publishers Ltd., Nature Publishing Group.

The YAC used comprised multiple human heavy chain V genes, multiple human heavy chain D and J genes, a murine $C_H1$ gene and a murine 3' enhancer gene. It lacks the $C_H1$ exon.

The transgenic founder mice were back crossed with animals that lacked endogenous immunoglobulin expression to create the Tg/TKO lines used in the immunisation studies described.

Example 2. Antigen for Immunisation

The immunisations used recombinant human PD-1 Fc chimera purchased from R&D, catalogue number 1086-PD, lot number FVQ081502B or FVQ081503A.

Recombinant human PD-1-TetTox protein was used in another separate immunisation. This is based on residues 1-167 of human PD-1 and comprises at the N terminus the tet toxin linked to PD-1 via a polylinker. Also included is an N-terminal His tag as well as leader sequence and restriction site for proteolytic cleavage.

CHO cell lines expressing human PD-1 on the surface were made in house.

Example 3. Immunisation Protocol

Tg/TKO mice aged 8-12 weeks of age each received an initial prime dose of either 50 ug or 10 ug of recombinant purified human PD-1-Fc protein emulsified in Complete Freund's Adjuvant and delivered subcutaneously, followed by three boosts of 10 µg of the recombinant protein, emulsified in Incomplete Freund's Adjuvant, also administered subcutaneously, given at various intervals following the initial priming. A final dose of 10 µg or 20 ug recombinant purified human PD-1 protein antigen was administered intraperitoneally, in phosphate buffered saline, in the absence of adjuvant.

A separate cohort of Tg/TKO mice aged 8-12 weeks of age each received an initial prime dose of 10 ug of recombinant purified human PD1-TetTox protein emulsified in Complete Freund's Adjuvant and delivered subcutaneously, followed by three boosts of 10 µg emulsified in Incomplete Freund's Adjuvant, also administered subcutaneously, given at various intervals following the initial priming. A final dose of 10 µg recombinant purified human PD-1-Tettox protein antigen was administered intraperitoneally, in phosphate buffered saline, in the absence of adjuvant.

Another cohort of animals was primed with 50 ug purified human PD-1-Fc protein as above, followed by three boosts of 10 million cells expressing human PD-1 at high levels on the surface. The boosts were given without adjuvant, two of them sub cutaneously and the third intraperitoneally. A final dose of 10 µg recombinant purified human PD-1-Fc protein was administered intraperitoneally, in phosphate buffered saline, in the absence of adjuvant.

Example 4. Serum ELISA

Serum was collected from mice before and after immunisation, and checked by ELISA for the presence of serum PD-1/Fc reactive heavy chain antibodies in response to immunisation with PD-1 antigen. Nunc Maxisorp plates (Nunc cat. no. 443404) were coated overnight at 4° C. with 50 µl/well of either a 1 µg/ml recombinant huPD-1-Fc solution in PBS (R&D 1086-PD) or of hPD-1 HIS in PBS R&D (8986-PD or 9047-PD). Plates were washed using PBS (prepared from PBS tablets, Oxoid cat. no. BRO014G) supplemented with 0.05% (v/v) Tween® 20 (Sigma P1379), followed by washes with PBS without added Tween 20. To block non-specific protein interactions, a solution of 3% (w/v) skimmed milk powder (Marvel®) in PBS was added to the wells and the plate was incubated for at least one hour at room temperature, then discarded.

Whole blood samples were centrifuged at 13000 rpm for 5 mins to separate blood from serum. Dilutions of serum were prepared in 3% Marvel®/PBS in polypropylene tubes or plates, pre-incubated for at least one hour at room temperature then transferred to the blocked ELISA plate and incubated for at least one hour. Unbound protein was removed by repetitive washing with PBS/Tween 20 followed by PBS. A 1:10,000 solution of biotin-conjugated, goat anti-mouse IgG, Fcgamma subclass 1 specific antibody (Jackson cat. no. 115-065-205), prepared in PBS/3% Marvel® was added to each well and incubated at room temperature for at least one hour. Unbound detection antibody was removed by repeated washing using PBS/Tween® 20 and PBS. Neutravidin-HRP solution (Pierce cat. no. 31030) in 3% Marvel®/PBS was added to the ELISA plates and allowed to bind for 30 minutes, then washed as above. The ELISA was developed using TMB substrate (Sigma cat. no. T0440) and the reaction was stopped after 7 minutes by the addition of 50 ul 0.5M $H_2SO_4$ solution (Sigma cat. no. 320501). Absorbances were read at 450 nm with the BMG Pherastar.

Mice were checked by ELISA for the presence of antibody in serum. All mice showed a robust immune response.

Example 5. Generation of Libraries from Immunised Mice

Tissue Collection and Homogenisation

Generation of libraries from immunised mice described above followed standard protocols of library generation as summarised below.

Total spleen, inguinal and brachial lymph nodes were used according to standard protocols.

RNA Extraction and RT-PCR

Spleen: 400 µl supernatant was used for preparation of total RNA. RNA was extracted using Qiagen RNeasy® kit (cat. no. 74104) following the manufacturer's protocol.

Lymph nodes: prepared by essentially the same process on the Kingfisher.

$V_H$ sequences were mined from the RNA samples using Superscript III RT-PCR high-fidelity kit (Invitrogen cat. no.

12574-035) according to the manufacturer's protocol. For each spleen and LN RNA sample, RT-PCR reactions were performed using a single $J_H$ primer in combination with primers for $V_H1$, $V_H2$, $V_H3$, $V_H4$ or $V_H6$ families.

RT-PCR products were pooled so that $V_H1$ products from lymph nodes 1-4 and spleen were combined. Amplified material was purified using the GeneJet™ purification kit (cat #K0702) according to the manufacturer's protocol, eluting in 50 ul water.

Cloning into Phagemid Vector

The phagemid vector, pUCG3, was employed in these studies. A conventional PCR-based method was used to construct the $V_H$ phagemid libraries from the amplified $V_H$ sequences. In short, the following procedure was used:

A linearised version of pUCG3 was created using PCR. Vector PCR product (3152 bp) was gel purified using Fermentas GeneJet Gel purification kit (cat. no. K0691), according to the manufacturer's instructions. Purified $V_H$ RT-PCR products were used to prime a PCR reaction from the linearised pUCG3 resulting in a heterogeneous population of $V_H$ cloned into pUCG3.

PCR products were analysed on a 1% (w/v) agarose gel.

Generation of Phagemid Library $V_H$/phagemid PCR products were pooled by animal-of-origin and purified using Fermentas PCR purification kit (cat. no. K0702) according to the manufacturer's instructions. The final elution was in 22 µl $H_2O$.

Eluted DNA was used to transform TG1 *E. coli* (Lucigen, cat. no. 60502-2) by electroporation using the Bio-Rad GenePulser Xcell pulsed at 2500V, 25 uF, 200W. Electroporated cells were pooled.

A 10-fold dilution series of the transformations was plated on 2xTY agar petri plates with 2% (w/v) glucose and 100 µg/ml ampicillin. Resulting colonies on these dishes were used to estimate library size. The remainder of the transformation was plated on large format 2xTY agar Bioassay dishes supplemented with 2% (w/v) glucose and 100 µg/ml ampicillin. All agar plates were incubated overnight at 30° C.

Libraries were harvested by adding 10 ml of 2xTY broth to the large format bioassay dishes. Bacterial colonies were gently scraped and OD600 recorded. Aliquots were stored at −80° C. in cryovials after addition of an equal volume of 50% (v/v) glycerol solution or used directly in a phage selection process.

Example 6. Selection Strategies for Isolation of PD-1 Binding $V_H$ Isolation and Optimisation Preparation of library phage stocks and phage display selections were performed according to published methods (Antibody Engineering, edited by Benny Lo, chapter 8, p 161-176, 2004). In most cases, phage display combined with a panning approach was used to isolate binding $V_H$ domains. However, a variety of different selection methods are well described in the art, including soluble selection and selections performed under stress (e.g., heat).

Standard methods were employed for optimisation, for example to increase $V_H$ affinity for antigen. These optimisation strategies are described in the art:
a) shuffling (Antibody Engineering, Edited by Benny Lo, chapter 19, p 327-343, 2004);
b) Targeted randomisation of CDR3 regions using randomised oligonucleotides and phage display technology (Main et al., J Pharmacol Exp Ther. 2006 December; 319(3): 1395-404.) and
c) Ribosome display.

Example 7: Screening of Periplasmic Extracts for Binding to CHO Human PD1 Cells and Inhibition of PD-L1 Binding PD-1

Following selections of the libraries, specific $V_H$ that bound to CHO cells expressing human PD-1 and inhibited the interaction between recombinant human PD-1 protein and recombinant human PD-L1 protein were identified by single point screening of bacterial periplasmic extracts.

Small-scale bacterial periplasmic extracts were prepared from 1 ml cultures, grown in deep well plates. Starter cultures were used to inoculate 96-well deep well plates (Fisher, cat. no. MPA-600-030X) containing 2XTY broth (Melford cat. no. M2130), supplemented with 0.1% (w/v) glucose and 100 µg/ml ampicillin at 37° C. with 250 rpm shaking. When $OD_{600}$ had reached 0.6-1, $V_H$ production was induced by adding 100 µl of 2XTY, supplemented with IPTG (final concentration 0.5 mM) and ampicillin and the cultures were grown overnight at 30° C. with shaking at 220 rpm. *E. coli* were pelleted by centrifugation at 3200 rpm for 10 mins and supernatants discarded. Cell pellets were resuspended in 120 µl of ice cold extraction buffer (50 mM MOPs, 0.5 mM EDTA, 0.5M Sucrose), then 180 µl of 1:5 diluted ice cold extraction buffer added. Cells were incubated on ice for 30 minutes and then centrifuged at 4500 rpm for 15 mins at 4° C. Supernatants were transferred to polypropylene plates for testing in assays.

Binding of His-tagged $V_H$ in the supernatants to CHO cell expressed human PD-1 was assessed using Fluorescence Microvolume Assay Technology (FMAT), a fluorescence-based platform that detects fluorescence localized to beads or cells settled at the bottom of microwells (Dietz et al., *Cytometry* 23:177-186 (1996), Miraglia et al., *J. Biomol. Screening* 4:193-204 (1999). A CHO TREX human PD-1 cell line was generated in-house using full-length human PD-1 sequence by standard procedures. All reagents were prepared in FMAT assay buffer (pH 7.4) containing PBS, 0.1% Bovine Serum Albumin, 0.01%, Sodium Azide. Peripreps were transferred into 384 well black clear-bottomed assay plates (Costar cat. no. 3655) and incubated for a minimum of 2 hours at room temperature with 1.5 nM Anti-His (Millipore cat. no. 05-949)/3 nM Goat Anti-Mouse Alexa Fluor-488 (Jackson Immunolabs cat. no. 115-545-071) and 2000 CHO human PD-1 cells prestained with DRAQ5 (Thermo Scientific cat. no. 62251). Plates were read in the FL2 (502 nm-537 nm) and FL5 (677-800 nm) channels on the TTP Mirrorball plate reader following excitation at 488 nm and 640 nm. Data was gated on FL5 perimeter and peak intensity and the FL2 median mean fluorescence intensity of the gated data used for determination of $V_H$ binding.

In parallel to the CHO PD-1 binding assay, periplasmic extracts were tested for their ability to inhibit the interaction of PD-L1 protein with PD-1 protein by single point screening in an HTRF inhibition assay. All samples and reagents were prepared in HTRF assay buffer containing PBS, 0.1% (w/v) BSA and 0.4M Potassium Fluoride. Periplasmic extracts were incubated with 25 nM strep tagged PD-L1 (Acro Biosystems cat no. PD-1-H5282), 1.5 nM Anti human-Fc Cryptate PAb (Cisbio cat. no. 61HFCKLB), 10 nM StrepMAB-Oyster 645 conjugate in black 384-shallow-well plates (Costar cat. no. 3676) for a minimum of 3 hours at room temperature. Total binding controls containing periplasmic extract sample buffer and non-specific binding controls containing excess untagged competitor were set up on each plate for data normalisation. Time-resolved fluorescent emission at 620 nm and 665 nm was measured following excitation at 337 nm on the BMG PHERAstar plate reader. Data was expressed as a % of the total binding control (% control) after subtraction of the background signal determined from the non-specific binding control wells.

Figure 1B:
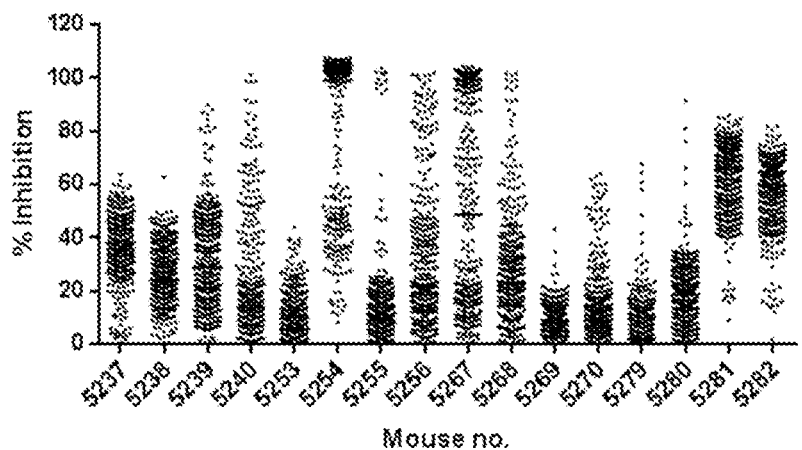

Families of $V_H$ were identified that bound to the CHO human PD-1 cells with FL2 fluorescence>1000 (FIG. 1a) and that inhibited PD-1 binding to PD-L1 (FIG. 1b).

Example 8. Sequencing

Each individual $V_H$ clone as identified above was sequenced from the phagemid and grouped based on $V_H$ germline and CDR3 amino acid similarity. Representative clones were further characterised. Further clones were generated by sequence optimisation of clone 1.1 as shown in table 1. Standard methods were used for optimisation. Clones 1.1 to 1.40 isolated as above were grouped into a single family. Clones 1.41-1.115 are sequence optimised variants clone 1.1.

Example 9. Preparation and Characterisation of Purified $V_H$ a) Preparation of Purified $V_H$ Purified $V_H$ were obtained by using the $V_H$ C-terminal 6×HIS tag for nickel-agarose affinity chromatographic purification of the periplasmic extracts. A starter culture of each $V_H$ was grown overnight in 2XTY media (2XTY broth (Melford cat. no. M2103) supplemented with 2% (w/v) glucose+100 µg/ml ampicillin at 30° C. with 250 rpm shaking. This overnight culture was then used to inoculate 50 ml-200 ml 2XTY media and incubated at 37° C. with 250 rpm shaking for approximately 6-8 hours (until $OD_{600}$=0.6-1.0). Cultures were centrifuged at 3200 rpm for 10 mins and the cell pellets resuspended in fresh 2XTY broth containing 100 µg/ml ampicillin+1 mM IPTG. Shake flasks were incubated overnight at 30° C. and 250 rpm. Cultures were again centrifuged at 3200 rpm for 10 mins and supernatants discarded. Cell pellets were resuspended in ice cold extraction buffer (20% (w/v) sucrose, 1 mM EDTA, 50 mM Tris-HCl pH 8.0 or 50 mM MOPS) by gently pipetting then diluted further with 1:5 diluted ice cold extraction buffer. Cells were incubated on ice for 30 minutes then centrifuged at 4500 rpm for 15 mins at 4° C. Supernatants were transferred to tubes containing imidazole (Sigma cat. no. I2399—final concentration 10 mM) and pre-equilibrated nickel agarose beads (Qiagen, Ni-NTA 50% soln, cat. no. 30210). $V_H$ binding was allowed to proceed for 2 hours at 4° C. with gentle shaking. The beads were transferred to a polyprep column (BioRad cat. no. 731-1550) and the supernatant discarded by gravity flow. Columns were washed 3 times with PBS+0.05% Tween® followed by 3 washes with 5 ml of PBS/20 mM Imidazole. $V_H$ were eluted from the columns using PBS/250 mM imidazole. The imidazole was removed from the purified $V_H$ preparations by buffer exchange with NAP-5 columns (GE Healthcare, 17-0853-01) and elution with PBS. Yields of purified $V_H$ were estimated spectrophotometrically and purity was assessed using SDS PAGE.

Alternatively $V_H$ were purified from the supernatants of W3110 E. coli with pJExpress vector. For this procedure up to 400 ml cultures were grown at 37° C. with 250 rpm shaking in TB media before being induced overnight with 1 mM IPTG overnight. The resulting supernatants were harvested and $V_H$ purified on AKTA Pure using a Ni-Sepharose excel column (HiScale 16, GE Healthcare). Yields of purified $V_H$ were estimated spectrophotometrically and purity was assessed using SDS PAGE.

b) Inhibition of Human PD-L1 and PD-L2 Binding to Recombinant Human PD-1

Purified $V_H$ were serially diluted in HTRF assay buffer and tested in the HTRF PD-1:PD-L1 Inhibition assay as described previously in Example 1 and $IC_{50}$ values determined. These are shown in Table 3 below.

TABLE 3

| Humabody ® | HTRF PD-1:PD-L1 IC50 (M) |
|---|---|
| 1.2 | 1.30E−08 |
| 1.3 | 2.30E−09 |
| 1.4 | 3.13E−09 |
| 1.5 | 2.66E−09 |
| 1.6 | 1.31E−08 |
| 1.7 | 4.40E−09 |
| 1.8 | 2.88E−08 |
| 1.9 | 9.13E−10 |
| 1.10 | 5.41E−08 |
| 1.11 | 5.16E−09 |
| 1.12 | 4.18E−09 |
| 1.13 | 1.70E−08 |
| 1.14 | 2.85E−08 |
| 1.15 | 3.78E−09 |
| 1.1 | 1.27E−09 |

For the PD-L2 inhibition assay, recombinant human PD-1 protein was labelled with Europium Trisbipyridine Cryptate (Cisbio cat no. 62EUSPEA) according to the manufacturer's protocol and PD-L2-Fc (Acro Biosystems cat no. PD2-H882R) was biotinylated according to EZ-link kit protocol (Thermo 21327) Serial dilutions of $V_H$ were incubated with 10 nM Streptavidin AlexaFluor-647 (Life Technologies cat no. S32357), 3 nM biotinylated PD-L2-Fc and Europium Cryptate labelled PD-1-Fc (167-fold dilution) in a 10 µl assay volume for a minimum of 3 hours at room temperature. For example data see FIG. 2 and Table 4.

TABLE 4

| Humabody ® | IC50 (M) |
|---|---|
| 1.9 | 7.5E−09 |
| 1.13 | 1.0E−08 |
| 1.5 | 2.2E−08 |
| 1.4 | 1.4E−08 |
| 1.1 | 4.9E−09 |
| 1.2 | 3.9E−08 | c) Humabody® 1.1 and Humabody® 1.57 Epitope Competition Assays

Sequence optimised single domain antibodies with improved activity and/or expression levels over that of the parental (non-optimised) single domain antibodies were initially identified by testing of bacterial periplasmic extracts for their ability to compete with the binding of the parental clone 1.1 or a partially optimised Humabody® 1.57 to CHO human PD-1 cells in an FMAT epitope competition assay.

Humabody® 1.1 or 1.57 $V_H$ sequence was amplified by PCR and sub-cloned into a vector enabling expression with a C terminally fused Strep tag. TG1 bacterial cultures transformed with the expression vector were cultured, periplasmic extracts prepared using extraction buffer (20% w/v sucrose, 1 mM EDTA, 50 mM Tris-HCl pH8.0) then Strep-tagged $V_H$ purified from the periplasm using Strep-Tactin affinity resin (Qiagen 30002).

For the epitope competition assay reagents were prepared in FMAT assay buffer. Bacterial periplasmic extracts, buffer (total binding controls) or excess His tagged $V_H$ competitor (non-specific binding control) were incubated with 1 nM 1.1Strep tagged protein or 1 nM 1.57-Strep tagged protein, 1.5 nM Strep-Tag® II monoclonal antibody (Millipore 71590), 2.5 nM Goat anti mouse Fc-Alexa Fluor 488 and 2000 CHO human PD-1 DRAQ5 stained cells per well in a 384 well black clear-bottomed assay plate. Plates were incubated for a minimum of 1.5 hours at room temperature then fluorescence measured in the FL2 (502 nm-537 nm) and FL5 (677-800 nm) channels on the Mirrorball plate reader (TTP) following excitation at 488 nm and 640 nm. Data was expressed as a % of the total binding control (i.e. % control) after subtraction of the background signal determined from the non-specific binding control wells. Clones that showed improved activity compared to the parent $V_H$ were purified and tested multipoint in the Epitope Competition Assay for $IC_{50}$ determination or were tested directly in the reporter gene assay described below (data shown in Table 5).

d) Reporter Gene Assays

The ability of the $V_H$ to increase functional responses in a transfected Jurkat cells as a result of PD-1:PD-L1 blockade was assessed using an NFAT-Luciferase Reporter Gene assay. A Jurkat reporter cell line expressing human PD-1 and a luciferase reporter gene under the control of a promoter with an NFAT response element and a CHO cell line expressing a T-Cell Receptor activator and human PD-L1 under the control of a tetracycline inducible promotor were generated by standard methods. Cells were prepared in bulk, then frozen and stored in liquid nitrogen.

CHO human PD-L1/TCR activator cells were thawed in a 37° C. water bath, washed once with PBS, resuspended in (Hams F12/10% FBS/1 µg/ml tetracycline) and plated at 10000 cells/well in a 96 well white TC treated assay plate. Plates were incubated at 37° C. overnight in a $CO_2$ incubator.

Samples were serially diluted in assay medium (RPMI+ 2% FBS). Jurkat PD-1 reporter cells were thawed in a 37° C. water bath, washed once with medium, then diluted into assay medium at $5e^5$ cells/ml. The media was removed from the CHO cells and 50 µl diluted sample or assay media (background control) added to the plates followed by 50 µl of the diluted Jurkat reporter cells. The plates were incubated for 6 hours at 37° C. in a $CO_2$ incubator, then removed from the incubator and equilibrated to room temperature for 10 mins. NanoGlo substrate (100 µl of substrate diluted 1:50 in NanGlo buffer Promega cat no. N1120) was added and the plates incubated for 10 mins at room temperature prior to measurement of luminescence signal (RLU). Data was expressed as fold/background signal.

Alternatively samples were tested using the PD-1/PD-L1 Blockade Bioassay System (Promega) according to the manufacturer's protocol.

Example $EC_{50}$ data for activity of optimised Humabody® in the reporter assays is shown in Table 5a below.

TABLE 5a

Monovalent single domain antibodies

| Humabody ® | 1.1 Epitope Competition (IC50) M | Reporter Assay EC50 (M) |
|---|---|---|
| 1.58 | 4.6E−09 | 7.1E−09 |
| 1.59 | 7.8E−09 | 2.4E−08 |

TABLE 5a-continued

Monovalent single domain antibodies

| Humabody ® | 1.1 Epitope Competition (IC50) M | Reporter Assay EC50 (M) |
|---|---|---|
| 1.42 | 3.5E−09 | 8.6E−09 |
| 1.43 | 1.3E−09 | 1.2E−08 |
| 1.44 | 1.9E−09 | 4.1E−08 |
| 1.45 | 2.5E−09 | 7.4E−08 |
| 1.46 | 1.8E−09 | 4.5E−08 |
| 1.47 | 4.4E−09 | 2.7E−08 |
| 1.48 | | 1.8E−08 |
| 1.51 | 4.7E−09 | 2.3E−08 |
| 1.53 | 5.4E−09 | 1.4E−08 |
| 1.57 | | 8.6E−09 |
| 1.62 | | 1.4E−08 |
| 1.63 | | 1.2E−08 |
| 1.64 | | 2.5E−08 |
| 1.65 | | 1.1E−08 |
| 1.67 | | 1.2E−08 |
| 1.69 | | 3.5E−08 |
| 1.70 | | 2.9E−08 |
| 1.71 | | 7.43E−09 |
| 1.72 | | 2.61E−08 |
| 1.92 | 7.9E−010 | 1.3E−08 |
| 1.93 | 1.5E−09 | |
| 1.91 | 1.4E−09 | |
| 1.95 | 2.0E−09 | |
| 1.97 | 1.7E−09 | |
| 1.100 | 1.5E−09 | |
| 1.98 | 1.1E−09 | 6.5E−09 |
| 1.101 | 3.0E−09 | |
| 1.96 | 1.6E−09 | |
| 1.94 | 4.2E−09 | |
| 1.89 | 2.4E−09 | 1.9E−08 |
| 1.90 | 1.6E−09 | |
| 1.99 | 1.4E−09 | 4.2E−09 |

TABLE 5b

Multivalent single domain antibodies

| Multivalent Humabody ® | $EC_{50}$ (M) |
|---|---|
| 1.57-4GS-1.57 | 1.0E−09 |
| 1.57-6GS-1.57 | 8.4E−10 |
| 1.57-9GS-1.57 | 1.0E−09 |
| 1.57-4GS-MSA binder | 1.0E−08 | e) Species Cross Reactivity Testing Purified $V_H$ were tested for their ability to bind to human PD-1 (R&D Systems cat no. 1086-PD), cynomolgus PD-1 (Acro Biosystems cat no. PD-1-05254) and mouse PD-1 (R&D Systems cat no. 1021-PD) in an HTRF Binding assay format. All reagents and serially diluted $V_H$ were prepared in assay buffer containing PBS, 0.1% BSA and 0.4M Potassium Fluoride. Samples or assay buffer (non-specific binding) were incubated with 2 nM human/cynomolgus or mouse PD-1, 1 nM Anti human-Fc Cryptate PAb (Cisbio cat. no. 61HFCKLB) and 30 nM anti His-D2 (CisBio cat no 61HISDLA) in black 384-shallow well assay plates for a minimum of 3 hours at room temperature. Time-resolved fluorescent emission at 620 nm and 665 nm was measured following excitation at 337 nm on the BMG PHERAstar plate reader. The HTRF ratio were calculated ((665 nm emission/620 nm emission) *10000) and the data corrected for (non-specific binding) to give the specific binding signal.

Humabody® 1.1 and variants 1.57, 1.92 showed binding to human (FIG. 3a) and cynomolgus PD-1 (FIG. 3b) recombinant protein, but did not cross react with mouse PD-1 protein (FIG. 3c).

EC50 values are shown in Table 6 below.

TABLE 6

| Humabody ® | human PD-1 EC$_{50}$ (M) | cyno PD-1 EC$_{50}$ (M) | mouse PD-1 EC$_{50}$ (M) |
|---|---|---|---|
| 1.1 | 4.0E−9 | 6.3E−9 | No binding |
| 1.57 | 5.9E−10 | 7.5E−10 | No binding |
| 1.92 | 2.6E−09 | 4.1E−09 | No binding |

Bivalent binding agents (1.57-4GS-1.57) and half-life extended binding agents (1.57-4GS-MSA binder were also tested and as with the single domain antibodies above, showed binding to human and cynomolgus PD-1 recombinant protein, but did not cross react with mouse PD-1 protein.

f) Inhibition of PD-11 and PD-L2 Binding to CHO Human PD-1 Cells

Purified V$_H$ were serially diluted in FMAT assay buffer and tested for binding to CHO human PD-1 cells as described above and for inhibition of human PD-L1 binding to CHO human PD-1 cells. The ability of purified monovalent and multivalent V$_H$ to inhibit PD-L1 and PD-L2 binding to CHO human PD-1 cells respectively was confirmed using an FMAT Inhibition assay (FIG. 4).

All reagents and serially diluted V$_H$ were prepared in FMAT assay buffer. V$_H$, buffer (total binding controls) or excess competitor (non-specific binding control) were incubated with 100 pM human Fc tagged human PDL-1 or 200 pM PD-L2, 3 nM anti human Fc-Alexa Fluor-488 and 2000 per well CHO human PD-1 DRAQ5 stained cells in a 384 well black clear-bottomed assay plates. Plates were incubated for 2 hours at room temperature then fluorescence measured in the FL2 (502 nm-537 nm) and FL5 (677-800 nm) channels on the Mirrorball plate reader (TTP) following excitation at 488 nm and 640 nm. Data was expressed as a % of the total binding control (i.e. % control) after subtraction of the background signal determined from the non-specific binding control wells.

IC50 values are shown below in Table 7. Example data are shown in FIGS. 4a and b.

TABLE 7

| Humabody ® | CHO PD-1 binding IC50 (M) | CHO PD-1: PD-L1 IC50 (M) | CHO PD-1: PD-L2 IC50 (M) |
|---|---|---|---|
| 1.64 | | 5.8E−09 | 9.0E−09 |
| 1.65 | | 5.8E−09 | 8.5E−09 |
| 1.63 | | 4.5E−09 | 6.9E−09 |
| 1.62 | | 5.7E−09 | 1.0E−08 |
| 1.57 | | 1.8E−09 | 2.3E−09 |
| 1.92 | 0.1E−09 | 2.8E−09 | 4.0E−09 |
| 1.93 | | 2.12E−09 | |
| 1.99 | | 1.86E−09 | |
| 1.91 | | 3.56E−09 | |
| 1.95 | | 3.59E−09 | |
| 1.97 | | 3.32E−09 | |
| 1.100 | | 2.61E−09 | |
| 1.98 | | 2.08E−09 | |
| 1.96 | | 2.45E−09 | |

TABLE 7-continued

| Humabody ® | CHO PD-1 binding IC50 (M) | CHO PD-1: PD-L1 IC50 (M) | CHO PD-1: PD-L2 IC50 (M) |
|---|---|---|---|
| 1.90 | | 3.00E−09 | |
| 1.80 | | 1.82E−09 | | g) Reporter Gene Assay

Functional activity of multivalent V$_H$ constructs was tested in the human PD-1 reporter gene assay as described above and EC$_{50}$ values determined. These are shown in Table 8 below. Example data shown in FIG. 9. Non blocking V$_H$(1) has SEQ ID NO. 587. Non-blocking V$_H$(2) has SEQ ID NO. 588. The blocking effect can be enhanced by 10 to 25 fold.

TABLE 8

| Humabody ® Construct | EC50 (M) |
|---|---|
| 1.57-4GS-1.57 | 1.0E−09 |
| 1.57-6GS-1.57 | 8.4E−10 |
| 1.57-9GS-1.57 | 1.0E−09 |
| 1.57-4GS-MSA binder | 1.0E−08 |
| 1.92-4GS-non-blocking VH(1) | 2.0E−09 |
| 1.92-4GS-non-blockering VH(2) | 1.2E−09 | h) Serum Stability

Serum stability of V$_H$ and multivalent V$_H$ constructs was assessed by measurement of their activity following incubation for 0, 1, 4 or 7 days in mouse serum (Sigma M5905). The pre-incubated samples were serially diluted and tested in the 1.57 epitope competition assay as previously described in Example 3. Minimal loss of activity was observed following incubation with serum (FIG. 5). Humabody® molecules tested were 1.57, 1.64, 1.57-4GS-MSA and 1.92. Example data shown in FIGS. 5a and b.

TABLE 9

| | IC 50 (M) | | | | | | | |
|---|---|---|---|---|---|---|---|---|
| | Day 0 | | Day 1 | | Day 4 | | Day 7 | |
| Constructs | Human | Mouse | Human | Mouse | Human | Mouse | Human | Mouse |
| 1.92 | 5.7E−09 | 4.4E−09 | 4.9E−09 | 4.4E−09 | 6.1E−09 | 4.7E−09 | 5.4E−09 | 5.2E−09 | i) Binding of V$_H$ to T-Cells

Figure 6:
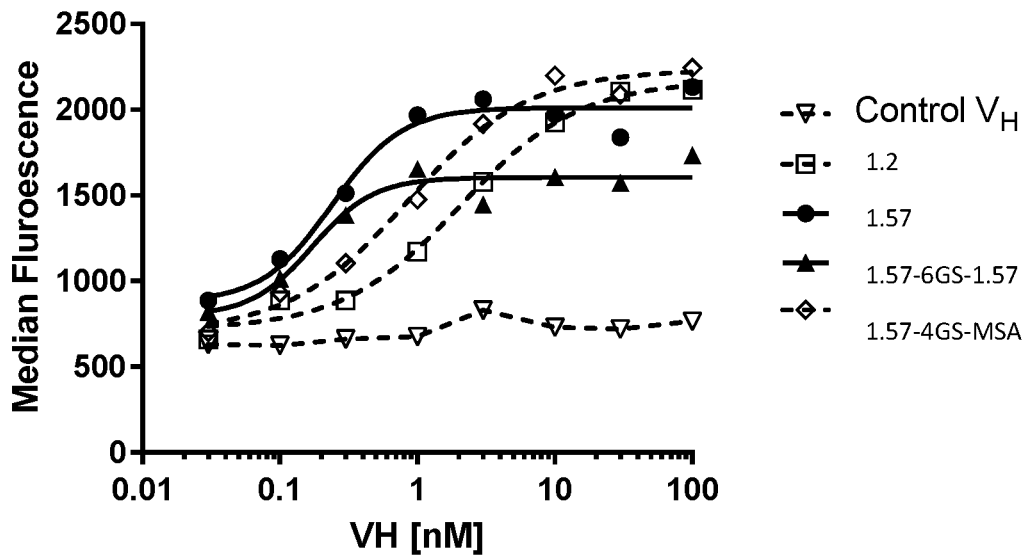

Binding of monovalent single domain antibodies and multivalent binding agents to T cells was measured using flow cytometry. Peripheral blood mononuclear cells (PBMCs) were isolated from human blood by density gradient centrifugation then CD4+ T cells purified using a negative selection isolation kit according to the manufacturer's protocol (Miltenyi Biotech cat no 130-096-533). T-cells were stimulated with 2.5 μg/ml PHA for 2-4 days in RPMI media supplemented with 10% FBS, 2 mM Glutamine, 1× Pen/Strep. Cells were transferred into 96 well plates (75000 per well), blocked for 10 mins with PBS/1% BSA, then incubated with serially diluted V$_H$ in staining buffer (PBS/1% BSA) for 1 hour at 4° C. Cells were washed with staining buffer by centrifugation then incubated with 10 μg/ml biotinylated Anti His antibody for 40 mins at 4° C. Cells were washed again then stained with Streptavidin Alexa Fluor-488 (10 μg/ml) and 1:5000 diluted Live Dead near IR stain (Molecular Probes cat no. L10119) for 30 mins at 4° C. After further washing cells were fixed and fluorescence measured by flow cytometry. EC$_{50}$ values are shown in table 10. Example binding curve data for staining of live cell gated CD4+ T cells is shown in FIG. 6.

TABLE 10

| | CD4+ T cell binding EC50 (M) | | | |
|---|---|---|---|---|
| Name | Donor 1 | Donor 2 | Donor 3 | Donor 4 |
| 1.92 | 0.8E-09 | 1.1E-09 | 1.2E-09 | 0.9E-09 | j) $V_H$ Single Domain Antibodies Demonstrate Good Stability

Purified $V_H$ were subjected to size exclusion chromatography. Briefly, purified $V_H$ were stored at either Na Acetate pH 5.5, 150 mM NaCl or PBS pH 7.4 for 0-14 days at either 4° C. or 40° C., and then analysed at various time points using a Waters H-Class Bio UPLC containing a PDA detector (detection at 280 nm) with separation on a Waters ACQUITY BEH 125 Å SEC column. Samples were injected in 10 μl volumes and were run in a mobile phase containing 200 mM NaCl, 100 mM sodium phosphate, pH 7.4+5% propan-1-ol at a flow rate of 0.4 ml/min. Data were collected for 6 minutes and the area of the monomer peak remaining after storage as compared to that present at the start (T=0) was calculated. Examples of anti-PD-1 $V_H$ single domain antibodies incubated at 40° C. for 14 days are illustrated in Table 11. At incubation at 4° C. for 14 days, no significant change was seen.

TABLE 11

| | 0 | 1 | 4 | 7 | 14 |
|---|---|---|---|---|---|
| 1.64 | 100.00 | 106.53 | 104.66 | 93.98 | 100.03 |
| 1.63 | 100.00 | 94.12 | 91.25 | 90.23 | 90.78 |
| 1.92 | 100.00 | 96.54 | 92.22 | 92.00 | 93.08 | k) Effects of PD-1 Specific Humabody® on Human T Cell Activation in a Mixed Lymphocyte Reaction Monocytes were isolated from human peripheral blood mononuclear cells (PBMCs) and differentiated into dendritic cells for 7 days using STEMCELL Technologies Dendritic Cell Differentiation media or GM-CSF and IL-4. Dendritic cells were cultured with allogeneic CD4+ T cells, isolated from PBMCs via magnetic separation. Co-cultures were incubated for 2 days in the presence of PD-1-specific Humabody® or control. T cell stimulation was measured by proliferation assay or cytokine quantification from the cell supernatant.

Humabody® 1.57 and 1.92 enhances IL-2 secretion from allogeneic dendritic cell/T cell co-culture in a concentration-dependent manner (FIGS. 7a and b). IL-2 levels were determined after 2 or 3 days by Homogenous Time Resolved Fluorescence assay (HTRF, CisBio).

It was also shown that in the absence of stimulation by dendritic cells, there is no impact of PD-1-specific Humabody® $V_H$ 1.57. This indicates that the Humabody® 1.57 is not eliciting a stimulatory signal directly so the mechanism is proposed to be blockade of the PD-1/PD-L1 inhibitory pathway.

l) Binding Kinetics

Binding kinetics were measured using the methods described below

Binding Kinetics to Human PD-1-huFc Using Surface Plasmon Resonance

Binding kinetics of certain $V_H$ single domain antibodies binding to human PD-1-huFc were measured by surface plasmon resonance (SPR) technology using Biacore T200 instrument (GE Healthcare). Recombinant human PD-1-huFc was immobilized by standard amine coupling to CM5 sensorschip (GE Healthcare) using in range of 0.1-0.01 mg/ml solution of antigen in 10 mM sodium acetate at pH 5.5. For the reference flow cell, a blank immobilisation was carried out. Single cycle kinetics assays were used to study the interaction, a five point, three-fold dilution series of each Humabody® was made with a top concentration of 30 nM. The binding kinetics were followed by flowing the Humabody® over the chip surface in HBS EP+ buffer at a flow rate of 30 μl/min. The contact time for each of the association steps was 180 seconds and the dissociation step was varied between 1200-3600 seconds. The data was fitted to a 1:1 binding model after double reference subtraction using the Biacore T200 Evaluation software. The calculated affinity and kinetic constants are shown in Table 13 below.

TABLE 13

| Humabody ® | ka (1/Ms) | kd (1/s) | KD (M) |
|---|---|---|---|
| 1.1 | 1.09E+05 | 7.35E-05 | 6.76E-10 |
| 1.47 | 1.91E+05 | 9.48E-05 | 4.97E-10 |
| 1.51 | 1.89E+05 | 5.98E-05 | 3.17E-10 |
| 1.52 | 2.05E+05 | 6.14E-05 | 2.99E-10 |
| 1.52 | 2.97E+05 | 7.61E-05 | 2.56E-10 |
| 1.44 | 2.09E+05 | 4.18E-05 | 2.00E-10 |
| 1.44 | 2.35E+05 | 4.00E-05 | 1.70E-10 |
| 1.49 | 2.63E+05 | 2.89E-05 | 1.10E-10 |
| 1.48 | 4.96E+05 | 5.24E-05 | 1.06E-10 |
| 1.54 | 5.30E+05 | 4.53E-05 | 8.56E-11 |
| 1.43 | 4.10E+05 | 2.79E-05 | 6.81E-11 |
| 1.50 | 4.02E+05 | 2.34E-05 | 5.81E-11 |
| 1.41 | 5.37E+05 | 2.96E-05 | 5.52E-11 |
| 1.42 | 5.32E+05 | 2.69E-05 | 5.05E-11 |
| 1.47 | 7.01E+05 | 3.14E-05 | 4.48E-11 |
| 1.55 | 5.35E+05 | 1.95E-05 | 3.64E-11 |
| 1.56 | 4.32E+05 | 1.53E-05 | 3.55E-11 |
| 1.57 | 5.37E+05 | 6.68E-08 | 1.24E-13 |
| 1.92 | 6.2E+05 | 3.67E-05 | 5.9E-11 |

Binding affinity and kinetic constant determination using strep tagged human PD-1

Single cycle kinetics assays were used to study the interaction between human PD-1 with Humabody® on a Biacore T200 instrument (GE Healthcare). Strep tagged recombinant human PD-1 was amine coupled to one flow cell of a CM-5 chip to create a low density surface (14 RU) using standard Biacore reagents. For the reference flow cell, a blank immobilisation was carried out. A five-point, three-fold dilution series of each Humabody® was made with a top concentration of 25 nM. The binding kinetics were followed by flowing the Humabody® over the chip surface in HBS EP+ buffer at a flow rate of 30 μl/min. The contact time for each of the association steps was 180 seconds and the dissociation step was 3300 seconds. The data was fitted to a 1:1 binding model after double reference subtraction using the Biacore T200 Evaluation software. The calculated affinity and kinetic constants are shown in Table 11 below.

TABLE 14

| Humabody ® | ka (1/Ms) | Kd (1/s) | $K_D$ (M) |
|---|---|---|---|
| 1.57 | 4.05E+05 | 3.17E-05 | 7.82E-11 |
| 1.57-4GS-1.57 | 8.88E+05 | 1.54E-05 | 1.73E-11 |
| 1.57-6GS-1.57 | 7.73E+05 | 1.32E-05 | 1.71E-11 |
| 1.57-9GS-1.57 | 6.30E+05 | 1.40E-05 | 2.22E-11 |
| 1.84 | 8.3E+05 | 7.6E-05 | 9.1E-11 |
| 1.104 | 7.8E+05 | 6.3E-05 | 8.0E-11 |
| 1.105 | 9.5E+05 | 8.7E-05 | 9.1E-11 |

TABLE 14-continued

| Humabody® | ka (1/Ms) | Kd (1/s) | $K_D$ (M) |
|---|---|---|---|
| 1.80 | 1.76E+05 | 5.2E−05 | 2.97E−11 |
| 1.77-4GS-non-blocking $V_H$ (3) | 5.5E+05 | 3.5e−05 | 6.3E−11 |
| 1.96 | 1.52E+06 | 1.2E−04 | 8.0E−11 |
| 1.89 | 1.6E+06 | 5.6E−05 | 3.42E−11 |

Non-blocking VH(3) has SEQ ID NO. 589.

Binding Affinity and Kinetic Constant Determination Using Human PD-1-Fc

Single cycle kinetics assays were used to study the interaction between human Fc tagged human PD-1 with Humabody® on a Biacore T200 instrument (GE Healthcare). Protein G was amine coupled to two flow cells of a CM-5 chip. Human Fc tagged recombinant human PD-1 was captured onto one of the flow cells. The other was used as the reference flow cell. A five point, three-fold dilution series of each Humabody® was made with a top concentration within the range of 50 to 150 nM. The binding kinetics were followed by flowing the Humabody® over the chip surface in HBS EP+ buffer at a flow rate of 30 µl/min. The contact time for each of the association steps was 180 seconds and the dissociation step was 3600 seconds. The data was fitted to a 1:1 binding model after double reference subtraction using the Biacore T200 Evaluation software. The calculated affinity and kinetic constants are shown in Table 15 below.

TABLE 15

| Humabody® | ka (1/Ms) | Kd (1/s) | $K_D$ (M) |
|---|---|---|---|
| 1.57 | 4.79 E+5 | 2.11 E−5 | 4.41 E−11 |
| 1.57-9GS-1.57 | 1.36 E+6 | 1.14 E−7 | 8.40 E−14 |
| 1.57-4GS-MSA | 3.40 E+5 | 1.99 E−5 | 5.86 E−11 |
|  | 4.35 E+5 | 2.32 E−5 | 5.33 E−11 |

Example 10. Multivalent Constructs

Multivalent constructs described above were generated by linking isolated $V_H$ nucleic acid sequences using a peptide linker (G4S)$_x$ wherein X is 2, 4, 6 or 9 and proteins were expressed. The techniques used were based on standard molecular biology techniques.

For example, a first blocking Humabody® nucleic acid sequence was linked to a second blocking Humabody® nucleic acid sequence. In one example, the first and second sequence were the same sequences. In another example, sequence the first and second sequence were not the same sequences. Such bivalent binding agents were optionally linked to a half-life extending Humabody® nucleic acid sequence (MSA binder). Constructs were also made and expressed where monovalent $V_H$ single domain antibodies were linked to a half-life extending Humabody® nucleic acid sequence (MSA binder).

Linker sequences used for these constructs are shown below in Table 16.

TABLE 16

| Linker | Peptide sequence | Nucleic acid sequence |
|---|---|---|
| 2GS | GGGGSGGGGS<br>SEQ ID No. 577 | GGAGGTGGAGGTTCAGGTGGAGGTGGTAGT<br>SEQ ID No. 578 |
| 4GS | GGGGSGGGGSGG<br>GGSGGGGS<br>SEQ ID No. 579 | GGAGGTGGAGGTTCAGGAGGTGGTGGTTCT<br>GGTGGTGGCGGTTCAGGTGGAGGTGGTAGT<br>SEQ ID No. 580 |
| 6GS | GGGGSGGGGSGG<br>GGSGGGGSGGGG<br>SGGGGS<br>SEQ ID No. 581 | GGTGGTGGCGGTTCAGGCGGAGGTGGCTCT<br>GGAGGTGGAGGTTCAGGAGGTGGTGGTTCT<br>GGCGGCGGTGGATCGGGTGGAGGTGGTAGT<br>SEQ ID No. 582 |
| 9GS | GGGGSGGGGSGG<br>GGSGGGGSGGGG<br>SGGGGSGGGGSG<br>GGGSGGGGS<br>SEQ ID No. 583 | GGAGGTGGAGGTTCAGGAGGTGGTGGTTCT<br>GGTGGTGGCGGTTCAGGTGGAGGTGGTAGT<br>GGAGGAGGTGGTTCTGGCGGAGGAGGATCG<br>GGTGGAGGTGGCTCAGGTGGTGGAGGTAGT<br>GGAGGCGGTGGCAGC<br>SEQ ID No. 584 |

Serum stability and binding to T cells of the multivalent binding agents was assayed as described in the examples above. Data is shown above.

Example 11 In Vivo Efficacy of Humabody® Compounds in HuGEMM PD-1 Model with Subcutaneous MC38 Mouse Colon Adenocarcinoma PD-1 HuGEMM mice are a genetically engineered mouse model (GEMM) with chimeric human/mouse PD-1 gene (h/mPD-1) containing humanized exon 2 in C57BL/6 mice. Mice were generated by Crown Biosciences and studies were run and performed by Crown.

Compounds administered were 1.57-4GS-MSA binder and Hel4. Compounds were dosed twice weekly intra peritoneal (i.p.).

MC38 mouse colon adenocarcinoma cells from Fudan IBS cell resource center (FDCC) were cultured in DMEM medium (Gibco) supplemented with 10% heat inactivated fetal bovine serum (Kang Yuan Biology) at 37° C. in an atmosphere of 5% $CO_2$ in air. Each mouse was inoculated subcutaneously at the right hind flank with MC38 cells (1×106) for tumor development. Totally 18 mice with desired tumor sizes were enrolled in this study. Mice were randomized into 3 experimental groups after stratification by the tumor sizes. The average tumor size of all these 18 mice was 85 mm3 at randomization. The day of randomization was denoted as day 0. The test articles were administered to the tumor-bearing mice from day 0 through day 14 with the schedule of BIW for 5 doses.

All the procedures related to animal handling, care, and the treatment in this study were performed according to guidelines approved by the Institutional Animal Care and Use Committee (IACUC) of CrownBio following the guidance of the Association for Assessment and Accreditation of Laboratory Animal Care (AAALAC). At the time of routine monitoring, the animals were checked for tumor growth, mobility, food and water consumption, body weight gain/loss, eye/hair matting and any other abnormal behaviours.

Tumor size were measured twice weekly in two dimensions using a caliper, and the volume is expressed in mm3 using the formula: TV=0.5 a×b2, where a and b are the long and short diameters of the tumor, respectively. The tumor size is then used for calculation of TGI (%).

All the data is expressed as Mean±SEM. Statistical analysis of difference in tumor volume was conducted using Repeat measures two-way ANOVA. All data were analyzed using GraphPad Prism 5 and $p<0.05$ was considered to be statistically significant. As shown in FIG. 8, administration of the binding agent reduced tumor volume.

The invention claimed is:

1. An isolated $V_H$ single domain antibody that binds to human programmed cell death 1 protein (PD-1) and blocks the interaction of PD-1 and PD-L1, comprising three complementarity determining regions CDR1, CDR2 and CDR3, wherein the CDR1 sequence comprises SEQ ID NO:438, the CDR2 sequence comprises SEQ ID NO:439, and the CDR3 sequence comprises SEQ ID NO:440.

2. The isolated $V_H$ single domain antibody of claim 1, comprising SEQ ID NO:441.

3. The isolated $V_H$ single domain antibody of claim 1, comprising a sequence with at least 70% homology to SEQ ID NO:441.

4. The isolated $V_H$ single domain antibody of claim 1, comprising a sequence with at least 80% homology to SEQ ID NO:441.

5. The isolated $V_H$ single domain antibody of claim 1, comprising a sequence with at least 90% homology to SEQ ID NO:441.

6. The isolated $V_H$ single domain antibody of claim 1, wherein said single domain antibody is conjugated to a single domain antibody that binds to human serum albumin.

7. The isolated $V_H$ single domain antibody of claim 1 obtained or obtainable from a transgenic rodent that expresses a transgene comprising human V, D and J regions, optionally wherein said rodent does not produce any functional endogenous light and heavy chains.

8. An isolated binding agent comprising the single domain antibody of claim 1.

9. The isolated binding agent of claim 8, wherein said single domain antibody is linked to a second antibody or an antibody fragment, wherein said second antibody or antibody fragment binds to and is an inhibitor of an immune checkpoint molecule selected from the group consisting of PD-L1, PD-L2, CTLA-4, TIM-3, LAG-3, CEACAM, VISTA, BTLA, TIGIT, LAIR1, CD160, 2B4 and TGFR beta.

10. The isolated binding agent of claim 9, wherein the immune checkpoint molecule is LAG-3.

11. The isolated binding agent of claim 8, wherein said single domain antibody is linked to a second antibody or an antibody fragment, wherein said second antibody or antibody fragment binds to and is an activator of a costimulatory molecule selected from the group consisting of an agonist of one or more of IL 2, IL-12, OX40, OX4OL, CD2, CD3, CD27, ICAM-1, LFA-1, CD11a, CD18, ICOS (CD278), 4-1 BB (CD137), GITR, CD30, CD40, BAFFR, HVEM, CD7, LIGHT, NKG2C, SLAMF7, NKp80, CD160, B7-H3, B7-H4 or CD83 ligand, CD8, CD28, CD4 and ICAM-1.

12. An immunoconjugate comprising the single domain antibody of claim 1 linked to a therapeutic agent, optionally wherein said therapeutic agent is a toxin, enzyme, radioisotope or other chemical moiety.

13. A pharmaceutical composition comprising the single domain antibody of claim 1 and a pharmaceutical carrier.

14. A kit comprising the single domain antibody of claim 1.

15. A bispecific molecule comprising the single domain antibody of claim 1 linked to a second functional moiety having a different binding specificity than said single domain antibody, wherein said second moiety is an antibody or an antibody fragment, wherein said second moiety binds to and is an inhibitor of an immune checkpoint molecule selected from the group consisting of PD-L1, PD-L2, CTLA-4, TIM-3, LAG-3, CEACAM, VISTA, BTLA, TIGIT, LAIR1, CD160, 2B4 and TGFR beta.

16. The bispecific molecule of claim 15, wherein the immune checkpoint molecule is LAG-3.

17. A bispecific molecule comprising the single domain antibody of claim 1 linked to a second functional moiety having a different binding specificity than said single domain antibody, wherein said second moiety is an antibody or an antibody fragment that binds to a costimulatory molecule selected from the group consisting of IL 2, IL-12, OX40, OX4OL, CD2, CD3, CD27, ICAM-1, LFA-1, CD11a, CD18, ICOS (CD278), 4-1 BB (CD137), GITR, CD30, CD40, BAFFR, HVEM, CD7, LIGHT, NKG2C, SLAMF7, NKp80, CD160, B7-H3, B7-H4 or CD83 ligand, CD8, CD28, CD4 and ICAM-1.

* * * * *

SEQUENCE LISTING

```
<160> NUMBER OF SEQ ID NOS: 589

<210> SEQ ID NO 1
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 4"

<400> SEQUENCE: 1

Asp Tyr Thr Met Thr
1               5

<210> SEQ ID NO 2
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 4"

<400> SEQUENCE: 2

Tyr Ile Ser Thr Gly Gly Thr Ile Lys Tyr Tyr Thr Asp Ser Val Lys
1               5                   10                  15

Gly

<210> SEQ ID NO 3
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 4"

<400> SEQUENCE: 3

Glu Ala Pro Leu Arg Leu Gly Glu Ser Pro His Asp Ala Phe Asp Ile
1               5                   10                  15

<210> SEQ ID NO 4
<211> LENGTH: 125
<212> TYPE: PRT
<213> ORGANISM: Homo sapiens
<220> FEATURE:
<221> NAME/KEY: source
<223> OTHER INFORMATION: /note="VH 1.1"

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
            35                  40                  45
Ser Tyr Ile Ser Thr Gly Gly Thr Ile Lys Tyr Tyr Thr Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Val Tyr Tyr Cys
                 85                  90                  95
Ala Arg Glu Ala Pro Leu Arg Leu Gly Glu Ser Pro His Asp Ala Phe
            100                 105                 110
Asp Ile Trp Gly Gln Gly Thr Met Val Thr Val Ser Ser
        115                 120                 125

<210> SEQ ID NO 5
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 8"

<400> SEQUENCE: 5

Asp Tyr Thr Met Thr
 1               5

<210> SEQ ID NO 6
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 8"

<400> SEQUENCE: 6

Tyr Ile Ser Thr Gly Gly Ser Ile Lys Tyr Tyr Thr Asp Ser Val Lys
 1               5                  10                  15
Gly

<210> SEQ ID NO 7
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 8"

<400> SEQUENCE: 7

Glu Ala Pro Leu Arg Leu Gly Glu Ser Pro His Asp Ala Phe Asp Ile
 1               5                  10                  15

<210> SEQ ID NO 8
<211> LENGTH: 125
<212> TYPE: PRT
<213> ORGANISM: Homo sapiens
<220> FEATURE:
<221> NAME/KEY: source
<223> OTHER INFORMATION: /note="VH 1.2"

<400> SEQUENCE: 8

Glu Val Gln Leu Leu Glu Ser Gly Gly Gly Leu Val Lys Pro Gly Gly
 1               5                  10                  15
Ser Leu Arg Leu Ser Cys Ala Ala Ser Gly Phe Thr Phe Ser Asp Tyr
             20                  25                  30
Thr Met Thr Trp Met Arg Gln Ala Pro Gly Lys Gly Leu Glu Trp Val
```

```
                    35                  40                  45
Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 9
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 12"

<400> SEQUENCE: 9

Asp Tyr Thr Met Thr
1               5

<210> SEQ ID NO 10
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 12"

<400> SEQUENCE: 10

Tyr Ile Ser Thr Gly Gly Ser Ile Lys Tyr Tyr Thr Asp Ser Val Lys
1               5                   10                  15

Gly

<210> SEQ ID NO 11
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 12"

<400> SEQUENCE: 11

Glu Ala Pro Leu Arg Leu Gly Glu Ser Pro His Asp Ala Phe Asp Ile
1               5                   10                  15

<210> SEQ ID NO 12
<211> LENGTH: 125
<212> TYPE: PRT
<213> ORGANISM: Homo sapiens
<220> FEATURE:
<221> NAME/KEY: source
<223> OTHER INFORMATION: /note="VH 1.3"

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 13
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 16"

<400> SEQUENCE: 13

Asp Tyr Tyr Met Ile
1               5

<210> SEQ ID NO 14
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 16"

<400> SEQUENCE: 14

Tyr Ile Ser Gly Gly Gly Thr Thr Lys Tyr Tyr Thr Asp Ser Val Lys
1               5                   10                  15

Gly

<210> SEQ ID NO 15
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 16"

<400> SEQUENCE: 15

Glu Ala Pro Leu Arg Leu Gly Glu Thr Pro His Asp Ala Phe Asp Ile
1               5                   10                  15

<210> SEQ ID NO 16
<211> LENGTH: 125
<212> TYPE: PRT
<213> ORGANISM: Homo sapiens
<220> FEATURE:
<221> NAME/KEY: source
<223> OTHER INFORMATION: /note="VH 1.4"

<400> SEQUENCE: 16

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ile Trp Met Arg Gln Ala Pro Gly Lys Gly Leu Glu Trp Val
```

```
                35                  40                  45
Ser Tyr Ile Ser Gly Gly Thr Thr Lys Tyr Tyr Thr Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Thr Pro His Asp Ala Phe
            100                 105                 110

Asp Ile Trp Gly Gln Gly Thr Met Val Thr Val Ser Ser
        115                 120                 125

<210> SEQ ID NO 17
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 20"

<400> SEQUENCE: 17

Asp Tyr Thr Met Thr
 1               5

<210> SEQ ID NO 18
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 20"

<400> SEQUENCE: 18

Tyr Ile Ser Thr Gly Gly Asn Thr Lys Tyr Tyr Thr Asp Ser Val Lys
 1               5                  10                  15

Gly

<210> SEQ ID NO 19
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 20"

<400> SEQUENCE: 19

Glu Ala Pro Leu Arg Leu Gly Glu Ser Pro His Asp Ala Phe Asp Ile
 1               5                  10                  15

<210> SEQ ID NO 20
<211> LENGTH: 125
<212> TYPE: PRT
<213> ORGANISM: Homo sapiens
<220> FEATURE:
<221> NAME/KEY: source
<223> OTHER INFORMATION: /note="VH 1.5"

<400> SEQUENCE: 20

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Asn Thr Lys Tyr Tyr Thr Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Trp Gly Gln Gly Thr Met Val Thr Val Ser Ser
        115                 120                 125

<210> SEQ ID NO 21
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 24"

<400> SEQUENCE: 21

Asp Tyr Thr Met Thr
1               5

<210> SEQ ID NO 22
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 24"

<400> SEQUENCE: 22

Tyr Ile Ser Thr Gly Gly Thr Ile Lys Tyr Tyr Thr Asp Ser Val Lys
1               5                   10                  15
Gly

<210> SEQ ID NO 23
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 24"

<400> SEQUENCE: 23

Glu Ala Pro Leu Arg Leu Gly Glu Ser Pro His Asp Ala Phe Asp Ile
1               5                   10                  15

<210> SEQ ID NO 24
<211> LENGTH: 125
<212> TYPE: PRT
<213> ORGANISM: Homo sapiens
<220> FEATURE:
<221> NAME/KEY: source
<223> OTHER INFORMATION: /note="VH 1.6"

<400> SEQUENCE: 24

Glu Val Gln Leu Leu Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 25
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 28"

<400> SEQUENCE: 25

Asp Tyr Thr Met Thr
1               5

<210> SEQ ID NO 26
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 28"

<400> SEQUENCE: 26

Tyr Ile Ser Thr Gly Gly Thr Ile Lys Tyr Tyr Thr Asp Ser Val Lys
1               5                  10                  15

Gly

<210> SEQ ID NO 27
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 28"

<400> SEQUENCE: 27

Glu Ala Pro Leu Arg Leu Gly Glu Ser Pro His Asp Ala Phe Asp Ile
1               5                  10                  15

<210> SEQ ID NO 28
<211> LENGTH: 125
<212> TYPE: PRT
<213> ORGANISM: Homo sapiens
<220> FEATURE:
<221> NAME/KEY: source
<223> OTHER INFORMATION: /note="VH 1.7"

<400> SEQUENCE: 28

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 29
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 32"

<400> SEQUENCE: 29

Asp Tyr Thr Met Thr
 1               5

<210> SEQ ID NO 30
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 32"

<400> SEQUENCE: 30

Tyr Ile Ser Thr Gly Gly Ser Ile Lys Tyr Tyr Thr Asp Ser Val Lys
 1               5                  10                  15

Gly

<210> SEQ ID NO 31
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 32"

<400> SEQUENCE: 31

Glu Ala Pro Leu Arg Leu Gly Glu Ser Pro His Asp Ala Phe Asp Ile
 1               5                  10                  15

<210> SEQ ID NO 32
<211> LENGTH: 125
<212> TYPE: PRT
<213> ORGANISM: Homo sapiens
<220> FEATURE:
<221> NAME/KEY: source
<223> OTHER INFORMATION: /note="VH 1.8"

<400> SEQUENCE: 32

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Gly Asp Thr Ala Val Tyr Tyr Cys
                 85                  90                  95
Ala Arg Glu Ala Pro Leu Arg Leu Gly Glu Ser Pro His Asp Ala Phe
            100                 105                 110
Asp Ile Trp Gly Gln Gly Thr Met Val Thr Val Ser Ser
        115                 120                 125
```

<210> SEQ ID NO 33
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 36"

<400> SEQUENCE: 33

```
Asp Tyr Thr Met Thr
 1               5
```

<210> SEQ ID NO 34
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 36"

<400> SEQUENCE: 34

```
Tyr Ile Ser Thr Gly Gly Thr Ile Lys Tyr Tyr Thr Asp Ser Val Lys
 1               5                  10                  15
Gly
```

<210> SEQ ID NO 35
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 36"

<400> SEQUENCE: 35

```
Glu Ala Pro Leu Arg Leu Gly Glu Ser Pro His Asp Ala Phe Asp Ile
 1               5                  10                  15
```

<210> SEQ ID NO 36
<211> LENGTH: 125
<212> TYPE: PRT
<213> ORGANISM: Homo sapiens
<220> FEATURE:
<221> NAME/KEY: source
<223> OTHER INFORMATION: /note="VH 1.9"

<400> SEQUENCE: 36

```
Gln Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Gly Asp Tyr
             20                  25                  30
Thr Met Thr Trp Met Arg Gln Ala Pro Gly Lys Gly Leu Glu Trp Val
```

```
                    35                  40                  45
Ser Tyr Ile Ser Thr Gly Gly Thr Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asp Ser Leu Arg Ala Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 37
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 40"

<400> SEQUENCE: 37

Asp Tyr Thr Met Ser
 1               5

<210> SEQ ID NO 38
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 40"

<400> SEQUENCE: 38

Tyr Ile Ser Leu Gly Gly Asn Thr Lys Tyr Tyr Thr Asp Ser Val Lys
 1               5                  10                  15
Gly

<210> SEQ ID NO 39
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 40"

<400> SEQUENCE: 39

Glu Ala Pro Leu Arg Leu Gly Glu Ser Pro His Asp Ala Phe Asp Ile
 1               5                  10                  15

<210> SEQ ID NO 40
<211> LENGTH: 125
<212> TYPE: PRT
<213> ORGANISM: Homo sapiens
<220> FEATURE:
<221> NAME/KEY: source
<223> OTHER INFORMATION: /note="VH 1.10"

<400> SEQUENCE: 40

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Ser Trp Met Arg Gln Ala Pro Gly Lys Gly Leu Glu Trp Ile
```

```
                35                  40                  45
Ser Tyr Ile Ser Leu Gly Gly Asn Thr Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 41
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 44"

<400> SEQUENCE: 41

Asp Tyr Asp Met Thr
 1               5

<210> SEQ ID NO 42
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 44"

<400> SEQUENCE: 42

Tyr Ile Ser Arg Gly Gly Ser Thr Lys Tyr Tyr Ala Asp Ser Val Lys
 1               5                  10                  15

Gly

<210> SEQ ID NO 43
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 44"

<400> SEQUENCE: 43

Glu Ala Pro Leu Arg Leu Gly Glu Thr Pro His Asp Ala Phe Asp Ile
 1               5                  10                  15

<210> SEQ ID NO 44
<211> LENGTH: 125
<212> TYPE: PRT
<213> ORGANISM: Homo sapiens
<220> FEATURE:
<221> NAME/KEY: source
<223> OTHER INFORMATION: /note="VH 1.11"

<400> SEQUENCE: 44

Glu Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Asp Met Thr Trp Ile Arg Gln Ala Pro Gly Lys Gly Gln Glu Trp Val
```

```
                35                  40                  45
Ser Tyr Ile Ser Arg Gly Gly Ser Thr Lys Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Thr Pro His Asp Ala Phe
            100                 105                 110

Asp Ile Trp Gly Gln Gly Thr Met Val Thr Val Ser Ser
        115                 120                 125

<210> SEQ ID NO 45
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 48"

<400> SEQUENCE: 45

Asp Tyr Tyr Met Gly
1               5

<210> SEQ ID NO 46
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 48"

<400> SEQUENCE: 46

Tyr Ile Ser Ser Ser Gly Ser Thr Ile Tyr Tyr Ala Asp Ser Val Lys
1               5                   10                  15
Gly

<210> SEQ ID NO 47
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 48"

<400> SEQUENCE: 47

Glu Ala Pro Leu Arg Leu Gly Glu Ser Pro His Asp Ala Phe Asp Ile
1               5                   10                  15

<210> SEQ ID NO 48
<211> LENGTH: 125
<212> TYPE: PRT
<213> ORGANISM: Homo sapiens
<220> FEATURE:
<221> NAME/KEY: source
<223> OTHER INFORMATION: /note="VH 1.12"

<400> SEQUENCE: 48

Glu Val Gln Leu Leu Glu Ser Gly Gly Gly Val Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Gly Trp Ile Arg Gln Ala Pro Gly Lys Gly Leu Glu Trp Ile
```

```
                35                  40                  45
Ser Tyr Ile Ser Ser Gly Ser Thr Ile Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 49
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 52"

<400> SEQUENCE: 49

Asp Tyr Thr Met Thr
 1               5

<210> SEQ ID NO 50
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 52"

<400> SEQUENCE: 50

Tyr Ile Ser Thr Gly Gly Thr Ile Lys Tyr Tyr Thr Asp Ser Val Lys
 1               5                  10                  15

Gly

<210> SEQ ID NO 51
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 52"

<400> SEQUENCE: 51

Glu Ala Pro Leu Arg Leu Gly Glu Ser Pro His Asp Ala Phe Asp Ile
 1               5                  10                  15

<210> SEQ ID NO 52
<211> LENGTH: 125
<212> TYPE: PRT
<213> ORGANISM: Homo sapiens
<220> FEATURE:
<221> NAME/KEY: source
<223> OTHER INFORMATION: /note="VH 1.13"

<400> SEQUENCE: 52

Glu Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 53
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 56"

<400> SEQUENCE: 53

Asp Tyr Thr Met Thr
 1               5

<210> SEQ ID NO 54
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 56"

<400> SEQUENCE: 54

Tyr Ile Ser Thr Gly Gly Thr Ile Lys Tyr Tyr Thr Asp Ser Val Lys
 1               5                  10                  15

Gly

<210> SEQ ID NO 55
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 56"

<400> SEQUENCE: 55

Glu Ala Pro Leu Arg Leu Gly Glu Ser Pro His Asp Ala Phe Asp Ile
 1               5                  10                  15

<210> SEQ ID NO 56
<211> LENGTH: 125
<212> TYPE: PRT
<213> ORGANISM: Homo sapiens
<220> FEATURE:
<221> NAME/KEY: source
<223> OTHER INFORMATION: /note="VH 1.14"

<400> SEQUENCE: 56

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 57
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 60"

<400> SEQUENCE: 57

Asp Asn Ser Met Ser
 1               5

<210> SEQ ID NO 58
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 60"

<400> SEQUENCE: 58

Tyr Ile Ser Ser Ser Gly Ser Thr Ile Tyr Tyr Ala Asp Ser Val Lys
 1               5                  10                  15

Gly

<210> SEQ ID NO 59
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 60"

<400> SEQUENCE: 59

Glu Ala Pro Leu Arg Leu Gly Glu Ser Pro His Asp Ala Phe Asp Ile
 1               5                  10                  15

<210> SEQ ID NO 60
<211> LENGTH: 125
<212> TYPE: PRT
<213> ORGANISM: Homo sapiens
<220> FEATURE:
<221> NAME/KEY: source
<223> OTHER INFORMATION: /note="VH 1.15"

<400> SEQUENCE: 60

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Asn
             20                  25                  30

Ser Met Ser Trp Ile Arg Gln Ala Pro Gly Lys Gly Leu Glu Trp Val
```

```
                    35                  40                  45
Ser Tyr Ile Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Thr Leu Arg Ala Glu Asp Thr Ala Val Tyr Tyr Cys
                 85                  90                  95

Ala Lys Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125
```

<210> SEQ ID NO 61
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 64"

<400> SEQUENCE: 61

```
Asp Tyr Thr Met Ser
 1               5
```

<210> SEQ ID NO 62
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 64"

<400> SEQUENCE: 62

```
Tyr Ile Ser Thr Gly Gly Ser Ile Lys Tyr Tyr Thr Asp Ser Val Lys
 1               5                  10                  15

Gly
```

<210> SEQ ID NO 63
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 64"

<400> SEQUENCE: 63

```
Glu Ala Pro Leu Arg Leu Gly Glu Ser Pro His Asp Ala Phe Asp Ile
 1               5                  10                  15
```

<210> SEQ ID NO 64
<211> LENGTH: 125
<212> TYPE: PRT
<213> ORGANISM: Homo sapiens
<220> FEATURE:
<221> NAME/KEY: source
<223> OTHER INFORMATION: /note="VH 1.16"

<400> SEQUENCE: 64

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Thr Met Ser Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 65
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 68"

<400> SEQUENCE: 65

Asp Tyr Thr Met Thr
1               5

<210> SEQ ID NO 66
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 68"

<400> SEQUENCE: 66

Tyr Ile Ser Thr Gly Gly Ser Ile Lys Tyr Tyr Thr Asp Ser Val Lys
1               5                   10                  15

Gly

<210> SEQ ID NO 67
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 68"

<400> SEQUENCE: 67

Glu Ala Pro Leu Arg Leu Gly Glu Ser Pro His Asp Ala Phe Asp Ile
1               5                   10                  15

<210> SEQ ID NO 68
<211> LENGTH: 125
<212> TYPE: PRT
<213> ORGANISM: Homo sapiens
<220> FEATURE:
<221> NAME/KEY: source
<223> OTHER INFORMATION: /note="VH 1.17"

<400> SEQUENCE: 68

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Val Asp Asp Thr Ala Val Tyr Tyr Cys
                 85                  90                  95
Ala Arg Glu Ala Pro Leu Arg Leu Gly Glu Ser Pro His Asp Ala Phe
            100                 105                 110
Asp Ile Trp Gly Gln Gly Thr Met Val Thr Val Ser Ser
        115                 120                 125

<210> SEQ ID NO 69
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 72"

<400> SEQUENCE: 69

Asp Tyr Thr Met Thr
 1               5

<210> SEQ ID NO 70
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 72"

<400> SEQUENCE: 70

Tyr Ile Ser Thr Gly Gly Thr Ile Lys Tyr Tyr Thr Asp Ser Val Lys
 1               5                  10                  15

Gly

<210> SEQ ID NO 71
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 72"

<400> SEQUENCE: 71

Glu Ala Pro Leu Arg Leu Gly Glu Ser Pro His Asp Ala Phe Asp Ile
 1               5                  10                  15

<210> SEQ ID NO 72
<211> LENGTH: 125
<212> TYPE: PRT
<213> ORGANISM: Homo sapiens
<220> FEATURE:
<221> NAME/KEY: source
<223> OTHER INFORMATION: /note="VH 1.18"

<400> SEQUENCE: 72

Gln Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 73
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 76"

<400> SEQUENCE: 73

Asp Tyr Thr Met Thr
 1               5

<210> SEQ ID NO 74
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 76"

<400> SEQUENCE: 74

Tyr Ile Ser Thr Gly Gly Ser Ile Lys Tyr Tyr Thr Asp Ser Val Lys
 1               5                  10                  15

Gly

<210> SEQ ID NO 75
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 76"

<400> SEQUENCE: 75

Glu Ala Pro Leu Arg Leu Gly Glu Thr Pro His Asp Ala Phe Asp Ile
 1               5                  10                  15

<210> SEQ ID NO 76
<211> LENGTH: 125
<212> TYPE: PRT
<213> ORGANISM: Homo sapiens
<220> FEATURE:
<221> NAME/KEY: source
<223> OTHER INFORMATION: /note="VH 1.19"

<400> SEQUENCE: 76

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Thr Met Thr Trp Met Arg Gln Ala Pro Gly Lys Gly Leu Glu Trp Val
```

```
                    35                  40                  45
Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Thr Pro His Asp Ala Phe
            100                 105                 110

Asp Ile Trp Gly Gln Gly Thr Met Val Thr Val Ser Ser
        115                 120                 125

<210> SEQ ID NO 77
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 80"

<400> SEQUENCE: 77

Asp Tyr Thr Met Thr
1               5

<210> SEQ ID NO 78
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 80"

<400> SEQUENCE: 78

Tyr Ile Ser Ser Gly Gly Ser Ile Lys Phe Tyr Ala Asp Ser Val Lys
1               5                   10                  15

Gly

<210> SEQ ID NO 79
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 80"

<400> SEQUENCE: 79

Glu Ala Pro Leu Arg Leu Gly Glu Ser Pro His Asp Ala Phe Asp Ile
1               5                   10                  15

<210> SEQ ID NO 80
<211> LENGTH: 125
<212> TYPE: PRT
<213> ORGANISM: Homo sapiens
<220> FEATURE:
<221> NAME/KEY: source
<223> OTHER INFORMATION: /note="VH 1.20"

<400> SEQUENCE: 80

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Ser Gly Gly Ser Ile Lys Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 81
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 84"

<400> SEQUENCE: 81

Asp Tyr Thr Met Thr
1               5

<210> SEQ ID NO 82
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 84"

<400> SEQUENCE: 82

Tyr Ile Ser Thr Gly Gly Ser Ile Lys Tyr Tyr Thr Asp Ser Val Lys
1               5                   10                  15

Gly

<210> SEQ ID NO 83
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 84"

<400> SEQUENCE: 83

Glu Ala Pro Leu Arg Leu Gly Glu Ser Pro His Asp Ala Phe Asp Thr
1               5                   10                  15

<210> SEQ ID NO 84
<211> LENGTH: 125
<212> TYPE: PRT
<213> ORGANISM: Homo sapiens
<220> FEATURE:
<221> NAME/KEY: source
<223> OTHER INFORMATION: /note="VH 1.21"

<400> SEQUENCE: 84

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Thr Trp Gly Gln Gly Thr Met Val Thr Val Ser Ser
        115                 120                 125

<210> SEQ ID NO 85
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 88"

<400> SEQUENCE: 85

Asp Tyr Thr Met Thr
1               5

<210> SEQ ID NO 86
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 88"

<400> SEQUENCE: 86

Tyr Ile Ser Thr Gly Gly Ser Ile Lys Tyr Tyr Thr Asp Ser Val Lys
1               5                   10                  15

Gly

<210> SEQ ID NO 87
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 88"

<400> SEQUENCE: 87

Glu Ala Pro Leu Arg Leu Gly Glu Ser Pro His Asp Ala Phe Asp Ile
1               5                   10                  15

<210> SEQ ID NO 88
<211> LENGTH: 125
<212> TYPE: PRT
<213> ORGANISM: Homo sapiens
<220> FEATURE:
<221> NAME/KEY: source
<223> OTHER INFORMATION: /note="VH 1.22"

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 89
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 92"

<400> SEQUENCE: 89

Asp Tyr Thr Met Ser
 1               5

<210> SEQ ID NO 90
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 92"

<400> SEQUENCE: 90

Tyr Ile Ser Thr Gly Gly Thr Ile Lys Tyr Tyr Thr Asp Ser Val Lys
 1               5                  10                  15

Gly

<210> SEQ ID NO 91
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 92"

<400> SEQUENCE: 91

Glu Ala Pro Leu Arg Leu Gly Glu Ser Pro His Asp Ala Phe Asp Ile
 1               5                  10                  15

<210> SEQ ID NO 92
<211> LENGTH: 125
<212> TYPE: PRT
<213> ORGANISM: Homo sapiens
<220> FEATURE:
<221> NAME/KEY: source
<223> OTHER INFORMATION: /note="VH 1.23"

<400> SEQUENCE: 92

Gln Ile Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Ser Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 93
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 96"

<400> SEQUENCE: 93

Asp Tyr Asp Met Tyr
1               5

<210> SEQ ID NO 94
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 96"

<400> SEQUENCE: 94

Tyr Ile Ser Arg Gly Gly Ser Val Thr Tyr Tyr Ala Asp Ser Val Lys
1               5                   10                  15

Gly

<210> SEQ ID NO 95
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 96"

<400> SEQUENCE: 95

Glu Ala Pro Leu Arg Leu Gly Glu Thr Pro His Ala Ala Phe Asp Ile
1               5                   10                  15

<210> SEQ ID NO 96
<211> LENGTH: 125
<212> TYPE: PRT
<213> ORGANISM: Homo sapiens
<220> FEATURE:
<221> NAME/KEY: source
<223> OTHER INFORMATION: /note="VH 1.24"

<400> SEQUENCE: 96

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Asp Met Tyr Trp Ile Arg Gln Ala Pro Gly Lys Gly Leu Glu Trp Val
```

```
                35                  40                  45
Ser Tyr Ile Ser Arg Gly Gly Ser Val Thr Tyr Tyr Ala Asp Ser Val
        50                  55                  60

Lys Gly Arg Phe Thr Ile Ser Arg Asp Asn Ala Lys Asn Ala Leu Tyr
 65                  70                  75                  80

Leu Gln Met Asn Ser Leu Arg Ala Glu Asp Met Ala Val Tyr Phe Cys
                85                  90                  95

Ala Thr Glu Ala Pro Leu Arg Leu Gly Glu Thr Pro His Ala Ala Phe
            100                 105                 110

Asp Ile Trp Gly Gln Gly Thr Met Val Thr Val Ser Ser
        115                 120                 125
```

<210> SEQ ID NO 97
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 100"

<400> SEQUENCE: 97

```
Asp Tyr Tyr Met Ser
 1               5
```

<210> SEQ ID NO 98
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 100"

<400> SEQUENCE: 98

```
Phe Ile Ser Ser Ser Gly Ser Thr Thr Tyr Tyr Ala Asp Ser Val Lys
 1               5                  10                  15

Gly
```

<210> SEQ ID NO 99
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 100"

<400> SEQUENCE: 99

```
Glu Ala Pro Leu Arg Leu Gly Glu Ser Pro His Asp Ala Phe Asp Phe
 1               5                  10                  15
```

<210> SEQ ID NO 100
<211> LENGTH: 125
<212> TYPE: PRT
<213> ORGANISM: Homo sapiens
<220> FEATURE:
<221> NAME/KEY: source
<223> OTHER INFORMATION: /note="VH 1.25"

<400> SEQUENCE: 100

```
Gln Val Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Phe Arg Gln Ala Pro Gly Lys Glu Arg Glu Trp Ile
```

```
                35                  40                  45
Ser Phe Ile Ser Ser Ser Gly Ser Thr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Phe Trp Gly Gln Gly Thr Met Val Thr Val Ser Ser
            115                 120                 125

<210> SEQ ID NO 101
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 104"

<400> SEQUENCE: 101

Asp Asn Ser Met Ser
1               5

<210> SEQ ID NO 102
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 104"

<400> SEQUENCE: 102

Tyr Ile Ser Ser Ser Gly Ser Thr Ile Tyr Tyr Ala Asp Ser Val Lys
1               5                   10                  15
Gly

<210> SEQ ID NO 103
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 104"

<400> SEQUENCE: 103

Glu Ala Pro Leu Arg Leu Gly Glu Ser Pro His Asp Ala Phe Asp Ile
1               5                   10                  15

<210> SEQ ID NO 104
<211> LENGTH: 125
<212> TYPE: PRT
<213> ORGANISM: Homo sapiens
<220> FEATURE:
<221> NAME/KEY: source
<223> OTHER INFORMATION: /note="VH 1.26"

<400> SEQUENCE: 104

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Ser Trp Ile Arg Gln Ala Pro Gly Lys Gly Leu Glu Trp Val
```

```
                35                  40                  45
Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Thr Leu Arg Ala Glu Asp Thr Ala Val Tyr Tyr Cys
                 85                  90                  95

Ala Lys Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 105
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 108"

<400> SEQUENCE: 105

Asp Tyr Thr Met Thr
 1               5

<210> SEQ ID NO 106
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 108"

<400> SEQUENCE: 106

Tyr Ile Ser Thr Gly Gly Ser Ile Lys Tyr Tyr Thr Asp Ser Val Lys
 1               5                  10                  15

Gly

<210> SEQ ID NO 107
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 108"

<400> SEQUENCE: 107

Glu Ala Pro Leu Arg Leu Gly Glu Ser Pro His Asp Ala Phe Asp Ile
 1               5                  10                  15

<210> SEQ ID NO 108
<211> LENGTH: 125
<212> TYPE: PRT
<213> ORGANISM: Homo sapiens
<220> FEATURE:
<221> NAME/KEY: source
<223> OTHER INFORMATION: /note="VH 1.27"

<400> SEQUENCE: 108

Gln Val Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                    35                  40                  45
Ser Tyr Ile Ser Thr Gly Gly Ser Ile Lys Tyr Tyr Thr Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                    85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 109
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 112"

<400> SEQUENCE: 109

Asp Tyr Asp Met Tyr
 1               5

<210> SEQ ID NO 110
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 112"

<400> SEQUENCE: 110

Tyr Ile Ser Arg Gly Gly Ser Val Thr Tyr Tyr Ala Asp Ser Val Lys
 1               5                  10                  15
Gly

<210> SEQ ID NO 111
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 112"

<400> SEQUENCE: 111

Glu Ala Pro Leu Arg Leu Gly Glu Thr Pro His Ala Ala Phe Asp Ile
 1               5                  10                  15

<210> SEQ ID NO 112
<211> LENGTH: 125
<212> TYPE: PRT
<213> ORGANISM: Homo sapiens
<220> FEATURE:
<221> NAME/KEY: source
<223> OTHER INFORMATION: /note="VH 1.28"

<400> SEQUENCE: 112

Gln Ile Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Asp Met Tyr Trp Ile Arg Gln Ala Pro Gly Lys Gly Leu Glu Trp Val
```

```
                35                  40                  45
Ser Tyr Ile Ser Arg Gly Gly Ser Val Thr Tyr Tyr Ala Asp Ser Val
 50                  55                  60

Lys Gly Arg Phe Thr Ile Ser Arg Asp Asn Ala Lys Asn Ala Leu Tyr
 65                  70                  75                  80

Leu Gln Met Asn Ser Leu Arg Ala Glu Asp Met Ala Val Tyr Phe Cys
                 85                  90                  95

Ala Thr Glu Ala Pro Leu Arg Leu Gly Glu Thr Pro His Ala Ala Phe
            100                 105                 110

Asp Ile Trp Gly Gln Gly Thr Met Val Thr Val Ser Ser
        115                 120                 125
```

<210> SEQ ID NO 113
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 116"

<400> SEQUENCE: 113

```
Asp Tyr Thr Met Ser
 1               5
```

<210> SEQ ID NO 114
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 116"

<400> SEQUENCE: 114

```
Tyr Ile Ser Thr Gly Gly Thr Ile Lys Tyr Tyr Thr Asp Ser Val Lys
 1               5                  10                  15

Gly
```

<210> SEQ ID NO 115
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 116"

<400> SEQUENCE: 115

```
Glu Ala Pro Leu Arg Leu Gly Glu Ser Pro His Asp Ala Phe Asp Ile
 1               5                  10                  15
```

<210> SEQ ID NO 116
<211> LENGTH: 125
<212> TYPE: PRT
<213> ORGANISM: Homo sapiens
<220> FEATURE:
<221> NAME/KEY: source
<223> OTHER INFORMATION: /note="VH 1.29"

<400> SEQUENCE: 116

```
Gln Val Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Thr Met Ser Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 117
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 120"

<400> SEQUENCE: 117

Asp Tyr Thr Met Thr
1               5

<210> SEQ ID NO 118
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 120"

<400> SEQUENCE: 118

Tyr Ile Ser Thr Gly Gly Ser Ile Lys Tyr Tyr Thr Asp Ser Val Lys
1               5                   10                  15

Gly

<210> SEQ ID NO 119
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 120"

<400> SEQUENCE: 119

Glu Ala Pro Leu Arg Leu Gly Glu Ser Pro His Asp Ala Phe Asp Ile
1               5                   10                  15

<210> SEQ ID NO 120
<211> LENGTH: 125
<212> TYPE: PRT
<213> ORGANISM: Homo sapiens
<220> FEATURE:
<221> NAME/KEY: source
<223> OTHER INFORMATION: /note="VH 1.30"

<400> SEQUENCE: 120

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
     50                  55                  60

Lys Gly Arg Phe Thr Ile Ser Arg Asp Asn Ala Arg Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 121
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 124"

<400> SEQUENCE: 121

Asp Tyr Thr Met Thr
1               5

<210> SEQ ID NO 122
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 124"

<400> SEQUENCE: 122

Tyr Ile Ser Thr Gly Gly Ser Thr Lys Tyr Tyr Thr Asp Ser Val Lys
1               5                   10                  15

Gly

<210> SEQ ID NO 123
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 124"

<400> SEQUENCE: 123

Glu Ala Pro Leu Arg Leu Gly Glu Ser Pro His Asp Ala Phe Asp Ile
1               5                   10                  15

<210> SEQ ID NO 124
<211> LENGTH: 125
<212> TYPE: PRT
<213> ORGANISM: Homo sapiens
<220> FEATURE:
<221> NAME/KEY: source
<223> OTHER INFORMATION: /note="VH 1.31"

<400> SEQUENCE: 124

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                    35                  40                  45
Ser Tyr Ile Ser Thr Gly Gly Ser Thr Lys Tyr Tyr Thr Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 125
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 128"

<400> SEQUENCE: 125

Asp Asp Tyr Met Met
 1               5

<210> SEQ ID NO 126
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 128"

<400> SEQUENCE: 126

Tyr Ile Ser Ser Gly Gly Ser Ile Ile Tyr Tyr Ala Asp Ser Val Lys
 1               5                  10                  15
Gly

<210> SEQ ID NO 127
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 128"

<400> SEQUENCE: 127

Glu Ala Pro Leu Arg Leu Gly Glu Ser Pro His Asp Ala Phe Asp Ile
 1               5                  10                  15

<210> SEQ ID NO 128
<211> LENGTH: 125
<212> TYPE: PRT
<213> ORGANISM: Homo sapiens
<220> FEATURE:
<221> NAME/KEY: source
<223> OTHER INFORMATION: /note="VH 1.32"

<400> SEQUENCE: 128

Gln Val Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Asp
             20                  25                  30

Tyr Met Met Trp Ile Arg Gln Ala Pro Gly Lys Gly Leu Glu Trp Val
```

```
                35                  40                  45
Ser Tyr Ile Ser Ser Gly Gly Ser Ile Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Arg Gly Gln Gly Thr Met Val Thr Val Ser Ser
        115                 120                 125

<210> SEQ ID NO 129
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 132"

<400> SEQUENCE: 129

Asp Tyr Asp Met Tyr
 1               5

<210> SEQ ID NO 130
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 132"

<400> SEQUENCE: 130

Tyr Ile Ser Arg Gly Gly Ser Val Thr Tyr Tyr Ala Asp Ser Val Lys
 1               5                  10                  15

Gly

<210> SEQ ID NO 131
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 132"

<400> SEQUENCE: 131

Glu Ala Pro Leu Arg Leu Gly Glu Thr Pro His Ala Ala Phe Asp Ile
 1               5                  10                  15

<210> SEQ ID NO 132
<211> LENGTH: 125
<212> TYPE: PRT
<213> ORGANISM: Homo sapiens
<220> FEATURE:
<221> NAME/KEY: source
<223> OTHER INFORMATION: /note="VH 1.33"

<400> SEQUENCE: 132

Gln Ile Thr Leu Lys Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Asp Met Tyr Trp Val Arg Gln Ala Pro Gly Lys Gly Leu Glu Trp Val
```

```
                  35                  40                  45
Ser Tyr Ile Ser Arg Gly Gly Ser Val Thr Tyr Tyr Ala Asp Ser Val
         50                  55                  60

Lys Gly Arg Phe Thr Ile Ser Arg Asp Asn Ala Lys Asn Ala Leu Tyr
 65                  70                  75                  80

Leu Gln Met Asn Ser Leu Arg Ala Glu Asp Met Ala Val Tyr Phe Cys
                 85                  90                  95

Ala Thr Glu Ala Pro Leu Arg Leu Gly Glu Thr Pro His Ala Ala Phe
            100                 105                 110

Asp Ile Trp Gly Gln Gly Thr Met Val Thr Val Ser Ser
        115                 120                 125
```

<210> SEQ ID NO 133
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 136"

<400> SEQUENCE: 133

```
Asp Tyr Thr Met Thr
 1               5
```

<210> SEQ ID NO 134
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 136"

<400> SEQUENCE: 134

```
Tyr Ile Ser Thr Gly Gly Ser Val Lys Tyr Tyr Thr Asp Ser Val Lys
 1               5                  10                  15

Gly
```

<210> SEQ ID NO 135
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 136"

<400> SEQUENCE: 135

```
Glu Ala Pro Leu Arg Leu Gly Glu Ser Pro His Asp Ala Phe Asp Ile
 1               5                  10                  15
```

<210> SEQ ID NO 136
<211> LENGTH: 125
<212> TYPE: PRT
<213> ORGANISM: Homo sapiens
<220> FEATURE:
<221> NAME/KEY: source
<223> OTHER INFORMATION: /note="VH 1.34"

<400> SEQUENCE: 136

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                    35                  40                  45
Ser Tyr Ile Ser Thr Gly Gly Ser Val Lys Tyr Tyr Thr Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 137
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 140"

<400> SEQUENCE: 137

Asp Tyr Thr Met Thr
 1               5

<210> SEQ ID NO 138
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 140"

<400> SEQUENCE: 138

Tyr Ile Ser Thr Gly Gly Ser Ile Lys Tyr Tyr Thr Asp Ser Val Lys
 1               5                  10                  15

Gly

<210> SEQ ID NO 139
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 140"

<400> SEQUENCE: 139

Glu Ala Pro Leu Arg Leu Gly Glu Ser Pro His Asp Ala Phe Asp Ile
 1               5                  10                  15

<210> SEQ ID NO 140
<211> LENGTH: 125
<212> TYPE: PRT
<213> ORGANISM: Homo sapiens
<220> FEATURE:
<221> NAME/KEY: source
<223> OTHER INFORMATION: /note="VH 1.35"

<400> SEQUENCE: 140

Glu Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 141
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 144"

<400> SEQUENCE: 141

Asp Tyr Thr Met Thr
 1               5

<210> SEQ ID NO 142
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 144"

<400> SEQUENCE: 142

Tyr Ile Ser Thr Gly Gly Thr Ile Lys Tyr Tyr Thr Asp Ser Val Lys
 1               5                  10                  15

Gly

<210> SEQ ID NO 143
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 144"

<400> SEQUENCE: 143

Glu Ala Pro Leu Arg Leu Gly Glu Ser Pro His Asp Ala Phe Asp Ile
 1               5                  10                  15

<210> SEQ ID NO 144
<211> LENGTH: 125
<212> TYPE: PRT
<213> ORGANISM: Homo sapiens
<220> FEATURE:
<221> NAME/KEY: source
<223> OTHER INFORMATION: /note="VH 1.36"

<400> SEQUENCE: 144

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 145
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 148"

<400> SEQUENCE: 145

Asp Tyr Thr Met Thr
1               5

<210> SEQ ID NO 146
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 148"

<400> SEQUENCE: 146

Tyr Ile Ser Thr Gly Gly Ser Ile Lys Tyr Tyr Thr Asp Ser Val Lys
1               5                   10                  15
Gly

<210> SEQ ID NO 147
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 148"

<400> SEQUENCE: 147

Glu Ala Pro Leu Arg Leu Gly Glu Ser Pro His Asp Ala Phe Asp Ile
1               5                   10                  15

<210> SEQ ID NO 148
<211> LENGTH: 125
<212> TYPE: PRT
<213> ORGANISM: Homo sapiens
<220> FEATURE:
<221> NAME/KEY: source
<223> OTHER INFORMATION: /note="VH 1.37"

<400> SEQUENCE: 148

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 149
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 152"

<400> SEQUENCE: 149

Asp Tyr Thr Met Thr
1               5

<210> SEQ ID NO 150
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 152"

<400> SEQUENCE: 150

Tyr Ile Ser Thr Gly Gly Thr Ile Lys Tyr Tyr Thr Asp Ser Val Lys
1               5                   10                  15

Gly

<210> SEQ ID NO 151
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 152"

<400> SEQUENCE: 151

Glu Ala Pro Leu Arg Leu Gly Glu Ser Pro His Asp Ala Phe Asp Ile
1               5                   10                  15

<210> SEQ ID NO 152
<211> LENGTH: 125
<212> TYPE: PRT
<213> ORGANISM: Homo sapiens
<220> FEATURE:
<221> NAME/KEY: source
<223> OTHER INFORMATION: /note="VH 1.38"

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 153
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 156"

<400> SEQUENCE: 153

Asp Tyr Thr Met Thr
1               5

<210> SEQ ID NO 154
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 156"

<400> SEQUENCE: 154

Tyr Ile Ser Thr Gly Gly Ser Ile Lys Tyr Tyr Thr Asp Ser Val Lys
1               5                   10                  15

Gly

<210> SEQ ID NO 155
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 156"

<400> SEQUENCE: 155

Glu Ala Pro Leu Arg Leu Gly Glu Ser Pro His Asp Ala Phe Asp Ile
1               5                   10                  15

<210> SEQ ID NO 156
<211> LENGTH: 125
<212> TYPE: PRT
<213> ORGANISM: Homo sapiens
<220> FEATURE:
<221> NAME/KEY: source
<223> OTHER INFORMATION: /note="VH 1.39"

<400> SEQUENCE: 156

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                  35                  40                  45

Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 157
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 160"

<400> SEQUENCE: 157

Asp Ser Ser Met Ser
 1               5

<210> SEQ ID NO 158
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 160"

<400> SEQUENCE: 158

Tyr Ile Ser Ser Gly Gly Gly Ile Ile Tyr Tyr Thr Asp Ser Val Lys
 1               5                  10                  15

Gly

<210> SEQ ID NO 159
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 160"

<400> SEQUENCE: 159

Glu Ala Pro Leu Arg Leu Gly Glu Ser Pro His Asp Ala Phe Asp Ile
 1               5                  10                  15

<210> SEQ ID NO 160
<211> LENGTH: 125
<212> TYPE: PRT
<213> ORGANISM: Homo sapiens
<220> FEATURE:
<221> NAME/KEY: source
<223> OTHER INFORMATION: /note="VH 1.40"

<400> SEQUENCE: 160

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Ser
             20                  25                  30

Ser Met Ser Trp Ile Arg Gln Ala Pro Gly Arg Gly Leu Glu Trp Ile
```

```
                35                  40                  45
Ser Tyr Ile Ser Ser Gly Gly Ile Ile Tyr Tyr Thr Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Val Glu Asp Thr Ala Val Tyr Tyr Cys
                85                  90                  95
Ala Lys Glu Ala Pro Leu Arg Leu Gly Glu Ser Pro His Asp Ala Phe
            100                 105                 110
Asp Ile Trp Gly His Gly Thr Met Val Thr Val Ser Ser
        115                 120                 125

<210> SEQ ID NO 161
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 164"

<400> SEQUENCE: 161

Asp Asn Ser Met Thr
1               5

<210> SEQ ID NO 162
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 164"

<400> SEQUENCE: 162

Tyr Ile Ser Ser Gly Gly Gly Val Ile Phe Tyr Ala Asp Ser Val Lys
1               5                   10                  15
Gly

<210> SEQ ID NO 163
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 164"

<400> SEQUENCE: 163

Glu Ala Pro Leu Arg Leu Gly Glu Ser Pro His Asp Ala Phe Asp Ile
1               5                   10                  15

<210> SEQ ID NO 164
<211> LENGTH: 125
<212> TYPE: PRT
<213> ORGANISM: Homo sapiens
<220> FEATURE:
<221> NAME/KEY: source
<223> OTHER INFORMATION: /note="VH 1.41"

<400> SEQUENCE: 164

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Asn
            20                  25                  30
Ser Met Thr Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 165
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 168"

<400> SEQUENCE: 165

Asp Asn Ser Met Thr
 1               5

<210> SEQ ID NO 166
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 168"

<400> SEQUENCE: 166

Tyr Ile Ser Ser Gly Gly Gly Val Lys Phe Tyr Ala Asp Ser Val Lys
 1               5                  10                  15
Gly

<210> SEQ ID NO 167
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 168"

<400> SEQUENCE: 167

Glu Ala Pro Leu Arg Leu Gly Glu Ser Pro His Asp Ala Phe Asp Ile
 1               5                  10                  15

<210> SEQ ID NO 168
<211> LENGTH: 125
<212> TYPE: PRT
<213> ORGANISM: Homo sapiens
<220> FEATURE:
<221> NAME/KEY: source
<223> OTHER INFORMATION: /note="VH 1.42"

<400> SEQUENCE: 168

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Asn
             20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Lys Phe Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 169
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 172"

<400> SEQUENCE: 169

Asp Ser Ser Met Thr
1               5

<210> SEQ ID NO 170
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 172"

<400> SEQUENCE: 170

Tyr Ile Ser Ser Gly Gly Gly Val Ile Phe Tyr Ala Asp Ser Val Lys
1               5                   10                  15
Gly

<210> SEQ ID NO 171
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 172"

<400> SEQUENCE: 171

Glu Ala Pro Leu Arg Leu Gly Glu Ser Pro His Asp Ala Phe Asp Ile
1               5                   10                  15

<210> SEQ ID NO 172
<211> LENGTH: 125
<212> TYPE: PRT
<213> ORGANISM: Homo sapiens
<220> FEATURE:
<221> NAME/KEY: source
<223> OTHER INFORMATION: /note="VH 1.43"

<400> SEQUENCE: 172

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 173
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 176"

<400> SEQUENCE: 173

Asp Asn Ser Met Thr
1               5

<210> SEQ ID NO 174
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 176"

<400> SEQUENCE: 174

Tyr Ile Ser Ser Gly Gly Ala Val Lys Phe Tyr Ala Asp Ser Val Lys
1               5                   10                  15

Gly

<210> SEQ ID NO 175
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 176"

<400> SEQUENCE: 175

Glu Ala Pro Leu Arg Leu Gly Glu Ser Pro His Asp Ala Phe Asp Ile
1               5                   10                  15

<210> SEQ ID NO 176
<211> LENGTH: 125
<212> TYPE: PRT
<213> ORGANISM: Homo sapiens
<220> FEATURE:
<221> NAME/KEY: source
<223> OTHER INFORMATION: /note="VH 1.44"

<400> SEQUENCE: 176

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Ala Val Lys Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125
```

<210> SEQ ID NO 177
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 180"

<400> SEQUENCE: 177

```
Asp Tyr Ser Met Ser
 1               5
```

<210> SEQ ID NO 178
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 180"

<400> SEQUENCE: 178

```
Tyr Ile Ser Ser Gly Gly Gly Val Ile Phe Tyr Ala Asp Ser Val Lys
 1               5                  10                  15

Gly
```

<210> SEQ ID NO 179
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 180"

<400> SEQUENCE: 179

```
Glu Ala Pro Leu Arg Leu Gly Glu Ser Pro His Asp Ala Phe Asp Ile
 1               5                  10                  15
```

<210> SEQ ID NO 180
<211> LENGTH: 125
<212> TYPE: PRT
<213> ORGANISM: Homo sapiens
<220> FEATURE:
<221> NAME/KEY: source
<223> OTHER INFORMATION: /note="VH 1.45"

<400> SEQUENCE: 180

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Ser Met Ser Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 181
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 184"

<400> SEQUENCE: 181

Asp Ser Ser Met Ser
1               5

<210> SEQ ID NO 182
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 184"

<400> SEQUENCE: 182

Tyr Ile Ser Ser Gly Gly Val Ile Phe Tyr Ala Asp Ser Val Lys
1               5                   10                  15

Gly

<210> SEQ ID NO 183
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 184"

<400> SEQUENCE: 183

Glu Ala Pro Leu Arg Leu Gly Glu Ser Pro His Asp Ala Phe Asp Ile
1               5                   10                  15

<210> SEQ ID NO 184
<211> LENGTH: 125
<212> TYPE: PRT
<213> ORGANISM: Homo sapiens
<220> FEATURE:
<221> NAME/KEY: source
<223> OTHER INFORMATION: /note="VH 1.46"

<400> SEQUENCE: 184

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Ser Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 185
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 188"

<400> SEQUENCE: 185

Asp Asn Ser Met Ser
 1               5

<210> SEQ ID NO 186
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 188"

<400> SEQUENCE: 186

Tyr Ile Ser Ser Gly Gly Gly Val Ile Phe Tyr Ala Asp Ser Val Lys
 1               5                  10                  15

Gly

<210> SEQ ID NO 187
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 188"

<400> SEQUENCE: 187

Glu Ala Pro Leu Arg Leu Gly Glu Ser Pro His Asp Ala Phe Asp Ile
 1               5                  10                  15

<210> SEQ ID NO 188
<211> LENGTH: 125
<212> TYPE: PRT
<213> ORGANISM: Homo sapiens
<220> FEATURE:
<221> NAME/KEY: source
<223> OTHER INFORMATION: /note="VH 1.47"

<400> SEQUENCE: 188

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Asn
             20                  25                  30

Ser Met Ser Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125
```

<210> SEQ ID NO 189
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 192"

<400> SEQUENCE: 189

```
Asp Ser Ser Met Thr
 1               5
```

<210> SEQ ID NO 190
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 192"

<400> SEQUENCE: 190

```
Tyr Ile Ser Ser Gly Gly Gly Val Lys Phe Tyr Ala Asp Ser Val Lys
 1               5                  10                  15

Gly
```

<210> SEQ ID NO 191
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 192"

<400> SEQUENCE: 191

```
Glu Ala Pro Leu Arg Leu Gly Glu Ser Pro His Asp Ala Phe Asp Ile
 1               5                  10                  15
```

<210> SEQ ID NO 192
<211> LENGTH: 125
<212> TYPE: PRT
<213> ORGANISM: Homo sapiens
<220> FEATURE:
<221> NAME/KEY: source
<223> OTHER INFORMATION: /note="VH 1.48"

<400> SEQUENCE: 192

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                    35                  40                  45
Ser Tyr Ile Ser Ser Gly Gly Val Lys Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 193
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 196"

<400> SEQUENCE: 193

Asp Ser Ser Met Ser
 1               5

<210> SEQ ID NO 194
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 196"

<400> SEQUENCE: 194

Tyr Ile Ser Thr Gly Gly Gly Val Lys Phe Tyr Ala Asp Ser Val Lys
 1               5                  10                  15

Gly

<210> SEQ ID NO 195
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 196"

<400> SEQUENCE: 195

Glu Ala Pro Leu Arg Leu Gly Glu Ser Pro His Asp Ala Phe Asp Ile
 1               5                  10                  15

<210> SEQ ID NO 196
<211> LENGTH: 125
<212> TYPE: PRT
<213> ORGANISM: Homo sapiens
<220> FEATURE:
<221> NAME/KEY: source
<223> OTHER INFORMATION: /note="VH 1.49"

<400> SEQUENCE: 196

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Ser
             20                  25                  30

Ser Met Ser Trp Met Arg Gln Ala Pro Gly Lys Gly Leu Glu Trp Val
```

```
                    35                  40                  45
Ser Tyr Ile Ser Thr Gly Gly Val Lys Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 197
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 200"

<400> SEQUENCE: 197

Asp Asn Ser Met Thr
1               5

<210> SEQ ID NO 198
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 200"

<400> SEQUENCE: 198

Tyr Ile Ser Ser Gly Gly Thr Ile Lys Phe Tyr Ala Asp Ser Val Lys
1               5                   10                  15
Gly

<210> SEQ ID NO 199
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 200"

<400> SEQUENCE: 199

Glu Ala Pro Leu Arg Leu Gly Glu Ser Pro His Asp Ala Phe Asp Ile
1               5                   10                  15

<210> SEQ ID NO 200
<211> LENGTH: 125
<212> TYPE: PRT
<213> ORGANISM: Homo sapiens
<220> FEATURE:
<221> NAME/KEY: source
<223> OTHER INFORMATION: /note="VH 1.50"

<400> SEQUENCE: 200

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Thr Ile Lys Phe Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 201
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 204"

<400> SEQUENCE: 201

Asp Ser Ser Met Thr
1               5

<210> SEQ ID NO 202
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 204"

<400> SEQUENCE: 202

Tyr Ile Ser Ser Gly Gly Ala Val Lys Phe Tyr Thr Asp Ser Val Lys
1               5                   10                  15

Gly

<210> SEQ ID NO 203
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 204"

<400> SEQUENCE: 203

Glu Ala Pro Leu Arg Leu Gly Glu Ser Pro His Asp Ala Phe Asp Ile
1               5                   10                  15

<210> SEQ ID NO 204
<211> LENGTH: 125
<212> TYPE: PRT
<213> ORGANISM: Homo sapiens
<220> FEATURE:
<221> NAME/KEY: source
<223> OTHER INFORMATION: /note="VH 1.51"

<400> SEQUENCE: 204

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Ala Val Lys Phe Tyr Thr Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 205
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 208"

<400> SEQUENCE: 205

Asp Asn Ser Met Thr
1               5

<210> SEQ ID NO 206
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 208"

<400> SEQUENCE: 206

Tyr Ile Ser Ser Gly Gly Gly Val Lys Tyr Tyr Ala Asp Ser Val Lys
1               5                   10                  15
Gly

<210> SEQ ID NO 207
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 208"

<400> SEQUENCE: 207

Glu Ala Pro Leu Arg Leu Gly Glu Ser Pro His Asp Ala Phe Asp Ile
1               5                   10                  15

<210> SEQ ID NO 208
<211> LENGTH: 125
<212> TYPE: PRT
<213> ORGANISM: Homo sapiens
<220> FEATURE:
<221> NAME/KEY: source
<223> OTHER INFORMATION: /note="VH 1.52"

<400> SEQUENCE: 208

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Lys Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 209
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 212"

<400> SEQUENCE: 209

Asp Asn Ser Met Thr
1               5

<210> SEQ ID NO 210
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 212"

<400> SEQUENCE: 210

Tyr Ile Ser Ser Gly Gly Ser Val Lys Phe Tyr Ala Asp Ser Val Lys
1               5                   10                  15

Gly

<210> SEQ ID NO 211
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 212"

<400> SEQUENCE: 211

Glu Ala Pro Leu Arg Leu Gly Glu Ser Pro His Asp Ala Phe Asp Ile
1               5                   10                  15

<210> SEQ ID NO 212
<211> LENGTH: 125
<212> TYPE: PRT
<213> ORGANISM: Homo sapiens
<220> FEATURE:
<221> NAME/KEY: source
<223> OTHER INFORMATION: /note="VH 1.53"

<400> SEQUENCE: 212

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Ser Val Lys Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 213
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 216"

<400> SEQUENCE: 213

Asp Asp Ser Met Thr
 1               5

<210> SEQ ID NO 214
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 216"

<400> SEQUENCE: 214

Tyr Ile Ser Ser Gly Gly Gly Val Ile Phe Tyr Ala Asp Ser Val Lys
 1               5                  10                  15

Gly

<210> SEQ ID NO 215
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 216"

<400> SEQUENCE: 215

Glu Ala Pro Leu Arg Leu Gly Glu Ser Pro His Asp Ala Phe Asp Ile
 1               5                  10                  15

<210> SEQ ID NO 216
<211> LENGTH: 125
<212> TYPE: PRT
<213> ORGANISM: Homo sapiens
<220> FEATURE:
<221> NAME/KEY: source
<223> OTHER INFORMATION: /note="VH 1.54"

<400> SEQUENCE: 216

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Asp
             20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 217
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 220"

<400> SEQUENCE: 217

Asp Asn Ser Met Thr
1               5

<210> SEQ ID NO 218
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 220"

<400> SEQUENCE: 218

Tyr Ile Ser Ser Gly Gly Gly Val Lys Phe Tyr Ala Asp Ser Val Lys
1               5                  10                  15
Gly

<210> SEQ ID NO 219
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 220"

<400> SEQUENCE: 219

Glu Ala Pro Leu Arg Leu Gly Glu Ser Pro His Asp Ala Phe Asp Ile
1               5                  10                  15

<210> SEQ ID NO 220
<211> LENGTH: 125
<212> TYPE: PRT
<213> ORGANISM: Homo sapiens
<220> FEATURE:
<221> NAME/KEY: source
<223> OTHER INFORMATION: /note="VH 1.55"

<400> SEQUENCE: 220

Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                 35                  40                  45
Ser Tyr Ile Ser Ser Gly Gly Val Lys Phe Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
        115                 120                 125

<210> SEQ ID NO 221
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 224"

<400> SEQUENCE: 221

Asp Asn Ser Met Thr
1               5

<210> SEQ ID NO 222
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 224"

<400> SEQUENCE: 222

Tyr Ile Ser Ser Gly Gly Ala Val Lys Phe Tyr Ala Asp Ser Val Lys
1               5                   10                  15
Gly

<210> SEQ ID NO 223
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 224"

<400> SEQUENCE: 223

Glu Ala Pro Leu Arg Leu Gly Glu Ser Pro His Asp Ala Phe Asp Ile
1               5                   10                  15

<210> SEQ ID NO 224
<211> LENGTH: 125
<212> TYPE: PRT
<213> ORGANISM: Homo sapiens
<220> FEATURE:
<221> NAME/KEY: source
<223> OTHER INFORMATION: /note="VH 1.56"

<400> SEQUENCE: 224

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Ala Val Lys Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Leu Gly Gln Gly Thr Met Val Thr Val Ser Ser
        115                 120                 125

<210> SEQ ID NO 225
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 228"

<400> SEQUENCE: 225

Asp Asn Ser Met Thr
1               5

<210> SEQ ID NO 226
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 228"

<400> SEQUENCE: 226

Tyr Ile Ser Ser Gly Gly Gly Val Ile Phe Tyr Ala Asp Ser Val Lys
1               5                   10                  15
Gly

<210> SEQ ID NO 227
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 228"

<400> SEQUENCE: 227

Glu Ala Pro Leu Arg Leu Gly Glu Ser Pro His Asp Ala Phe Asp Ile
1               5                   10                  15

<210> SEQ ID NO 228
<211> LENGTH: 125
<212> TYPE: PRT
<213> ORGANISM: Homo sapiens
<220> FEATURE:
<221> NAME/KEY: source
<223> OTHER INFORMATION: /note="VH 1.57"

<400> SEQUENCE: 228

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                    35                  40                  45
Ser Tyr Ile Ser Ser Gly Gly Val Ile Phe Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 229
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 232"

<400> SEQUENCE: 229

Asp Asn Thr Met Thr
 1               5

<210> SEQ ID NO 230
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 232"

<400> SEQUENCE: 230

Tyr Ile Ser Thr Gly Gly Val Lys Phe Tyr Ala Asp Ser Val Lys
 1               5                  10                  15

Gly

<210> SEQ ID NO 231
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 232"

<400> SEQUENCE: 231

Glu Ala Pro Leu Arg Leu Gly Glu Ser Pro His Asp Ala Phe Asp Ile
 1               5                  10                  15

<210> SEQ ID NO 232
<211> LENGTH: 125
<212> TYPE: PRT
<213> ORGANISM: Homo sapiens
<220> FEATURE:
<221> NAME/KEY: source
<223> OTHER INFORMATION: /note="VH 1.58"

<400> SEQUENCE: 232

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 233
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 236"

<400> SEQUENCE: 233

Asp Asn Ser Met Ser
1               5

<210> SEQ ID NO 234
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 236"

<400> SEQUENCE: 234

Tyr Ile Ser Ser Gly Gly Ser Val Lys Phe Tyr Ala Asp Ser Val Lys
1               5                   10                  15
Gly

<210> SEQ ID NO 235
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 236"

<400> SEQUENCE: 235

Glu Ala Pro Leu Arg Leu Gly Glu Ser Pro His Asp Ala Phe Asp Ile
1               5                   10                  15

<210> SEQ ID NO 236
<211> LENGTH: 125
<212> TYPE: PRT
<213> ORGANISM: Homo sapiens
<220> FEATURE:
<221> NAME/KEY: source
<223> OTHER INFORMATION: /note="VH 1.59"

<400> SEQUENCE: 236

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Thr Met Thr Trp Met Arg Gln Ala Pro Gly Lys Gly Leu Glu Trp Val
```

```
                35                  40                  45
Ser Tyr Ile Ser Thr Gly Gly Val Lys Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 237
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 240"

<400> SEQUENCE: 237

Asp Asn Ser Met Thr
1               5

<210> SEQ ID NO 238
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 240"

<400> SEQUENCE: 238

Tyr Ile Ser Thr Gly Gly Val Lys Tyr Tyr Ala Asp Ser Val Lys
1               5                   10                  15

Gly

<210> SEQ ID NO 239
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 240"

<400> SEQUENCE: 239

Glu Ala Pro Leu Arg Leu Gly Glu Ser Pro His Asp Ala Phe Asp Ile
1               5                   10                  15

<210> SEQ ID NO 240
<211> LENGTH: 125
<212> TYPE: PRT
<213> ORGANISM: Homo sapiens
<220> FEATURE:
<221> NAME/KEY: source
<223> OTHER INFORMATION: /note="VH 1.60"

<400> SEQUENCE: 240

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Ser Trp Met Arg Gln Ala Pro Gly Lys Gly Leu Glu Trp Val
```

```
                35                  40                  45
Ser Tyr Ile Ser Ser Gly Gly Ser Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 241
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 244"

<400> SEQUENCE: 241

Asp Tyr Thr Met Ser
1               5

<210> SEQ ID NO 242
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 244"

<400> SEQUENCE: 242

Tyr Ile Ser Thr Gly Gly Gly Val Lys Phe Tyr Ala Asp Ser Val Lys
1               5                   10                  15

Gly

<210> SEQ ID NO 243
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 244"

<400> SEQUENCE: 243

Glu Ala Pro Leu Arg Leu Gly Glu Ser Pro His Asp Ala Phe Asp Ile
1               5                   10                  15

<210> SEQ ID NO 244
<211> LENGTH: 125
<212> TYPE: PRT
<213> ORGANISM: Homo sapiens
<220> FEATURE:
<221> NAME/KEY: source
<223> OTHER INFORMATION: /note="VH 1.61"

<400> SEQUENCE: 244

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
```

```
                35                  40                  45
Ser Tyr Ile Ser Thr Gly Gly Val Lys Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 245
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 248"

<400> SEQUENCE: 245

Asp Ser Ser Met Thr
1               5

<210> SEQ ID NO 246
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 248"

<400> SEQUENCE: 246

Tyr Ile Ser Ser Gly Gly Ala Val Lys Phe Tyr Thr Asp Ser Val Lys
1               5                   10                  15

Gly

<210> SEQ ID NO 247
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 248"

<400> SEQUENCE: 247

Glu Ala Pro Leu Arg Leu Gly Glu Ser Pro His Asp Ala Phe Asp Ile
1               5                   10                  15

<210> SEQ ID NO 248
<211> LENGTH: 125
<212> TYPE: PRT
<213> ORGANISM: Homo sapiens
<220> FEATURE:
<221> NAME/KEY: source
<223> OTHER INFORMATION: /note="VH 1.62"

<400> SEQUENCE: 248

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Ala Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 249
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 252"

<400> SEQUENCE: 249

Asp Ser Ser Met Thr
1               5

<210> SEQ ID NO 250
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 252"

<400> SEQUENCE: 250

Tyr Ile Ser Ser Gly Gly Val Lys Phe Tyr Thr Asp Ser Val Lys
1               5                   10                  15

Gly

<210> SEQ ID NO 251
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 252"

<400> SEQUENCE: 251

Glu Ala Pro Leu Arg Leu Gly Glu Ser Pro His Asp Ala Phe Asp Ile
1               5                   10                  15

<210> SEQ ID NO 252
<211> LENGTH: 125
<212> TYPE: PRT
<213> ORGANISM: Homo sapiens
<220> FEATURE:
<221> NAME/KEY: source
<223> OTHER INFORMATION: /note="VH 1.63"

<400> SEQUENCE: 252

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 253
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 256"

<400> SEQUENCE: 253

Asp Ser Ser Met Thr
 1               5

<210> SEQ ID NO 254
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 256"

<400> SEQUENCE: 254

Tyr Ile Ser Ser Gly Gly Gly Val Lys Phe Tyr Ala Asp Ser Val Lys
 1               5                  10                  15

Gly

<210> SEQ ID NO 255
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 256"

<400> SEQUENCE: 255

Glu Ala Pro Leu Arg Leu Gly Glu Ser Pro His Asp Ala Phe Asp Ile
 1               5                  10                  15

<210> SEQ ID NO 256
<211> LENGTH: 125
<212> TYPE: PRT
<213> ORGANISM: Homo sapiens
<220> FEATURE:
<221> NAME/KEY: source
<223> OTHER INFORMATION: /note="VH 1.64"

<400> SEQUENCE: 256

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 257
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 260"

<400> SEQUENCE: 257

Asp Ser Ser Met Thr
1               5

<210> SEQ ID NO 258
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 260"

<400> SEQUENCE: 258

Tyr Ile Ser Ser Gly Gly Val Lys Phe Tyr Ala Asp Ser Val Lys
1               5                   10                  15
Gly

<210> SEQ ID NO 259
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 260"

<400> SEQUENCE: 259

Glu Ala Pro Leu Arg Leu Gly Glu Ser Pro His Asp Ala Phe Asp Ile
1               5                   10                  15

<210> SEQ ID NO 260
<211> LENGTH: 125
<212> TYPE: PRT
<213> ORGANISM: Homo sapiens
<220> FEATURE:
<221> NAME/KEY: source
<223> OTHER INFORMATION: /note="VH 1.65"

<400> SEQUENCE: 260

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                    35                  40                  45
Ser Tyr Ile Ser Ser Gly Gly Val Lys Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 261
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 264"

<400> SEQUENCE: 261

Asp Ser Ser Met Thr
1               5

<210> SEQ ID NO 262
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 264"

<400> SEQUENCE: 262

Tyr Ile Ser Ser Gly Gly Gly Val Lys Phe Tyr Thr Asp Ser Val Lys
1               5                   10                  15

Gly

<210> SEQ ID NO 263
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 264"

<400> SEQUENCE: 263

Glu Ala Pro Leu Arg Leu Gly Glu Ser Pro His Asp Ala Phe Asp Thr
1               5                   10                  15

<210> SEQ ID NO 264
<211> LENGTH: 125
<212> TYPE: PRT
<213> ORGANISM: Homo sapiens
<220> FEATURE:
<221> NAME/KEY: source
<223> OTHER INFORMATION: /note="VH 1.66"

<400> SEQUENCE: 264

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Lys Phe Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asp Ser Leu Arg Ala Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Thr Ser Gly Gln Gly Thr Met Val Thr Val Ser Ser
        115                 120                 125

<210> SEQ ID NO 265
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 268"

<400> SEQUENCE: 265

Gly Ser Ser Met Thr
 1               5

<210> SEQ ID NO 266
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 268"

<400> SEQUENCE: 266

Tyr Ile Ser Ser Gly Gly Val Ile Phe Tyr Ala Asp Ser Val Lys
 1               5                  10                  15
Gly

<210> SEQ ID NO 267
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 268"

<400> SEQUENCE: 267

Glu Ala Pro Leu Arg Leu Gly Glu Ser Pro His Asp Ala Phe Asp Ile
 1               5                  10                  15

<210> SEQ ID NO 268
<211> LENGTH: 125
<212> TYPE: PRT
<213> ORGANISM: Homo sapiens
<220> FEATURE:
<221> NAME/KEY: source
<223> OTHER INFORMATION: /note="VH 1.67"

<400> SEQUENCE: 268

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Gly Ser
             20                  25                  30

Ser Met Thr Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 269
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 272"

<400> SEQUENCE: 269

Asp Asn Ser Met Thr
1               5

<210> SEQ ID NO 270
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 272"

<400> SEQUENCE: 270

Tyr Ile Ser Ser Gly Gly Val Ile Phe Tyr Ala Asp Ser Val Lys
1               5                   10                  15
Gly

<210> SEQ ID NO 271
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 272"

<400> SEQUENCE: 271

Glu Ala Pro Leu Arg Leu Gly Glu Ser Pro His Asp Ala Phe Asp Ile
1               5                   10                  15

<210> SEQ ID NO 272
<211> LENGTH: 125
<212> TYPE: PRT
<213> ORGANISM: Homo sapiens
<220> FEATURE:
<221> NAME/KEY: source
<223> OTHER INFORMATION: /note="VH 1.68"

<400> SEQUENCE: 272

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asp Asn
            20                  25                  30

Ser Met Thr Trp Met Arg Gln Ala Pro Gly Lys Gly Leu Glu Trp Val
```

-continued

```
                35                  40                  45
Ser Tyr Ile Ser Ser Gly Gly Val Ile Phe Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
               100                 105                 110

Asp Ile Ser Gly Arg Gly Thr Thr Val Thr Val Ser Ser
            115                 120                 125

<210> SEQ ID NO 273
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 276"

<400> SEQUENCE: 273

Asp Asn Ser Met Ser
1               5

<210> SEQ ID NO 274
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 276"

<400> SEQUENCE: 274

Tyr Ile Ser Ser Gly Gly Gly Val Ile Phe Tyr Ala Asp Ser Val Lys
1               5                  10                  15

Gly

<210> SEQ ID NO 275
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 276"

<400> SEQUENCE: 275

Glu Ala Pro Leu Arg Leu Gly Glu Ser Pro His Asp Ala Phe Asp Ile
1               5                  10                  15

<210> SEQ ID NO 276
<211> LENGTH: 125
<212> TYPE: PRT
<213> ORGANISM: Homo sapiens
<220> FEATURE:
<221> NAME/KEY: source
<223> OTHER INFORMATION: /note="VH 1.69"

<400> SEQUENCE: 276

Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asp Asn
            20                  25                  30

Ser Met Ser Trp Met Arg Gln Ala Pro Gly Lys Gly Leu Glu Trp Val
```

```
                35                  40                  45
Ser Tyr Ile Ser Ser Gly Gly Val Ile Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                     85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
            115                 120                 125

<210> SEQ ID NO 277
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 280"

<400> SEQUENCE: 277

Asp Ser Ser Met Thr
 1               5

<210> SEQ ID NO 278
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 280"

<400> SEQUENCE: 278

Tyr Ile Ser Ser Gly Gly Ala Val Lys Phe Tyr Thr Asp Ser Val Lys
 1               5                  10                  15

Gly

<210> SEQ ID NO 279
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 280"

<400> SEQUENCE: 279

Glu Ala Pro Leu Arg Leu Gly Glu Ser Pro His Asp Ala Phe Asp Ile
 1               5                  10                  15

<210> SEQ ID NO 280
<211> LENGTH: 125
<212> TYPE: PRT
<213> ORGANISM: Homo sapiens
<220> FEATURE:
<221> NAME/KEY: source
<223> OTHER INFORMATION: /note="VH 1.70"

<400> SEQUENCE: 280

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Gly Asp Ser
                20                  25                  30

Ser Met Thr Trp Met Arg Gln Ala Pro Gly Lys Gly Leu Glu Trp Val
```

35                  40                  45
Ser Tyr Ile Ser Ser Gly Gly Ala Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 281
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 284"

<400> SEQUENCE: 281

Gly Ser Ser Met Thr
1               5

<210> SEQ ID NO 282
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 284"

<400> SEQUENCE: 282

Tyr Ile Ser Ser Gly Gly Val Lys Phe Tyr Thr Asp Ser Val Lys
1               5                   10                  15

Gly

<210> SEQ ID NO 283
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 284"

<400> SEQUENCE: 283

Glu Ala Pro Leu Arg Leu Gly Glu Ser Pro His Asp Ala Phe Asp Ile
1               5                   10                  15

<210> SEQ ID NO 284
<211> LENGTH: 125
<212> TYPE: PRT
<213> ORGANISM: Homo sapiens
<220> FEATURE:
<221> NAME/KEY: source
<223> OTHER INFORMATION: /note="VH 1.71"

<400> SEQUENCE: 284

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Gly Ser
            20                  25                  30

Ser Met Thr Trp Met Arg Gln Ala Pro Gly Lys Gly Leu Glu Trp Val

```
                35                  40                  45
Ser Tyr Ile Ser Ser Gly Gly Val Lys Phe Tyr Thr Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
        115                 120                 125

<210> SEQ ID NO 285
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 288"

<400> SEQUENCE: 285

Asp Ser Ser Met Ser
 1               5

<210> SEQ ID NO 286
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 288"

<400> SEQUENCE: 286

Tyr Ile Ser Ser Gly Gly Gly Val Ile Phe Tyr Ala Asp Ser Val Lys
 1               5                  10                  15
Gly

<210> SEQ ID NO 287
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 288"

<400> SEQUENCE: 287

Glu Ala Pro Leu Arg Leu Gly Glu Ser Pro His Asp Ala Phe Asp Ile
 1               5                  10                  15

<210> SEQ ID NO 288
<211> LENGTH: 125
<212> TYPE: PRT
<213> ORGANISM: Homo sapiens
<220> FEATURE:
<221> NAME/KEY: source
<223> OTHER INFORMATION: /note="VH 1.72"

<400> SEQUENCE: 288

Gln Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Asp Ser
             20                  25                  30
Ser Met Ser Trp Met Arg Gln Ala Pro Gly Lys Gly Leu Glu Trp Val
```

```
              35                  40                  45
Ser Tyr Ile Ser Ser Gly Gly Val Ile Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 289
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 292"

<400> SEQUENCE: 289

Asp Ser Ser Met Thr
 1               5

<210> SEQ ID NO 290
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 292"

<400> SEQUENCE: 290

Tyr Ile Ser Ala Gly Gly Gly Val Arg Phe Tyr Thr Asp Ser Val Lys
 1               5                  10                  15

Gly

<210> SEQ ID NO 291
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 292"

<400> SEQUENCE: 291

Glu Ala Pro Leu Arg Leu Gly Glu Ser Pro His Asp Ala Phe Asp Ile
 1               5                  10                  15

<210> SEQ ID NO 292
<211> LENGTH: 125
<212> TYPE: PRT
<213> ORGANISM: Homo sapiens
<220> FEATURE:
<221> NAME/KEY: source
<223> OTHER INFORMATION: /note="VH 1.73"

<400> SEQUENCE: 292

Gln Val Gln Leu Val Glu Ser Gly Gly Gly Leu Val Lys Pro Gly Gly
 1               5                  10                  15

Ser Leu Arg Leu Ser Cys Ala Ala Thr Gly Phe Thr Phe Ser Asp Ser
            20                  25                  30

Ser Met Thr Trp Met Arg Gln Ala Pro Gly Lys Gly Leu Glu Trp Val
```

```
            35                  40                  45
Ser Tyr Ile Ser Ala Gly Gly Val Arg Phe Tyr Thr Asp Ser Val
     50                   55                  60

Lys Gly Arg Phe Thr Ile Ser Arg Asp Asn Ala Lys Asn Ser Leu Tyr
 65                   70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 293
<211> LENGTH: 375
<212> TYPE: DNA
<213> ORGANISM: Homo sapiens
<220> FEATURE:
<221> NAME/KEY: source
<223> OTHER INFORMATION: /note="VH 1.1"

<400> SEQUENCE: 293
caggtgcagc tggtggagtc tgggggaggc ttggtcaagc ctggagggtc cctgagactc      60
tcctgtgcag cctctggatt caccttcagt gactacacca tgacctggat gcggcaggct     120
ccagggaagg ggctggagtg gtttcctac ataagtactg gtggtactat caaatattac      180
acagactctg tgaagggccg attcaccatc tccagggaca acgccaagaa ctcactgtat     240
ctgcaaatga acagcctgag agccgacgac acggccgtgt attactgtgc gcgagaggcc     300
cctttacgtt tggggagtc cccccatgat gcttttgata tctggggcca agggacaatg      360
gtcaccgtct cctca                                                     375

<210> SEQ ID NO 294
<211> LENGTH: 375
<212> TYPE: DNA
<213> ORGANISM: Homo sapiens
<220> FEATURE:
<221> NAME/KEY: source
<223> OTHER INFORMATION: /note="VH 1.2"

<400> SEQUENCE: 294
gaggtgcagc tgttggagtc tgggggaggc ttggtcaagc ctggagggtc cctgagactc      60
tcctgtgcag cctctggatt caccttcagt gactacacca tgacctggat gcgccaggct     120
ccagggaagg ggctggagtg gtttcatat ataagtactg gtggtagtat caaatattac      180
acagactctg tgaagggccg attcaccatc tccagggaca acgccaagaa ctcactgtat     240
ctgcaaatga acagcctgag agccgacgac acggccgtgt attactgtgc gagagaggcc     300
cctttacgtt tggggagtc cccccatgat gcttttgata tctggggcca agggacaatg      360
gtcactgtct cctca                                                     375

<210> SEQ ID NO 295
<211> LENGTH: 375
<212> TYPE: DNA
<213> ORGANISM: Homo sapiens
<220> FEATURE:
<221> NAME/KEY: source
<223> OTHER INFORMATION: /note="VH 1.3"

<400> SEQUENCE: 295
caggtgcagc tggtggagtc tgggggaggc ttggtcaagc ctggagggtc cctgagactc      60
```

```
tcctgtgcag cctctggatt caccttcagt gactacacca tgacctggat gcgccaggct      120
ccagggaagg ggctggagtg ggtttcttac ataagtactg tggtagtat  caaatattat     180 acagactctg tgaagggccg attcaccatc tccagggaca acgccaagaa ctcactgtat      240
ctgcaaatga acagcctgag agccgacgac acggccgtgt attactgtgc gagagaggcc      300
cctttacgtt tggggagtc  ccccatgat  gcttttgata tctggggcca agggacaatg      360
gtcactgtct cctca                                                       375
```

<210> SEQ ID NO 296
<211> LENGTH: 375
<212> TYPE: DNA
<213> ORGANISM: Homo sapiens
<220> FEATURE:
<221> NAME/KEY: source
<223> OTHER INFORMATION: /note="VH 1.4"

<400> SEQUENCE: 296

```
caagtgcagc tggtggagtc tgggggaggc ttggtcaagc ctggagggtc cctgagactc       60
tcctgtgcag cctctggatt caccttcagt gactactaca tgatctggat gcgccaggct      120
ccagggaagg ggctggagtg ggtttcctac attagtggtg gtggtactac caaatattac      180
acagactctg tgaagggccg attcaccatc tccagggaca acgccaagaa ctcactgtat      240
ctgcaaatga acagcctgag agccgacgac acggccgtgt actactgtgc gagagaggcc      300
cctttacgtt tggggagac  ccccatgat  gcttttgata tctggggcca agggacaatg      360
gtcactgtct cctca                                                       375
```

<210> SEQ ID NO 297
<211> LENGTH: 375
<212> TYPE: DNA
<213> ORGANISM: Homo sapiens
<220> FEATURE:
<221> NAME/KEY: source
<223> OTHER INFORMATION: /note="VH 1.5"

<400> SEQUENCE: 297

```
gaagtgcagc tggtggagtc tgggggaggc ttggtcaagc ctggagggtc cctgagactc       60
tcctgtgcag cctctggatt caccttcagt gactacacca tgacctggat gcgccaggct      120
ccagggaagg ggctggagtg ggtttcatac ataagtactg tggtaatac  caaatattac     180 acagactctg tgaagggccg cttcaccatc tccagggaca acgccaagaa ctcactgtat      240
ctgcaaatga acagcctgag agccgacgac acggccgtat attactgtgc gagagaggcc      300
cctttacgtt tggggagtc  ccccatgat  gcttttgata tctggggcca agggacaatg      360
gtcactgtct cttca                                                       375
```

<210> SEQ ID NO 298
<211> LENGTH: 375
<212> TYPE: DNA
<213> ORGANISM: Homo sapiens
<220> FEATURE:
<221> NAME/KEY: source
<223> OTHER INFORMATION: /note="VH 1.6"

<400> SEQUENCE: 298

```
gaggtgcagc tgttggagtc tgggggaggc ttggtcaagc ctggagggtc cctgagactc       60
tcctgtgcag cctctggatt caccttcagt gactacacca tgacctggat gcggcaggct      120
ccagggaagg ggctggagtg ggtttcctac ataagtactg gtggtactat caaatattac      180
```

```
acagactctg tgaagggccg attcaccatc tccagggaca acgccaagaa ctcactgtat    240
ctgcaaatga gcagcctgag agccgacgac acggccgtgt attactgtgc gcgagaggcc    300
cctttacgtt tgggggagtc cccccatgat gcttttgata tctggggcca agggacaatg    360
gtcactgtct cctca                                                     375
```

<210> SEQ ID NO 299
<211> LENGTH: 375
<212> TYPE: DNA
<213> ORGANISM: Homo sapiens
<220> FEATURE:
<221> NAME/KEY: source
<223> OTHER INFORMATION: /note="VH 1.7"

<400> SEQUENCE: 299

```
gaagtgcagc tggtggagtc tgggggaggc ttggtcaagc ctggagggtc cctgagactc    60
tcctgtgcag cctctggatt caccttcagt gactacacca tgacctggat cgcccaggct    120
ccagggaagg ggctggagtg ggtttcctac ataagtactg tggtactat caaatattac    180 acagactctg tgaagggccg attcaccatc tccagggaca acgccaagaa ctcactgtat    240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcactgtct cttca                                                     375
```

<210> SEQ ID NO 300
<211> LENGTH: 375
<212> TYPE: DNA
<213> ORGANISM: Homo sapiens
<220> FEATURE:
<221> NAME/KEY: source
<223> OTHER INFORMATION: /note="VH 1.8"

<400> SEQUENCE: 300

```
gaggtgcagc tggtggagtc tgggggaggc ttggtcaagc ctggagggtc cctgagactc    60
tcctgtgcag cctctggatt caccttcagt gactacacca tgacctggat cgcccaggct    120
ccagggaagg ggctggagtg ggtttcatac ataagtactg tggtagtat taaatattac    180 acagactctg tgaagggccg attcaccatc tccagggaca acgccaagaa ctcactgtat    240
ctgcaaatga acagcctgag agccggcgac acggccgtgt attactgtgc gagagaggcc    300
cctttacgtt tgggggagtc cccccatgat gcttttgata tctggggcca agggacaatg    360
gtcaccgtct cttca                                                     375
```

<210> SEQ ID NO 301
<211> LENGTH: 375
<212> TYPE: DNA
<213> ORGANISM: Homo sapiens
<220> FEATURE:
<221> NAME/KEY: source
<223> OTHER INFORMATION: /note="VH 1.9"

<400> SEQUENCE: 301

```
caggtgcagc tggtggagtc tgggggaggc ttggtcaagc ctggagggtc cctgagactc    60
tcctgtgcag cctctggatt caccttcggt gactacacca tgacctggat cgggcaggct    120
ccagggaagg ggctggagtg ggtttcctac ataagtactg tggtactat caaatattac    180 acagactctg tgaagggccg attcaccatc tccagggaca acgccaagaa ctcactgtat    240
ctgcaaatgg acagcctgag agccgacgac acggccgtgt attactgtgc gcgagaggcc    300
```

```
cctttacgtt tgggggagtc cccccatgat gcttttgata tctggggcca agggacaatg    360
gtcactgtct cttca                                                     375
```

<210> SEQ ID NO 302
<211> LENGTH: 375
<212> TYPE: DNA
<213> ORGANISM: Homo sapiens
<220> FEATURE:
<221> NAME/KEY: source
<223> OTHER INFORMATION: /note="VH 1.10"

<400> SEQUENCE: 302

```
caggtgcagc tggtggagtc tgggggaggc ttggtcaagc ctggagggtc cctgagactc     60
tcctgtgcag cctctggatt caccttcagt gactacacca tgagctggat cgccaggct    120 ccagggaagg ggctggagtg gatttcatac ataagtcttg gtggtaatac caaatattac   180
acagactctg tgaagggccg attcaccatc tccagggaca cgccaagaa ctcactgtat    240 ctgcaaatga acagcctgcg agccgacgac acggccgtgt attactgtgc gagagaggcc   300
cctttacgtt tgggggagtc cccccatgat gcttttgata tctggggcca agggacaatg   360
gtcaccgtct cctca                                                     375
```

<210> SEQ ID NO 303
<211> LENGTH: 375
<212> TYPE: DNA
<213> ORGANISM: Homo sapiens
<220> FEATURE:
<221> NAME/KEY: source
<223> OTHER INFORMATION: /note="VH 1.11"

<400> SEQUENCE: 303

```
gaggtgcagc tgttggagtc tgggggaggc ttggtcaagc ctggagggtc cctgagactc     60
tcctgtgcag cctctggatt caccttcagt gactatgaca tgacctggat ccgccaggct   120
ccagggaagg ggcaggagtg ggtttcatat attagtcgtg gtggtagtac caaatactac   180
gcagactctg tgaagggccg attcaccatc tccagggaca cgccaagaa ctcactgtat    240 ctgcaaatga acagcctgag agccgaggac acggccgtat actactgtgc gagagaggcc   300
cctttacgtt tggggagac ccccacgat gcttttgata tctggggcca agggacaatg    360
gtcaccgtct cttca                                                     375
```

<210> SEQ ID NO 304
<211> LENGTH: 375
<212> TYPE: DNA
<213> ORGANISM: Homo sapiens
<220> FEATURE:
<221> NAME/KEY: source
<223> OTHER INFORMATION: /note="VH 1.12"

<400> SEQUENCE: 304

```
gaggtgcagc tgttggagtc tgggggaggc gtggtcaagc ctggagggtc cctgagactc     60
tcctgtgcag cctctggatt caccttcagt gactactata tgggctggat ccgccaggct   120
ccagggaagg ggctggagtg gatttcatac attagtagta gtggtagtac catatactac   180
gcagactctg tgaagggccg attcaccatc tccagggaca cgccaagaa ctcactgtat    240 ctgcaaatga acagcctgag agccgaggac acggccgtgt attactgtgc gagagaggcc   300
cctttgcgtt tgggggagtc cccccatgat gcttttgata tctggggcca agggacaatg   360
gtcactgtct cttca                                                     375
```

<210> SEQ ID NO 305
<211> LENGTH: 375
<212> TYPE: DNA
<213> ORGANISM: Homo sapiens
<220> FEATURE:
<221> NAME/KEY: source
<223> OTHER INFORMATION: /note="VH 1.13"

<400> SEQUENCE: 305

```
gaggtgcagc tgttggagtc tgggggaggc ttggtcaagc ctggagggtc cctgagactc      60
tcctgtgcag cctctggatt caccttcagt gactacacca tgacctggat gcggcaggct     120
ccagggaagg ggctggagtg ggtttcctac ataagtactg gtggtactat caaatattac     180
acagactctg tgaagggccg attcaccatc tccaggaca acgccaagaa ctcactgtat     240
ctgcaaatga acagcctgag agccgacgac acggccgtgt attactgtgc gcgagaggcc     300
cctttacgtt tggggagtc cccccatgat gcttttgata tctggggcca aggacaatg     360
gtcactgtct cttca                                                      375
```

<210> SEQ ID NO 306
<211> LENGTH: 375
<212> TYPE: DNA
<213> ORGANISM: Homo sapiens
<220> FEATURE:
<221> NAME/KEY: source
<223> OTHER INFORMATION: /note="VH 1.14"

<400> SEQUENCE: 306

```
gaggtgcagc tggtggagtc tgggggaggc ttggtacagc ctggcaggtc cctgagactc      60
tcctgtgcag cctctggatt caccttcagt gactacacca tgacctggat gcggcaggct     120
ccagggaagg ggctggagtg ggtttcctac ataagtactg gtggtactat caaatattac     180
acagactctg tgaagggccg attcaccatc tccaggaca acgccaagaa ctcactgtat     240
ctgcaaatga acagcctgag agccgacgac acggccgtgt attactgtgc gcgagaggcc     300
cctttacgtt tggggagtc cccccatgat gcttttgata tctggggcca aggacaatg     360
gtcaccgtct cctca                                                      375
```

<210> SEQ ID NO 307
<211> LENGTH: 375
<212> TYPE: DNA
<213> ORGANISM: Homo sapiens
<220> FEATURE:
<221> NAME/KEY: source
<223> OTHER INFORMATION: /note="VH 1.15"

<400> SEQUENCE: 307

```
caggtgcagc tggtggagtc tgggggaggc ttggtcaagc ctggagggtc cctgagactc      60
tcctgtgcag cctctggatt caccttcagt gacaattcca tgagctggat ccgccaggct     120
ccagggaagg ggctggagtg ggtttcatac attagtagta gtggtagtac catatactac     180
gcagactctg tgaagggccg attcaccatc tccaggaca acgccaagaa ctcactgtat     240
ctgcaaatga acaccctgag agccgaggac acggccgtgt attactgtgc gaaagaggcc     300
cctttacgtt tggggagtc cccccatgat gcttttgata tctggggcca aggacaatg     360
gtcaccgtct cttca                                                      375
```

<210> SEQ ID NO 308
<211> LENGTH: 375

```
<212> TYPE: DNA
<213> ORGANISM: Homo sapiens
<220> FEATURE:
<221> NAME/KEY: source
<223> OTHER INFORMATION: /note="VH 1.16"

<400> SEQUENCE: 308
gaagtgcagc tggtggagtc tgggggaggc ttggtcaagc ctggagggtc cctgagactc      60
tcctgtgcag cctctggatt caccttcagt gactacacca tgagctggat gcgccaggct     120
ccagggaagg ggctggagtg ggtttcatac ataagtactg gtggtagtat caaatattac     180
acagactctg tgaagggccg attcaccatc tccagggaca cgccaagaa ctcactgtat      240 ctgcaaatga acagcctgag agccgacgac acggccgtgt attactgtgc gagagaggcc     300
cctttacgtt tggggagtc cccccatgat gcttttgata tctggggcca aggacaatg      360 gtcaccgtct cctca                                                      375

<210> SEQ ID NO 309
<211> LENGTH: 375
<212> TYPE: DNA
<213> ORGANISM: Homo sapiens
<220> FEATURE:
<221> NAME/KEY: source
<223> OTHER INFORMATION: /note="VH 1.17"

<400> SEQUENCE: 309
gaggtgcagc tggtggagtc tgggggaggc ttggtcaagc ctggagggtc cctgagactc      60
tcctgtgcag cctctggatt caccttcagt gactacacca tgacctggat gcgccaggct     120
ccagggaagg ggctggagtg ggtttcatac ataagtactg gtggcagtat caaatattac     180
acagactctg tgaagggccg attcaccatc tccagggaca cgccaagaa ctcactgtat      240 ctgcaaatga acagcctgag agtcgacgac acggccgtgt attactgtgc gagagaggcc     300
cctttacgtt tggggagtc cccccatgat gcttttgata tctggggcca aggacaatg      360 gtcaccgtct cctca                                                      375

<210> SEQ ID NO 310
<211> LENGTH: 375
<212> TYPE: DNA
<213> ORGANISM: Homo sapiens
<220> FEATURE:
<221> NAME/KEY: source
<223> OTHER INFORMATION: /note="VH 1.18"

<400> SEQUENCE: 310
caggtgcagc tgttggagtc tgggggaggc ttggtcaagc ctggagggtc cctgagactc      60
tcctgtgcag cctctggatt caccttcagt gactacacca tgacctggat gcggcaggct     120
ccagggaagg ggctggagtg ggtttcctac ataagtactg gtggtactat caaatattac     180
acagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tggggagtc cccccatgat gcttttgata tctggggcca aggacaatg      360 gtcactgtct cttca                                                      375

<210> SEQ ID NO 311
<211> LENGTH: 375
<212> TYPE: DNA
<213> ORGANISM: Homo sapiens
<220> FEATURE:
<221> NAME/KEY: source
```

<223> OTHER INFORMATION: /note="VH 1.19"

<400> SEQUENCE: 311

```
caggtgcagc tggtggagtc tgggggaggc ttggtcaagc ctggagggtc cctgagactc      60
tcctgtgcag cctctggatt caccttcagt gactacacca tgacctggat gcgccaggct     120
ccagggaagg ggctggagtg ggtttcatac ataagtactg gtggtagtat caaatattac     180
acagactctg tgaagggccg attcaccatc tccaggaca acgccaagaa ctcactgtat      240
ctgcaaatga acagcctgag agccgaggac acggccgtat actactgtgc gagagaggcc     300
cctttacgtt tgggggagac cccccacgat gcttttgata tctggggcca agggacaatg     360
gtcaccgtct cttca                                                      375
```

<210> SEQ ID NO 312
<211> LENGTH: 375
<212> TYPE: DNA
<213> ORGANISM: Homo sapiens
<220> FEATURE:
<221> NAME/KEY: source
<223> OTHER INFORMATION: /note="VH 1.20"

<400> SEQUENCE: 312

```
gaggtgcagc tgttggagtc tgggggaggc ttggtcaagc ctggagggtc cctgagactc      60
tcctgtgcag cctctggatt caccttcagt gactacacca tgacctggat gcgccaggct     120
ccagggaagg ggctggagtg ggtttcatac attagtagtg gtggtagtat caaattctac     180
gcagactctg tgaagggccg attcaccatc tccaggaca acgccaaaaa ctcactgtat      240
ctgcaaatga acagcctgag agccgaggac acggccgtgt attactgtgc gagagaggcc     300
cctttacgtt tgggggagtc cccccatgat gcttttgata tctggggcca agggacaatg     360
gtcaccgtct cctca                                                      375
```

<210> SEQ ID NO 313
<211> LENGTH: 375
<212> TYPE: DNA
<213> ORGANISM: Homo sapiens
<220> FEATURE:
<221> NAME/KEY: source
<223> OTHER INFORMATION: /note="VH 1.21"

<400> SEQUENCE: 313

```
gaggtgcagc tggtggagtc tgggggaggc ttggtcaagc ctggagggtc cctgagactc      60
tcctgtgcag cctctggatt caccttcagt gactacacca tgacctggat gcgccaggct     120
ccagggaagg ggctggagtg ggtttcatat ataagtactg gtggtagtat caaatattac     180
acagactctg tgaagggccg attcaccatc tccaggaca acgccaagaa ctcactgtat      240
ctgcaaatga acagcctgag agccgacgac acggccgtgt attactgtgc gagagaggcc     300
cctttacgtt tgggggagtc cccccatgat gcttttgata tctggggcca agggacaatg     360
gtcaccgtct cttca                                                      375
```

<210> SEQ ID NO 314
<211> LENGTH: 375
<212> TYPE: DNA
<213> ORGANISM: Homo sapiens
<220> FEATURE:
<221> NAME/KEY: source
<223> OTHER INFORMATION: /note="VH 1.22"

<400> SEQUENCE: 314

```
gaagtgcagc tggtggagtc tgggggaggc ttggtcaagc ctggagggtc cctgagactc    60
tcctgtgcag cctctggatt caccttcagt gactacacca tgacctggat gcgccaggct   120
ccagggaagg ggctggagtg ggtttcatac ataagtactg gtggtagtat caaatattac   180
acagactctg tgaagggccg attcaccatc tccaggaca acgccaagaa ctcattgtat    240
ctgcaaatga acagcctgag agccgacgac acggccgtgt attactgtgc gagagaggcc   300
cctttacgtt tggggagtc cccccatgat gcttttgata tctggggcca agggacaatg   360
gtcactgtct cttca                                                   375

<210> SEQ ID NO 315
<211> LENGTH: 375
<212> TYPE: DNA
<213> ORGANISM: Homo sapiens
<220> FEATURE:
<221> NAME/KEY: source
<223> OTHER INFORMATION: /note="VH 1.23"

<400> SEQUENCE: 315
cagatcacct tgaaggagtc tgggggaggc ttggtcaagc ctggagggtc cctgagactc    60
tcctgtgcag cctctggatt caccttcagt gactacacca tgagctggat gcggcaggct   120
ccagggaagg ggctggagtg ggtttcctac ataagtactg gtggtactat caaatattac   180
acagactctg tgaagggccg attcaccatc tccaggaca acgccaagaa ctcactgtat    240
ctgcaaatga acagcctgag agccgacgac acggccgtgt attactgtgc gcgagaggcc   300
cctttacgtt tggggagtc cccccatgat gcttttgata tctggggcca agggacaatg   360
gtcaccgtct cctca                                                   375

<210> SEQ ID NO 316
<211> LENGTH: 375
<212> TYPE: DNA
<213> ORGANISM: Homo sapiens
<220> FEATURE:
<221> NAME/KEY: source
<223> OTHER INFORMATION: /note="VH 1.24"

<400> SEQUENCE: 316
caggtcacct tgaaggagtc tgggggaggc ttggtcaagc ctggagggtc cctgagactc    60
tcctgtgcag cctctggatt caccttcagt gactatgaca tgtactggat ccgccaggct   120
ccagggaagg ggctggagtg ggtttcatat attagtcgtg gtggtagtgt aacatactac   180
gcagactctg tgaagggccg attcaccatt tccaggaca acgccaagaa cgcactgtat    240
ctgcaaatga acagcctgag agccgaggac atggccgtat attttgtgc gacagaggcc    300 cctttacgtt tgggggagac ccccatgct gcttttgata tctggggcca agggacaatg   360
gtcaccgtct cctca                                                   375

<210> SEQ ID NO 317
<211> LENGTH: 375
<212> TYPE: DNA
<213> ORGANISM: Homo sapiens
<220> FEATURE:
<221> NAME/KEY: source
<223> OTHER INFORMATION: /note="VH 1.25"

<400> SEQUENCE: 317
caggtcacct tgaaggagtc tgggggaggc ttggtcaagc ctggagggtc cctgagactc    60
tcctgtgcag cctctggatt caccttcagt gactactaca tgagctggtt ccgccaggct   120
```

```
ccagggaagg aacgggagtg gatttcattt attagtagta gtggtagtac cacatactac    180
gcagactctg tgaagggccg attcaccatc tccagggaca acgccaagaa ctcactgtat    240
ctgcaaatga acagcctgag agccgaggat acggccgtct attactgtgc gagagaggcc    300
cctttacgtt tgggggagtc cccccatgat gcttttgatt tctggggcca agggacaatg    360
gtcaccgtct cttca                                                    375

<210> SEQ ID NO 318
<211> LENGTH: 375
<212> TYPE: DNA
<213> ORGANISM: Homo sapiens
<220> FEATURE:
<221> NAME/KEY: source
<223> OTHER INFORMATION: /note="VH 1.26"

<400> SEQUENCE: 318
caggtcacct tgaaggagtc tggggggaggc ttggtcaagc ctggagggtc cctgagactc     60
tcctgtgcag cctctggatt caccttcagt gacaattcca tgagctggat ccgccaggct    120
ccagggaagg ggctggagtg ggtttcatac attagtagta gtggtagtac catatactac    180
gcagactctg tgaagggccg attcaccatc tccagggaca acgccaagaa ctcactgtat    240
ctgcaaatga acaccctgag agccgaggac acggccgtgt attactgtgc gaaagaggcc    300
cctttacgtt tgggggagtc cccccatgat gcttttgata tctggggcca agggacaatg    360
gtcaccgtct cctca                                                    375

<210> SEQ ID NO 319
<211> LENGTH: 375
<212> TYPE: DNA
<213> ORGANISM: Homo sapiens
<220> FEATURE:
<221> NAME/KEY: source
<223> OTHER INFORMATION: /note="VH 1.27"

<400> SEQUENCE: 319
caggtcacct tgaaggagtc tggggggaggc ttggtcaagc ctggagggtc cctgagactc     60
tcctgtgcag cctctggatt caccttcagt gactacacca tgacctggat gcgccaggct    120
ccagggaagg ggctggagtg ggtttcatac ataagtactg gtggtagtat caaatattac    180
acagactctg tgaagggccg attcaccatc tccagggaca acgccaagaa ctcactgtat    240
ctgcaaatga acagcctgag agccgacgac acggccgtgt attactgtgc gagagaggcc    300
cctttacgtt tgggggagtc cccccatgat gcttttgata tctggggcca agggacaatg    360
gtcaccgtct cttca                                                    375

<210> SEQ ID NO 320
<211> LENGTH: 375
<212> TYPE: DNA
<213> ORGANISM: Homo sapiens
<220> FEATURE:
<221> NAME/KEY: source
<223> OTHER INFORMATION: /note="VH 1.28"

<400> SEQUENCE: 320
cagatcacct tgaaggagtc tggggggaggc ttggtcaagc ctggagggtc cctgagactc     60
tcctgtgcag cctctggatt caccttcagt gactatgaca tgtactggat ccgccaggct    120
ccagggaagg ggctggagtg ggtttcatat attagtcgtg gtggtagtgt aacatactac    180
gcagactctg tgaagggccg attcaccatt tccagggaca acgccaagaa cgcactgtat    240
```

```
ctgcaaatga acagcctgag agccgaggac atggccgtat attttgtgc gacagaggcc      300 cctttacgtt tggggagac cccccatgct gcttttgata tctggggcca agggacaatg      360
gtcaccgtct cttca                                                       375

<210> SEQ ID NO 321
<211> LENGTH: 375
<212> TYPE: DNA
<213> ORGANISM: Homo sapiens
<220> FEATURE:
<221> NAME/KEY: source
<223> OTHER INFORMATION: /note="VH 1.29"

<400> SEQUENCE: 321
caggtcacct tgaaggagtc tggggggaggc ttggtcaagc ctggagggtc cctgagactc      60
tcctgtgcag cctctggatt caccttcagt gactacacca tgagctggat gcggcaggct     120
ccagggaagg ggctggagtg ggtttcctac ataagtactg gtggtactat caaatattac     180
acagactctg tgaagggccg attcaccatc tccaggaca acgccaagaa ctcactgtat     240
ctgcaaatga acagcctgag agccgacgac acggccgtgt attactgtgc gcgagaggcc     300
cctttacgtt tggggagtc cccccatgat gcttttgata tctggggcca agggacaatg     360
gtcaccgtct cttca                                                       375

<210> SEQ ID NO 322
<211> LENGTH: 375
<212> TYPE: DNA
<213> ORGANISM: Homo sapiens
<220> FEATURE:
<221> NAME/KEY: source
<223> OTHER INFORMATION: /note="VH 1.30"

<400> SEQUENCE: 322
caggtcacct tgaaggagtc tggggggaggc ttggtcaagc ctggagggtc cctgagactc      60
tcctgtgcag cctctggatt caccttcagt gactacacca tgacctggat gcgccaggct     120
ccagggaagg ggctggagtg ggtttcatac ataagtactg gtggtagtat caaatattac     180
acagactctg tgaagggccg attcaccatc tccaggaca acgccaggaa ctcactatat     240
ctgcagatga acagcctgag agccgaggac acggccgtgt attactgtgc gagagaggcc     300
cctttacgtt tggggagtc cccccatgat gcttttgata tctggggcca agggacaatg     360
gtcaccgtct cttca                                                       375

<210> SEQ ID NO 323
<211> LENGTH: 375
<212> TYPE: DNA
<213> ORGANISM: Homo sapiens
<220> FEATURE:
<221> NAME/KEY: source
<223> OTHER INFORMATION: /note="VH 1.31"

<400> SEQUENCE: 323
caggtcacct tgaaggagtc tggggggaggc ttggtcaagc ctggagggtc cctgagactc      60
tcctgtgcag cctctggatt caccttcagt gactacacca tgacctggat gcgccaggct     120
ccagggaagg ggctggagtg ggtttcatac ataagtactg gtggtagtac caaatattac     180
acagactctg tgaagggccg attcaccatc tccaggaca acgccaagaa ctcactgtat     240
ctgcaaatga acagcctgag agccgacgac acggccgtgt attactgtgc gagagaggcc     300
cctttacgtt tggggagtc cccccatgat gcttttgata tctggggcca agggacaatg     360
```

```
gtcactgtct cctca                                              375

<210> SEQ ID NO 324
<211> LENGTH: 375
<212> TYPE: DNA
<213> ORGANISM: Homo sapiens
<220> FEATURE:
<221> NAME/KEY: source
<223> OTHER INFORMATION: /note="VH 1.32"

<400> SEQUENCE: 324
caggtcacct tgaaggagtc tggggggaggc ttggtcaagc cgggagggtc cctgagactc     60
tcctgtgcag cctctggatt caccttcagt gacgactaca tgatgtggat ccgccaggct    120
ccagggaagg ggctggagtg ggtttcatac attagtagtg gtggtagtat tatatactac    180
gcagactctg tgaagggccg attcaccatt tccaggaca acgccaagaa ctcactgtat    240
ctgcaaatga acagcctgag agccgaggac acggccgtgt attactgtgc gagagaggcc    300
cctttacgtt tgggggagtc cccccatgat gcttttgata tcaggggcca agggacaatg    360
gtcactgtct cctca                                              375

<210> SEQ ID NO 325
<211> LENGTH: 375
<212> TYPE: DNA
<213> ORGANISM: Homo sapiens
<220> FEATURE:
<221> NAME/KEY: source
<223> OTHER INFORMATION: /note="VH 1.33"

<400> SEQUENCE: 325
caggtcacct tgaaggagtc tggggggaggc ttggtcaagc ctggagggtc cctgagactc     60
tcctgtgcag cctctggatt caccttcagt gactatgaca tgtactgggt ccgccaggct    120
ccagggaagg ggctggagtg ggtttcatat attagtcgtg gtggtagtgt aacatactac    180
gcagactctg tgaagggccg attcaccatt tccaggaca acgccaagaa cgcactgtat    240
ctgcaaatga acagcctgag agccgaggac atggccgtat attttttgcgc gacagaggcc    300 cctttacgtt tgggggagac cccccatgct gcttttgata tctggggcca agggacaatg    360
gtcaccgtct cctca                                              375

<210> SEQ ID NO 326
<211> LENGTH: 375
<212> TYPE: DNA
<213> ORGANISM: Homo sapiens
<220> FEATURE:
<221> NAME/KEY: source
<223> OTHER INFORMATION: /note="VH 1.34"

<400> SEQUENCE: 326
gaggtgcagc tggtggagtc tggggggaggc ttggtcaagc ctggagggtc cctgagactc     60
tcctgtgcag cctctggatt caccttcagt gactacacca tgacctggat gcgccaggct    120
ccagggaagg ggctggagtg ggtttcatac ataagtactg gtggtagtgt taaatattac    180
acagactctg tgaagggccg attcaccatc tccaggaca acgccaagaa ctcactgtat    240
ctgcaaatga acagcctgag agccgacgac acggccgtgt attactgtgc gagagaggcc    300
cctttacgtt tgggggagtc cccccatgat gcttttgata tctggggcca agggacaatg    360
gtcactgtct cctca                                              375

<210> SEQ ID NO 327
```

```
<211> LENGTH: 375
<212> TYPE: DNA
<213> ORGANISM: Homo sapiens
<220> FEATURE:
<221> NAME/KEY: source
<223> OTHER INFORMATION: /note="VH 1.35"

<400> SEQUENCE: 327
gaggtgcagc tgttggagtc tgggggaggc ttggtcaagc ctggagggtc cctgagactc       60
tcctgtgcag cctctggatt caccttcagt gactacacca tgacctggat gcgccaggct      120
ccagggaagg ggctggagtg ggtttcttac ataagtactg gtggtagtat caaatattac      180
acagactctg tgaagggccg attcaccatc tccaggggaca cgccaagaa ctcactgtat      240 ctgcaaatga acagcctgag agtcgacgac acggccgtgt attactgtgc gagagaggcc      300
cctttacgtt tgggggagtc cccccatgat gcttttgata tctggggcca agggacaatg      360
gtcaccgtct cctca                                                       375

<210> SEQ ID NO 328
<211> LENGTH: 375
<212> TYPE: DNA
<213> ORGANISM: Homo sapiens
<220> FEATURE:
<221> NAME/KEY: source
<223> OTHER INFORMATION: /note="VH 1.36"

<400> SEQUENCE: 328
gaagtgcagc tggtggagtc tgggggaggc ttggtcaagc ctggagggtc cctgagactc       60
tcctgtgcag cctctggatt caccttcagt gactacacca tgacctggat gcggcaggct      120
ccagggaagg ggctggagtg ggtttcctac ataagtactg gtggtactat caaatattat      180
acagactctg tgaagggccg attcaccatc tccaggggaca cgccaagaa ttcactgttt      240 ctgcaaatga acagcctgag agccgacgac acggccgttt attactgtgc gagagaggcc      300
cctttacgtt tgggggagtc cccccatgat gcttttgata tctggggcca agggacaatg      360
gtcactgtct cttca                                                       375

<210> SEQ ID NO 329
<211> LENGTH: 375
<212> TYPE: DNA
<213> ORGANISM: Homo sapiens
<220> FEATURE:
<221> NAME/KEY: source
<223> OTHER INFORMATION: /note="VH 1.37"

<400> SEQUENCE: 329
caggtgcagc tggtggagtc tgggggaggc ttggtcaagc ctggagggtc cctgagactc       60
tcctgtgcag cctctggatt caccttcagt gactacacca tgacctggat gcgccaggct      120
ccagggaagg ggctggagtg ggtttcttac ataagtactg gtggtagtat caaatattat      180
acagactctg tgaagggccg attcaccatc tccaggggaca cgccaagaa ttcactgttt      240 ctgcaaatga acagcctgag agccgacgac acggccgtgt attactgtgc gagagaggcc      300
cctttacgtt tgggggagtc cccccatgat gcttttgata tctggggcca agggacaatg      360
gtcaccgtct cctca                                                       375

<210> SEQ ID NO 330
<211> LENGTH: 375
<212> TYPE: DNA
<213> ORGANISM: Homo sapiens
<220> FEATURE:
```

```
<221> NAME/KEY: source
<223> OTHER INFORMATION: /note="VH 1.38"

<400> SEQUENCE: 330
gaggtgcagc tggtggagtc tggggggaggc ttggtccagc ctggggggtc cctgagactc    60
tcctgtgcag cctctggatt caccttcagt gactacacca tgacctggat gcggcaggct   120
ccagggaagg ggctggagtg ggtttcctac ataagtactg gtggtactat caaatattac   180
acagactctg tgaagggccg attcaccatc tccaggdaca cgccaagaa ctcactgtat   240 ctgcaaatga acagcctgag agccgacgac acggccgtgt attactgtgc gcgagaggcc   300
cctttacgtt tgggggagtc cccccatgat gcttttgata tctggggcca agggacaatg   360
gtcaccgtct cctca                                                    375

<210> SEQ ID NO 331
<211> LENGTH: 375
<212> TYPE: DNA
<213> ORGANISM: Homo sapiens
<220> FEATURE:
<221> NAME/KEY: source
<223> OTHER INFORMATION: /note="VH 1.39"
<220> FEATURE:
<221> NAME/KEY: modified_base
<222> LOCATION: (273)..(273)
<223> OTHER INFORMATION: a, c, t, g, unknown or other

<400> SEQUENCE: 331
caggtgcagc tgcaggagtc ggggggaggc ttggtcaagc ctggagggtc cctgagactc    60
tcctgtgcag cctctggatt caccttcagt gactacacca tgacctggat gcgccaggct   120
ccagggaagg ggctggagtg ggtttcatac ataagtactg gtggtagtat caaatattac   180
acagactctg tgaagggccg attcaccatc tccaggdaca cgccaagaa ctcactgtat   240 ctgcaaatga acagcctgag agccgacgac acngccgtgt attactgtgc gagagaggcc   300
cctttacgtt tgggggagtc cccccatgat gcttttgata tctggggcca agggacaatg   360
gtcactgtct cttca                                                    375

<210> SEQ ID NO 332
<211> LENGTH: 375
<212> TYPE: DNA
<213> ORGANISM: Homo sapiens
<220> FEATURE:
<221> NAME/KEY: source
<223> OTHER INFORMATION: /note="VH 1.40"

<400> SEQUENCE: 332
gaggtgcagc tggtggagtc tggggggaggc ttggtcaagc ctggagggtc cctgagactc    60
tcctgtgcag cctctggatt caccttcagt gactcctcca tgagctggat ccgccaggct   120
ccagggaggg ggctggaatg gatttcatac attagtagtg gtggtggtat catatactac   180
acagactctg tgaagggccg attcaccatc tccaggdaca cgccaagaa ctcactgtat   240 ctacagatga acagcctgag agtcgaggac acggccgtgt attactgtgc gaaagaggcc   300
cctttacgtt tgggggagtc cccccatgat gcttttgata tctggggcca cgggacaatg   360
gtcaccgtct cttca                                                    375

<210> SEQ ID NO 333
<211> LENGTH: 375
<212> TYPE: DNA
<213> ORGANISM: Homo sapiens
<220> FEATURE:
```

<221> NAME/KEY: source
<223> OTHER INFORMATION: /note="VH 1.41"

<400> SEQUENCE: 333

```
caggtgcagc tggttgagtc tggggggaggc ttggtcaagc ctggagggtc cctgagactc     60
tcctgtgcag cctctggatt caccttcagt gacaactcca tgacctggat gcggcaggct    120
ccagggaagg ggctggagtg ggtttcctac ataagttctg gtggtggtgt catattttac    180
gcagactctg tgaagggccg attcaccatc tccaggaca acgccaagaa ctcactgtat     240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                      375
```

<210> SEQ ID NO 334
<211> LENGTH: 375
<212> TYPE: DNA
<213> ORGANISM: Homo sapiens
<220> FEATURE:
<221> NAME/KEY: source
<223> OTHER INFORMATION: /note="VH 1.42"

<400> SEQUENCE: 334

```
caggtgcagc tggtggagtc tggggggaggc ttggtcaagc ctggagggtc cctgagactc     60
tcctgtgcag cctctggatt caccttcagt gacaactcca tgacctggat gcggcaggct    120
ccagggaagg ggctggagtg ggtttcctac ataagttctg gtggtggtgt catattttac    180
gcagactctg tgaagggccg attcaccatc tccaggaca acgccaagaa ctcactgtat     240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                      375
```

<210> SEQ ID NO 335
<211> LENGTH: 375
<212> TYPE: DNA
<213> ORGANISM: Homo sapiens
<220> FEATURE:
<221> NAME/KEY: source
<223> OTHER INFORMATION: /note="VH 1.43"

<400> SEQUENCE: 335

```
caggtgcagc tggtggagtc tggggggaggc ttggtcaagc ctggagggtc cctgagactc     60
tcctgtgcag cctctggatt caccttcagt gacaactcca tgacctggat gcggcaggct    120
ccagggaagg ggctggagtg ggtttcctac ataagttctg gtggtggtgt catattttac    180
gcagactctg tgaagggccg attcaccatc tccaggaca acgccaagaa ctcactgtat     240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                      375
```

<210> SEQ ID NO 336
<211> LENGTH: 375
<212> TYPE: DNA
<213> ORGANISM: Homo sapiens
<220> FEATURE:
<221> NAME/KEY: source
<223> OTHER INFORMATION: /note="VH 1.44"

<400> SEQUENCE: 336

```
caggtgcagc tggtggagtc tgggggaggc ttggtcaagc ctggagggtc cctgagactc      60
tcctgtgcag cctctggatt caccttcagt gacaactcca tgacctggat gcggcaggct     120
ccagggaagg ggctggagtg ggtttcctac ataagttctg gtggtgctgt caaattttac     180
gcagactctg tgaagggccg attcaccatc tccaggaca  acgccaagaa ctcactgtat     240
ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                      375
```

<210> SEQ ID NO 337
<211> LENGTH: 375
<212> TYPE: DNA
<213> ORGANISM: Homo sapiens
<220> FEATURE:
<221> NAME/KEY: source
<223> OTHER INFORMATION: /note="VH 1.45"

<400> SEQUENCE: 337

```
caggtgcagc tggtggagtc tgggggaggc ttggtcaagc ctggagggtc cctgagactc      60
tcctgtgcag cctctggatt caccttcagt gactactcca tgtcctggat gcggcaggct     120
ccagggaagg ggctggagtg ggtttcctac ataagttctg gtggtggtgt catattttac     180
gcagactctg tgaagggccg attcaccatc tccaggaca  acgccaagaa ctcactgtat     240
ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                      375
```

<210> SEQ ID NO 338
<211> LENGTH: 375
<212> TYPE: DNA
<213> ORGANISM: Homo sapiens
<220> FEATURE:
<221> NAME/KEY: source
<223> OTHER INFORMATION: /note="VH 1.46"

<400> SEQUENCE: 338

```
caggtgcagc tggtggagtc tgggggaggc ttggtcaagc ctggagggtc cctgagactc      60
tcctgtgcag cctctggatt caccttcagt gacagctcca tgtcctggat gcggcaggct     120
ccagggaagg ggctggagtg ggtttcctac ataagttctg gtggtggtgt catattttac     180
gcagactctg tgaagggccg attcaccatc tccaggaca  acgccaagaa ctcactgtat     240
ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                      375
```

<210> SEQ ID NO 339
<211> LENGTH: 375
<212> TYPE: DNA
<213> ORGANISM: Homo sapiens
<220> FEATURE:
<221> NAME/KEY: source
<223> OTHER INFORMATION: /note="VH 1.47"

<400> SEQUENCE: 339

```
caggtgcagc tggtggagtc tgggggaggc ttggtcaagc ctggagggtc cctgagactc      60
tcctgtgcag cctctggatt caccttcagt gacaactcca tgtcctggat gcggcaggct     120
```

```
ccagggaagg ggctggagtg ggtttcctac ataagttctg gtggtggtgt catattttac    180
gcagactctg tgaagggccg attcaccatc tccaggaca acgccaagaa ctcactgtat     240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                     375
```

```
<210> SEQ ID NO 340
<211> LENGTH: 375
<212> TYPE: DNA
<213> ORGANISM: Homo sapiens
<220> FEATURE:
<221> NAME/KEY: source
<223> OTHER INFORMATION: /note="VH 1.48"

<400> SEQUENCE: 340
caggtgcagc tggtggagtc tgggggaggc ttggtcaagc ctggagggtc cctgagactc    60
tcctgtgcag cctctggatt caccttcagt gacagctcca tgacctggat gcggcaggct    120
ccagggaagg ggctggagtg ggtttcctac ataagttctg gtggtggtgt caaattttac    180
gcagactctg tgaagggccg attcaccatc tccaggaca acgccaagaa ctcactgtat     240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                     375
```

```
<210> SEQ ID NO 341
<211> LENGTH: 375
<212> TYPE: DNA
<213> ORGANISM: Homo sapiens
<220> FEATURE:
<221> NAME/KEY: source
<223> OTHER INFORMATION: /note="VH 1.49"

<400> SEQUENCE: 341
caggtgcaac tggttgaaag cggcggcggg ttagtaaaac ccggaggctc cctgcgactg    60
agttgcgcgg ccagtgggtt cacatttagc gattccagca tgtcatggat gcgtcaagct    120
cccggtaaag gcttagagtg ggtttcgtac attagcacag gtggtggtgt caaattctat    180
gctgattctg tcaaaggccg ttttaccatc tcccggata atgcaaagaa ctcgttgtat    240
ttgcagatga acagcttacg cgccgacgat actgcagtct attattgcgc acgcgaagct    300
cctctgcgct taggtgagag cccacatgac gcctttgata tatgggggca aggaacaatg    360
gtgaccgtgt ccagc                                                     375
```

```
<210> SEQ ID NO 342
<211> LENGTH: 375
<212> TYPE: DNA
<213> ORGANISM: Homo sapiens
<220> FEATURE:
<221> NAME/KEY: source
<223> OTHER INFORMATION: /note="VH 1.50"

<400> SEQUENCE: 342
caggtgcagc tggtggagtc tgggggaggc ttggtcaagc ctggagggtc cctgagactc    60
tcctgtgcag cctctggatt caccttcagt gacaactcca tgacctggat gcggcaggct    120
ccagggaagg ggctggagtg ggtttcctac ataagttctg gtggtactat caaattttac    180
gcagactctg tgaagggccg attcaccatc tccaggaca acgccaagaa ctcactgtat     240
```

```
ctgcaaatga acagcctgag agccgacgac acggccgtgt attactgtgc gcgagaggcc    300
cctttacgtt tggggagtc cccccatgat gcttttgata tctggggcca agggacaatg    360
gtcaccgtct cctca                                                    375
```

<210> SEQ ID NO 343
<211> LENGTH: 375
<212> TYPE: DNA
<213> ORGANISM: Homo sapiens
<220> FEATURE:
<221> NAME/KEY: source
<223> OTHER INFORMATION: /note="VH 1.51"

<400> SEQUENCE: 343

```
caggtgcagc tggtggagtc tgggggaggc ttggtcaagc ctggagggtc cctgagactc    60
tcctgtgcag cctctggatt caccttcagt gacagctcca tgacctggat gcggcaggct   120
ccagggaagg ggctggagtg ggtttcctac ataagttctg gtggtgctgt caaattttac   180
acagactctg tgaagggccg attcaccatc tccaggaca acgccaagaa ctcactgtat   240
ctgcaaatga acagcctgag agccgacgac acggccgtgt attactgtgc gcgagaggcc   300
cctttacgtt tggggagtc cccccatgat gcttttgata tctggggcca agggacaatg   360
gtcaccgtct cctca                                                    375
```

<210> SEQ ID NO 344
<211> LENGTH: 375
<212> TYPE: DNA
<213> ORGANISM: Homo sapiens
<220> FEATURE:
<221> NAME/KEY: source
<223> OTHER INFORMATION: /note="VH 1.52"

<400> SEQUENCE: 344

```
caggtgcagc tggtggagtc tgggggaggc ttggtcaagc ctggagggtc cctgagactc    60
tcctgtgcag cctctggatt caccttcagt gacaactcca tgacctggat gcggcaggct   120
ccagggaagg ggctggagtg ggtttcctac ataagttctg gtggtggtgt caaatattac   180
gcagactctg tgaagggccg attcaccatc tccaggaca acgccaagaa ctcactgtat    240
ctgcaaatga acagcctgag agccgacgac acggccgtgt attactgtgc gcgagaggcc   300
cctttacgtt tggggagtc cccccatgat gcttttgata tctggggcca agggacaatg    360
gtcaccgtct cctca                                                    375
```

<210> SEQ ID NO 345
<211> LENGTH: 375
<212> TYPE: DNA
<213> ORGANISM: Homo sapiens
<220> FEATURE:
<221> NAME/KEY: source
<223> OTHER INFORMATION: /note="VH 1.53"

<400> SEQUENCE: 345

```
caggtgcagc tggtggagtc tgggggaggc ttggtcaagc ctggagggtc cctgagactc    60
tcctgtgcag cctctggatt caccttcagt gacaactcca tgacctggat gcggcaggct   120
ccagggaagg ggctggagtg ggtttcctac ataagttctg gtggtagtgt caaattttac   180
gcagactctg tgaagggccg attcaccatc tccaggaca acgccaagaa ctcactgtat    240
ctgcaaatga acagcctgag agccgacgac acggccgtgt attactgtgc gcgagaggcc   300
cctttacgtt tggggagtc cccccatgat gcttttgata tctggggcca agggacaatg    360
```
gtcaccgtct cctca                                                           375

<210> SEQ ID NO 346
<211> LENGTH: 375
<212> TYPE: DNA
<213> ORGANISM: Homo sapiens
<220> FEATURE:
<221> NAME/KEY: source
<223> OTHER INFORMATION: /note="VH 1.54"

<400> SEQUENCE: 346
caggtgcagc tggtggagtc tgggggaggc ttggtcaagc ctggagggtc cctgagactc        60
tcctgtgcag cctctggatt caccttcagt gacgactcca tgacctggat gcggcaggct       120
ccagggaagg ggctggagtg ggtttcctac ataagttctg gtggtggtgt catattttac       180
gcagactctg tgaagggccg attcaccatc tccaggaca acgccaagaa ctcactgtat        240
ctgcaaatga acagcctgag agccgacgac acggccgtgt attactgtgc gcgagaggcc      300
cctttacgtt tgggggagtc cccccatgat gcttttgata tctggggcca agggacaatg      360
gtcaccgtct cctca                                                           375

<210> SEQ ID NO 347
<211> LENGTH: 375
<212> TYPE: DNA
<213> ORGANISM: Homo sapiens
<220> FEATURE:
<221> NAME/KEY: source
<223> OTHER INFORMATION: /note="VH 1.55"

<400> SEQUENCE: 347
caggtgcagc tggtggagtc tgggggaggc ttggtcaagc ctggagggtc cctgagactc        60
tcctgtgcag cctctggatt caccttcagt gacaactcca tgacctggat gcggcaggct       120
ccagggaagg ggctggagtg ggtttcctac ataagttctg gtggtggtgt caaattttac       180
gcagactctg tgaagggccg attcaccatc tccaggaca acgccaagaa ctcactgtat        240
ctgcaaatga acagcctgag agccgacgac acggccgtgt attactgtgc gcgagaggcc      300
cctttacgtt tgggggagtc ccctcatgat gcttttgata tctcgggcca agggacaatg      360
gtcaccgtct cctca                                                           375

<210> SEQ ID NO 348
<211> LENGTH: 375
<212> TYPE: DNA
<213> ORGANISM: Homo sapiens
<220> FEATURE:
<221> NAME/KEY: source
<223> OTHER INFORMATION: /note="VH 1.56"

<400> SEQUENCE: 348
caggtgcagc tggtggagtc tgggggaggc ttggtcaagc ctggagggtc cctgagactc        60
tcctgtgcag cctctggatt caccttcagt gacaactcca tgacctggat gcggcaggct       120
ccagggaagg ggctggagtg ggtttcctac ataagttctg gtggtgctgt caaattttac       180
gcagactctg tgaagggccg attcaccatc tccaggaca acgccaagaa ctcactgtat        240
ctgcaaatga acagcctgag agccgacgac acggccgtgt attactgtgc gcgagaggcc      300
cctttacgtt tgggggagtc cccccatgat gcttttgata tcttgggcca agggacaatg      360
gtcaccgtct cctca                                                           375

```
<210> SEQ ID NO 349
<211> LENGTH: 375
<212> TYPE: DNA
<213> ORGANISM: Homo sapiens
<220> FEATURE:
<221> NAME/KEY: source
<223> OTHER INFORMATION: /note="VH 1.57"

<400> SEQUENCE: 349
caggtgcagc tggtggagtc tgggggaggc ttggtcaagc ctggagggtc cctgagactc      60
tcctgtgcag cctctggatt caccttcagt gacaactcca tgacctggat gcggcaggct     120
ccagggaagg ggctggagtg ggtttcctac ataagttctg gtggtggtgt catattttac     180
gcagactctg tgaagggccg attcaccatc tccagggaca acgccaagaa ctcactgtat     240
ctgcaaatga acagcctgag agccgacgac acggccgtgt attactgtgc gcagagggcc     300
cctttacgtt tgggggagtc cccccatgat gcttttgata tctcgggcca agggacaatg     360
gtcaccgtct cctca                                                       375

<210> SEQ ID NO 350
<211> LENGTH: 375
<212> TYPE: DNA
<213> ORGANISM: Homo sapiens
<220> FEATURE:
<221> NAME/KEY: source
<223> OTHER INFORMATION: /note="VH 1.58"

<400> SEQUENCE: 350
caggtgcagc tggtggagtc tgggggaggc ttggtcaagc ctggagggtc cctgagactc      60
tcctgtgcag cctctggatt caccttcagt gacaacacca tgacctggat gcggcaggct     120
ccagggaagg ggctggagtg ggtttcctac ataagtactg gtggtggtgt caaattttac     180
gcagactctg tgaagggccg attcaccatc tccagggaca acgccaagaa ctcactgtat     240
ctgcaaatga acagcctgag agccgacgac acggccgtgt attactgtgc gcagagggcc     300
cctttacgtt tgggggagtc cccccatgat gcttttgata tctggggcca agggacaatg     360
gtcaccgtct cctca                                                       375

<210> SEQ ID NO 351
<211> LENGTH: 375
<212> TYPE: DNA
<213> ORGANISM: Homo sapiens
<220> FEATURE:
<221> NAME/KEY: source
<223> OTHER INFORMATION: /note="VH 1.59"

<400> SEQUENCE: 351
caggtgcagc tggtggagtc tgggggaggc ttggtcaagc ctggagggtc cctgagactc      60
tcctgtgcag cctctggatt caccttcagt gacaactcca tgtcctggat gcggcaggct     120
ccagggaagg ggctggagtg ggtttcctac ataagttctg gtggtagtgt caaattttac     180
gcagactctg tgaagggccg attcaccatc tccagggaca acgccaagaa ctcactgtat     240
ctgcaaatga acagcctgag agccgacgac acggccgtgt attactgtgc gcagaggcc      300 cctttacgtt tgggggagtc cccccatgat gcttttgata tctggggcca agggacaatg     360
gtcaccgtct cctca                                                       375

<210> SEQ ID NO 352
<211> LENGTH: 375
<212> TYPE: DNA
<213> ORGANISM: Homo sapiens
```

```
<220> FEATURE:
<221> NAME/KEY: source
<223> OTHER INFORMATION: /note="VH 1.60"

<400> SEQUENCE: 352
caggtgcagc tggtggagtc tggggggaggc ttggtcaagc ctggagggtc cctgagactc     60
tcctgtgcag cctctggatt caccttcagt gacaactcca tgacctggat gcggcaggct    120
ccagggaagg gctggagtg gtttcctac ataagtactg gtggtggtgt caaatattac      180
gcagactctg tgaagggccg attcaccatc tccagggaca acgccaagaa ctcactgtat    240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                      375

<210> SEQ ID NO 353
<211> LENGTH: 375
<212> TYPE: DNA
<213> ORGANISM: Homo sapiens
<220> FEATURE:
<221> NAME/KEY: source
<223> OTHER INFORMATION: /note="VH 1.61"

<400> SEQUENCE: 353
caggtgcagc tggtggagtc tggggggaggc ttggtcaagc ctggagggtc cctgagactc     60
tcctgtgcag cctctggatt caccttcagt gactacacca tgtcctggat gcggcaggct    120
ccagggaagg gctggagtg gtttcctac ataagtactg gtggtggtgt caaattttac      180
gcagactctg tgaagggccg attcaccatc tccagggaca atgccaagaa ctcactgtat    240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                      375

<210> SEQ ID NO 354
<211> LENGTH: 375
<212> TYPE: DNA
<213> ORGANISM: Homo sapiens
<220> FEATURE:
<221> NAME/KEY: source
<223> OTHER INFORMATION: /note="VH 1.62"

<400> SEQUENCE: 354
caggtgcagc tggtggagtc tggggggaggc ttggtcaagc ctggagggtc cctgagactc     60
tcctgtgcag cctctggatt caccttcagt gacagctcca tgacctggat gcggcaggct    120
ccagggaagg gctggagtg gtttcctac ataagttctg gtggtgctgt caaattttac      180
acagactctg tgaagggccg attcaccatc tccagggaca acgccaagaa ctcactgtat    240
ctgcaaatga acagcctgag agccgacgac acggccgtgt attactgtgc gcgagaggcc    300
cctttacgtt tgggggagtc cccccatgat gcttttgata tctcgggcca agggacaatg    360
gtcaccgtct cctca                                                      375

<210> SEQ ID NO 355
<211> LENGTH: 375
<212> TYPE: DNA
<213> ORGANISM: Homo sapiens
<220> FEATURE:
<221> NAME/KEY: source
<223> OTHER INFORMATION: /note="VH 1.63"
```

<400> SEQUENCE: 355

```
gaggtgcagc tggtggagtc tggggggaggc ttggtcaagc ctggagggtc cctgagactc    60
tcctgtgcag cctctggatt caccttcagt gacagctcca tgacctggat gcggcaggct   120
ccagggaagg ggctggagtg ggtttcctac ataagttctg gtggtggtgt caaattttac   180
acagactctg tgaagggccg attcaccatc tccagggaca cgccaagaa ctcactgtat   240
ctgcaaatga acagcctgag agccgacgac acggccgtgt attactgtgc gcagagggcc   300
cctttacgtt tgggggagtc cccccatgat gcttttgata tctcgggcca agggacaatg   360
gtcaccgtct cctca                                                    375
```

<210> SEQ ID NO 356
<211> LENGTH: 375
<212> TYPE: DNA
<213> ORGANISM: Homo sapiens
<220> FEATURE:
<221> NAME/KEY: source
<223> OTHER INFORMATION: /note="VH 1.64"

<400> SEQUENCE: 356

```
gaggtgcagc tggtggagtc tggggggaggc ttggtcaagc ctggagggtc cctgagactc    60
tcctgtgcag cctctggatt caccttcagt gacagctcca tgacctggat gcggcaggct   120
ccagggaagg ggctggagtg ggtttcctac ataagttctg gtggtggtgt caaattttac   180
gcagactctg tgaagggccg attcaccatc tccagggaca cgccaagaa ctcactgtat   240
ctgcaaatga acagcctgag agccgacgac acggccgtgt attactgtgc gcagagggcc   300
cctttacgtt tgggggagtc cccccatgat gcttttgata tctcgggcca agggacaatg   360
gtcaccgtct cctca                                                    375
```

<210> SEQ ID NO 357
<211> LENGTH: 375
<212> TYPE: DNA
<213> ORGANISM: Homo sapiens
<220> FEATURE:
<221> NAME/KEY: source
<223> OTHER INFORMATION: /note="VH 1.65"

<400> SEQUENCE: 357

```
caggtgcagc tggtggagtc tggggggaggc ttggtcaagc ctggagggtc cctgagactc    60
tcctgtgcag cctctggatt caccttcagt gacagctcca tgacctggat gcggcaggct   120
ccagggaagg ggctggagtg ggtttcctac ataagttctg gtggtggtgt caaattttac   180
gcagactctg tgaagggccg attcaccatc tccagggaca cgccaagaa ctcactgtat   240
ctgcaaatga acagcctgag agccgacgac acggccgtgt attactgtgc gcagagggcc   300
cctttacgtt tgggggagtc cccccatgat gcttttgata tctcgggcca agggacaatg   360
gtcaccgtct cctca                                                    375
```

<210> SEQ ID NO 358
<211> LENGTH: 375
<212> TYPE: DNA
<213> ORGANISM: Homo sapiens
<220> FEATURE:
<221> NAME/KEY: source
<223> OTHER INFORMATION: /note="VH 1.66"

<400> SEQUENCE: 358

```
caggtgcagc tggtggagtc tggggggaggc ttggtcaagc ctggagggtc cctgagactc    60
```

```
tcctgtgcag cctctggatt caccttcagt gacagctcca tgacctggat gcggcaggct    120
ccagggaagg ggctggagtg ggtttcctac ataagttctg gtggtggtgt caaattttac    180
acagactctg tgaagggccg attcaccatc tccagggaca acgccaagaa ctcactgtat    240
ctgcaaatgg acagcctgag agccgacgac acggccgtgt attactgtgc gcgagaggcc    300
cctttacgtt tgggggagtc cccccatgat gcttttgata cctcgggcca agggacaatg    360
gtcaccgtct cctca                                                     375
```

<210> SEQ ID NO 359
<211> LENGTH: 375
<212> TYPE: DNA
<213> ORGANISM: Homo sapiens
<220> FEATURE:
<221> NAME/KEY: source
<223> OTHER INFORMATION: /note="VH 1.67"

<400> SEQUENCE: 359

```
caggtgcagc tggtggagtc tgggggaggc ttggtcaagc ctggagggtc cctgagactc     60
tcctgtgcag cctctggatt caccttcagt ggcagctcca tgacctggat gcggcaggct    120
ccagggaagg ggctggagtg ggtttcctac ataagttctg gtggcggtgt catattttac    180
gcagactctg tgaagggccg attcaccatc tccagggaca acgccaagaa ctcactgtat    240
ctgcaaatga acagcctgag ggccgacgac acggccgtgt actactgtgc gcgagaggcc    300
cctttacgtt tgggggagtc cccccatgac gctttcgata tctcgggcca agggacaatg    360
gtcaccgtct cctca                                                     375
```

<210> SEQ ID NO 360
<211> LENGTH: 375
<212> TYPE: DNA
<213> ORGANISM: Homo sapiens
<220> FEATURE:
<221> NAME/KEY: source
<223> OTHER INFORMATION: /note="VH 1.68"

<400> SEQUENCE: 360

```
caggtgcagc tggtggagtc tgggggaggc ttggtcaagc ctggagggtc cctgagactc     60
tcctgtgcag cctctggatt caccttcggt gacaactcca tgacctggat gcggcaggct    120
ccagggaagg ggctggagtg ggtttcctac ataagttctg gtggtggtgt catattttac    180
gcagactctg tgaagggccg attcaccatc tccagggaca acgccaagaa ctcactgtat    240
ctgcaaatga acagcctgag agccgacgac acggccgtgt attactgtgc gcgagaggcc    300
cctttacgtt tgggggagtc cccccatgat gcttttgata tctcgggccg agggacaacg    360
gtcaccgtct cctca                                                     375
```

<210> SEQ ID NO 361
<211> LENGTH: 375
<212> TYPE: DNA
<213> ORGANISM: Homo sapiens
<220> FEATURE:
<221> NAME/KEY: source
<223> OTHER INFORMATION: /note="VH 1.69"

<400> SEQUENCE: 361

```
caggtgcagc tggtggagtc tgggggaggc ttggtcaagc ctggagggtc cctgagactc     60
tcctgtgcag cctctggatt caccttcagt gacaactcca tgtcctggat gcggcaggct    120
ccagggaagg ggctggagtg ggtttcctac ataagttctg gtggtggtgt catattttac    180
```

```
gcagactctg tgaagggccg attcaccatc tccagggaca acgccaagaa ctcactgtat      240
ctgcaaatga acagcctgag ggccgacgac acggccgtgt attactgtgc gcgagaggcc      300
cctttacgtt tgggggagtc cccccatgat gcttttgata tctcgggcca agggacaatg      360
gtcaccgtct cttca                                                      375

<210> SEQ ID NO 362
<211> LENGTH: 375
<212> TYPE: DNA
<213> ORGANISM: Homo sapiens
<220> FEATURE:
<221> NAME/KEY: source
<223> OTHER INFORMATION: /note="VH 1.70"

<400> SEQUENCE: 362
caggtgcagc tggtggagtc tgggggaggt ttggtcaagc ctggagggtc cctgagactc       60
tcctgtgcag cctctggatt caccttcggt gacagctcca tgacctggat gcggcaggct      120
ccagggaagg ggctggagtg ggtttcctac ataagttctg gtggtgctgt caagttttac      180
acagactctg tgaagggccg attcaccatc tccagggaca acgccaagaa ctcactgtat      240
ctgcaaatga acagcctgag agccgacgac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 363
<211> LENGTH: 375
<212> TYPE: DNA
<213> ORGANISM: Homo sapiens
<220> FEATURE:
<221> NAME/KEY: source
<223> OTHER INFORMATION: /note="VH 1.71"

<400> SEQUENCE: 363
caggtgcagc tggtggagtc tgggggaggc ttggtcaagc ctggagggtc cctgaggctc       60
tcctgtgcag cctcaggatt caccttcggt ggcagctcca tgacctggat gcggcaggct      120
ccagggaagg ggctggagtg ggtttcctac ataagttctg gtggtggtgt caaattttac      180
acagactctg tgaagggccg attcaccatc tccagggaca acgccaagaa ctcactgtat      240
ctgcaaatga acagcctgag agccgacgac acggccgtgt attactgtgc gcgagaggcc      300
cctttacgtt tgggggagtc cccccatgat gcttttgata tctcgggcca ggggacaatg      360
gtcaccgtct cctca                                                      375

<210> SEQ ID NO 364
<211> LENGTH: 375
<212> TYPE: DNA
<213> ORGANISM: Homo sapiens
<220> FEATURE:
<221> NAME/KEY: source
<223> OTHER INFORMATION: /note="VH 1.72"

<400> SEQUENCE: 364
caggtgcagc tggtggagtc tgggggaggc ttggtcaagc ctggagggtc cctgagactc       60
tcctgtgcag cctctggatt caccttcagt gacagctcca tgtcctggat gcggcaggct      120
ccagggaagg ggctggagtg ggtttcctac ataagttctg gtggtggtgt catattttac      180
gcagactctg tgaagggccg attcaccatc tccagggaca acgccaagaa ctcgctgtat      240
ctgcaaatga acagcctgag agccgacgac acggccgtgt attactgtgc gcgagaggcc      300
```

```
cctttacgtt tgggggagtc cccccatgat gcttttgata tctcgggcca agggacaatg    360
gtcaccgtct cttca                                                    375
```

<210> SEQ ID NO 365
<211> LENGTH: 375
<212> TYPE: DNA
<213> ORGANISM: Homo sapiens
<220> FEATURE:
<221> NAME/KEY: source
<223> OTHER INFORMATION: /note="VH 1.73"

<400> SEQUENCE: 365

```
caggtgcagc tggtggagtc tgggggaggc ttggtcaagc ctggagggtc cctgagactc     60
tcctgtgcag ccactggatt caccttcagt gacagctcca tgacctggat gcggcaggct   120
ccagggaagg gctggagtg gtttcctac ataagtgctg gtggtggtgt cagattttac     180
acagactctg tgaagggccg attcaccatc tccagggaca cgccaagaa ctcactgtat    240 ctgcaaatga acagcctgag gccgacgac acggccgtgt attactgtgc gcgagaggcc   300
cctttacgtt tgggggagtc cccccatgat gcttttgata tctcgggcca agggacaatg    360
gtcaccgtct catca                                                    375
```

<210> SEQ ID NO 366
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 369"

<400> SEQUENCE: 366

Asp Ser Ser Met Thr
1               5

<210> SEQ ID NO 367
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 369"

<400> SEQUENCE: 367

Tyr Ile Ser Ser Gly Gly Gly Val Lys Phe Tyr Thr Asp Ser Val Lys
1               5                   10                  15

Gly

<210> SEQ ID NO 368
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 369"

<400> SEQUENCE: 368

Glu Ala Pro Leu Arg Leu Gly Glu Ser Pro His Asp Ala Phe Asp Ile
1               5                   10                  15

<210> SEQ ID NO 369
<211> LENGTH: 125
<212> TYPE: PRT
<213> ORGANISM: Homo sapiens
<220> FEATURE:

<221> NAME/KEY: source
<223> OTHER INFORMATION: /note="VH 1.74"

<400> SEQUENCE: 369

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 370
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 373"

<400> SEQUENCE: 370

Asp Ser Ser Met Thr
1               5

<210> SEQ ID NO 371
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 373"

<400> SEQUENCE: 371

Tyr Ile Ser Ser Gly Gly Gly Val Lys Phe Tyr Thr Asp Ser Val Lys
1               5                   10                  15

Gly

<210> SEQ ID NO 372
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 373"

<400> SEQUENCE: 372

Glu Ala Pro Leu Arg Leu Gly Glu Ser Pro His Asp Ala Phe Asp Ile
1               5                   10                  15

<210> SEQ ID NO 373
<211> LENGTH: 125
<212> TYPE: PRT
<213> ORGANISM: Homo sapiens
<220> FEATURE:

<221> NAME/KEY: source
<223> OTHER INFORMATION: /note="VH 1.75"

<400> SEQUENCE: 373

Glu Val Gln Leu Val Glu Ser Gly Gly Gly Leu Val Lys Pro Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 374
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 377"

<400> SEQUENCE: 374

Asp Ser Ser Met Thr
1               5

<210> SEQ ID NO 375
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 377"

<400> SEQUENCE: 375

Tyr Ile Ser Ser Gly Gly Gly Val Lys Phe Tyr Ala Asp Ser Val Lys
1               5                   10                  15

Gly

<210> SEQ ID NO 376
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 377"

<400> SEQUENCE: 376

Glu Ala Pro Leu Arg Leu Gly Glu Ser Pro His Asp Ala Phe Asp Ile
1               5                   10                  15

<210> SEQ ID NO 377
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.76"

<400> SEQUENCE: 377

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 378
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 381"

<400> SEQUENCE: 378

Asp Ser Ser Met Thr
1               5

<210> SEQ ID NO 379
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 381"

<400> SEQUENCE: 379

Tyr Ile Ser Ser Gly Gly Gly Val Lys Phe Tyr Thr Asp Ser Val Lys
1               5                   10                  15

Gly

<210> SEQ ID NO 380
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 381"

<400> SEQUENCE: 380

Glu Ala Pro Leu Arg Leu Gly Glu Ser Pro His Asp Ala Phe Asp Ile
1               5                   10                  15

<210> SEQ ID NO 381
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.77"

<400> SEQUENCE: 381

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Ser
            20                  25                  30
Ser Met Thr Trp Met Arg Gln Ala Pro Gly Lys Gly Leu Glu Trp Val
        35                  40                  45
Ser Tyr Ile Ser Ser Gly Gly Gly Val Lys Phe Tyr Thr Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
        115                 120                 125

<210> SEQ ID NO 382
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 385"

<400> SEQUENCE: 382

Asp Ser Ser Met Thr
1               5

<210> SEQ ID NO 383
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 385"

<400> SEQUENCE: 383

Tyr Ile Ser Ser Gly Gly Gly Val Lys Phe Tyr Ala Asp Ser Val Lys
1               5                   10                  15
Gly

<210> SEQ ID NO 384
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 385"

<400> SEQUENCE: 384

Glu Ala Pro Leu Arg Leu Gly Glu Ser Pro His Asp Ala Phe Asp Ile
1               5                   10                  15

<210> SEQ ID NO 385
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.78"

<400> SEQUENCE: 385

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 386
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 389"

<400> SEQUENCE: 386

Asp Ser Ser Met Thr
1               5

<210> SEQ ID NO 387
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 389"

<400> SEQUENCE: 387

Tyr Ile Ser Ser Gly Gly Gly Val Lys Phe Tyr Ala Asp Ser Val Lys
1               5                   10                  15

Gly

<210> SEQ ID NO 388
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 389"

<400> SEQUENCE: 388

Glu Ala Pro Leu Arg Leu Gly Glu Ser Pro His Asp Ala Phe Asp Ile
1               5                   10                  15

<210> SEQ ID NO 389
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.79"

<400> SEQUENCE: 389

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Lys Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 390
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 393"

<400> SEQUENCE: 390

Asp Ser Ser Met Thr
1               5

<210> SEQ ID NO 391
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 393"

<400> SEQUENCE: 391

Tyr Ile Ser Ser Gly Gly Gly Val Lys Phe Tyr Ala Asp Ser Val Lys
1               5                   10                  15

Gly

<210> SEQ ID NO 392
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 393"

<400> SEQUENCE: 392

Glu Ala Pro Leu Arg Leu Gly Glu Ser Pro His Asp Ala Phe Asp Ile
1               5                   10                  15

<210> SEQ ID NO 393
<211> LENGTH: 125
<212> TYPE: PRT
<213> ORGANISM: Homo sapiens
<220> FEATURE:

<221> NAME/KEY: source
<223> OTHER INFORMATION: /note="VH 1.80"

<400> SEQUENCE: 393

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 394
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 397"

<400> SEQUENCE: 394

Asp Ser Ser Met Thr
1               5

<210> SEQ ID NO 395
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 397"

<400> SEQUENCE: 395

Tyr Ile Ser Ser Gly Gly Gly Val Lys Phe Tyr Ala Asp Ser Val Lys
1               5                   10                  15
Gly

<210> SEQ ID NO 396
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 397"

<400> SEQUENCE: 396

Glu Ala Pro Leu Arg Leu Gly Glu Ser Pro His Asp Ala Phe Asp Ile
1               5                   10                  15

<210> SEQ ID NO 397
<211> LENGTH: 125
<212> TYPE: PRT
<213> ORGANISM: Homo sapiens
<220> FEATURE:

<221> NAME/KEY: source
<223> OTHER INFORMATION: /note="VH 1.81"

<400> SEQUENCE: 397

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Val Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 398
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 401"

<400> SEQUENCE: 398

Asp Thr Ser Met Thr
1               5

<210> SEQ ID NO 399
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 401"

<400> SEQUENCE: 399

Tyr Ile Ser Ser Gly Gly Gly Val Lys Phe Tyr Thr Asp Ser Val Lys
1               5                   10                  15

Gly

<210> SEQ ID NO 400
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 401"

<400> SEQUENCE: 400

Glu Ala Pro Leu Arg Leu Gly Glu Ser Pro His Asp Ala Phe Asp Ile
1               5                   10                  15

<210> SEQ ID NO 401
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.82"

<400> SEQUENCE: 401

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Thr
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 402
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 405"

<400> SEQUENCE: 402

Asp Glu Ser Met Thr
1               5

<210> SEQ ID NO 403
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 405"

<400> SEQUENCE: 403

Tyr Ile Ser Ser Gly Gly Gly Val Lys Phe Tyr Thr Asp Ser Val Lys
1               5                   10                  15

Gly

<210> SEQ ID NO 404
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 405"

<400> SEQUENCE: 404

Glu Ala Pro Leu Arg Leu Gly Glu Ser Pro His Asp Ala Phe Asp Ile
1               5                   10                  15

<210> SEQ ID NO 405
<211> LENGTH: 125
<212> TYPE: PRT
<213> ORGANISM: Homo sapiens
<220> FEATURE:
```

-continued

```
<221> NAME/KEY: source
<223> OTHER INFORMATION: /note="VH 1.83"

<400> SEQUENCE: 405
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Phe Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

```
<210> SEQ ID NO 406
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 409"

<400> SEQUENCE: 406
```

Asp Glu Ser Met Thr
1               5

```
<210> SEQ ID NO 407
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 409"

<400> SEQUENCE: 407
```

Tyr Ile Ser Ser Gly Gly Gly Val Lys Phe Tyr Thr Asp Ser Val Lys
1               5                   10                  15

Gly

```
<210> SEQ ID NO 408
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 409"

<400> SEQUENCE: 408
```

Glu Ala Pro Leu Arg Leu Gly Glu Ser Pro His Asp Ala Phe Asp Ile
1               5                   10                  15

```
<210> SEQ ID NO 409
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.84"

<400> SEQUENCE: 409

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 410
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 413"

<400> SEQUENCE: 410

Asp Tyr Ser Met Thr
1               5

<210> SEQ ID NO 411
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 413"

<400> SEQUENCE: 411

Tyr Ile Ser Ser Gly Gly Gly Val Lys Phe Tyr Thr Asp Ser Val Lys
1               5                   10                  15

Gly

<210> SEQ ID NO 412
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 413"

<400> SEQUENCE: 412

Glu Ala Pro Leu Arg Leu Gly Glu Ser Pro His Asp Ala Phe Asp Ile
1               5                   10                  15

<210> SEQ ID NO 413
<211> LENGTH: 125
<212> TYPE: PRT
<213> ORGANISM: Homo sapiens
<220> FEATURE:

<221> NAME/KEY: source
<223> OTHER INFORMATION: /note="VH 1.85"

<400> SEQUENCE: 413

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Ser Met Thr Trp Met Arg Gln Ala Pro Gly Lys Gly Leu Glu Trp Val
        35                  40                  45
Ser Tyr Ile Ser Ser Gly Gly Gly Val Lys Phe Tyr Thr Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
        115                 120                 125

<210> SEQ ID NO 414
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 417"

<400> SEQUENCE: 414

Asp Ala Ser Met Thr
1               5

<210> SEQ ID NO 415
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 417"

<400> SEQUENCE: 415

Tyr Ile Ser Ser Gly Gly Gly Val Lys Phe Tyr Thr Asp Ser Val Lys
1               5                   10                  15
Gly

<210> SEQ ID NO 416
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 417"

<400> SEQUENCE: 416

Glu Ala Pro Leu Arg Leu Gly Glu Ser Pro His Asp Ala Phe Asp Ile
1               5                   10                  15

<210> SEQ ID NO 417
<211> LENGTH: 125
<212> TYPE: PRT
<213> ORGANISM: Homo sapiens
<220> FEATURE:

<221> NAME/KEY: source
<223> OTHER INFORMATION: /note="VH 1.86"

<400> SEQUENCE: 417

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 418
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 421"

<400> SEQUENCE: 418

Asp Lys Ser Met Thr
1               5

<210> SEQ ID NO 419
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 421"

<400> SEQUENCE: 419

Tyr Ile Ser Ser Gly Gly Gly Val Lys Phe Tyr Thr Asp Ser Val Lys
1               5                   10                  15

Gly

<210> SEQ ID NO 420
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 421"

<400> SEQUENCE: 420

Glu Ala Pro Leu Arg Leu Gly Glu Ser Pro His Asp Ala Phe Asp Ile
1               5                   10                  15

<210> SEQ ID NO 421
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.87"

<400> SEQUENCE: 421
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Lys
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

```
<210> SEQ ID NO 422
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 425"

<400> SEQUENCE: 422
```

Asp Arg Ser Met Thr
1               5

```
<210> SEQ ID NO 423
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 425"

<400> SEQUENCE: 423
```

Tyr Ile Ser Ser Gly Gly Gly Val Lys Phe Tyr Thr Asp Ser Val Lys
1               5                   10                  15

Gly

```
<210> SEQ ID NO 424
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 425"

<400> SEQUENCE: 424
```

Glu Ala Pro Leu Arg Leu Gly Glu Ser Pro His Asp Ala Phe Asp Ile
1               5                   10                  15

```
<210> SEQ ID NO 425
<211> LENGTH: 125
<212> TYPE: PRT
<213> ORGANISM: Homo sapiens
<220> FEATURE:
```

```
<221> NAME/KEY: source
<223> OTHER INFORMATION: /note="VH 1.88"

<400> SEQUENCE: 425

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Arg
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 426
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 429"

<400> SEQUENCE: 426

Asp Tyr Ser Met Thr
1               5

<210> SEQ ID NO 427
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 429"

<400> SEQUENCE: 427

Tyr Ile Ser Ser Gly Gly Gly Val Lys Phe Tyr Ala Asp Ser Val Lys
1               5                   10                  15

Gly

<210> SEQ ID NO 428
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 429"

<400> SEQUENCE: 428

Glu Ala Pro Leu Arg Leu Gly Glu Ser Pro His Asp Ala Phe Asp Ile
1               5                   10                  15

<210> SEQ ID NO 429
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.89"

<400> SEQUENCE: 429

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 430
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 433"

<400> SEQUENCE: 430

Asp Val Ser Met Thr
1               5

<210> SEQ ID NO 431
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 433"

<400> SEQUENCE: 431

Tyr Ile Ser Ser Gly Gly Gly Val Lys Phe Tyr Ala Asp Ser Val Lys
1               5                   10                  15

Gly

<210> SEQ ID NO 432
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 433"

<400> SEQUENCE: 432

Glu Ala Pro Leu Arg Leu Gly Glu Ser Pro His Asp Ala Phe Asp Ile
1               5                   10                  15

<210> SEQ ID NO 433
<211> LENGTH: 125
<212> TYPE: PRT
<213> ORGANISM: Homo sapiens
<220> FEATURE:

<221> NAME/KEY: source
<223> OTHER INFORMATION: /note="VH 1.90"

<400> SEQUENCE: 433

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Val
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 434
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 437"

<400> SEQUENCE: 434

Asp Gln Ser Met Thr
1               5

<210> SEQ ID NO 435
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 437"

<400> SEQUENCE: 435

Tyr Ile Ser Ser Gly Gly Gly Val Lys Phe Tyr Ala Asp Ser Val Lys
1               5                   10                  15

Gly

<210> SEQ ID NO 436
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 437"

<400> SEQUENCE: 436

Glu Ala Pro Leu Arg Leu Gly Glu Ser Pro His Asp Ala Phe Asp Ile
1               5                   10                  15

<210> SEQ ID NO 437
<211> LENGTH: 125
<212> TYPE: PRT
<213> ORGANISM: Homo sapiens
<220> FEATURE:

<221> NAME/KEY: source
<223> OTHER INFORMATION: /note="VH 1.91"

<400> SEQUENCE: 437

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Gln
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 438
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 441"

<400> SEQUENCE: 438

Asp Glu Ser Met Thr
1               5

<210> SEQ ID NO 439
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 441"

<400> SEQUENCE: 439

Tyr Ile Ser Ser Gly Gly Gly Val Lys Phe Tyr Ala Asp Ser Val Lys
1               5                   10                  15

Gly

<210> SEQ ID NO 440
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 441"

<400> SEQUENCE: 440

Glu Ala Pro Leu Arg Leu Gly Glu Ser Pro His Asp Ala Phe Asp Ile
1               5                   10                  15

<210> SEQ ID NO 441
<211> LENGTH: 125
<212> TYPE: PRT
<213> ORGANISM: Homo sapiens
<220> FEATURE:

<221> NAME/KEY: source
<223> OTHER INFORMATION: /note="VH 1.92"

<400> SEQUENCE: 441

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 442
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 445"

<400> SEQUENCE: 442

Asp Ala Ser Met Thr
1               5

<210> SEQ ID NO 443
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 445"

<400> SEQUENCE: 443

Tyr Ile Ser Ser Gly Gly Gly Val Lys Phe Tyr Ala Asp Ser Val Lys
1               5                   10                  15

Gly

<210> SEQ ID NO 444
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 445"

<400> SEQUENCE: 444

Glu Ala Pro Leu Arg Leu Gly Glu Ser Pro His Asp Ala Phe Asp Ile
1               5                   10                  15

<210> SEQ ID NO 445
<211> LENGTH: 125
<212> TYPE: PRT
<213> ORGANISM: Homo sapiens
<220> FEATURE:

<221> NAME/KEY: source
<223> OTHER INFORMATION: /note="VH 1.93"

<400> SEQUENCE: 445

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 446
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 449"

<400> SEQUENCE: 446

Asp Trp Ser Met Thr
1               5

<210> SEQ ID NO 447
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 449"

<400> SEQUENCE: 447

Tyr Ile Ser Ser Gly Gly Gly Val Lys Phe Tyr Ala Asp Ser Val Lys
1               5                   10                  15

Gly

<210> SEQ ID NO 448
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 449"

<400> SEQUENCE: 448

Glu Ala Pro Leu Arg Leu Gly Glu Ser Pro His Asp Ala Phe Asp Ile
1               5                   10                  15

<210> SEQ ID NO 449
<211> LENGTH: 125
<212> TYPE: PRT
<213> ORGANISM: Homo sapiens
<220> FEATURE:

<221> NAME/KEY: source
<223> OTHER INFORMATION: /note="VH 1.94"

<400> SEQUENCE: 449

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Trp
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 450
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 453"

<400> SEQUENCE: 450

Asp Gly Ser Met Thr
1               5

<210> SEQ ID NO 451
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 453"

<400> SEQUENCE: 451

Tyr Ile Ser Ser Gly Gly Gly Val Lys Phe Tyr Ala Asp Ser Val Lys
1               5                   10                  15

Gly

<210> SEQ ID NO 452
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 453"

<400> SEQUENCE: 452

Glu Ala Pro Leu Arg Leu Gly Glu Ser Pro His Asp Ala Phe Asp Ile
1               5                   10                  15

<210> SEQ ID NO 453
<211> LENGTH: 125
<212> TYPE: PRT
<213> ORGANISM: Homo sapiens
<220> FEATURE:

<221> NAME/KEY: source
<223> OTHER INFORMATION: /note="VH 1.95"

<400> SEQUENCE: 453

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Gly
            20                  25                  30
Ser Met Thr Trp Met Arg Gln Ala Pro Gly Lys Gly Leu Glu Trp Val
        35                  40                  45
Ser Tyr Ile Ser Ser Gly Gly Val Lys Phe Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
            115                 120                 125

<210> SEQ ID NO 454
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 457"

<400> SEQUENCE: 454

Asp Thr Ser Met Thr
1               5

<210> SEQ ID NO 455
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 457"

<400> SEQUENCE: 455

Tyr Ile Ser Ser Gly Gly Gly Val Lys Phe Tyr Ala Asp Ser Val Lys
1               5                   10                  15
Gly

<210> SEQ ID NO 456
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 457"

<400> SEQUENCE: 456

Glu Ala Pro Leu Arg Leu Gly Glu Ser Pro His Asp Ala Phe Asp Ile
1               5                   10                  15

<210> SEQ ID NO 457
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.96"

<400> SEQUENCE: 457
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Thr
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

```
<210> SEQ ID NO 458
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 461"

<400> SEQUENCE: 458
```

Asp Ile Ser Met Thr
1               5

```
<210> SEQ ID NO 459
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 461"

<400> SEQUENCE: 459
```

Tyr Ile Ser Ser Gly Gly Gly Val Lys Phe Tyr Ala Asp Ser Val Lys
1               5                   10                  15

Gly

```
<210> SEQ ID NO 460
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 461"

<400> SEQUENCE: 460
```

Glu Ala Pro Leu Arg Leu Gly Glu Ser Pro His Asp Ala Phe Asp Ile
1               5                   10                  15

```
<210> SEQ ID NO 461
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.97"

<400> SEQUENCE: 461

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ile
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 462
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 465"

<400> SEQUENCE: 462

Asp Lys Ser Met Thr
1               5

<210> SEQ ID NO 463
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 465"

<400> SEQUENCE: 463

Tyr Ile Ser Ser Gly Gly Gly Val Lys Phe Tyr Ala Asp Ser Val Lys
1               5                   10                  15
Gly

<210> SEQ ID NO 464
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 465"

<400> SEQUENCE: 464

Glu Ala Pro Leu Arg Leu Gly Glu Ser Pro His Asp Ala Phe Asp Ile
1               5                   10                  15

<210> SEQ ID NO 465
<211> LENGTH: 125
<212> TYPE: PRT
<213> ORGANISM: Homo sapiens
<220> FEATURE:

<221> NAME/KEY: source
<223> OTHER INFORMATION: /note="VH 1.98"

<400> SEQUENCE: 465

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Lys
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 466
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 469"

<400> SEQUENCE: 466

Asp Arg Ser Met Thr
1               5

<210> SEQ ID NO 467
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 469"

<400> SEQUENCE: 467

Tyr Ile Ser Ser Gly Gly Gly Val Lys Phe Tyr Ala Asp Ser Val Lys
1               5                   10                  15

Gly

<210> SEQ ID NO 468
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 469"

<400> SEQUENCE: 468

Glu Ala Pro Leu Arg Leu Gly Glu Ser Pro His Asp Ala Phe Asp Ile
1               5                   10                  15

<210> SEQ ID NO 469
<211> LENGTH: 125
<212> TYPE: PRT
<213> ORGANISM: Homo sapiens
<220> FEATURE:

<221> NAME/KEY: source
<223> OTHER INFORMATION: /note="VH 1.99"

<400> SEQUENCE: 469

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Arg
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 470
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 473"

<400> SEQUENCE: 470

Asp Leu Ser Met Thr
1               5

<210> SEQ ID NO 471
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 473"

<400> SEQUENCE: 471

Tyr Ile Ser Ser Gly Gly Gly Val Lys Phe Tyr Ala Asp Ser Val Lys
1               5                   10                  15

Gly

<210> SEQ ID NO 472
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 473"

<400> SEQUENCE: 472

Glu Ala Pro Leu Arg Leu Gly Glu Ser Pro His Asp Ala Phe Asp Ile
1               5                   10                  15

<210> SEQ ID NO 473
<211> LENGTH: 125
<212> TYPE: PRT
<213> ORGANISM: Homo sapiens
<220> FEATURE:

<221> NAME/KEY: source
<223> OTHER INFORMATION: /note="VH 1.100"

<400> SEQUENCE: 473

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Leu
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 474
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 477"

<400> SEQUENCE: 474

Asp Phe Ser Met Thr
1               5

<210> SEQ ID NO 475
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 477"

<400> SEQUENCE: 475

Tyr Ile Ser Ser Gly Gly Gly Val Lys Phe Tyr Ala Asp Ser Val Lys
1               5                   10                  15

Gly

<210> SEQ ID NO 476
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 477"

<400> SEQUENCE: 476

Glu Ala Pro Leu Arg Leu Gly Glu Ser Pro His Asp Ala Phe Asp Ile
1               5                   10                  15

<210> SEQ ID NO 477
<211> LENGTH: 125
<212> TYPE: PRT
<213> ORGANISM: Homo sapiens
<220> FEATURE:

<221> NAME/KEY: source
<223> OTHER INFORMATION: /note="VH 1.101"

<400> SEQUENCE: 477

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 478
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 481"

<400> SEQUENCE: 478

Asp Glu Ser Val Thr
1               5

<210> SEQ ID NO 479
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 481"

<400> SEQUENCE: 479

Tyr Ile Ser Ser Gly Gly Gly Val Lys Phe Tyr Thr Asp Ser Val Lys
1               5                   10                  15

Gly

<210> SEQ ID NO 480
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 481"

<400> SEQUENCE: 480

Glu Ala Pro Leu Arg Leu Gly Glu Ser Pro His Asp Ala Phe Asp Ile
1               5                   10                  15

<210> SEQ ID NO 481
<211> LENGTH: 125
<212> TYPE: PRT
<213> ORGANISM: Homo sapiens
<220> FEATURE:

<221> NAME/KEY: source
<223> OTHER INFORMATION: /note="VH 1.102"

<400> SEQUENCE: 481

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Glu
            20                  25                  30
Ser Val Thr Trp Met Arg Gln Ala Pro Gly Lys Gly Leu Glu Trp Val
        35                  40                  45
Ser Tyr Ile Ser Ser Gly Gly Gly Val Lys Phe Tyr Thr Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
        115                 120                 125

<210> SEQ ID NO 482
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 485"

<400> SEQUENCE: 482

Asp Glu Ser Gln Thr
1               5

<210> SEQ ID NO 483
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 485"

<400> SEQUENCE: 483

Tyr Ile Ser Ser Gly Gly Gly Val Lys Phe Tyr Thr Asp Ser Val Lys
1               5                   10                  15
Gly

<210> SEQ ID NO 484
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 485"

<400> SEQUENCE: 484

Glu Ala Pro Leu Arg Leu Gly Glu Ser Pro His Asp Ala Phe Asp Ile
1               5                   10                  15

<210> SEQ ID NO 485
<211> LENGTH: 125
<212> TYPE: PRT
<213> ORGANISM: Homo sapiens
<220> FEATURE:

<221> NAME/KEY: source
<223> OTHER INFORMATION: /note="VH 1.103"

<400> SEQUENCE: 485

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Gln Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 486
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 489"

<400> SEQUENCE: 486

Asp Glu Ser Phe Thr
1               5

<210> SEQ ID NO 487
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 489"

<400> SEQUENCE: 487

Tyr Ile Ser Ser Gly Gly Gly Val Lys Phe Tyr Thr Asp Ser Val Lys
1               5                   10                  15

Gly

<210> SEQ ID NO 488
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 489"

<400> SEQUENCE: 488

Glu Ala Pro Leu Arg Leu Gly Glu Ser Pro His Asp Ala Phe Asp Ile
1               5                   10                  15

<210> SEQ ID NO 489
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.104"

<400> SEQUENCE: 489
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Phe Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

```
<210> SEQ ID NO 490
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 493"

<400> SEQUENCE: 490
```

Asp Glu Ser Leu Thr
1               5

```
<210> SEQ ID NO 491
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 493"

<400> SEQUENCE: 491
```

Tyr Ile Ser Ser Gly Gly Gly Val Lys Phe Tyr Thr Asp Ser Val Lys
1               5                   10                  15

Gly

```
<210> SEQ ID NO 492
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 493"

<400> SEQUENCE: 492
```

Glu Ala Pro Leu Arg Leu Gly Glu Ser Pro His Asp Ala Phe Asp Ile
1               5                   10                  15

```
<210> SEQ ID NO 493
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.105"

<400> SEQUENCE: 493

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Glu
            20                  25                  30
Ser Leu Thr Trp Met Arg Gln Ala Pro Gly Lys Gly Leu Glu Trp Val
        35                  40                  45
Ser Tyr Ile Ser Ser Gly Gly Gly Val Lys Phe Tyr Thr Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
        115                 120                 125

<210> SEQ ID NO 494
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 497"

<400> SEQUENCE: 494

Asp Glu Ser Lys Thr
1               5

<210> SEQ ID NO 495
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 497"

<400> SEQUENCE: 495

Tyr Ile Ser Ser Gly Gly Gly Val Lys Phe Tyr Thr Asp Ser Val Lys
1               5                   10                  15
Gly

<210> SEQ ID NO 496
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 497"

<400> SEQUENCE: 496

Glu Ala Pro Leu Arg Leu Gly Glu Ser Pro His Asp Ala Phe Asp Ile
1               5                   10                  15

<210> SEQ ID NO 497
<211> LENGTH: 125
<212> TYPE: PRT
<213> ORGANISM: Homo sapiens
<220> FEATURE:

<221> NAME/KEY: source
<223> OTHER INFORMATION: /note="VH 1.106"

<400> SEQUENCE: 497

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Lys Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 498
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 501"

<400> SEQUENCE: 498

Asp Glu Ser Tyr Thr
1               5

<210> SEQ ID NO 499
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 501"

<400> SEQUENCE: 499

Tyr Ile Ser Ser Gly Gly Gly Val Lys Phe Tyr Thr Asp Ser Val Lys
1               5                   10                  15

Gly

<210> SEQ ID NO 500
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 501"

<400> SEQUENCE: 500

Glu Ala Pro Leu Arg Leu Gly Glu Ser Pro His Asp Ala Phe Asp Ile
1               5                   10                  15

<210> SEQ ID NO 501
<211> LENGTH: 125
<212> TYPE: PRT
<213> ORGANISM: Homo sapiens
<220> FEATURE:

<221> NAME/KEY: source
<223> OTHER INFORMATION: /note="VH 1.107"

<400> SEQUENCE: 501

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Tyr Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 502
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 505"

<400> SEQUENCE: 502

Asp Glu Ser Ala Thr
1               5

<210> SEQ ID NO 503
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 505"

<400> SEQUENCE: 503

Tyr Ile Ser Ser Gly Gly Gly Val Lys Phe Tyr Ala Asp Ser Val Lys
1               5                   10                  15

Gly

<210> SEQ ID NO 504
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 505"

<400> SEQUENCE: 504

Glu Ala Pro Leu Arg Leu Gly Glu Ser Pro His Asp Ala Phe Asp Ile
1               5                   10                  15

<210> SEQ ID NO 505
<211> LENGTH: 125
<212> TYPE: PRT
<213> ORGANISM: Homo sapiens
<220> FEATURE:

<221> NAME/KEY: source
<223> OTHER INFORMATION: /note="VH 1.108"

<400> SEQUENCE: 505

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Ala Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 506
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 509"

<400> SEQUENCE: 506

Asp Glu Ser Phe Thr
1               5

<210> SEQ ID NO 507
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 509"

<400> SEQUENCE: 507

Tyr Ile Ser Ser Gly Gly Gly Val Lys Phe Tyr Ala Asp Ser Val Lys
1               5                   10                  15

Gly

<210> SEQ ID NO 508
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 509"

<400> SEQUENCE: 508

Glu Ala Pro Leu Arg Leu Gly Glu Ser Pro His Asp Ala Phe Asp Ile
1               5                   10                  15

<210> SEQ ID NO 509
<211> LENGTH: 125
<212> TYPE: PRT
<213> ORGANISM: Homo sapiens
<220> FEATURE:

<221> NAME/KEY: source
<223> OTHER INFORMATION: /note="VH 1.109"

<400> SEQUENCE: 509

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Phe Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 510
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 513"

<400> SEQUENCE: 510

Asp Glu Ser Asn Thr
1               5

<210> SEQ ID NO 511
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 513"

<400> SEQUENCE: 511

Tyr Ile Ser Ser Gly Gly Gly Val Lys Phe Tyr Ala Asp Ser Val Lys
1               5                   10                  15

Gly

<210> SEQ ID NO 512
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 513"

<400> SEQUENCE: 512

Glu Ala Pro Leu Arg Leu Gly Glu Ser Pro His Asp Ala Phe Asp Ile
1               5                   10                  15

<210> SEQ ID NO 513
<211> LENGTH: 125
<212> TYPE: PRT
<213> ORGANISM: Homo sapiens
<220> FEATURE:

<221> NAME/KEY: source
<223> OTHER INFORMATION: /note="VH 1.110"

<400> SEQUENCE: 513

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Asn Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 514
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 517"

<400> SEQUENCE: 514

Asp Glu Ser Trp Thr
1               5

<210> SEQ ID NO 515
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 517"

<400> SEQUENCE: 515

Tyr Ile Ser Ser Gly Gly Gly Val Lys Phe Tyr Ala Asp Ser Val Lys
1               5                   10                  15

Gly

<210> SEQ ID NO 516
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 517"

<400> SEQUENCE: 516

Glu Ala Pro Leu Arg Leu Gly Glu Ser Pro His Asp Ala Phe Asp Ile
1               5                   10                  15

<210> SEQ ID NO 517
<211> LENGTH: 125
<212> TYPE: PRT
<213> ORGANISM: Homo sapiens
<220> FEATURE:

<221> NAME/KEY: source
<223> OTHER INFORMATION: /note="VH 1.111"

<400> SEQUENCE: 517

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Trp Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 518
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 521"

<400> SEQUENCE: 518

Asp Glu Ser Ile Thr
1               5

<210> SEQ ID NO 519
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 521"

<400> SEQUENCE: 519

Tyr Ile Ser Ser Gly Gly Gly Val Lys Phe Tyr Ala Asp Ser Val Lys
1               5                   10                  15

Gly

<210> SEQ ID NO 520
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 521"

<400> SEQUENCE: 520

Glu Ala Pro Leu Arg Leu Gly Glu Ser Pro His Asp Ala Phe Asp Ile
1               5                   10                  15

<210> SEQ ID NO 521
<211> LENGTH: 125
<212> TYPE: PRT
<213> ORGANISM: Homo sapiens
<220> FEATURE:

<221> NAME/KEY: source
<223> OTHER INFORMATION: /note="VH 1.112"

<400> SEQUENCE: 521

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Ile Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 522
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 525"

<400> SEQUENCE: 522

Asp Glu Ser Ser Thr
1               5

<210> SEQ ID NO 523
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 525"

<400> SEQUENCE: 523

Tyr Ile Ser Ser Gly Gly Gly Val Lys Phe Tyr Ala Asp Ser Val Lys
1               5                   10                  15

Gly

<210> SEQ ID NO 524
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 525"

<400> SEQUENCE: 524

Glu Ala Pro Leu Arg Leu Gly Glu Ser Pro His Asp Ala Phe Asp Ile
1               5                   10                  15

<210> SEQ ID NO 525
<211> LENGTH: 125
<212> TYPE: PRT
<213> ORGANISM: Homo sapiens
<220> FEATURE:

```
<221> NAME/KEY: source
<223> OTHER INFORMATION: /note="VH 1.113"

<400> SEQUENCE: 525
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Ser Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

```
<210> SEQ ID NO 526
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 529"

<400> SEQUENCE: 526
```

Asp Glu Ser His Thr
1               5

```
<210> SEQ ID NO 527
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 529"

<400> SEQUENCE: 527
```

Tyr Ile Ser Ser Gly Gly Gly Val Lys Phe Tyr Ala Asp Ser Val Lys
1               5                   10                  15

Gly

```
<210> SEQ ID NO 528
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 529"

<400> SEQUENCE: 528
```

Glu Ala Pro Leu Arg Leu Gly Glu Ser Pro His Asp Ala Phe Asp Ile
1               5                   10                  15

```
<210> SEQ ID NO 529
<211> LENGTH: 125
<212> TYPE: PRT
<213> ORGANISM: Homo sapiens
<220> FEATURE:
```

```
<221> NAME/KEY: source
<223> OTHER INFORMATION: /note="VH 1.114"

<400> SEQUENCE: 529
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser His Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

```
<210> SEQ ID NO 530
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 533"

<400> SEQUENCE: 530
```

Asp Glu Ser Gly Thr
1               5

```
<210> SEQ ID NO 531
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 533"

<400> SEQUENCE: 531
```

Tyr Ile Ser Ser Gly Gly Gly Val Lys Phe Tyr Ala Asp Ser Val Lys
1               5                   10                  15

Gly

```
<210> SEQ ID NO 532
<211> LENGTH: 16
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 533"

<400> SEQUENCE: 532
```

Glu Ala Pro Leu Arg Leu Gly Glu Ser Pro His Asp Ala Phe Asp Ile
1               5                   10                  15

```
<210> SEQ ID NO 533
<211> LENGTH: 125
<212> TYPE: PRT
<213> ORGANISM: Homo sapiens
<220> FEATURE:
```

<221> NAME/KEY: source
<223> OTHER INFORMATION: /note="VH 1.115"

<400> SEQUENCE: 533

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asp | Glu |
|---|---|---|---|---|---|---|---|---|---|---|---|---|---|---|---|
| | | | 20 | | | | | 25 | | | | | 30 | | |

| Ser | Gly | Thr | Trp | Met | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Tyr | Ile | Ser | Ser | Gly | Gly | Val | Lys | Tyr | Ala | Asp | Ser | Val |
|---|---|---|---|---|---|---|---|---|---|---|---|---|---|
| 50 | | | | | 55 | | | | 60 | | | | |

| Lys | Gly | Arg | Phe | Thr | Ile | Ser | Arg | Asp | Asn | Ala | Lys | Asn | Ser | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Ala | Pro | Leu | Arg | Leu | Gly | Glu | Ser | Pro | His | Asp | Ala | Phe |
|---|---|---|---|---|---|---|---|---|---|---|---|---|---|---|---|
| | | | 100 | | | | | 105 | | | | | 110 | | |

| Asp | Ile | Ser | Gly | Gln | Gly | Thr | Met | Val | Thr | Val | Ser | Ser |
|---|---|---|---|---|---|---|---|---|---|---|---|---|
| | | 115 | | | | | 120 | | | | | 125 |

<210> SEQ ID NO 534
<211> LENGTH: 375
<212> TYPE: DNA
<213> ORGANISM: Homo sapiens
<220> FEATURE:
<221> NAME/KEY: source
<223> OTHER INFORMATION: /note="VH 1.74"

<400> SEQUENCE: 534

```
gaggtgcagc tggtggagtc tgggggaggc ttggtcaagc ctggagggtc cctgagactc      60
tcctgtgcag cctctggatt caccttcagt gacagctcca tgacctggat tcggcaggct     120
ccagggaagg ggctggagtg gtttcctac ataagttctg gtggtggtgt caaattttac      180
acagactctg tgaagggccg attcaccatc tccagggaca cgccaagaa ctcactgtat      240
ctgcaaatga acagcctgag agccgacgac acggccgtgt attactgtgc gcgagaggcc     300
cctttacgtt tgggggagtc cccccatgat gcttttgata tctcgggcca agggacaatg     360
gtcaccgtct cctca                                                     375
```

<210> SEQ ID NO 535
<211> LENGTH: 375
<212> TYPE: DNA
<213> ORGANISM: Homo sapiens
<220> FEATURE:
<221> NAME/KEY: source
<223> OTHER INFORMATION: /note="VH 1.75"

<400> SEQUENCE: 535

```
gaggtgcagc tggtggagtc tgggggaggc ttggtcaagc ctggagggtc cctgagactc      60
tcctgtgcag cctctggatt caccttcagt gacagctcca tgacctggat tcggcaggct     120
ccagggaagg ggctggagtg gtttcctac ataagttctg gtggtggtgt caaattttac      180
acagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375
```

<210> SEQ ID NO 536
<211> LENGTH: 375
<212> TYPE: DNA
<213> ORGANISM: Homo sapiens
<220> FEATURE:
<221> NAME/KEY: source
<223> OTHER INFORMATION: /note="VH 1.76"

<400> SEQUENCE: 536

| gaggtgcagc tggtggagtc tgggggaggc ttggtcaagc ctggagggtc cctgagactc | 60 |
| tcctgtgcag cctctggatt caccttcagt gacagctcca tgacctggat tcggcaggct | 120 |
| ccagggaagg gctggagtg gtttcctac ataagttctg gtggtggtgt caaattttac | 180 |
| gcagactctg tgaagggccg attcaccatc tccagggaca acgccaagaa ctcactgtat | 240 |
| ctgcaaatga acagcctgag agccgacgac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 537
<211> LENGTH: 375
<212> TYPE: DNA
<213> ORGANISM: Homo sapiens
<220> FEATURE:
<221> NAME/KEY: source
<223> OTHER INFORMATION: /note="VH 1.77"

<400> SEQUENCE: 537

| gaggtgcagc tggtggagtc tgggggaggc ttggtcaagc ctggagggtc cctgagactc | 60 |
| tcctgtgcag cctctggatt caccttcagt gacagctcca tgacctggat gcggcaggct | 120 |
| ccagggaagg gctggagtg gtttcctac ataagttctg gtggtggtgt caaattttac | 180 |
| acagactctg tgaagggccg attcaccatc tccagggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 538
<211> LENGTH: 375
<212> TYPE: DNA
<213> ORGANISM: Homo sapiens
<220> FEATURE:
<221> NAME/KEY: source
<223> OTHER INFORMATION: /note="VH 1.78"

<400> SEQUENCE: 538

| gaggtgcagc tggtggagtc tgggggaggc ttggtcaagc ctggagggtc cctgagactc | 60 |
| tcctgtgcag cctctggatt caccttcagt gacagctcca tgacctggat tcggcaggct | 120 |
| ccagggaagg gctggagtg gtttcctac ataagttctg gtggtggtgt caaattttac | 180 |
| gcagactctg tgaagggccg attcaccatc tccagggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 539
<211> LENGTH: 375
<212> TYPE: DNA

<213> ORGANISM: Homo sapiens
<220> FEATURE:
<221> NAME/KEY: source
<223> OTHER INFORMATION: /note="VH 1.79"

<400> SEQUENCE: 539

```
gaggtgcagc tggtggagtc tggggggaggc ttggtcaagc ctggagggtc cctgagactc      60
tcctgtgcag cctctggatt caccttcagt gacagctcca tgacctggaa gcggcaggct     120
ccagggaagg ggctggagtg ggtttcctac ataagttctg gtggtggtgt caaattttac     180
gcagactctg tgaagggccg attcaccatc tccaggaca acgccaagaa ctcactgtat      240
ctgcaaatga acagcctgag agccgaagac acggccgtgt attactgtgc gcgagaggcc     300
cctttacgtt tgggggagtc ccccatgat gcttttgata tctcgggcca agggacaatg      360
gtcaccgtct cctca                                                      375
```

<210> SEQ ID NO 540
<211> LENGTH: 375
<212> TYPE: DNA
<213> ORGANISM: Homo sapiens
<220> FEATURE:
<221> NAME/KEY: source
<223> OTHER INFORMATION: /note="VH 1.80"

<400> SEQUENCE: 540

```
gaggtgcagc tggtggagtc tggggggaggc ttggtcaagc ctggagggtc cctgagactc      60
tcctgtgcag cctctggatt caccttcagt gacagctcca tgacctggat gcggcaggct     120
ccagggaagg ggctggagtg ggtttcctac ataagttctg gtggtggtgt caaattttac     180
gcagactctg tgaagggccg attcaccatc tccaggaca acgccaagaa ctcactgtat      240
ctgcaaatga acagcctgag agccgaagac acggccgtgt attactgtgc gcgagaggcc     300
cctttacgtt tgggggagtc ccccatgat gcttttgata tctcgggcca agggacaatg      360
gtcaccgtct cctca                                                      375
```

<210> SEQ ID NO 541
<211> LENGTH: 375
<212> TYPE: DNA
<213> ORGANISM: Homo sapiens
<220> FEATURE:
<221> NAME/KEY: source
<223> OTHER INFORMATION: /note="VH 1.81"

<400> SEQUENCE: 541

```
gaggtgcagc tggtggagtc tggggggaggc ttggtcaagc ctggagggtc cctgagactc      60
tcctgtgcag cctctggatt caccttcagt gacagctcca tgacctgggt gcggcaggct     120
ccagggaagg ggctggagtg ggtttcctac ataagttctg gtggtggtgt caaattttac     180
gcagactctg tgaagggccg attcaccatc tccaggaca acgccaagaa ctcactgtat      240
ctgcaaatga acagcctgag agccgaagac acggccgtgt attactgtgc gcgagaggcc     300
cctttacgtt tgggggagtc ccccatgat gcttttgata tctcgggcca agggacaatg      360
gtcaccgtct cctca                                                      375
```

<210> SEQ ID NO 542
<211> LENGTH: 375
<212> TYPE: DNA
<213> ORGANISM: Homo sapiens
<220> FEATURE:
<221> NAME/KEY: source
<223> OTHER INFORMATION: /note="VH 1.82"

<400> SEQUENCE: 542

```
gaggtgcagc tggtggagtc tgggggaggc ttggtcaagc ctggagggtc cctgagactc      60
tcctgtgcag cctctggatt caccttcagt gacacctcca tgacctggat gcggcaggct     120
ccagggaagg ggctggagtg ggtttcctac ataagttctg gtggtggtgt caaattttac     180
acagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca aggacaatg      360
gtcaccgtct cctca                                                      375
```

<210> SEQ ID NO 543
<211> LENGTH: 375
<212> TYPE: DNA
<213> ORGANISM: Homo sapiens
<220> FEATURE:
<221> NAME/KEY: source
<223> OTHER INFORMATION: /note="VH 1.83"

<400> SEQUENCE: 543

```
gaggtgcagc tggtggagtc tgggggaggc ttggtcaagc ctggagggtc cctgagactc      60
tcctgtgcag cctctggatt caccttcagt gacgaatcca tgacctggtt tcggcaggct     120
ccagggaagg ggctggagtg ggtttcctac ataagttctg gtggtggtgt caaattttac     180
acagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca aggacaatg      360
gtcaccgtct cctca                                                      375
```

<210> SEQ ID NO 544
<211> LENGTH: 375
<212> TYPE: DNA
<213> ORGANISM: Homo sapiens
<220> FEATURE:
<221> NAME/KEY: source
<223> OTHER INFORMATION: /note="VH 1.84"

<400> SEQUENCE: 544

```
gaggtgcagc tggtggagtc tgggggaggc ttggtcaagc ctggagggtc cctgagactc      60
tcctgtgcag cctctggatt caccttcagt gacgaatcca tgacctggat gcggcaggct     120
ccagggaagg ggctggagtg ggtttcctac ataagttctg gtggtggtgt caaattttac     180
acagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca aggacaatg      360
gtcaccgtct cctca                                                      375
```

<210> SEQ ID NO 545
<211> LENGTH: 375
<212> TYPE: DNA
<213> ORGANISM: Homo sapiens
<220> FEATURE:
<221> NAME/KEY: source
<223> OTHER INFORMATION: /note="VH 1.85"

<400> SEQUENCE: 545

```
gaggtgcagc tggtggagtc tgggggaggc ttggtcaagc ctggagggtc cctgagactc      60
```

-continued

```
tcctgtgcag cctctggatt caccttcagt gactattcca tgacctggat gcggcaggct      120
ccagggaagg ggctggagtg ggtttcctac ataagttctg gtggtggtgt caaattttac      180
acagactctg tgaagggccg attcaccatc tccagggaca cgccaagaa ctcactgtat       240 ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 546
<211> LENGTH: 375
<212> TYPE: DNA
<213> ORGANISM: Homo sapiens
<220> FEATURE:
<221> NAME/KEY: source
<223> OTHER INFORMATION: /note="VH 1.86"

<400> SEQUENCE: 546
gaggtgcagc tggtggagtc tgggggaggc ttggtcaagc ctggagggtc cctgagactc      60
tcctgtgcag cctctggatt caccttcagt gacgcctcca tgacctggat gcggcaggct      120
ccagggaagg ggctggagtg ggtttcctac ataagttctg gtggtggtgt caaattttac      180
acagactctg tgaagggccg attcaccatc tccagggaca cgccaagaa ctcactgtat       240 ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 547
<211> LENGTH: 375
<212> TYPE: DNA
<213> ORGANISM: Homo sapiens
<220> FEATURE:
<221> NAME/KEY: source
<223> OTHER INFORMATION: /note="VH 1.87"

<400> SEQUENCE: 547
gaggtgcagc tggtggagtc tgggggaggc ttggtcaagc ctggagggtc cctgagactc      60
tcctgtgcag cctctggatt caccttcagt gacaaatcca tgacctggat gcggcaggct      120
ccagggaagg ggctggagtg ggtttcctac ataagttctg gtggtggtgt caaattttac      180
acagactctg tgaagggccg attcaccatc tccagggaca cgccaagaa ctcactgtat       240 ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 548
<211> LENGTH: 375
<212> TYPE: DNA
<213> ORGANISM: Homo sapiens
<220> FEATURE:
<221> NAME/KEY: source
<223> OTHER INFORMATION: /note="VH 1.88"

<400> SEQUENCE: 548
gaggtgcagc tggtggagtc tgggggaggc ttggtcaagc ctggagggtc cctgagactc      60
tcctgtgcag cctctggatt caccttcagt gaccgttcca tgacctggat gcggcaggct      120
ccagggaagg ggctggagtg ggtttcctac ataagttctg gtggtggtgt caaattttac      180
```

```
acagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                      375
```

<210> SEQ ID NO 549
<211> LENGTH: 375
<212> TYPE: DNA
<213> ORGANISM: Homo sapiens
<220> FEATURE:
<221> NAME/KEY: source
<223> OTHER INFORMATION: /note="VH 1.89"

<400> SEQUENCE: 549

```
gaggtgcagc tggtggagtc tgggggaggc ttggtcaagc ctggagggtc cctgagactc     60
tcctgtgcag cctctggatt caccttcagt gactattcca tgacctggat gcggcaggct    120
ccagggaagg gactggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                      375
```

<210> SEQ ID NO 550
<211> LENGTH: 375
<212> TYPE: DNA
<213> ORGANISM: Homo sapiens
<220> FEATURE:
<221> NAME/KEY: source
<223> OTHER INFORMATION: /note="VH 1.90"

<400> SEQUENCE: 550

```
gaggtgcagc tggtggagtc tgggggaggc ttggtcaagc ctggagggtc cctgagactc     60
tcctgtgcag cctctggatt caccttcagt gacgtgtcca tgacctggat gcggcaggct    120
ccagggaagg gactggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                      375
```

<210> SEQ ID NO 551
<211> LENGTH: 375
<212> TYPE: DNA
<213> ORGANISM: Homo sapiens
<220> FEATURE:
<221> NAME/KEY: source
<223> OTHER INFORMATION: /note="VH 1.91"

<400> SEQUENCE: 551

```
gaggtgcagc tggtggagtc tgggggaggc ttggtcaagc ctggagggtc cctgagactc     60
tcctgtgcag cctctggatt caccttcagt gaccagtcca tgacctggat gcggcaggct    120
ccagggaagg gactggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
```

```
cctttacgtt tggggagtc cccccatgat gcttttgata tctcgggcca agggacaatg    360
gtcaccgtct cctca                                                   375

<210> SEQ ID NO 552
<211> LENGTH: 375
<212> TYPE: DNA
<213> ORGANISM: Homo sapiens
<220> FEATURE:
<221> NAME/KEY: source
<223> OTHER INFORMATION: /note="VH 1.92"

<400> SEQUENCE: 552
gaggtgcagc tggtggagtc tgggggaggc ttggtcaagc ctggagggtc cctgagactc    60
tcctgtgcag cctctggatt caccttcagt gacgaatcca tgacctggat gcggcaggct   120
ccagggaagg ggctggagtg ggtttcctac ataagttctg gtggtggtgt caaattttac   180
gcagactctg tgaagggccg attcaccatc tccaggaca acgccaagaa ctcactgtat    240
ctgcaaatga acagcctgag agccgaagac acggccgtgt attactgtgc gcgagaggcc    300
cctttacgtt tggggagtc cccccatgat gcttttgata tctcgggcca agggacaatg   360
gtcaccgtct cctca                                                   375

<210> SEQ ID NO 553
<211> LENGTH: 375
<212> TYPE: DNA
<213> ORGANISM: Homo sapiens
<220> FEATURE:
<221> NAME/KEY: source
<223> OTHER INFORMATION: /note="VH 1.93"

<400> SEQUENCE: 553
gaggtgcagc tggtggagtc tgggggaggc ttggtcaagc ctggagggtc cctgagactc    60
tcctgtgcag cctctggatt caccttcagt gacgcctcca tgacctggat gcggcaggct   120
ccagggaagg ggctggagtg ggtttcctac ataagttctg gtggtggtgt caaattttac   180
gcagactctg tgaagggccg attcaccatc tccaggaca acgccaagaa ctcactgtat    240
ctgcaaatga acagcctgag agccgaagac acggccgtgt attactgtgc gcgagaggcc    300
cctttacgtt tggggagtc cccccatgat gcttttgata tctcgggcca agggacaatg   360
gtcaccgtct cctca                                                   375

<210> SEQ ID NO 554
<211> LENGTH: 375
<212> TYPE: DNA
<213> ORGANISM: Homo sapiens
<220> FEATURE:
<221> NAME/KEY: source
<223> OTHER INFORMATION: /note="VH 1.94"

<400> SEQUENCE: 554
gaggtgcagc tggtggagtc tgggggaggc ttggtcaagc ctggagggtc cctgagactc    60
tcctgtgcag cctctggatt caccttcagt gactggtcca tgacctggat gcggcaggct   120
ccagggaagg ggctggagtg ggtttcctac ataagttctg gtggtggtgt caaattttac   180
gcagactctg tgaagggccg attcaccatc tccaggaca acgccaagaa ctcactgtat    240
ctgcaaatga acagcctgag agccgaagac acggccgtgt attactgtgc gcgagaggcc    300
cctttacgtt tggggagtc cccccatgat gcttttgata tctcgggcca agggacaatg   360
gtcaccgtct cctca                                                   375
```

<210> SEQ ID NO 555
<211> LENGTH: 375
<212> TYPE: DNA
<213> ORGANISM: Homo sapiens
<220> FEATURE:
<221> NAME/KEY: source
<223> OTHER INFORMATION: /note="VH 1.95"

<400> SEQUENCE: 555

```
gaggtgcagc tggtggagtc tgggggaggc ttggtcaagc ctggagggtc cctgagactc      60
tcctgtgcag cctctggatt caccttcagt gacggctcca tgacctggat gcggcaggct     120
ccagggaagg ggctggagtg ggtttcctac ataagttctg gtggtggtgt caaattttac     180
gcagactctg tgaagggccg attcaccatc tccaggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca aggacaatg     360
gtcaccgtct cctca                                                      375
```

<210> SEQ ID NO 556
<211> LENGTH: 375
<212> TYPE: DNA
<213> ORGANISM: Homo sapiens
<220> FEATURE:
<221> NAME/KEY: source
<223> OTHER INFORMATION: /note="VH 1.96"

<400> SEQUENCE: 556

```
gaggtgcagc tggtggagtc tgggggaggc ttggtcaagc ctggagggtc cctgagactc      60
tcctgtgcag cctctggatt caccttcagt gacacctcca tgacctggat gcggcaggct     120
ccagggaagg ggctggagtg ggtttcctac ataagttctg gtggtggtgt caaattttac     180
gcagactctg tgaagggccg attcaccatc tccaggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca aggacaatg     360
gtcaccgtct cctca                                                      375
```

<210> SEQ ID NO 557
<211> LENGTH: 375
<212> TYPE: DNA
<213> ORGANISM: Homo sapiens
<220> FEATURE:
<221> NAME/KEY: source
<223> OTHER INFORMATION: /note="VH 1.97"

<400> SEQUENCE: 557

```
gaggtgcagc tggtggagtc tgggggaggc ttggtcaagc ctggagggtc cctgagactc      60
tcctgtgcag cctctggatt caccttcagt gacatttcca tgacctggat gcggcaggct     120
ccagggaagg ggctggagtg ggtttcctac ataagttctg gtggtggtgt caaattttac     180
gcagactctg tgaagggccg attcaccatc tccaggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca aggacaatg     360
gtcaccgtct cctca                                                      375
```

<210> SEQ ID NO 558
<211> LENGTH: 375

```
<212> TYPE: DNA
<213> ORGANISM: Homo sapiens
<220> FEATURE:
<221> NAME/KEY: source
<223> OTHER INFORMATION: /note="VH 1.98"

<400> SEQUENCE: 558
gaggtgcagc tggtggagtc tgggggaggc ttggtcaagc ctggagggtc cctgagactc      60
tcctgtgcag cctctggatt caccttcagt gacaaatcca tgacctggat gcggcaggct     120
ccagggaagg gctggagtg gtttcctac ataagttctg gtggtggtgt caaattttac      180
gcagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 559
<211> LENGTH: 375
<212> TYPE: DNA
<213> ORGANISM: Homo sapiens
<220> FEATURE:
<221> NAME/KEY: source
<223> OTHER INFORMATION: /note="VH 1.99"

<400> SEQUENCE: 559
gaggtgcagc tggtggagtc tgggggaggc ttggtcaagc ctggagggtc cctgagactc      60
tcctgtgcag cctctggatt caccttcagt gaccgttcca tgacctggat gcggcaggct     120
ccagggaagg gctggagtg gtttcctac ataagttctg gtggtggtgt caaattttac      180
gcagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 560
<211> LENGTH: 375
<212> TYPE: DNA
<213> ORGANISM: Homo sapiens
<220> FEATURE:
<221> NAME/KEY: source
<223> OTHER INFORMATION: /note="VH 1.100"

<400> SEQUENCE: 560
gaggtgcagc tggtggagtc tgggggaggc ttggtcaagc ctggagggtc cctgagactc      60
tcctgtgcag cctctggatt caccttcagt gacctgtcca tgacctggat gcggcaggct     120
ccagggaagg gctggagtg gtttcctac ataagttctg gtggtggtgt caaattttac      180
gcagactctg tgaagggccg attcaccatc tccagggaca cgccaagaa ctcactgtat      240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 561
<211> LENGTH: 375
<212> TYPE: DNA
<213> ORGANISM: Homo sapiens
<220> FEATURE:
<221> NAME/KEY: source
```

<223> OTHER INFORMATION: /note="VH 1.101"

<400> SEQUENCE: 561

```
gaggtgcagc tggtggagtc tggggggaggc ttggtcaagc ctggagggtc cctgagactc   60
tcctgtgcag cctctggatt caccttcagt gacttttcca tgacctggat gcggcaggct  120
ccagggaagg ggctggagtg ggtttcctac ataagttctg gtggtggtgt caaattttac  180
gcagactctg tgaagggccg attcaccatc tccaggaca acgccaagaa ctcactgtat  240
ctgcaaatga acagcctgag agccgaagac acggccgtgt attactgtgc gcgagaggcc  300
cctttacgtt tgggggagtc cccccatgat gcttttgata tctcgggcca agggacaatg  360
gtcaccgtct cctca                                                    375
```

<210> SEQ ID NO 562
<211> LENGTH: 375
<212> TYPE: DNA
<213> ORGANISM: Homo sapiens
<220> FEATURE:
<221> NAME/KEY: source
<223> OTHER INFORMATION: /note="VH 1.102"

<400> SEQUENCE: 562

```
gaggtgcagc tggtggagtc tggggggaggc ttggtcaagc ctggagggtc cctgagactc   60
tcctgtgcag cctctggatt caccttcagt gacgaatccg tgacctggat gcggcaggct  120
ccagggaagg ggctggagtg ggtttcctac ataagttctg gtggtggtgt caaattttac  180
acagactctg tgaagggccg attcaccatc tccaggaca acgccaagaa ctcactgtat  240
ctgcaaatga acagcctgag agccgaagac acggccgtgt attactgtgc gcgagaggcc  300
cctttacgtt tgggggagtc cccccatgat gcttttgata tctcgggcca agggacaatg  360
gtcaccgtct cctca                                                    375
```

<210> SEQ ID NO 563
<211> LENGTH: 375
<212> TYPE: DNA
<213> ORGANISM: Homo sapiens
<220> FEATURE:
<221> NAME/KEY: source
<223> OTHER INFORMATION: /note="VH 1.103"

<400> SEQUENCE: 563

```
gaggtgcagc tggtggagtc tggggggaggc ttggtcaagc ctggagggtc cctgagactc   60
tcctgtgcag cctctggatt caccttcagt gacgaatccc agacctggat gcggcaggct  120
ccagggaagg ggctggagtg ggtttcctac ataagttctg gtggtggtgt caaattttac  180
acagactctg tgaagggccg attcaccatc tccaggaca acgccaagaa ctcactgtat  240
ctgcaaatga acagcctgag agccgaagac acggccgtgt attactgtgc gcgagaggcc  300
cctttacgtt tgggggagtc cccccatgat gcttttgata tctcgggcca agggacaatg  360
gtcaccgtct cctca                                                    375
```

<210> SEQ ID NO 564
<211> LENGTH: 375
<212> TYPE: DNA
<213> ORGANISM: Homo sapiens
<220> FEATURE:
<221> NAME/KEY: source
<223> OTHER INFORMATION: /note="VH 1.104"

<400> SEQUENCE: 564

```
gaggtgcagc tggtggagtc tggggaggc ttggtcaagc ctggagggtc cctgagactc      60
tcctgtgcag cctctggatt caccttcagt gacgaatcct ttacctggat gcggcaggct    120
ccagggaagg ggctggagtg ggtttcctac ataagttctg tggtggtgt caaattttac    180 acagactctg tgaagggccg attcaccatc tccagggaca cgccaagaa ctcactgtat    240 ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375

<210> SEQ ID NO 565
<211> LENGTH: 375
<212> TYPE: DNA
<213> ORGANISM: Homo sapiens
<220> FEATURE:
<221> NAME/KEY: source
<223> OTHER INFORMATION: /note="VH 1.105"

<400> SEQUENCE: 565
gaggtgcagc tggtggagtc tggggaggc ttggtcaagc ctggagggtc cctgagactc      60
tcctgtgcag cctctggatt caccttcagt gacgaatccc tgacctggat gcggcaggct    120
ccagggaagg ggctggagtg ggtttcctac ataagttctg tggtggtgt caaattttac    180 acagactctg tgaagggccg attcaccatc tccagggaca cgccaagaa ctcactgtat    240 ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375

<210> SEQ ID NO 566
<211> LENGTH: 375
<212> TYPE: DNA
<213> ORGANISM: Homo sapiens
<220> FEATURE:
<221> NAME/KEY: source
<223> OTHER INFORMATION: /note="VH 1.106"

<400> SEQUENCE: 566
gaggtgcagc tggtggagtc tggggaggc ttggtcaagc ctggagggtc cctgagactc      60
tcctgtgcag cctctggatt caccttcagt gacgaatcca aaacctggat gcggcaggct    120
ccagggaagg ggctggagtg ggtttcctac ataagttctg tggtggtgt caaattttac    180 acagactctg tgaagggccg attcaccatc tccagggaca cgccaagaa ctcactgtat    240 ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375

<210> SEQ ID NO 567
<211> LENGTH: 375
<212> TYPE: DNA
<213> ORGANISM: Homo sapiens
<220> FEATURE:
<221> NAME/KEY: source
<223> OTHER INFORMATION: /note="VH 1.107"

<400> SEQUENCE: 567
gaggtgcagc tggtggagtc tggggaggc ttggtcaagc ctggagggtc cctgagactc      60
tcctgtgcag cctctggatt caccttcagt gacgaatcct ataccctggat gcggcaggct   120
```

| | |
|---|---|
| ccagggaagg ggctggagtg ggtttcctac ataagttctg gtggtggtgt caaattttac | 180 |
| acagactctg tgaagggccg attcaccatc tccagggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 568
<211> LENGTH: 375
<212> TYPE: DNA
<213> ORGANISM: Homo sapiens
<220> FEATURE:
<221> NAME/KEY: source
<223> OTHER INFORMATION: /note="VH 1.108"

<400> SEQUENCE: 568

| | |
|---|---|
| gaggtgcagc tggtggagtc tgggggaggc ttggtcaagc ctggagggtc cctgagactc | 60 |
| tcctgtgcag cctctggatt caccttcagt gacgaatccg cgacctggat gcggcaggct | 120 |
| ccagggaagg ggctggagtg ggtttcctac ataagttctg gtggtggtgt caaattttac | 180 |
| gcagactctg tgaagggccg attcaccatc tccagggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 569
<211> LENGTH: 375
<212> TYPE: DNA
<213> ORGANISM: Homo sapiens
<220> FEATURE:
<221> NAME/KEY: source
<223> OTHER INFORMATION: /note="VH 1.109"

<400> SEQUENCE: 569

| | |
|---|---|
| gaggtgcagc tggtggagtc tgggggaggc ttggtcaagc ctggagggtc cctgagactc | 60 |
| tcctgtgcag cctctggatt caccttcagt gacgaatcct tcacctggat gcggcaggct | 120 |
| ccagggaagg ggctggagtg ggtttcctac ataagttctg gtggtggtgt caaattttac | 180 |
| gcagactctg tgaagggccg attcaccatc tccagggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 570
<211> LENGTH: 375
<212> TYPE: DNA
<213> ORGANISM: Homo sapiens
<220> FEATURE:
<221> NAME/KEY: source
<223> OTHER INFORMATION: /note="VH 1.110"

<400> SEQUENCE: 570

| | |
|---|---|
| gaggtgcagc tggtggagtc tgggggaggc ttggtcaagc ctggagggtc cctgagactc | 60 |
| tcctgtgcag cctctggatt caccttcagt gacgaatcca cacctggat gcggcaggct | 120 |
| ccagggaagg ggctggagtg ggtttcctac ataagttctg gtggtggtgt caaattttac | 180 |
| gcagactctg tgaagggccg attcaccatc tccagggaca acgccaagaa ctcactgtat | 240 |

```
ctgcaaatga acagcctgag agccgaagac acggccgtgt attactgtgc gcgagaggcc    300
cctttacgtt tggggagtc cccccatgat gcttttgata tctcgggcca agggacaatg    360
gtcaccgtct cctca                                                     375
```

<210> SEQ ID NO 571
<211> LENGTH: 375
<212> TYPE: DNA
<213> ORGANISM: Homo sapiens
<220> FEATURE:
<221> NAME/KEY: source
<223> OTHER INFORMATION: /note="VH 1.111"

<400> SEQUENCE: 571

```
gaggtgcagc tggtggagtc tgggggaggc ttggtcaagc ctggagggtc cctgagactc    60
tcctgtgcag cctctggatt caccttcagt gacgaatcct ggacctggat gcggcaggct    120
ccagggaagg ggctggagtg ggtttcctac ataagttctg gtggtggtgt caaattttac    180
gcagactctg tgaagggccg attcaccatc tccaggggaca cgccaagaa ctcactgtat    240 ctgcaaatga acagcctgag agccgaagac acggccgtgt attactgtgc gcgagaggcc    300
cctttacgtt tggggagtc cccccatgat gcttttgata tctcgggcca agggacaatg    360
gtcaccgtct cctca                                                     375
```

<210> SEQ ID NO 572
<211> LENGTH: 375
<212> TYPE: DNA
<213> ORGANISM: Homo sapiens
<220> FEATURE:
<221> NAME/KEY: source
<223> OTHER INFORMATION: /note="VH 1.112"

<400> SEQUENCE: 572

```
gaggtgcagc tggtggagtc tgggggaggc ttggtcaagc ctggagggtc cctgagactc    60
tcctgtgcag cctctggatt caccttcagt gacgaatcca tcacctggat gcggcaggct    120
ccagggaagg ggctggagtg ggtttcctac ataagttctg gtggtggtgt caaattttac    180
gcagactctg tgaagggccg attcaccatc tccaggggaca cgccaagaa ctcactgtat    240 ctgcaaatga acagcctgag agccgaagac acggccgtgt attactgtgc gcgagaggcc    300
cctttacgtt tggggagtc cccccatgat gcttttgata tctcgggcca agggacaatg    360
gtcaccgtct cctca                                                     375
```

<210> SEQ ID NO 573
<211> LENGTH: 375
<212> TYPE: DNA
<213> ORGANISM: Homo sapiens
<220> FEATURE:
<221> NAME/KEY: source
<223> OTHER INFORMATION: /note="VH 1.113"

<400> SEQUENCE: 573

```
gaggtgcagc tggtggagtc tgggggaggc ttggtcaagc ctggagggtc cctgagactc    60
tcctgtgcag cctctggatt caccttcagt gacgaatcca gcacctggat gcggcaggct    120
ccagggaagg ggctggagtg ggtttcctac ataagttctg gtggtggtgt caaattttac    180
gcagactctg tgaagggccg attcaccatc tccaggggaca cgccaagaa ctcactgtat    240 ctgcaaatga acagcctgag agccgaagac acggccgtgt attactgtgc gcgagaggcc    300
cctttacgtt tggggagtc cccccatgat gcttttgata tctcgggcca agggacaatg    360
```
gtcaccgtct cctca 375

<210> SEQ ID NO 574
<211> LENGTH: 375
<212> TYPE: DNA
<213> ORGANISM: Homo sapiens
<220> FEATURE:
<221> NAME/KEY: source
<223> OTHER INFORMATION: /note="VH 1.114"

<400> SEQUENCE: 574
gaggtgcagc tggtggagtc tgggggaggc ttggtcaagc ctggagggtc cctgagactc    60
tcctgtgcag cctctggatt caccttcagt gacgaatccc acacctggat gcggcaggct   120
ccagggaagg gctggagtg gttttcctac ataagttctg gtggtggtgt caaattttac   180
gcagactctg tgaagggccg attcaccatc tccagggaca cgccaagaa ctcactgtat   240
ctgcaaatga acagcctgag agccgaagac acggccgtgt attactgtgc gcgagaggcc   300
cctttacgtt tggggagtc ccccatgat gcttttgata tctcgggcca agggacaatg   360
gtcaccgtct cctca                                                   375

<210> SEQ ID NO 575
<211> LENGTH: 375
<212> TYPE: DNA
<213> ORGANISM: Homo sapiens
<220> FEATURE:
<221> NAME/KEY: source
<223> OTHER INFORMATION: /note="VH 1.115"

<400> SEQUENCE: 575
gaggtgcagc tggtggagtc tgggggaggc ttggtcaagc ctggagggtc cctgagactc    60
tcctgtgcag cctctggatt caccttcagt gacgaatccg ggacctggat gcggcaggct   120
ccagggaagg gctggagtg gttttcctac ataagttctg gtggtggtgt caaattttac   180
gcagactctg tgaagggccg attcaccatc tccagggaca cgccaagaa ctcactgtat   240
ctgcaaatga acagcctgag agccgaagac acggccgtgt attactgtgc gcgagaggcc   300
cctttacgtt tggggagtc ccccatgat gcttttgata tctcgggcca agggacaatg   360
gtcaccgtct cctca                                                   375

<210> SEQ ID NO 576
<211> LENGTH: 288
<212> TYPE: PRT
<213> ORGANISM: Homo sapiens
<220> FEATURE:
<221> NAME/KEY: source
<223> OTHER INFORMATION: /note="Human PD-1 protein"

<400> SEQUENCE: 576

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg

```
                85                  90                  95
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 577
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 2GS linker sequence"

<400> SEQUENCE: 577

Gly Gly Gly Gly Ser Gly Gly Gly Gly Ser
1               5                   10

<210> SEQ ID NO 578
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 2GS linker sequence"

<400> SEQUENCE: 578
ggaggtggag gttcaggtgg aggtggtagt                                    30

<210> SEQ ID NO 579
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 4GS linker sequence"

<400> SEQUENCE: 579
```

Gly Gly Gly Gly Ser Gly Gly Gly Gly Ser Gly Gly Gly Ser Gly
1               5                   10                  15

Gly Gly Gly Ser
            20

<210> SEQ ID NO 580
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 4GS linker sequence"

<400> SEQUENCE: 580
ggaggtggag gttcaggagg tggtggttct ggtggtggcg gttcaggtgg aggtggtagt      60

<210> SEQ ID NO 581
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6GS linker sequence"

<400> SEQUENCE: 581

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 582
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 6GS linker sequence"

<400> SEQUENCE: 582
ggtggtggcg gttcaggcgg aggtggctct ggaggtggag gttcaggagg tggtggttct      60
ggcggcggtg gatcgggtgg aggtggtagt                                      90

<210> SEQ ID NO 583
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 9GS linker sequence"

<400> SEQUENCE: 583

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Gly Gly Gly Gly Ser
        35                  40                  45

<210> SEQ ID NO 584
<211> LENGTH: 135
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic 9GS linker sequence"

<400> SEQUENCE: 584
ggaggtggag gttcaggagg tggtggttct ggtggtggcg gttcaggtgg aggtggtagt        60
ggaggaggtg gttctggcgg aggaggatcg ggtggaggtg gctcaggtgg tggaggtagt       120
ggaggcggtg gcagc                                                       135

<210> SEQ ID NO 585
<211> LENGTH: 5
<212> TYPE: PRT
<213> ORGANISM: Homo sapiens
<220> FEATURE:
<221> NAME/KEY: source
<223> OTHER INFORMATION: /note="C terminal end of human VH"

<400> SEQUENCE: 585

Val Thr Val Ser Ser
1               5

<210> SEQ ID NO 586
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 586

His His His His His His
1               5

<210> SEQ ID NO 587
<211> LENGTH: 127
<212> TYPE: PRT
<213> ORGANISM: Homo sapiens

<400> SEQUENCE: 587

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Gly Gly Ser Tyr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 588
<211> LENGTH: 123
<212> TYPE: PRT
```

```
<213> ORGANISM: Homo sapiens

<400> SEQUENCE: 588

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
            35                  40                  45

Ser Gly Ile Thr Trp Asn Ala Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
            115                 120

<210> SEQ ID NO 589
<211> LENGTH: 127
<212> TYPE: PRT
<213> ORGANISM: Homo sapiens

<400> SEQUENCE: 589

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
            35                  40                  45

Ser Gly Ile Ser Trp Asn Gly Gly Ser Met Gly Tyr Ala Ala Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Val Trp Gly Gln Gly Thr Met Val Thr Val Ser Ser
            115                 120                 125
```